(12) United States Patent
Karras

(10) Patent No.: US 7,307,069 B2
(45) Date of Patent: Dec. 11, 2007

(54) ANTISENSE OLIGONUCLEOTIDE MODULATION OF STAT3 EXPRESSION

(75) Inventor: James G. Karras, San Marcos, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 11/376,033

(22) Filed: Mar. 15, 2006

(65) Prior Publication Data

US 2006/0217339 A1 Sep. 28, 2006

Related U.S. Application Data

(62) Division of application No. 10/773,678, filed on Feb. 6, 2004, now Pat. No. 7,098,192.

(51) Int. Cl.
| C07H 21/04 | (2006.01) |
| C07H 21/02 | (2006.01) |
| A61K 48/00 | (2006.01) |
| C12Q 1/68  | (2006.01) |

(52) U.S. Cl. .................. 514/44; 435/6; 435/325; 435/375; 536/23.1; 536/24.3; 536/24.5

(58) Field of Classification Search ............... None
See application file for complete search history.

(56) References Cited

U.S. PATENT DOCUMENTS

| 5,686,242 A | 11/1997 | Bruice et al. |
| 5,719,042 A | 2/1998 | Kishimoto et al. |
| 5,801,154 A | 9/1998 | Baracchini et al. |
| 5,844,082 A | 12/1998 | Kishimoto et al. |
| 6,110,667 A | 8/2000 | Lopez-Nieto et al. |
| 6,159,694 A | 12/2000 | Karras |
| 6,248,586 B1 | 6/2001 | Monia et al. |
| 6,514,725 B1 | 2/2003 | Kishimoto et al. |
| 6,727,064 B2 | 4/2004 | Karras |
| 6,727,084 B1 | 4/2004 | Hoyoux et al. |

FOREIGN PATENT DOCUMENTS

| EP | 0 676 469 A2 | 10/1995 |
| WO | WO 96/16175 | 5/1996 |
| WO | WO 00/61602 | 10/2000 |

OTHER PUBLICATIONS

Scherer et al., Approaches for the sequence-specific knockdown of mRNA, 2003, Nat. Biotechnol., 21(12), pp. 1457-1465.*
Mahato et al., Modulation of gene expression by antisense and antigene oligodeoxynucleotides and small interfering RNA, Jan. 2005, Expert Opinion on Drug Delivery, vol. 2, No. 1, pp. 3-28.*
Groothuis, The blood-brain and blood-tumor barriers: A review of strategies for increasing drug delivery, Jan. 2000, Neuro-Oncology, 2(1), pp. 45-59.*
Aberg, et al., "Selective Introduction of Antisense Oligonucleotides into Single Adult CNS Progenitor Cells Using Electroporation Demonstrates the Requirement of STAT3 Activation for CNTF-Induced Gliogenesis," *Molecular and Cellular Neuroscience*, vol. 17, pp. 426-443 (2001).
Agrawal, "Antisense oligonucleotides: towards clinical trials," *TIBECH*, vol. 14, pp. 376-387 (1996).
Barton, et al., "Signal transducer and activator of transcription 3 (STAT3) activation in prostate cancer: Direct STAT3 inhibition induces apoptosis in prostate cancer lines," *Molecular Cancer Therapeutics*, vol. 3:1, pp. 11-20 (2004).
Braasch, et al., "Novel Antisense and Peptide Nucleic Acid Strategies for Controlling Gene Expression," *Biochemistry*, vol. 41:14, pp. 4503-4510 (2002).
Branch, "A good antisense molecule is hard to find," *TIBS*, vol. 23, pp. 45-50 (1998).
Catlett-Falcone, et al., "Constitutive Activation of Stat3 Signaling Confers Resistance to Apoptosis in Human U266 Myeloma Cells," *Immunity*, vol. 10, pp. 105-115 (1999).
Epling-Burnette, et al., "Inhibition of STAT3 signaling leads to apoptosis of leukemic large granular lymphocytes and decreased Mcl-1 expression," *J. of Clinical Investigation*, vol. 107:3, pp. 351-361 (2001).
Ernst, et al., "The Carboxyl-terminal Domains of gp130-related Cytokine Receptors are Necessary for Suppressing Embryonic Stem Cell Differentiation," *J. of Biological Chemistry*, vol. 274:14, pp. 9729-9737 (1999).
Gerwitz, et al., "Facilitating oligonucleotide delivery: Helping antisense deliver on its promise," *Proc. Natl. Acad. Sci*, vol. 93, pp. 3161-3163 (1996).
Grandis, et al., "Requirement of Stat3 but not Stat1 Activation for Epidermal Growth Factor Receptor—mediated Cell Growth In Vitro," *J. Clin. Invest.*, vol. 102:7, pp. 1385-1392 (1998).
James, "Towards gene-inhibition therapy: a review of progress and prosects in the field of antiviral antisense nucleic acids and ribozymes," *Antiviral Chemistry & Chemotherapy*, vol. 2:4, pp. 191-214 (1991).
Karras, et al., "STAT3 Regulates the Growth and Immunoglobulin Production of BCL1 B Cell Lymphona through Control of Cell Cycle Progression," *Cellular Immunology*, vol. 202, pp. 124-135 (2000).

(Continued)

*Primary Examiner*—Jon E. Angell
*Assistant Examiner*—Amy H. Bowman
(74) *Attorney, Agent, or Firm*—Charles E. Cohen; Manisha A. Desai

(57) ABSTRACT

Compounds, compositions and methods are provided for inhibiting the expression of human STAT3. The compositions comprise antisense oligonucleotides targeted to nucleic acids encoding STAT3. Methods of using these oligonucleotides for inhibition of STAT3 expression and for promotion of apoptosis are provided. Methods for treatment of diseases, particularly inflammatory diseases and cancers, associated with overexpression or constitutive activation of STAT3 or insufficient apoptosis are also provided.

13 Claims, No Drawings

OTHER PUBLICATIONS

Konnikova, et al., "Knockdown of STAT3 expression by RNAi induces apoptosis in astrocytoma cells," *BMC Cancer*, vol. 3:23, pp. 1-9 (2003).

Lamy, "Dysregulation of CD95/CD95 Ligand-Apoptotic Pathway in CD3+ Large Granular Lymphocyte Leukemia," *Blood*, vol. 92:12, pp. 4771-4777 (1998).

Lui, et al., "Serine phosphorylation of STAT3 is essential for Mcl-1 expression and macrophage survival," *Blood*, vol. 102:1, pp. 344-352 (2003).

Mahboubi, et al., "Desensitization of Signaling by Oncostatin M in Human Vascular Cells Involves Cytoplasmic Tyr Residue 759 in gp130 but is Not Mediated by Either Src Homology 2 Domain-containing Tyrosine Phosphatase 2 or Suppressor of Cytokine Signaling 3*," *J. of Biological Chemistry*, vol. 278:27, pp. 25014-25023 (2003).

Milner, et al., "Selecting effective antisense reagents on combinatorial oligonucleotide arrays," *Nature Biotechnology*, vol. 15, pp. 537-541 (1997).

Mora, et al., "Constitutive Activation of Stat3 in Human Prostate Tumors and Cell Lines: Direct Inhibition of Stat3 Signaling Induces Apoptosis of Prostate Cancer Cells," *Cancer Research*, vol. 62, pp. 6659-6666 (2002).

Niu, et al., "Gene Therapy with Dominant-negative Stat3 Suppresses Growth of the Murine Melanoma B16 Tumor in Vivo," *Cancer Research*, vol. 59, pp. 5059-5063 (1999).

Niu, et al., "Constitutivie Stat3 activity up-regulates VEGF expression and tumor angiogenesis," *Oncogene*, vol. 21, pp. 2000-2008 (2002).

Song, et al., "Activation of Stat3 by receptor tyrosine kinases and cytokines regulates survival in human non-small cell carcinoma cells," *Oncogene*, vol. 22, pp. 4150-4165 (2003).

Tamm, et al., "Antisense therapy in oncology: new hope for an old idea?" *The Lancet*, vol. 358, pp. 489-497 (2001).

Akira, et al., "Molecular Cloning of APRF, a Novel IFN-Stimulated Gene Factor 3 p91-Related Transcription Factor Involved in the gp130-Mediated Signaling Pathway," *Cell*, vol. 77, pp. 63-71 (1994).

Zhong, et al., "Stat3: A STAT Family Member Activated by Tyrosine Phosphorylation in Response to Epidermal Growth Factor and Interleukin-6," *Science*, vol. 264, pp. 95-98 (1994).

STAT3 Antisense Oligonucleotide Sequence Search Results, 2007.

Matzura, et al., RNAdraw: an integrated program for RNA secondary structure calculation and analysis under 32-bit Microsoft Windows, *Computer Applications in the Biosciences* 12(3):247-249 (1996).

Olie, et al., "A Novel Antisense Oligonucleotide Targeting Survivin Expression Induces Apoptosis and Sensitizes Lung Cancer Cells to Chemotherapy," *Cancer Research*, 60:2805-2809 (2000).

* cited by examiner

SEQUENCE LISTING

<160> NUMBER OF SEQ ID NOS: 406

<210> SEQ ID NO 1
<211> LENGTH: 2787
<212> TYPE: DNA
<213> ORGANISM: Homo sapiens

<400> SEQUENCE: 1

```
cagctggaat tcggggcggc ggcgcagact gggaggggga gccgggggtt ccgacgtcgc      60
agccgaggga acaagcccca accggatcct ggacaggcac cccggcttgg cgctgtctct     120 cccctcggc tcggagaggc ccttcggcct gagggagcct cgccgcccgt ccccggcaca     180
cgcgcagccc cggcctctcg gcctctgccg gagaaacagg atggcccaat ggaatcagct     240
acagcagctt gacacacggt acctggagca gctccatcag ctctacagtg acagcttccc     300
aatggagctg cggcagtttc tggccccttg gattgagagt caagattggg catatgcggc     360
cagcaaagaa tcacatgcca ctttggtgtt tcataatctc ctgggagaga ttgaccagca     420
gtatagccgc ttcctgcaag agtcgaatgt tctctatcag cacaatctac gaagaatcaa     480
gcagtttctt cagagcaggt atcttgagaa gccaatggag attgcccgga ttgtggcccg     540
```

```
gtgcctgtgg gaagaatcac gccttctaca gactgcagcc actgcggccc agcaaggggg      600
ccaggccaac caccccacag cagccgtggt gacggagaag cagcagatgc tggagcagca      660
ccttcaggat gtccggaaga gagtgcagga tctagaacag aaaatgaaag tggtagagaa      720
tctccaggat gactttgatt tcaactataa acccctcaag agtcaaggag acatgcaaga      780
tctgaatgga acaaccagt cagtgaccag gcagaagatg cagcagctgg aacagatgct      840
cactgcgctg gaccagatgc ggagaagcat cgtgagtgag ctggcggggc ttttgtcagc      900
gatggagtac gtgcagaaaa ctctcacgga cgaggagctg gctgactgga agaggcggca      960
acagattgcc tgcattggag gcccgcccaa catctgccta gatcggctag aaaactggat     1020
aacgtcatta gcagaatctc aacttcgac ccgtcaacaa attaagaaac tggaggagtt     1080
gcaccaaaaa gtttcctaca aggggaccc cattgtacag caccggccga tgctggagga     1140
gaggatcgtg gagctgttca gaaacttaat gaaaagtgcc tttgtggtgg agcggcagcc     1200
ctgcatgccc atgcatcctg accggcccct cgtcatcaag accggcgtcc agttcactac     1260
taaagtcagg ttgctggtca agttccctga gttgaattat cagcttaaaa ttaaagtgtg     1320
cattgacaaa gactctgggg acgttgcagc tctcagagga tcccggaaat ttaacattct     1380
gggcacaaac acaaaagtga tgaacatgga agaatccaac aacggcagcc tctctgcaga     1440
attcaaacac ttgaccctga gggagcagag atgtgggaat gggggccgag ccaattgtga     1500
tgcttccctg attgtgactg aggagctgca cctgatcacc tttgagaccg aggtgtatca     1560
ccaaggtctc aagattgacc tagagaccca ctccttgtca gttgtggtga tctccaacat     1620
ctgtcagatg ccaaatgcct gggcgtccat cctgtggtac aacatgctga ccaacaatcc     1680
caagaatgtg aacttcttca ctaagccgcc aattggaacc tgggaccaag tggccgaggt     1740
gctcagctgg cagttctcgt ccaccaccaa gcggggggctg agcatcgagc agctgacaac     1800
gctggctgag aagctcctag ggcctggtgt gaactactca gggtgtcaga tcacatgggc     1860
taacttctgc aaagaaaaca tggctggcaa gggcttctcc tactgggtct ggctagacaa     1920
tatcatcgac cttgtgaaaa agtatatctt ggccctttgg aatgaagggt acatcatggg     1980
tttcatcagc aaggagcggg agcgggccat cttgagcact aagcccccag gcaccttcct     2040
gctgcgcttc agtgaaagca gcaaagaagg aggcgtcact ttcacttggg tggagaagga     2100
catcagcggt aagacccaga tccagtccgt ggaaccatac acaaagcagc agctgaacaa     2160 catgtcatttt gctgaaatca tcatgggcta taagatcatg gatgctacca atatcctgtt     2220
gtctccactt gtctatctct atcctgacat tcccaaggag gaggcattcg ggaagtattg     2280
tcggccagag agccaggagc atcctgaagc tgacccaggt agcgctgccc cataccctgaa     2340 gaccaagttt atctgtgtga caccaacgac ctgcagcaat accattgacc tgccgatgtc     2400
cccccgcgct ttagattcat tgatgcagtt tggaaataat ggtgaaggtg ctgaaccctc     2460
agcaggaggg cagtttgagt ccctcacctt tgacatggag ttgacctcgg agtgcgctac     2520
ctcccccatg tgaggagctg agaacggaag ctgcagaaag atacgactga ggcgcctacc     2580
tgcattctgc caccctcac acagccaaac cccagatcat ctgaaactac taactttgtg     2640
gttccagatt ttttttaatc tcctacttct gctatctttg agcaatctgg gcacttttaa     2700
aaatagagaa atgagtgaat gtgggtgatc tgcttttatc taaatgcaaa taaggatgtg     2760
ttctctgaga cccatgatca ggggatg                                       2787
```

<210> SEQ ID NO 2

-continued

```
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 2
gtctgcgccg ccgccccgaa                                               20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 3
ggccgaaggg cctctccgag                                               20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 4
tcctgtttct ccggcagagg                                               20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 5
catcctgttt ctccggcaga                                               20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 6
gccatcctgt ttctccggca                                               20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 7
gggccatcct gtttctccgg                                               20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 8
```

-continued ttgggccatc ctgtttctcc                                              20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 9
cattgggcca tcctgtttct                                              20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 10
tccattgggc catcctgttt                                              20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 11
attccattgg gccatcctgt                                              20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 12
tgattccatt gggccatcct                                              20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 13
gctgattcca ttgggccatc                                              20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 14
tagctgattc cattgggcca                                              20

<210> SEQ ID NO 15
<211> LENGTH: 20
<212> TYPE: DNA

```
<213> ORGANISM: Artificial Sequence
<220> FEATURE:
<223> OTHER INFORMATION: Description of Artificial Sequence: Synthetic

<400> SEQUENCE: 15
tgtagctgat tccattgggc                                          20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 16
ctgtagagct gatggagctg                                          20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 17
cccaatcttg actctcaatc                                          20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 18
cccaggagat tatgaaacac                                          20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 19
acattcgact cttgcaggaa                                          20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 20
tctgaagaaa ctgcttgatt                                          20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 21
ggccacaatc cgggcaatct                                          20
```

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 22
tggctgcagt ctgtagaagg                    20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 23
ctgctccagc atctgctgct                    20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 24
tttctgttct agatcctgca                    20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 25
tagttgaaat caaagtcatc                    20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 26
ttccattcag atcttgcatg                    20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 27
tctgttccag ctgctgcatc                    20

<210> SEQ ID NO 28
<211> LENGTH: 20
<212> TYPE: DNA
<213> ORGANISM: Artificial Sequence
<220> FEATURE:

<223> OTHER INFORMATION: Description of Artificial Sequence: Synthetic

<400> SEQUENCE: 28
tcactcacga tgcttctccg          20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 29
gagttttctg cacgtactcc          20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 30
atctgttgcc gcctcttcca          20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 31
ctagccgatc taggcagatg          20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 32
cgggtctgaa gttgagattc          20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 33
cggccggtgc tgtacaatgg          20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 34
tttcattaag tttctgaaca          20

```
<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 35
aggatgcatg ggcatgcagg                                               20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 36
gaccagcaac ctgactttag                                               20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 37
atgcacactt taattttaag                                               20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 38
ttccgggatc ctctgagagc                                               20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 39
ttccatgttc atcacttttg                                               20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 40
gtcaagtgtt tgaattctgc                                               20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
```

<400> SEQUENCE: 41
caatcaggga agcatcacaa                                          20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 42
tacacctcgg tctcaaaggt                                          20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 43
tgacaaggag tgggtctcta                                          20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 44
cgcccaggca tttggcatct                                          20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 45
cattcttggg attgttggtc                                          20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 46
cacttggtcc caggttccaa                                          20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 47
cccgcttggt ggtggacgag                                          20

<210> SEQ ID NO 48
<211> LENGTH: 20

```
<212> TYPE: DNA
<213> ORGANISM: Artificial Sequence
<220> FEATURE:
<223> OTHER INFORMATION: Description of Artificial Sequence: Synthetic

<400> SEQUENCE: 48
agttcacacc aggccctagg                                           20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 49
gttttctttg cagaagttag                                           20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 50
atattgtcta gccagaccca                                           20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 51
aacccatgat gtacccttca                                           20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 52
gcttagtgct caagatggcc                                           20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 53
gctgctttca ctgaagcgca                                           20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 54
```
gtgaaagtga cgcctccttc                                              20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 55
ctgatgtcct tctccaccca                                              20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 56
actggatctg ggtcttaccg                                              20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 57
aaatgacatg ttgttcagct                                              20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 58
gcccatgatg atttcagcaa                                              20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 59
tattggtagc atccatgatc                                              20

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 60
atagacaagt ggagacaaca                                              20

<210> SEQ ID NO 61
<211> LENGTH: 20
<212> TYPE: DNA
<213> ORGANISM: Artificial Sequence

```
<220> FEATURE:
<223> OTHER INFORMATION: Description of Artificial Sequence: Synthetic

<400> SEQUENCE: 61
ttgggaatgt caggatagag                                                    20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 62
ctcctggctc tctggccgac                                                    20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 63
acctgggtca gcttcaggat                                                    20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 64
cacagataaa cttggtcttc                                                    20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 65
atcggcaggt caatggtatt                                                    20

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 66
ccaaactgca tcaatgaatc                                                    20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 67
ggttcagcac cttcaccatt                                                    20
```

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 68
gagggactca aactgccctc                                               20

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 69
caactccatg tcaaaggtga                                               20

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 70
ttctcagctc ctcacatggg                                               20

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 71
cgttctcagc tcctcacatg                                               20

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 72
tccgttctca gctcctcaca                                               20

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 73
cttccgttct cagctcctca                                               20

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 74
agcttccgtt ctcagctcct                                            20

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 75
agaatgcagg taggcgcctc                                            20

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 76
accacaaagt tagtagtttc                                            20

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 77
tgctcaaaga tagcagaagt                                            20

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 78
attcactcat ttctctattt                                            20

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 79
catttagata aaagcagatc                                            20

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 80
acatccttat ttgcatttag                                            20

<210> SEQ ID NO 81

<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 81

```
gatcatgggt ctcagagaac                                                 20
```

<210> SEQ ID NO 82
<211> LENGTH: 2869
<212> TYPE: DNA
<213> ORGANISM: Mus musculus

<400> SEQUENCE: 82

```
gccgcgacca gccaggccgg ccagtcgggc tcagcccgga gacagtcgag acccctgact      60
gcagcaggat ggctcagtgg aaccagctgc agcagctgga cacacgctac ctgaagcagc     120
tgcaccagct gtacagcgac acgttcccca tggagctgcg gcagttcctg gcaccttgga     180
ttgagagtca agactgggca tatgcagcca gcaaagagtc acatgccacg ttggtgtttc     240
ataatctctt gggtgaaatt gaccagcaat atagccgatt cctgcaagag tccaatgtcc     300
tctatcagca caaccttcga agaatcaagc agtttctgca gagcaggtat cttgagaagc     360
caatggaaat tgcccggatc gtggcccgat gcctgtggga gagtctcgc tcctccaga      420
cggcagccac ggcagcccag caaggggggcc aggccaacca cccaacagcc gccgtagtga     480
cagagaagca gcagatgttg gagcagcatc ttcaggatgt ccggaagcga gtgcaggatc     540
tagaacagaa aatgaaggtg gtggagaacc tccaggacga ctttgatttc aactacaaaa     600
ccctcaagag ccaaggagac atgcaggatc tgaatggaaa caaccagtct gtgaccagac     660
agaagatgca gcagctggaa cagatgctca gccctggga ccagatgcgg agaagcattg      720
tgagtgagct ggcgggggctc ttgtcagcaa tggagtacgt gcagaagaca ctgactgatg     780
aagagctggc tgactggaag aggcggcagc agatcgcgtg catcggaggc cctcccaaca     840
tctgcctgga ccgtctggaa aactggataa cttcattagc agaatctcaa cttcagaccc     900
gccaacaaat taagaaactg gaggagctgc agcagaaagt gtcctacaag ggcgacccta     960
tcgtgcagca ccgccccatg ctggaggaga ggatcgtgga gctgttcaga aacttaatga    1020
agagtgcctt cgtggtggag cggcagccct gcatgcccat gcacccggac cggcccttag    1080
tcatcaagac tggtgtccag tttaccacga agtcaggtt gctggtcaaa tttcctgagt     1140
tgaattatca gcttaaaatt aaagtgtgca ttgataaaga ctctgggggat gttgctgccc    1200
tcagagggtc tcggaaattt aacattctgg gcacgaacac aaaagtgatg aacatggagg    1260
agtctaacaa cggcagcctg tctgcagagt tcaagcacct gaccttagg gagcagagat      1320
gtgggaatgg aggccgtgcc aattgtgatg cctccttgat cgtgactgag gagctgcacc    1380
tgatcaccctt cgagactgag gtgtaccacc aaggcctcaa gattgaccta gagacccact    1440
ccttgccagt tgtggtgatc tccaacatct gtcagatgcc aaatgcttgg gcatcaatcc    1500
tgtggtataa catgctgacc aataacccca agaacgtgaa cttcttcact aagccgccaa    1560
ttggaacctg ggaccaagtg gccgaggtgc tcagctggca gttctcgtcc accaccaagc    1620
gagggctgag catcgagcag ctgacaacgc tggctgagaa gctcctaggg cctggtgtga    1680
actactcagg gtgtcagatc acatgggcta aattctgcaa agaaaacatg gctggcaagg    1740
gcttctcctt ctgggtctgg ctagacaata tcatcgacct tgtgaaaaag tatatcttgg    1800
ccctttggaa tgaagggtac atcatgggtt tcatcagcaa ggagcgggag cgggccatcc    1860
```

-continued

```
taagcacaaa gccccgggc accttcctac tgcgcttcag cgagagcagc aaagaaggag    1920
gggtcacttt cacttgggtg aaaaggaca tcagtggcaa gacccagatc cagtctgtag    1980
agccatacac caagcagcag ctgaacaaca tgtcatttgc tgaaatcatc atgggctata    2040
agatcatgga tgcgaccaac atcctggtgt ctccacttgt ctacctctac cccgacattc    2100
ccaaggagga ggcatttgga aagtactgta ggcccgagag ccaggagcac cccgaagccg    2160
acccaggtag tgctgccccg tacctgaaga ccaagttcat ctgtgtgaca ccaacgacct    2220
gcagcaatac cattgacctg ccgatgtccc cccgcacttt agattcattg atgcagtttg    2280
gaaataacgg tgaaggtgct gagccctcag caggagggca gtttgagtcg ctcacgtttg    2340
acatggatct gacctcggag tgtgctacct cccccatgtg aggagctgaa accagaagct    2400
gcagagacgt gacttgagac acctgccccg tgctccaccc ctaagcagcc gaacccata    2460 tcgtctgaaa ctcctaactt tgtggttcca gatttttttt tttaatttcc tacttctgct    2520
atctttgggc aatctgggca cttttaaaa gagagaaatg agtgagtgtg ggtgataaac    2580
tgttatgtaa agaggagaga cctctgagtc tggggatggg gctgagagca aagggaggc    2640 aaagggaac acctcctgtc ctgcccgcct gccctccttt ttcagcagct cggggttgg    2700 ttgttagaca agtgcctcct ggtgcccatg gctacctgtt gccccactct gtgagctgat    2760
accccattct gggaactcct ggctctgcac tttcaacctt gctaatatcc acatagaagc    2820
taggactaag cccaggaggt tcctctttaa attaaaaaaa aaaaaaaaa                2869
```

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 83
gttccactga gccatcctgc                                                 20

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 84
ttcaggtagc gtgtgtccag                                                 20

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 85
atgtgactct ttgctggctg                                                 20

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic

```
<400> SEQUENCE: 86
ccaagagatt atgaaacacc                                              20

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 87
gctccaacat ctgctgcttc                                              20

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 88
gctcttcatc agtcagtgtc                                              20

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 89
atctgacacc ctgagtagtt                                              20

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 90
gccagaccca gaaggagaag                                              20

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 91
cgctccttgc tgatgaaacc                                              20

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 92
aacttggtct tcaggtacgg                                              20

<210> SEQ ID NO 93
<211> LENGTH: 20
```

```
<212> TYPE: DNA
<213> ORGANISM: Artificial Sequence
<220> FEATURE:
<223> OTHER INFORMATION: Description of Artificial Sequence: Synthetic

<400> SEQUENCE: 93
atcaatgaat ctaaagtgcg                                          20

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 94
tcagcacctt caccgttatt                                          20

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 95
actcaaactg ccctcctgct                                          20

<210> SEQ ID NO 96
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 96
ggtttcagct cctcacatgg                                          20

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 97
taaaaaaaaa aatctggaac                                          20

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 98
aagatagcag aagtaggaaa                                          20

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 99
```
aaaaagtgcc cagattgccc                                              20

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 100
atcacccaca ctcactcatt                                              20

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 101
cctttgcctc ccttctgctc                                              20

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 102
tgaaaaagga gggcaggcgg                                              20

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 103
caccaggagg cacttgtcta                                              20

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 104
aacctcctgg gcttagtcct                                              20

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 105
aaaaagtgcg cagattgccc                                              20

<210> SEQ ID NO 106
<211> LENGTH: 20
<212> TYPE: DNA
<213> ORGANISM: Artificial Sequence

```
<220> FEATURE:
<223> OTHER INFORMATION: Description of Artificial Sequence: Synthetic

<400> SEQUENCE: 106
aaaaagtccg ctgattgccc                                                    20

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 107
aaaaactccg ctgaatgccc                                                    20

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 108
atgtgattct ttgctggccg                                                    20

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 109
agctgattcc attgggccat                                                    20

<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 110
ccaggagatt atgaaacacc                                                    20

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 111
accgtgtgtc aagctgctgt                                                    20

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 112
ccattgggaa gctgtcactg                                                    20
```

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 113
tgtgattctt tgctggccgc                                          20

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 114
gcggctatac tgctggtcaa                                          20

<210> SEQ ID NO 115
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 115
gctccagcat ctgctgcttc                                          20

<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 116
gattcttccc acaggcaccg                                          20

<210> SEQ ID NO 117
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 117
tgattcttcc cacaggcacc                                          20

<210> SEQ ID NO 118
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 118
atcctgaagg tgctgctcca                                          20

<210> SEQ ID NO 119
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 119
cggacatcct gaaggtgctg                                              20

<210> SEQ ID NO 120
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 120
cccgccagct cactcacgat                                              20

<210> SEQ ID NO 121
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 121
agtcagccag ctcctcgtcc                                              20

<210> SEQ ID NO 122
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 122
ccagtcagcc agctcctcgt                                              20

<210> SEQ ID NO 123
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 123
cgcctcttcc agtcagccag                                              20

<210> SEQ ID NO 124
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 124
ggccggtgct gtacaatggg                                              20

<210> SEQ ID NO 125
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 125
atcctctcct ccagcatcgg                                              20

<210> SEQ ID NO 126

<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 126
ccgctccacc acaaaggcac          20

<210> SEQ ID NO 127
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 127
cgtccccaga gtctttgtca          20

<210> SEQ ID NO 128
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 128
ttgtgtttgt gcccagaatg          20

<210> SEQ ID NO 129
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 129
gctcggcccc cattcccaca          20

<210> SEQ ID NO 130
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 130
aggcatttgg catctgacag          20

<210> SEQ ID NO 131
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 131
cttgggattg ttggtcagca          20

<210> SEQ ID NO 132
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 132

```
ctcggccact tggtcccagg                                                20
```

<210> SEQ ID NO 133
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 133

```
ccccgcttgg tggtggacga                                                20
```

<210> SEQ ID NO 134
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 134

```
cccccgcttg gtggtggacg                                                20
```

<210> SEQ ID NO 135
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 135

```
ggagaagccc ttgccagcca                                                20
```

<210> SEQ ID NO 136
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 136

```
ttcattccaa agggccaaga                                                20
```

<210> SEQ ID NO 137
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 137

```
cccgctcctt gctgatgaaa                                                20
```

<210> SEQ ID NO 138
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 138

```
gtgctcaaga tggcccgctc                                                20
```

<210> SEQ ID NO 139
<211> LENGTH: 20
<212> TYPE: DNA

```
<213> ORGANISM: Artificial Sequence
<220> FEATURE:
<223> OTHER INFORMATION: Description of Artificial Sequence: Synthetic

<400> SEQUENCE: 139
cccaagtgaa agtgacgcct                                              20

<210> SEQ ID NO 140
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 140
acccaagtga aagtgacgcc                                              20

<210> SEQ ID NO 141
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 141
ccgaatgcct cctccttggg                                              20

<210> SEQ ID NO 142
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 142
gccgacaata cttcccgaat                                              20

<210> SEQ ID NO 143
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 143
gatgctcctg gctctctggc                                              20

<210> SEQ ID NO 144
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 144
tcaatgaatc taaagcgcgg                                              20

<210> SEQ ID NO 145
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 145
gactcaaact gccctcctgc                                              20
```

```
<210> SEQ ID NO 146
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 146
atcacccaca ttcactcatt                                              20

<210> SEQ ID NO 147
<211> LENGTH: 17
<212> TYPE: DNA
<213> ORGANISM: Artificial Sequence
<220> FEATURE:
<223> OTHER INFORMATION: Description of Artificial Sequence: Synthetic

<400> SEQUENCE: 147
aaaagtgccc agattgc                                                 17

<210> SEQ ID NO 148
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 148
aaaagtgccc agattgctca                                              20

<210> SEQ ID NO 149
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 149
taaaagtgcc cagattgctc                                              20

<210> SEQ ID NO 150
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 150
aagcagatca cccacattca                                              20

<210> SEQ ID NO 151
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 151
aaaaagaggc ctgattgccc                                              20

<210> SEQ ID NO 152
<211> LENGTH: 20
<212> TYPE: DNA
<213> ORGANISM: Artificial Sequence
<220> FEATURE:
```

<223> OTHER INFORMATION: Description of Artificial Sequence: Synthetic

<400> SEQUENCE: 152
tctggcaaag tgtcagtatg  20

<210> SEQ ID NO 153
<211> LENGTH: 74424
<212> TYPE: DNA
<213> ORGANISM: H. sapiens
<220> FEATURE:
<223> OTHER INFORMATION: Antisense oligonucleotide

<400> SEQUENCE: 153

| | | | | | |
|---|---|---|---|---|---|
| agagcgggca | ggagggagct | gtatcagggg | catttaaagt | gccttgacgt | cacgcactgc | 60 |
| caggaactca | gctgagtttt | cagcaggaca | ttccggtcat | cttccctccc | tcccccggg | 120 |
| cttctgtgcc | caagtcctcg | gctcttccct | cgctgtggcg | gagggaggag | caccgaactg | 180 |
| tcggaacagc | cagcacaggg | gcgtatcagt | ctcctcttgg | ctccgccctt | tctcctagct | 240 |
| gctctcctca | ttggtcagtg | ggcggggctt | cggctgtacc | gcacacgcac | tgggacctct | 300 |
| gggtggccga | acgagctggc | ctttcatgaa | ttatgcatga | cggcgtgcct | cggccaggct | 360 |
| ggggctgggc | gaggattggc | tgaaggggct | gtaattcagc | ggtttccgga | gctgcggcgg | 420 |
| cgcagactgg | gaggggagc | cggggttcc | gacgtcgcag | ccgagggaac | aagccccaac | 480 |
| cggatcctgg | acaggcaccc | cggcttggcg | ctgtctctcc | ccctcggctc | ggagaggccc | 540 |
| ttcggcctga | gggagcctcg | ccgcccgtcc | ccggcacacg | cgcagcccg | gcctctcggc | 600 |
| ctctgccgga | gaaacaggtg | aaggggggtgc | agggtggggc | cgttggggag | gcctggggac | 660 |
| ccggggggctc | cgcagcggca | ggggccctct | gggaccttgg | ggatgttgtg | atggacgctg | 720 |
| cagtggggcc | gggagagatg | aagagacgcg | gagggtcgcc | ctgagggaag | actcttcggg | 780 |
| atgacaggag | cgggcctcgg | aagggactcg | gggcgctgga | gggaagtttc | gttcttcgga | 840 |
| gaaacagaac | gcgctcgagg | gggcaccgtg | gggcgaggc | gcactcggtt | gcggcggcag | 900 |
| gagtgaggga | cagtcccccg | atttcctgct | ccctgggggcc | ctggggacgt | tccgccacc | 960 |
| ggagcgactg | tcacgccgac | ggggatcacc | ggcgcgagtg | gggggtcgga | aagcgcctcc | 1020 |
| tccccgcccg | gtcggcggct | cccgctgagc | cacttcctcc | gcttgccctg | ttccgctcc | 1080 |
| ttcaggagac | agctgtgccc | ttttggaggc | aggaataggt | gtgtctgtcg | cctgcagcct | 1140 |
| tacgggctgg | ctggtcgtgg | gtaggcttta | ttgcataaga | atcaagtttc | ctgtagggaa | 1200 |
| attgacagac | cggtactctt | tctaaattcc | ctcgcatctt | tttctaggtt | aaattatgct | 1260 |
| cccccacgt | cccgccttg | taaaaagag | aaaaaagac | aaaataaaat | ccccatcaac | 1320 |
| ccgtcaagcc | agctctagag | agagaaataa | acctcttgac | attgtccttt | tccaaatacc | 1380 |
| tggtaaagtc | ggccagaaga | taaataattg | agccattgca | tttactggat | tgtggtgttg | 1440 |
| cttaattgca | taggacggaa | tgaaccaatt | gagagtggga | gttttctgtc | tcagagccaa | 1500 |
| gatcttgggt | aaatgcagag | gagagggaaa | caaagacagg | ctggccttga | aaaaccatg | 1560 |
| tgtgcaaact | ttacatgcat | ttgggggggtg | tggttgcact | gaagttaaca | agattcaaac | 1620 |
| cgtcgcccaa | gttggtattt | ccatgtttgg | tacacatcac | tctgtgccat | atcaggtcgt | 1680 |
| tgttaagtgt | ggtgacaaaa | tcagtggtta | gtcattttt | taattaaaaa | tgtgtatagt | 1740 |
| gtgtacctgc | tggtcttact | gtatgtgcaa | ctaaaggttt | acatagtctg | tgtatgggtt | 1800 |
| gtaaattttt | ggctggctgt | gctgataaag | cattgggctt | gaataaagca | aagcagaaaa | 1860 |
| tcatctcaat | cttttatatg | tggatttaga | ctgtgttatg | acttggttca | gccagttttc | 1920 |

-continued

```
tatcttattt tatattaaat atgtctgtgt tctctgagtc agcacattta tttccttatt      1980
acatgttcca gacaggagtg ctagcccagt ttttgttcag tttgcacagt gggatgggga      2040
aacaagtctg gaatttaaaa aaaaatgttt tagaggttgg agccttgatt ttagtctcta      2100
tattagcaca tccatcacaa agaaccatta gtaaattcat gaatcttttg ttttttatgt      2160
agttcatttg agaagaataa tcacttagaa atatccacag tgccaggcat ggtggtgcac      2220
acctctgatc ccagctaatt gaaggctgag gtgggaggat tccttgagtc caggagttga      2280
gtctggtctg ggcaacatgg tgagaggcca ggaattgggt ctagagtcta gtctaagcac      2340
cataatgaga acccatcttt aagaaagaaa gaaaggaaag gaggaagaaa ggaaagaaaa      2400
agaaataccc acagcacagt tatgaattaa cccacaaagg acttgtgagg tgggtagttc      2460
acataacaat taccctaata tcgtagataa gaaaattgag gccaaaggat caagacactt      2520
ggccaacgca gcagagtgcc atagtggtgg aatttgtgcc tccttctgta tattttgtga      2580
aaagtatcag tgaaattctt tttttttttt ttttgagtc agagtcttgc tctgttgccc      2640
aggctagagt gcagtggcgc aatcttggct cactgcaacc tctgcctcct gggttcaagc      2700
gattctcctg cctcagcctc ccaagtagct gggactacag gcgtgcgcca ccacgcccag      2760 ctaattttg tattttagt agagaccggg gttttaccat attggccagg ctggtcttga      2820
actcctgacc ttgtgatttg cccacctcta tctcccaaag tgctgggatt acaggtgtga      2880
gccaccgcgc ccagtaagta tcagtgaaat tctaacatat atctgaacag taaaatacca      2940
ccaataggct gaaagacttc atgggaggta aatattcaat aaacaggtga aaaagaaat      3000 acaaatggag cttgcttaga ttattttct aattgctatg tctaacttgg gaagtgagga      3060 actgttttg gtcagcataa tttaccatca gaatttagct atttactaat gaaaagaaat      3120
actaatctag gtttgtttta gattaaggac agtcatgacc taaatgtcat ttaaaccaga      3180
gtgcattgtg gcttgatcag tggtcatttc tgtctctaga aagttgcttt aacttctctg      3240
cctctacgtg tctcttgaca ttcagatatg aggtggggta gaggtggtga ccaactttcc      3300
agacgcctga gtccaaacct tcttagctta tggttttctt aggtgatgtg caaatcaaca      3360
aatatatact tttttttttt ttttttgag ttggagttgc actctatcac ccaggctgga      3420
gtgcagtggc atgatcgtgg ctcactgcaa cctcctcctc ccgggttcaa gtgattctcg      3480
cacctcagcc tcctgagtag ctgggattac aggtgcccgc cactacgccc ggctaatttt      3540
tgtattttta gtagagataa ggtttcacta tattgaccag gctggtctca aactcctgac      3600
ctcaagagat ctgcccacct cagcctccca agtgctggg attacaggcg tgaaccacct      3660
tgcctggcca acatatatat accttttgca actttgtcag agtttgctatg aagaataagt      3720 tgtatcttgt tcacagaaat tgcagtctac tgggggagct gataaatgtt ttaaccatcc      3780
aatgtaacat gttgtcatca aagagatggt gagactttac acttgtgcta acaaggtagc      3840
tgttctacat aaaagaacat acagtacaga tgtagaactt ttctgttatc atagaacgtt      3900
ctattggaca gtgctaggct gaatgctaca gatcttcaga gaaggagag gttatgaggc       3960 ctggagttgt ctagaaagtc ttttttgccaa agagggattt caactgggtc ccaaataatg      4020
ggtggaattt gataggtgta aagaatttgc ggtggtttat gcctgtaatc ccagcacttt      4080
gggaggctga ggcaggagga ttgcttgagc ccaggagttt gagaccagct tgggcaacgt      4140
ggtaaaactc cctctcccct aaaaataaaa aaaattagcc aggcctggtg gcgtggacct      4200
gtagtcccag ctactggtga gactaaggtg ggaggatcac caagcccg gggttaagg       4260
```

```
ctgcagtgag ccgtgatccc gccaccgcac tccagcctgg gtgacagagt gagaccctgt    4320
ctccaaaaaa aaaaaaaatt cctggtagcc cggtagacta ggagggtaag taggggagaa    4380
gtgattactt acaaaagaca ttgaatacag gaccaaggaa tttcagttct gttcttttgt    4440
aggggaagct tttaaaactt tcggggcgcc gggcgcggtg gctcacgcct gtaatcccag    4500
cactttggga ggcccagacg cgcggatcac gaggccagga gatcgagacc atcctggcta    4560
acacggtgaa accccatctc tactaaaaat acaaaaaaaa gtagccgggc gttgtggcgg    4620
gcgtctgtag tcccagctac tcgggaggct gaggcaggag aagagcgtga actcgggagg    4680
cggagcttgc agtgagccga tatcgcacca ctgcactcca gcctgggcga cagagcgaga    4740
ctccgtctca aaaaaaaaa aaataaataa ataaataaat aaataaaact ttggagccga    4800
agcactgatg tttaatcata gagtgcttac tatgtgttag gcacaggcct gattgcctga    4860
tgctggttaa tttgtacaaa gtaaatcagt gcatatgccc tctgccctag gggagttatt    4920
aactggagtc tgacattgta caaggtagg tatcctgact agtttgattt ggtactttgg    4980
gtgaaaaaag tatagtgtgc ttaagtgcag aagtgttttt tgaggatttt tgattggata    5040
caaaccacca ctcatatttt atgtctttgg cacttaaaaa tttcaccata acttttgagt    5100
catttataaa aaccactgaa agagtacttg agggacatcc ccgaatcctg aagaacttct    5160
ggtgttctgg agcagcctca gtgagatcca ggaggatggc attgctgggc tggcccagcc    5220
cttattgatt atggtgtaaa gaattaatat ggtggttata tactctttgt tagacacctt    5280
ggcttacaag acgtaagcgt aaagtgtagt gcgctttagt cagtatggcc acatggtcct    5340
ttggtggtaa attgtttgag atgcctccag ttttaaaag gagtagcata tcgggccagg    5400
agcagtggct catgcctata atcccagcac tttggaaggc cgaggcaaga ggattgcttg    5460
agcccaggag ttcaagacca gcctgggcaa catagtgaga ccactttgtt tctttaaaaa    5520
aaaaaaaaag gcaaaacag gctgggcatg gtggctgatg cctgtaatcc cagcgctttg    5580
tgaggcagag gtgagcggat cacttgaggt caggagtttg agaccagcct ggccaacatg    5640
gtaaaacccc gtctctacta aaaatacaaa aattagccag gtgtggtggc acacgcctgt    5700
agttccagct actctggagg ctgagccagg agaattgctt gaacctggga ggtggaggct    5760
gcagtgagcc aagatcctgc cactgcactc cagactgggg gacagagtga gacattctga    5820
cagtgctaca ctgaatgcta catgtcttca gaggaaggag aggttatgag gcctgggaat    5880
aacatatgga agaatgaatt tctgttatgg tcagttctca tttgtcatgt taggattact    5940
gcaactctta cccagccggg tgtggtggct catgcctgta attccagcac tttgggaggc    6000
tgtgggcgga tcacgaggtc aggagatcga gaccatcctg gctaacacgg tgaaactccg    6060
cctctactaa aaatacaaaa aattagccca gcgtggtggc agacgcctgt agtcccagct    6120
actcaggagg ctgaggcagg agaatggcat gagtcctgga ggcggagctt gcagtgagct    6180
gagatcgtgc cactgcactc cagcctgggc aacagagtgg gactccatct caaaaaaaaa    6240
agaaaaaaaa aaggattacc gcaactcttt aattcagatc agcaaacatg ttgagagcca    6300
ggtattgcgt caggcaggat ccaaggataa tgaatatttg tccgttttca tgaaactgga    6360
gatgttgcag ggaccgaggt gtgtgctatg ccagtatgga agtaggacag gggagacgac    6420
agggcagtga gtggttcaag actctggctc tgaagtcaaa cagatctggg actgaatcct    6480
ggatctgcca cttcctagtc agaatctgag cctctatttt cttatctgta aagaagatt    6540
ataacagtgc ttatcttgta ggtactgttg acgattcaat aagataatgt ggataaaatg    6600
cttagcatag tgcctggcac atagtaagag ctcggtaaat ctaagttctt actaaatatc    6660
```

```
caagaaaaga gattaattct tttcaggagt gagagaaagt catcattatt gagggctttt      6720
atcagatggg aacacctgaa tagggtttta taggatgaat aggaattctt tccacgaagt      6780
tgcgttacaa aaagttgcat tcaaggctga aggaacatga gggtgcagag gcttaaaaca      6840
gccttgtgtg ttcagggagc tataagtaga agttcttaat ttaggagaac taaaccaagg      6900
ggaaaggagg ccaaggaacc acagttctta tcccttttct gttaataatt gggtttaaat      6960
gtcattaaaa taagttattt tgtccttttt agaaaagtaa taacatgcta ttataaaaaa      7020
aaagacttgt aggaatataa aatgtgtgtt ttacatgtat cctgttaatt gacttgcttt      7080
tattcagatt ttttgcagcc ctttctgttt accaggttat cttggagaca tatttattcc      7140
aaattccttt tttttttttt ttttgagatg gagtctcgct ctgtcgccca ggctggagtg      7200
cagtggcgct atcttggctc attgcaagct ccgcctcccg ggttcacgcc actctcctgc      7260
ctcagcctcc cgagtagctg ggactacagg cgcccgccac cacgcccagc taatgttttt      7320 tttttttatat ttttagtagc gacagggttt caccgtgtta gccaggatgg tctcaatctc      7380
ctcacattgt gatccgcctg cctcggcctc ccaaagtgct gggattacag gcgtgagcca      7440
gcacgcctgg ccttccaaat tccttttaac agcctagcaa aagaataata aggaaggtaa      7500 atctgccccct acaagaaaat aatgcttcga cgatccggct ttccttcctg ctaccccccag     7560 ccataagaat aaatgacctt gctcatcact gaaattttac ctgacctttg aatttttaac      7620
tgcgtcagcc aaagaactta tattttgagt attcctaagg tgattgctat tgtagttttg      7680
aaacacttgg ttggtatgtt tgagggtttc atggtccaaa gttactatag cagttaaaag      7740
agtggactat caggtcagac ctattgggct ttaatcccag ttctgccttc tcttagacct      7800
tgggcctgtt gttttcactt ctctggtttt cagtttctct gtccacaatt gtggaaacga      7860
ggtccacttg tagagtaatt gagaggatga agcaagatga tgcatatcaa gtactttgca      7920
tagtgccggg cagacaggta acattcaagt gctaataatt actattatta ctatttattt      7980
tttgagacag gttctcactc tgtcacctag gctggagtgc agcggtgaga tcacagctca      8040
tgacagcctt gacctcctag gctcaagtga tcctcctgcc tcagccttcg ggtagctgg      8100 ggctacaggt gtgtgctacc accctcagct aattttctaa ttttttttgag tcaggatctc      8160 gtcacgttgc ctaggctgaa ttactcttat taaaaactat aatatcaggc cgagtgcggt      8220
ggctcacgcc tgtaatccca gcactttggg aggccaaggc gggtggatca cctgaggtca      8280
ggagttcaag accagcctgc caacagagt gagaccccccc ccgtctctac taaaaatata      8340
aaaattagcc agttgtggtg gtgggcacct gtaatcccag ctactcggga ggctgaggca      8400
ggataatcgc ttgaacccgg gaggcggagg ttgcggtgaa ccgagatcgt gccactgcac      8460
tacagcctgg gtgacagagt gagactctgt ctcaaaaaaa ccgaaaaaca aaaagcataa      8520
ttagggtggt aacgcttata catagggca ggtggaataa aacataatta ggaggtcggg      8580
catggtggct cacgcctgta attccagcac tttgggaggc cgaggcgggt caggagttca      8640
agaccagcct gcccaacata gtgagacccc gtctctacta aaatataaa atttagcctg      8700 ttgtggtggc gggtgcctgt agtcccagct acccgggagg ctgaggcagg agaattgctt      8760
ttgaacccag gaggtggggg ttgcagtgag ctgagatcgc gccgctgcac tccagcctgg      8820
gagacagagc aagactccgt cacaaaaaca aaaacaaaa aactgtcata tcaaaaacta      8880
aactaaaatg gtaatatctg ttagatatta caaagtcagg caaattatga ttcatggcag      8940
ccactaatga cccaaaggag agaaagaata attagcagat tctaacctaa tgggaaaaaa      9000
```

```
actaaatgaa tagggatggg ggacttacat tctgttagag gaaattgagg ctgtcatata   9060
aaaggaatag gtaaggcaaa ctgtaaattc ctgttttacac aaatgccctt ctgataaatc  9120
tctgcattgc ccacagtcca tgattacctc tcccttattt taagtaatat ttaacacatt  9180
aaaaatggat taccacccaa ggaattgctc ccgacccaga aagtgcaggt agtgttgaag  9240
gtttgagggg aagaggaatg attagagttg gttgtgtctc aggaagaagc caacaggagg  9300
aaccttattt tgagtcaggt aaagaaggtg ggagtgagga ggcatcccgg tggccaggta  9360
tgaagctggg agctgattgc tgcacattac tcagctgaat taaatgtgcc ctcacatctg  9420
tgtgtgtgcg tacatgcaaa tgtacatgtg tatgagttag ttggaggggt agacctttat  9480
tttcctgtcc tgtaactttc ctttgcaaac taatctgtat tcagaacagt gttgcagtta  9540
agaaccaccc agcttgtcca tgaaacaggt tctctcaccc catctcccca gttttagaga  9600
aggcaggaaa gaaaggcag tgcttttctt ttttcctggc cgtatgcggg gcaggaagaa  9660
gccagcagag cttgaaagag aaagtaaacc ttctgggaaa taaacggctt ggcttcccta  9720
ttgtggagga ggagtgcaaa ttattagggg gatgtttggg tagttttgt agaagccatt   9780
tctgaaaact gatttggatt agtgaaggta agcccaattt aggaaaaccc tgcccagtct  9840
ggtgtcagcc acctgtttcc cgctttgttt gattgatttg attagtttgt ggtattctga  9900
cctctcattt ttattacaag agttggaaga tttgagtctg aacttgagca cctgcttcgg  9960
tgaaagcttc ctaaaatgca tgtttttca catttttct catgttcatt ttgttttgct   10020
ttttagcaaa cacttttct gacagaatct aaaagcatta gactttctt gttttcccct   10080
tctctcccca caatgtaatc ttgaaaaccc aaatgttagc tgtgtaaatt acctctcccg  10140
taaaccaaac aaagtgcaat attgcattga gttagcattg aaatagtcgg cctttgaatt  10200
tttttctact tgtggtttag acataataaa tatttcatct cagactgact ttctcgacaa  10260
atcagttttg catttgggcc tcttttcatc agtatgttta gggaaagcac atttattgaa  10320
acattaacca aaatgaaaca taattaggag gccgggagcg atggctcacg cctgtaatcc  10380
cagcactttg ggagaccaag gcatgtggat tgcttgaggt caggagttca agaccatcct  10440
tgccgacttg gtgaaatcct gtttctactg aaaatacaaa aaactagctg ggtgtggtga  10500
cgcgtgcctg taatcccagc tactctggag gctaaagcaa gagaatcgct tgaacctggg  10560
aggcagaggt tgcagtgagt cgagatcgtg ccactgcact ccagcctggg caacagagac  10620
tccgtctcaa acaaccaaaa aaacaaaaac aagcataatt agggtggtaa cgcttataca  10680
taggggcagg tggaataatt gaagcattct ggagccagaa ataatcaact gattaagaat  10740
aatctggctg ggtgcggtgg ctcacgcctg taatcccagc tactcaggag gctgaggcag  10800
gagaatcgct tgaacctggg aggtggaggt tgcagtgagc cgagatcgcg ccattgcact  10860
ccagcctggg ctatgagca agactccatc tcaaaaaaaa aaaaaaaaa atcctgttt    10920
ctgcagaaat atcccaggtg tcctgggtca gcagtgcccc atagattcca cggacgttta  10980
ccctaagttt tccaatggga gttcatacct ctatacccag tgagaatatt ttctgagtaa  11040
tgggaatgag attggagatg tagggtagag aagatccata cagtctttgg gttaaacttt  11100
ttcctctttg cctaggaaag attaatgcta atcttaacca cagatttgta gtaagaatgt  11160
atcagttttg tcattcagtt ctagactcca gttttctta ttgtaatacc aatatttag    11220
agtaaatttt gaaatgaatc agtacaaaag atatgtagta agtggaaagt tagtccgcac  11280
cttatccttg ggactctttc ccagggacag ctagttacct actatttatc tctcctgagt  11340
tacttcatat gtatgcatgc aaacatgtta ttctctgggt gttgttcctt ccatatatag  11400
```

```
cagcaaatac accaaactct gtattttgct ttttgtcact ttatcttaga gaatactcaa    11460
tgcaaataca tgtgtatata cctcatgttt aaaaaatcta catagtaaaa ttagccaggc    11520
atggtagtgt gtgcctgtaa tcccagctac tcgggaggct gtggtgggag aatcacttga    11580
accctgagat cacaccactg gactccagcc tgggccacag agcaagattc tgtctcaaaa    11640
aacaaaaaca aaaacaaaaa aactacagag tagtattcta ggctatgcat atcataaatt    11700
tgatttccta atgataggca tagatgattt gcctgggcgg caaattagcg ttggctgtgt    11760
ctcaggaaga agccaacagg aggaacctta ttttgagtca ggttccaaag acagaaacat    11820
tgtctgacat ttgttttttgg gcttatatga ataaatctgt acacatatat ttttaatgtt    11880
ttaatcgtaa tatgtatact atttggaaat gtggcttttt agttaacaga gtgcatgttt    11940
taccccattg cacttaaaca ttaacttggg gataattaaa tgagtctgtc acttggacag    12000
gcaggaattg taccccccac aaacccataa accgccaatt ttttttttttt gagacagagc    12060 ctcattctgt tgcccaggct ggagtgcagt ggtgcgatct gggcccactg taagctcagc    12120
ctcccgggtt catgccattc tcctgcctca gcctcccaag tagctgggac tacaggcgcc    12180
cgtcacaatg cccggctaat ttttttgtatt tttagtagag tcgggttttc accatgttag    12240
ccaggatggt ctctatctcc tgaccttgtg atccgcccgc tttggcctcc caaagtgctg    12300
gaattacagg tgtgagccac cgcacctggc cggtttttttt tttttttttt gagatggagt    12360
cttgctctgt tgccaggctg gagtgcaatg gcatgatctc cgctcactgc aacctccacc    12420
tcccgggttc aagtgattct cctgcctcag cctcctgagt agctgggact acaggcgtgt    12480
gccaccacgc acagctaatt tttgtaattt tagtagagat ggggtttcat taataatcat    12540
taatattaga caactgtcag actcacagtg gtggatacaa actttctcaa attctgattt    12600
ttactctaaa gctcaaattt tatcattggc aacaaatatt gtcagttgct ttccctgaac    12660
agacagcttc ccttctttca tttttgagaa aatatctgcc agtatcccag ttggtttatc    12720
aatcattctt tctctttttt tttttgagac ggagtctcac tctgtcaccc aggctggagt    12780
gcagtggcat gatctcggct cactgcaacc tccacctccc aggttccagc aattctcctg    12840
cctcagcctc ccgagtagct gggattacag gggctagcag ccacacctgg ctaattttg    12900 cattttttagt agagacaggg ttttaccatg ttggccaggc tgatcttgaa ctcctgacct    12960
catgatatgc ccaccttggc ctcccaaagt gctgggatta caggtgtgag ccattgcgcc    13020
cggctctatt atttctttc tttctttctt tttcttttt tttttgaga tggagtttcg    13080 ctcttgttgc ccaggctgga gtgcaatggc gcgatctcgg ctcaccacaa cctccgcctc    13140
ccgaattcaa gtgattctct tgcctaagcc tcccgagtag ctgggattac aggcatgtgc    13200
caccacaccc gtctagtttt gtattttat tagagatggg ggtttctcca tgttggtcag    13260
gctggtctcg aactcccaac ctcaggagat ctgcctgcct cagcctccca agtactggg    13320 attacagttt tgagccacct gacccggttt gcttattatt tctttaaat ttaaaaaata    13380 ataaataaag gggccatgag agcgaagagt ttgagaaagg ttggtctaaa ggttttaaca    13440
taagaatccc tgggttattt gcttaaaaag aagaaagaat ctatggatct gcctgagagg    13500
gtctgatgta gttatctgg ggtcatcctc acaggcatag cagatatct gattcagatg    13560 gtccttggtc cttagtttga gaaatgtggc tttacaaggc ccatagaata taagtcttc    13620 tttggattag tgaagtcatg tccacagggt ttagaaaatg ttttgtttt agagataaag    13680 gtaagtggaa gagtagacat gtagtgaatg agggaaaatg ttttagagat ttcttttat    13740
```

```
tctgtttact cttcttggta tgcacgtacc tgaatattaa ggatattta tgaagtcatg    13800
acattaccag attaatgttg gttttgtttt aaggtacttc ctgactgctg gggttaattc    13860
ctacagacga ttctggtaaa gaatagcctt taagtttta aagtgttgac ttatttcaga    13920
tgtcttaata aagttaactt ccagttatta catgtaacgt atataaagct ctcattttcc    13980
tttattctcg ttaattgttt gcataacaaa ttcaaaggga aatttgcttg cagagatca    14040
gatagcagag atgagattta aaaacaggta atttggctac tagcctggga gtttgaagat    14100
tccaagttg catccatgtg tagtcactta acatttctgt ccttatctgt aaatgggaat    14160
aacacctact tgatagggtt gttacattat cttggccacc tcaggttctc tttggctgag    14220
tgattgactg gaaaacgcaa tgtgaattca tgcttcagac tgggttcttt tttttttttt    14280
tttttgagat ggagtttcac tcttattgcc caggctggag tgcaatggca cgatctcagc    14340
tcactgcaac ctctgcctcc caggttcaag cgattctcct gcctcaggct cccgagtagc    14400
tgggattaca ggcatgcacc accatgcctg gctaattttt ttgtattttt agtagagacg    14460
gggtttcact gtgttggtca gactggtttc aaactcctga cctcaggtga tccacctgct    14520
tcagtctccc aaagtgctgg gattacaggc atgagccacc gcacccagcc caggctaggt    14580
tctatatggg tgtgcttttt agaatttaga tcatgggcta tccccaacac aaactggata    14640
atgtttcttt ctagattctc tctaagcgtg tattctcttt ctttcctagg cacagccacc    14700
acttcactta cattgtggga ttataatttc atgagtagtg gaatttcctt aaccttctct    14760
tgtgtgggag ctgaaggaca aaatgagata ttctctgaag agtggttaca tcatgcaaaa    14820
ctatgatgtg taatgaggtc acttagtttt ctaagtacat tatacatttt gataagattt    14880
tcatagaaaa gcttgtctcc ttgggagat cactcatctt ccatcttgac tattatttaa    14940
actttatggg tcagatttat cttttaaaa acttaaccat aaagctcaat taattttttt    15000
tttttttt tgagacggag tctcgctctg ttgcccaggc tggagtgtag tggcgcgatc    15060
tcggctcact gcaagctctg cctcccaggt tcatgccatt ctcctgcctc agcctcctga    15120
ctagatggga ctacaggcgc cgccacgat gcccggctaa ttttttgtat ttttagtaga    15180
gacggggttt caccgtgtta ggatggtctc gatctcctga cctcgtgatc cacccgcctc    15240
ggcctcccaa agtgctggga ttacaagcgt gagccaccgc gcccggctca attaatatat    15300
tttaaaaatt aatagacttt attattttta ttttattta tttttgaggc agagtctcgc    15360
tctgtcaccc aggctgagtg cagtggtgtg atcttggctc actgcaaaact ccacctcccg    15420
ggctcaagtg attctcctgc ctcagcctcc taagtagcta ggattacagg tgcctgccac    15480
catacccggc tagttttgt aatttagta gatacgtgtt ttctttcttt tcttttcttt    15540
tttttgagat ggagtttcac tctttttgcc caggctggag tgcaatggca tgatctcggc    15600
tcactgcaac ctccgcctcc caggttcaag tgattctcct gcctcagcct cccaagtagc    15660
tgagattata gttgtctgcc accacgcctg gctaattttt tgtatgttg atagagacag    15720
ggtttcacta tgttagccag gatgtctcga tctcttgacc tcgtgatccg cctgccttgg    15780
cctcccaaag tgctgggatt acaggcgtga gccactgcgg ccagtctaga ctttattttt    15840
taaagcagtg ttagttttac agaaaaatta tgtggaaagt acagagagtt tccatatacc    15900
ccttactttc tcccacaact tctattatta acatcttgca ttagtatagt acgtccctta    15960
caactaatga accaactcga tacattatta ttaaccaaat tcctgagttt attttatttc    16020
tattttatt ttattattat tatttttag aggtagggtc tcactgtgtt gtccaggcca    16080
ggttgcagtg gcatcatcat agcttgctat agcctgaaac tcctgggctc aagcaatcct    16140
```

```
cctgcctcag tctcccaaag tgttggaatt acaggtgtga gccactctgt ccagcctgaa    16200
gtccatagtt tacattacat ttcactctgt tgagcattct atggattttg acaaatgtgt    16260
gatgatgtat atttgccagt acacaattat ataaaatagt tttactgccc tagaaacccc    16320
ctgtgctcca cctattcatt cctctgctga accactggca accactgatc tttataata    16380 tctccatagt tttgtctttt ccagaatgtc atatagttgg acatacagtg tgtagccttt    16440
tcagattggc ttctttcagt aaatgatatg catttcaggt ttcttcatgt ttttttgtgg    16500
cttgataggt tgtttctttt cattggtgag taatactcta ttgtatggat ataccacatg    16560
ttgtttatca acattcacc tgaaggatag acatcttggt tgcttccaag tttgagcagt    16620
tatgaataaa gctgctataa acattccagt gcaggacttt tcacctcctc tggataaata    16680
tcaaggagtg caattgctag atcatatggt aagagtatgt ttagttttgt aagaagctat    16740
caaactatat tcaaagtgac tgtaccatta tacattccca tcagcagtga gtgagagttc    16800
ctgttactcc acatcttcac cagcatttag tggtgtcagt gttttggatt ttagccattt    16860
taatgggtgt ataatggtat acctattaaa attggttttt tttggagaca gagtttcaca    16920
gtttcactct tgttgccctg gctggagtgc aatggcgcaa tctcggctca ctgcagcctc    16980
cgcctcccag tttcaagtga ttctcctgcc tcagcctccc aagtagctgg gattacaggt    17040
gcacgccacc atgttctgct aattttttg tattttagta gagatggggt ttcactgtgt    17100
tacccaggct ggtcttgaac tcctgagctc aggtaatcca cctgcctcag cttcccaaag    17160
tgttaggatt acaggcatga gccaccgcac ctggcctcaa tttttttttt tttttttttg    17220
agacagagtt ttgctcctgt tgaccaggct ggagtgcagt ggcacaatct cggctcactg    17280
caacctccgc ctcctgagtt caagcgattc tcctgccaca gcctcctgag tagctgggat    17340
tataggcgcc cgccactacg cctggctaat tttttttttt tttttaatta gagacgaggt    17400
ttctccatgt tggtcaggct ggtcttgaac tccccgttct caggtgatcc gcctgcctca    17460
gcctcccaaa gtgctgagat tacaggtgtg agccaccgtg cccgcctgt tttggctttt    17520 actgtgaaga cgtgttagcc gctgtgatga ctagcaagtg tggccctcca cccagtcgct    17580
ctgggctccc agctcctgca tcctgctgca aacttgacat cttccctcaa gtaacttgta    17640
gttgtctcct gtctacttgc ccaaaatata actcttaaac ttttctctct gcaagtttgt    17700
gcctctctcc ctgtctgact tccccatcta aataaatggt agaccaccat ctactccttt    17760
gtgcaagcca gaaatctagg aatcatcctt aaattccctg ttctgtctta tctctgcttt    17820
cattcaaagc atcagcaaat cctgttggtt ctacctctga agttttctca aatactgtta    17880
cttgactcat cctgacttt gtttctgctt tatgttaggc taaatgccct gaaaactctt    17940
ttgtacaaaa cacctagaaa tactggataa actgggctta acagggaggc ccggtgtggt    18000
ggctcacgcc tgtaatccca gaactttggg aggccaaggt gggtggatca cctgaggtca    18060
ggagttccag accagcctgg ccaatacgta gtgaaacccc acctctacta aaaaaaaaaa    18120
aaaaaattag ctgggtgttg tggtgcacac ctgtaggtgg tgcatgcttg aacttgggag    18180
gcggaggttg cagcgagctg agatcgcgcc actgcacttc agcctgggtg acagagcagg    18240
attctgtctc ttaaaaaaaa aaacaaaaaa agaaaaacag gaaatcttc agaagcaaaa    18300 accaaacaat ctcaccaaag aaatgagaag atggctgggc gcggtggctc acgcctgtaa    18360
tcccagcact ttgggaggcc gaggcgggca gatcacccga gatgggcaga tcacccgagg    18420
tcaggaattc gagaccagcc tggccaatat ggtgaaaccc cgtctctgct aaaaatacaa    18480
```

```
aaattagcca ggtgtggtgg caggcgcctg taatcccagc tactcaggag gctgaggcag    18540
gagaatcgct tgaacctggg aggcggaggt tgcagtgagc cgagatcatg ccactgtact    18600
ctagcctgga cgacagagca agactctgtc tcaaaaaaaa aaaaggctgg gtgtggtggc    18660
tcatgcctat aatcctagca ctttgggagg ccaaggtggg cggatcactt gaggccaggt    18720
gaacatggcg aaaccccatc tctactaaaa atactaaagt tagctgggca tggtggtggg    18780
tgcctgtaat cccagctact cgggaggcga ggcaggagaa tcgcttgaac caggaggtgg    18840
aggttacagt gaaccgagat ctcgccaccg cactctagtc tgggcgacag agcaagactc    18900
cgtctcaaaa aacaacaaca aaaaaccaac acatggccaa agtgcagtga cttacatctg    18960
tataatccca atgttttggg aggctgaggc aggaggatcg cttgagtcca ggaatttgag    19020
accagcctgg gcaacataga cctcatcacc aaaaaaaaaa tattttttaa ttagctgggt    19080
ttggcagcat gtacctgtag tcctagctac tcaggaggct gaggtgggag gatcacttag    19140
gcccaggagt tgatagttc gaggttatag tgagctatga tcctgccact gcactccagc    19200
ctgggccaca gagtgagacc ctgtctctta gaaacaaaac aaaacaaaaa aagaaactg     19260 aattaaaaac aacaagaaca aaaatgctgc tttttgttat tgagttgtag cccaagtttc    19320
ttgagggtaa agcattgaaa agcaggcagt aatagatttg ctgtttaaag agatttactt    19380
gcagcactat tcacaatagc aaagacatgg aatcaaccta aatgcccatc agtgacaaat    19440
tggataaaga aaatgtggta catacactgt ggaatactat gcagccataa aaaacaacga    19500
gatcatgttt tgtttgtttt gtttgtttgt ttgtttttga gatggagtct tgctctattg    19560
cccaggctgg aatgcaggtg gcacgatttc agctcactgc aacctccgcc tcccaggttc    19620
aagcaattct ctgcctcagc ctcccgagta gctgggatta caggtgccct ccaccatgcc    19680
tggctaattt ttgtatttct agtagagatg gggtttcacc gtgttgggca ggctgttctt    19740
gaactcctga cctcatgatc ctcccacctc ggcctcccaa agtgccggga ttacgtgtga    19800
gccaccgtgc tcggctgaga tcatgttttt gcaggaacat ggatggagct ggaggctatt    19860
atccttagca aagtaatgca ggaacagaaa accgaagacc acgtgttctc acttataagt    19920
gggagctaaa tgataaggac ttgtgaacac aaagaaggaa accacagata ctgggggttta   19980 cttgagggtg gagagtggga ggagggagag gaacagaaaa gataactatt gggtattggg    20040
cttaatactt aatattttat caaaataagc tgtacaacaa acccctctga catgagttta    20100
cctatataac aaacttgcac gtgtaacccc aaacctaaaa taaagttaa aaaaaaaaa     20160 aaaggctggt tgcattggga ggctgaggca ggcagagcac ttgaggccag gaattcgaga    20220
ccagcttggc taacgtggag aaaccctgtc tctactaaaa attcaaaaat tagccaggtg    20280
tggtggtgca tgcctgcagt cccagctacc agggaggctg aggcaggaga attgcttgaa    20340
ctcaggaggc agaggttgca gtgagctgag attgcaccac tgcattccag cctgggcgac    20400
agggcgagac cttgtctcaa aaacaaaac aaaacaaaac aaaacctgt cactttggga    20460 atatctcaaa cctagtcatc caagtggttg tacgatttta gtgtctgcat atcaatattt    20520
agtgtgatct actttcttag attctcaaat actgccaatg gcacatgtc atgaaataat    20580 gtcttttaga ggacaagaga gtgctaaagt ctcattattg cagtttaaga aaaacaattc    20640
tgtaacagtt taactttata ggaaatgcct tttgttatt tatttttttt cttttgaggc    20700 ttagatttt attttatgt tttagagat gggtcttcc tatgttaccc aggctggcct    20760
tgaattcctg ggctcaagtg atcttcctgc ttcagcctcc tgagtagctg ggactagacg    20820
tccactactg ctcctggctg gaagtttaga ttttaattta aactcttcta ttgggaaact    20880
```

-continued

| | | | | | |
|---|---|---|---|---|---|
| ttgtatgttt | gctttaccac | ttaacatttg | catgcattat | tgtacctatt | gtctcctact | 20940 |
| taaggaaggg | cagtttatgc | tgttatatga | agtgaattaa | cctcctatgg | tacttcagtt | 21000 |
| ttctctatgc | taaaagtgtg | ttctagattt | ttgaaaaact | tacttaattt | tcattcattt | 21060 |
| attcaaatat | ttgagcattc | tgtagttgct | ggggaaatag | cagtgaactg | aagaatgtct | 21120 |
| ttgttcttat | ggggcttaag | ttcctagttg | atcatattgg | aaggagatac | atgaaaaaag | 21180 |
| aaatatatga | acaatggagg | gcgatgagta | ctgtaaagga | gaattcagca | ggggagatgt | 21240 |
| tgctgtttta | gatagagggg | tgtcaagaga | cattgtgcag | agacctgaac | gaagtgaggg | 21300 |
| agcaagccat | ggagatatct | agggaaagag | cctatcaggt | ggagagaaga | gtcctagggc | 21360 |
| agaaacgggc | aaggtgtgtt | ccaggagcag | agagggaca | gctgtgagca | aggggagagt | 21420 |
| tgtagggaag | gaggcaaaga | gagacatctg | gggcaaaatg | gattgactgg | tgggccgtgg | 21480 |
| taggactttg | gattttttcc | tgagtggggtt | ttgagcaggg | gaatgaaatg | atctgactct | 21540 |
| ggttttttt | ttttttggag | acaaaatctt | gctctgttgc | cgaggctgaa | gtgcagtggc | 21600 |
| gcaatctcgg | ctcattgcaa | catctacttc | ctggttcaa | gctatgctcc | tgcctcagcc | 21660 |
| tcccgagtag | ctaggattac | aggcttgggc | caccatgccg | gcgaatttct | gtttttattt | 21720 |
| ttatttttta | tttattttta | tgtttatgtt | ttttgagacg | gagtctcgct | gtgtcaccca | 21780 |
| ggctggagtg | cagtggcgcg | atctcagctc | actgcaacct | ctgcctcccc | ggttcaagca | 21840 |
| acttctcctg | cctcagcctc | ccgagtagct | gagattacag | gcgcctgcca | ctacacctgg | 21900 |
| ctaattttg | tattttagt | agaaacggga | tttcaccttg | ttggccaggc | tggtctcgaa | 21960 |
| ctcctgacct | taatttatct | gctcgccttg | gcctcccaaa | gtgctgggat | gacaggtttg | 22020 |
| agccaccgtg | ccagccagga | ctcttatttt | gaaaggatct | gtaatgtgga | gaatagaagg | 22080 |
| tagagggaca | aggatgaaag | catccaggcc | agttagccta | gtccagctat | ctaggtaaga | 22140 |
| gatgctggtg | gcctggatta | aggctgcgtc | agtgggaggt | tgtgagaaag | gctcaccttc | 22200 |
| cttttttttt | tttttttttt | tttttgagac | aggatcttac | tctgtctccc | aggctggagt | 22260 |
| gcagtggtgc | aatctcagct | tactacaacc | tccgcctcct | gggctcaagt | gatacccca | 22320 |
| cctcagcctc | ccaagtagct | gggatcacag | gcttgcgcca | ctatatccgg | ctaattttg | 22380 |
| tatatttcgt | agagacaggg | ttttgccatg | ttgcctaggc | tggtctcaaa | ctcctgagct | 22440 |
| caagtgatcc | acccgcctca | gcctcctaaa | gtgctgggat | tataggcctg | agccattgtg | 22500 |
| cccggtcact | tccagatttt | gaagacagag | ccaacaggat | ttgttaatgg | attaggtgtg | 22560 |
| gcaggaggag | ggggaggaag | agagagagag | actggagttg | aagttaaggc | tcatttcaag | 22620 |
| gttttttagcc | tcaacatgtg | caggaatgga | gttgtcactt | gctagaatgg | gggagactgg | 22680 |
| aggagaagcc | ggctgggaga | ggttttaat | gaaggggttg | gctttggata | cattaagttt | 22740 |
| gacatgcatt | ttagacatcc | aggtggagat | attgaagagg | cagttggcta | taagtgtctg | 22800 |
| atgttcatat | tagcggatgg | ggctagagac | ataaatttga | gaattgtcag | tgtataaacg | 22860 |
| ttgttttgaa | agaaagtggg | gctgaataat | ttagaaagga | gtgcatagag | aaaataagtt | 22920 |
| tactattaaa | atagctttaa | caggccgggc | acggtggctc | atgcctgtaa | tcccagcact | 22980 |
| ttgggaggct | ggggtgggca | gatcaaaagg | tcaggagttt | gagaccagcc | tggccaatat | 23040 |
| ggtgaaaccc | tgtctctact | gaaaatacaa | aaattagcca | ggcgttgtac | cggcaccctg | 23100 |
| tagtcccagc | tacttgggag | gttgaggcag | gagaatcact | tcaacccggg | aggtggaggt | 23160 |
| tgcagtgagc | caagatcacg | ccactgcact | ccatcctggg | caacagagca | agactccgtc | 23220 |

```
tcaaaaaaaa aaacaaaaaa aaacaaaaaa aaaaaacttt aacagcaaag cctcttcctt    23280
taaaattatg aatttttttc ttatggaagt tggactcttt cattattaag tctacattca    23340
atcactatgt tagtaaaaat gttgttctag ttgccgaatg caataaacca gctcagactt    23400
agtggcctaa agcagcaatc atttgactat gttcgaagat gccgtgggca ggaatttaga    23460
taacagcagg gatggcttgt ctttgctctg cgatgtctga ggtctcactg agaaaactca    23520
agcggctggg ggtaataatc atctggaatt ttctttactc ctgtatctga tgtctgggct    23580
gcgatgactc aaaggctgat ttcagctgag actgtagacc acgtgcctac ttgtggcctc    23640
cccttttgcc ttgggtttct cacagaatgt ggctggttct ggagaatgag acttccaatg    23700
aaatcaggtg gaaatgacat ctcgccgctt tcagcatgct ctattggttg aacagttat    23760 ggacttagct agattcaaag gaagggaaca aagacccct cctctcagag agtggggcat    23820
aatgagagaa tttagggcca tgttatccaa ccaccacaaa tgccttctga atttgaggtt    23880
ctgcctcaaa agttcatagt tcctttgact gaaggacttc tatatatcca agcatcgtca    23940
gccccaggta tattgttcca tgtaagtgac caggactacc ttagtatttc gtatagggaa    24000
agtgacctga ataaatttga gaaaagaatc ttccttctct ccagtaagca ctgaggtaag    24060
cattgagcca tattataggt ttatgacttt gagactcaga aatttaaatt cttggccagg    24120
cgcagtggct cacgcctgta accccaacac tttgggaggc caaggcaggc agatcacttg    24180
aggtcaggag tttgagacca acctggccaa aatggtgaaa ctccatctct acgaaaaata    24240
caaaaattag ccaggtgtgg tggcgggcac ctgtaatccc agctacttgg gaggctgagg    24300
taagagaatg gcttaagttc tctttatctg ctttatttca gttgcctctc ttagatgaat    24360
attaatgact tacatagcat tttagatcag tggatgtttt tgtgattctt ttatttgagc    24420
tttggccaaa gataacagta cccacaggtt ttttccagct actcgctctt ctcccttcag    24480
tggccctcga gcctggaaaa tctgacatga caatgtgctt gctcaaccta ccactgtttt    24540
tcttttgaaa agtttggcag cctgtttctg actcctatga aggtgaattc ctcagcattc    24600
acagtttatt agaaaatac tttgcttctc tccaaactcg aaattcaaga taaccaaacc    24660
tatatatagg ctgatctttc aggatgcagt tgtcatgttg atgccatgct tttcagtatc    24720
gtggccatca tctgttcagt aggggaggtg tacttctgta atgggaggtg gtggttatgt    24780
gtgtgtgcaa gtgtttattt ggtgtcttaa gttagcctgt gggaagttct aaatcaggat    24840
ggtacgtggt tgccagcaga gagctgctcc tcaagtgaag gaggtagaat caaagccaat    24900
aggaaagagc ctcagatgct tatatatgta ccgtggggat tcagagtgaa agcagtcatt    24960
ggactagggg tgggggttagg gagagcctgt ctgacagaca caagaaaggg atggataacg    25020
ccacccagag aaaaaagcat tttaggcaag aacaaatatg aaaaaggaac aaagtctgtg    25080 ggtgggggc aaggaggaga taagttgact tgaaggaaga caacacttat gaaagtcacc    25140
tggaggctgg gtgccatggc tcatgcctat aatcgcagca ctttgggagg ccgaggtagg    25200
aggacaactt gagcccagga gttcgagacc atcctgggca acatggtgag actgagtctc    25260
taccaaaaaa aaaaaaaaa gaaaattatc cagacatggt ggcatgtgcc tgtaatccca    25320
gttactcagg aggctgaggt gggagggttg cttgagccca ggaggttgag gctgcagtga    25380
gctgtgatcg tattattgca ctccagcctg ggtaacagag caagaccctg tctcaaaaaa    25440
tgaaagtcat ctgtaggctg gagagaggaa ctggaagggg ctaaagttgg ctgagtagtt    25500
acagagcctg agataagggt aaagattttg cattggacaa tgagatgtta gtgtgtgttt    25560
ttgagctggg gagtgctgtg atttttactct tattgaagaa tcactgaagg attattcttg    25620
```

-continued

```
aatcagtgat tcttgatcat tcttgaattt ttcaaacagc aaaactggaa gagttggcct    25680
attcctcaga atattttcta attgggcgca gtgtcctcac ttgggagaac ctggctacac    25740
actttagttg taattcactc cagtcgttca ttcattcaat acctatttt tcagcaccta    25800 ttatgagcca gacactatgc tggatgccag ggttcagggt aggacacgct agtgagcaaa    25860
agccaagact cttcttgtct tcatggggct ttcagtccag catagtggtt atgagtccaa    25920
gttaatggag tcacagtact tgggtgcaag tcatggtgat ggtgatagaa ggaaggcatg    25980
tgtgagggcc agtggcaggc aggagcctgg tgttttgag gacctgaaga aggagcagag    26040
tgagtgccag gaacttagcc accagctggt accagccata cgagaggggc agagccagcc    26100
aggatgtcgg tcatgctagt aatgagtaca aacacttaca tgctgcacgc tattgggctc    26160
ctgagtgcta cgtgttcatt agctcgatga atttgtacag caaccctgtg aggtaagcac    26220
tgttctctcc ccttctata gatgaggaaa ttaaggcaca aagaggataa ataactggca    26280
ccagctacac gctaagtgat cgaagtggtg gaaccaggat tcaaatccat gctattctgc    26340
cttaagataa caaatcttgt tttttagcct aagaacagag cagtcatcag gagggttta    26400 agtaggggtg tggcaagatc aagtttgtgt cttgaaaagg tctctctacc cacagtgtgg    26460
aaaatggcct ggaggcaagc acacagatgt tgggagacag ttaacagctc ttgccatggc    26520
cccctatgca ttttggctct gatgtttctg cctgatttt ctcttgcctc tgcctctttt    26580
cctgagggga tggcaggttt taccattcag ctggagtaca aaccctgaac cctttttggt    26640
taaatatcta cttgcttttc ctacagtatt attttgagtt gctgtggctg taatgtcttg    26700
agggaatcga gcttgacagt aatttataga acaaacagtt tttagagact gtgtggccca    26760
attgccctct caatgttggc actcctgcca tgacatttac catgctgagc atgtgaccgc    26820
catctgaata ccaaatgcca caggaacctg ggaggttgtc acttactcct cccttctct    26880 gagtcacctt tgcccttcag tcagtcacca agtcccatca catgtagctc tgtaatgtca    26940
cagaagatgg atgtctgcct caaaacactt acaatgctgc tacctaaatt gggcagccac    27000
gacctcccac caggattatt gcagcctgag ggatctttt gaaatgtaaa tcaaactatc    27060
acttgtctgt ttaaagcttt tcaaagactt accccattgc ccttggaaga aagtgcagat    27120
atcttgacag gagagccttc tccagcctcc tcttctgccg tggtctcctt gtacagtctc    27180
tacagtgtac tgcttcatta gaaccctgga gattattatt tgctagttct gggctaagaa    27240
ctggcacctg gctttgtaga gctcctcagg agattctgag gcgtattcag agttgagccc    27300
tgatctctgc tctgatttcg aggttctcgt tatatttatt aatgatcacg aaaaaattta    27360
ttattattct ttggcctcac tttagcatca tctgaggaat ttttttttt ttttgacaga    27420 gttttgctct tgttgcccag gctggagtgc aatggcgtga tctcagctca ctgcaacctc    27480
cgcctcccgg gttcaagaga ttctcctgcc tcagcctccc aagtagctga aattacaggc    27540
atccaccacc atgcctgcta atgtttttgt attttttagt agaggtgggc tttcacagtg    27600
ttggtcaggc tggttttgaa ctcctgacgt cagctgatcc acccacctag gccccccaga    27660
gtgctgggat tacaggtgtg agccaccgtg cccagccgta gctttcgaaa tttgaaacct    27720
ggtcccactg tcagaggttc caatttggca ctggtttggt tcccaggcat cttttcttgct    27780 gtatatattt tttagtgtca gccagggtgg agacctctgt attacttcat ggggaagaat    27840
ttgggagaag atgttgtgag gagacaggtt ctagtcctag agtgatttat cctttctcgt    27900
acagatttcc aggtatttga ggggccactc ttctgtaatt catgttttc tctcctaacc    27960
```

-continued

```
tcactcctgt tgcctgcatc ttcttgctga gcaaaatatt caaggtcttc aactcctcac   28020
accctggttg tccctccctg gatgtgtttg gttgttttag tgttccattt caattttgat   28080
acacagaatt agaatagcat ccagatgtgg gtctgttaca gctagactac tagatccttc   28140
aaaatccaag tactagtatg tctattaaaa taccataaga tcacattggc tagttacaat   28200
ggttggtttg tgggttactt aaaaatcaac taaaattctt tttttttttt tgagatggag   28260
ttttgctctt gttgcctagg ctggaatgca atgacacaat cttggctcac tgccacctct   28320
gcctcccagg ttcaagcaat tcccctgcct tagcctcctg agtagctggg attacaggca   28380
tgtgccacca tggccagcta attctgtatt tttagtagag atgaggtttt ccatgttggg   28440
tcaggctggt ctcgaactcc cgacctcagg tgatccacct gcctcagcct cccaaagtgc   28500
tgggattaca ggcgtgagcc actgagcctg gccaaaattc ccactttcta atactcctgt   28560
agtagctggg tacggtgggt cacatctgta atcccagcac ttttggaggc tgaggctgga   28620
ggatcgcttg agcctaggag ttcgagacca gcctgggcaa gatggccaga cgccatctct   28680
aatttaaaaa aagaaaaaa caagactcct atagtggtga agaacagaca ttccgaaaac   28740
agactgtgcg ttatgattcc agctccatgc ctttactacc tgtgttgtga ctttggataa   28800
atcacttaaa aatcttttt tttttttttt tttttgaga cggagtcttg ctctgccgcc   28860
caggctggag tgcagtggcg cgatctcggc tcactgcaag ctctgcctcc caggttcaca   28920
ccattctcct gcctcagcct cccaagtagc tgggactgca ggtgcccgcc actacacctg   28980
gctaattttt tgtattttta gtagagacgg ggtttcaccg tgttagccag gatggtctcg   29040
atctcctgtc ctcgtgatcc acccgcctca gcctctcaaa gtgttgggat tacaggcgtg   29100
agccaccgca cccggccaaa tcacttaaaa ttctgtgcct cagtttctcc tctgtaaagt   29160
gggataaaaa tagtacctat ctgatagggt tgttacaatt atgaaatgag caaataagta   29220
tgtcaagtgt ttaaaacagc gcctggcttc ttgtaaaaag tgctatataa atcatagcta   29280
taatcattac ttatttcgac tgctctttaa ccaaggttct tattttttcat cttttctttt   29340 tgttttgaat atcacttagt gttttcacct tttactcttt ttaggaccta gagccatcct   29400
aggtgaaata cgtatggaga tatttgatca ggtcaccacc cagctctcct gacctccctt   29460
ctctccttaa attaacatgc caaatcacag catcactgac tccttccctc ccgatatgat   29520
aagagtgtgc attgaaatgc atgtatttta cttagcaggg aaagctgatt agtgattatc   29580
acacttaacc cctagtgaat ctgatggatt aacctgcttt ccaggacact aaggaaatgg   29640
gtttaagata agaaatatct ggctgggtgc ggtggcttta cgcctgtaat cccagcactt   29700
tgggaggccg aggtgggcag atcacgaggt caggtgattg agatcatcct ggctaacacg   29760
atgaaacccc ctctttacta aaaatacaaa aaattagccg ggtgtggtgg cgggcgcctg   29820
gagtcccagc tactcgggag gctgaggcaa gagaatggtg tgaacccagg aggcagagct   29880
tgcagtgagc tgagattgtg cccaccgcat tccagcctgg gcaacagagt gagactacat   29940
ctcaaaaaaa aaaaaaaaa aagtaagaaa tgtccatgaa agggagaccc tgggggaaag   30000
gaacaataac tgcagctctg aggatctggc accagcagca ccagcacaga gggatgctgt   30060
acaaccatta ttgattttaa ctttacaaca gttcttcaaa ggagagagag ttccctgttt   30120
tactgaagag aaagcccatt tggtagtgaa ataccattcc caaagacaaa tagctaataa   30180
atgtcaggca gggttttgca cccaggccca tccagctccc gtctctactg tcctttcccc   30240
cacaccacac tgatacagag gaatgtgtct ggttggggaa gtggaagtgt tcccaagtgg   30300
ggaggtcatc tgatgcacaa atttggtctg ttttgtgggt tttcttgttt tagttttagt   30360
```

```
ttttgtagag ctcagacctg ttcttaggca gctttaacaa tcaactgtgc actcagtaat    30420
tgacaaatca tgtttgttac ttttaatttta gagggaatta ggtttgttaa gctcttgctc    30480
cttctttaga gatggggtct agctctgtca cccaggctgg agcgcagtgg tatgatcaca    30540
gctcactgca gtctcaatct gctcaagtga tcctcctgcc tcagcctcca tgggactaca    30600
agcatgggcc accatgctag gctaatttta aaaaatttt tttgtagagg caaggtctca    30660
cggtgttgcc caggctggtc ttgaactcct gagctcaagc aatccctctt ccaccttggc    30720
ctctcaaagt gctagaatta taggcatgag ccaccatgcc tggcctttac ttctttcata    30780
tattcaaatt ttgtcatatt agtagggaac ataactcaa gttttcttat agattgatgt    30840
tcatttttac aagcttgatc gtcattggtt tttaatttta aagcaaatcc tgttatatgt    30900
aattgaacat tacagtaatt atagtaattt gtttcagatt gggcactcaa gtgttaatat    30960
tttgtctctt taggaaatca aaactagatt tatatataga cttcttattg caagtatcta    31020
gtcttaaatc ttacaaaggt actatttgga cttaaaacta tgaaattgtg tgcttactat    31080
ataagtgtac ttatttttgag ttatgtttta aacttgaaat tccattctta atgtctagag    31140
taattatgaa tggttaaatt atgaatgact ctaatagttt aaagctacag tatttattta    31200
tttatttatt taatttattt tttgagatgg agtttcgctc ttgtcgccca ggctggagtg    31260
tagtggcacc atcttggttc actgcaacct ctgcctcgcg ggttcaagtg attctcctgc    31320
ctcagcctcc caagtggctg ggattacagg tgtatttcac catgcctggc taattttgt    31380 attttttagta gagacaggct tttgccatgt tagcctggc ggtctcgaac tcctgacctc    31440
aggtgaccta ccctcctcag cctcccaagg attacaagca tgagccacca cacctggcct    31500
acagtatttt aatgtggact ctctgtcatc cattatgctg tttatcctgt ggtgaaaatt    31560
ttatgaagat tgaatgtttt tctctagcgt gaattgcttt ctcttacttt tctcattttt    31620
ttccttccta atctacttgc agatacttca gattattttt agaacgtggt atggtgagaa    31680
caaataaatt ggggtttcca atcttaata aattatgtgg ccctcagtgg gattagcagg    31740
gttgtattga aaacaccaat agaaacaaaa tagttctttt atgcgcttta aataaaaatt    31800
tcttttcagg ccaggcgcag tggctcacac ctgtaatccc agcaccctgg gaggctgagg    31860
caggcagatc acctcaggtc aggagtttaa gacaagcctg gccaacatgg tgaagcgccg    31920
tctctactaa aaatacaaaa attagccggg tatgatggcg catgcctgta atcccagcta    31980
ctccagaggc tgaggcatga gaatcacttg aactcaggag atggaggttg cagtgagctg    32040
agatggtgcc actgcactct agcctgggca acagagtgag attctgtctc aaacaacaac    32100
aacaacaata acaaaacatc tcttttcagg ccaggtactg tggctcacgc ctgtaatccc    32160
agcactttgg gaggccaaaa caggagggtc gcttgagacc aggagtttga gaccagcttg    32220
ggcagctggt ctctatttga acaaacaaac aaacaaacac aatactcttt tcatagaaaa    32280
atgtttacta cacaataaac tttaaaagaa tatgcagctg tattaatgct atgactccaa    32340
tgtaaaaaaa aaaaatata tatatatata tacacacaca caaacacatt ctgaaataga    32400
tttaaaggaa ttacatcaac atgtcaattt ttattttttc ggagacaggg tctcgctgtg    32460
tcacccaagc tggagtacag tggtgcaatc acagctcact gcagccttga cttcctggcc    32520
tcaagtgatc ctcccccctc agcctcccaa agtgctgggg tcacagacca ccacacctgg    32580
caacatgtca gttttgttc tgcatagtgg gatggtggga tatggatgtt tttatcttt    32640 attttctttt ttatattttt ctaaattttc cacattgaac attatttat aatctttcaa    32700
```

```
acatatctct taaaaggact ggttcctata gaattcagtg caagaaatct tctgtgtttc   32760
tttatacttt ggttgccttg atcactgggc ctttcctgac agcaaagaag aggttagtgt   32820
aggcagcaga taaacacag gtatgctcta tttaaaatgc atgtatttat aataaaagta   32880
taggtggtac ccaaaggaaa atgtcatgac acattgcaaa gtggaacaga agttatcttt   32940
agatcacttt ctgttctgga ttattgtatg agcctgattt tcgtctctct ttccgccttc   33000
cctcaccctc gttgtaaatc cactagtgca tggatgtgaa gtacaagtct taactttaaa   33060 aagtttatg aagctgtgta gtaaatccct tttgtaagtg gtcttgactg cgtttctcaa    33120
tatatctttt ggtttcatta gattcaagta tataaatgag aactgtaact ttggacagac   33180
tttttcagtc atctttacgg taataagttc ccaattagac aatagttatt tgttttatga   33240
cttgctgttg gtaggttatc cccaagggac tgagaaattc ctgttttgaa aagtccaaaa   33300
agtctttgat gacttgctgt ttcattttt tcttttctct tcagttatag aaaacaggat    33360
tacacccacc ttgcctttgt acagtgcatc tactatctgc tgacttaacc tgagtaaatg   33420
ctttgaattg agccccatat aatgtcctaa ggcagcctat atggagtaat gaattgtctt   33480
ctctcttatg cacccagagt ggtagttggc actcaagttg ttcctcagat aactttgtgt   33540
gttctggggc tcaatgaagt agttattaag tcacaggctt ggggagaaca ttcatcctat   33600
ggcattgaat gaagtgttgc ccaattctag aatgtctaat aaaattttt taaaaaccca    33660 caggcttaga attattccgt agatatgaag taatgtagtt agaacttagt ggagttcttt   33720
agattaactt gtaatttgaa aaaccaaaat tgaaattgtg aaataacatg ggctctttga   33780
ggtcttttcc agtaaaacag ttacagtaaa gctgcttggc agtgattttc ctagacactt   33840
tggctagtca tctcctgtga ctgctgttaa ttaaatatgg tttgtagcta agcagcctgt   33900
aaggagaaga ctatggaagt atttgcatat tctctccttg aaaatactac ctggtctttg   33960
gctttaagtt atacttttat tttcccctgt agaataacta ttaaagtatt acctatggtg   34020
attagactaa gaagtaaaac atgaaatcag tcattgttgg tgccctggtg ccttcttttt   34080
tttttttttg agacagagtc tcactctgtt gcccaggctg gagtgcaatg gcacgatctt   34140
ggctcactgc aacctctgcc tcccaggttc aagcgattct cctgcctcag cctcccaagt   34200
agctgagact acaggcgccc accaccacgc ctggctaatt tttgaatttt tagtagagac   34260
agggtttcac tatattggct aggctggtct caaactcctg accttgtgat ccgcccacct   34320
cagcctccca aagtgctggg attataggtg ttagccactg tgcccagcct ggtgctttaa   34380
ttttatggaa aaaactacta gctggttct gtttaagaa ataacacagg ccgggtgcca    34440
tgacttgcgc ttgtactccc agcagtttgg gaggccgagg cgggcggatc acgaggtcag   34500
gagtttgaga ccagcctggc caacatagtg aaacccgtc tctactaaaa atacaaaaat    34560
tagccgggcg tggtggggca tgcctgtagt cccagctact cgggaggctg aggcaggaga   34620
atcgcttgaa cctgggaggt ggaggctgca gtgagccaag atcgccccac tgcacaccag   34680
cccgggtgac agtatttcat ctcaaaaaaa aaaaaaaaa aagaacaca attattgtac    34740 tacttactag ccctcctctg tcccagcta aaaataagaa cagcaacaac caaaaaatcc    34800
ttagttatgt actggaaatg aattagataa ttttcaataa cttacacgtt tttaggatat   34860
gttagtttga aaatgcaaat attcatgcat gaccccagtg ttaatctatg atggagcagg   34920
tatagtggga tgctgtttca tgatttaatt tggaccttca gggagtagac tgtgatgcct   34980
ctgcatttgt atccaagaca aataattaaa tagtctattt ttggctgggc atgatgcctc   35040
atgcctgcag tcccagcact ttgggaggct gaggtgggag gatcgcttga ggccaggagt   35100
```

```
tcaagatcag tctgggcaac aaaatgagac cttgtctcta caaaaactac aaaaaattag    35160
ctgaacattg tggcttgtgc ccctagtccc agctactcag gtccctgagt taggaggatt    35220
gcttgagccc aggagttgga ggttacagtg atctatattt gccactgcac tccagcctgg    35280
gtgacagaga gagaccctgt ctcaaaaaat aaagtctgtt tttaaaatta attttaaaca    35340
ctggagttta ttacaaaaag cagttggttc ttttttttaaa tcattttttt ttaggagaac    35400
caccgctttt tggctacatt gtctagagta gcagtgttca ataaaaataa gatccaagtc    35460
acatatgtaa tgttaagttt tcttttagtt tcttttctt ttcttttctt ttctcttctt    35520
tctttctttc tttctttttt tttttttga tatgcagtct cactctgttg cccaggctgg    35580
agtgcagtgg cacgatctcg gcccactgca acctccgcct cccgggttca agcaattctc    35640
ctgcctcagc ctcccgagta gctgggacta caggcatgtg ccaccatacc cagctaattt    35700 ttgtatttt agtagagatg gagctttgcc atgttggcca gtctggtctc aaactcctga    35760
cctcgggtga tccacatgct tggcctccc taagtgctgg gattacaggc atgagccacc    35820
atgccctacc aatgttaagt tttctagtag ccatattaaa agaagtaaaa agaaatgggt    35880
gaagttaatt ttaataatat attttattta acccaatata tctaaaatat tatcatttca    35940
acatgaacaa gatactttac attcttttgt ttttcactaa gtcctcaaaa tccagtgtgt    36000
attttatatt gacagcatag ttcagtttga agcagccaca tttcaagtgc tcagtagcca    36060
catgtggcta gtgactccat actgactgt gtaggtttag agtttcagta aatttgtatg    36120
caatagaatc tacataaatt ggcatattat gcagatttct ttgtatgcac atcagttctt    36180
gcatagcata agtcaggtca tgatgctttt agtctatgag gcagattttt tttttttttt    36240
ttttgagaca gagtctcact tggtcaccca ggctggagtg tagatgcaca atcttggctc    36300
actgcaacct ccatgtgagg cagattttaa cttggcccta atgcaaatat tgtaagagag    36360
atctaatggc ctttgatttc ttacagaggg caatcaatac atgccatggt tacaatgctt    36420
cagcatatag tatgcacgtc agccactgct tttactctgg ctagtgctta gtgtacctgt    36480
accactgccc aggcagcatt tgtcctgtgg caggtgaatc ttagggtgga aggtggcaag    36540
taacattgct tttttttgag agggagtctt gctgtattgc ccaggctgga gtgcagtggt    36600
gcgatctcgg ctcactacaa cctccacctc ccgggttcaa gtgattctcc tgcctcagcc    36660
tcctgagtag ctgggattac agacggccac caccatgctc ggctaatttt tgtattttta    36720
gtagagacgg ggtttcacta tgttggccag gctggtctcg aactcctgac ctcgtgatcc    36780
acccgcctcg gcctcccaaa gttctgggat tacaggtgtg agccaccgtg cccagcctac    36840 attttttaaat taattaatta taagcaggat ctcactgtgt tggccagact ggtcttgaac    36900
tgataagagt tcaagaccag cctaggcaac atggtaaaac cctgtctact aaaaaataca    36960
aaaaaaaaaa ttagctgggc atggtggtgc gtgcctataa tcccagctac ttgggaggct    37020
gaggcaggaa aatcgcttga acccgggaga ctgaagttgc agtgaggtga gattgcacca    37080
ctgcactcca gcctaggcga ttccatctca aaaacaataa caacaaaata acattgttgg    37140
aatatttagt taatttatag aagcgtattg gcctaattgg ggcaaatacc ttattctgac    37200
attctctcta tttgctttac tgagcttttt caccagtgga attaagccc ttgatacatg    37260 aggagggaaa ataccttgga gctgtgctgc acatgtaaag tacacaggag atttagaaaa    37320
cttcgtagca aaaaaagag tgtaaagtat ctcattaata gttttttgtgg gctggacacg    37380 gtggctcaag cctatactct tggcacattg ggaggctgag atgcatgagt ctaggagttt    37440
```

```
gagaccagcc tgggcaacac agtaggaccc cgtctctaca aaaataatca gccagatgtg   37500
gtgcgcatct gtagtcccag ttacttgaga ggctgaggtg ggaggatcgt ttgagctggg   37560
aagttgaggc tacagtgagc tgtgattgaa ccactgcact ccagcctggg tgacagagtg   37620
cctgtctcca aaaataaat aaataaataa taatatgttt tgtatgttca tatgttgcaa    37680
taacattttg gatatattaa atgaaataaa atacattaaa attaatttca cctgtttctt   37740
ttcttttctt tttttttttt tttttgaga tggagtctcg ctatgtcatc aggctggagt    37800
gcagtggcac gatctcggct cactgcaacc tcctcctcct gggttcaagc gattcttctg   37860
cctcagcctc cctagtagct gggattaaag gcatgtgcca ccacacccag ctaattttg    37920 tattttagt agagacgggg tttcaccata ttggccagga tggtctcgat ctcctgacct    37980
catgatccgc ctgccttggc ctcccaaagt tctgggatta caggcgtgag ccactgcacc   38040
cagcctcttt taacttttta agtatggcta ccagaaaatt taaaatgcat gtgtggcctg   38100
tattctattt ctgttggatg ctgctgcctt agattattaa ttattcaatg taaagactgc   38160
tgggaggtac tacctgcact tccctgaata tatgcttgag agctccacca gccgtcttca   38220
cagtagcaag aggggtattc tgagtctgtc ccccaaagag ggaggagaa gtgcagccct    38280 ctcaggttct gtcagaaaac ctgatcccag gccaggcgtg gtagcttacg cctgtaatcc   38340
cagcactttg ggaggttgag gcaggaggat tgcttaagcc caggagttcg agaccagcct   38400
gggcaacaca gtgaagaccc tatctctaca aaatttttt taaaaaatt agccaggtgc     38460 agcaatgctg cctgtactcc cagctgcttg ggaggctgag gtaggaggat tgcctgagcc   38520
caggagttag aggttgcagg agttagaggt tccacgatcg caccttcat tccgttacat    38580 ttgctgcctt gagaacagaa gacctgctgg ttttgttgcc agtttgctca gtcatttta    38640 tgaaaagcc agtgctaact aggtgcttct tcgtgccttc tctgagaatc aagaactcta    38700
gtatgtttgc gtgtgttcag tctctcatta aatgttctca ctatcccaga gaaccatctc   38760
attggacctt ggtctgtaca taccttcatc tttggctctg acttgtaatt atttttagaa   38820
cttctctttt tttttttttg gagacagagt tttgctctag ttgccagact ggaatgcagt   38880
ggcacgatct cagctcacct caacctctgc cttccaggtt caagcaattc tcctgcctca   38940
acctcttgag tagctgtaat tacaggcatg tgccaccacg cctggctaat tttgtgtttt   39000
tagtagagac agggtttctc caagttggtc aggctggtct caaactcccg acctcaggtg   39060
atctgcccgc cttggcctcc caaagtgctg ggattacagg cgtaagccac tgcgcctggc   39120
ctaattttag aacttgttaa aacaacttgg cctctattga tatttccatg acccatgcta   39180
ttcagaaaga ggattacagg taattagctg gctgggtttc tcataccaga gcatttcact   39240
gggatgttcc tgaacctggg acaactttta tgcctggcat ttttctttcc ttctctgttg   39300
tcccagacta agcaattttt aaaatagtta ttatttgttg agtaggagaa tctcaggcag   39360
atcttcctgg atcctcattt atacttttaa acctgtagtc ttggaattag tgctctgtcc   39420
cccaacccca aacatccaat ttctacattt tggctacagt acaggtttac tgtgtataac   39480 taaagggct gtggaggaga aagaaaggaa ccgacatttg ttgggcatct gttatgtgcc     39540
atgcactgag ctggatgctg taggaatatc tcaataccct tgaggagtgg gaattattat   39600 ctctattta tagacaaggg aatagaaatc tgggagttaa gtaatttttt aatttccacc    39660
acttctggta gataatggat tctagaacct ggcataatag ccacttgtca tcccagtgta   39720
aaagagatgt gtgccagat ggggtggctc acatatgtaa tcccagcact ttgggaagcc    39780
gaggcaggag gatgacttga gcccaggagt tcaagaccag cctgggcatg ttttgtttgt   39840
```

```
ctcacgaaac attttttaaa aaatgagtgt ggcatggtgt tgtgtgccta tagtcccagc   39900
tcctcgggag gctgaggtgg gaggatctct tgagcccatg atcatgccat tgcactctag   39960
cctgggccac agagcaagac tctgtcttca aaaaataata aaaaggagct gtgattatcc   40020
caaggtgggg attgtgaatg tgtttgtatt gttctaaact gggagaaaca ggctgggtgt   40080
gttggcttat gcctgtaatc tcagcacttt gggaggccaa ggtgggagga tcacttgagt   40140
ccaggagttc aaggccaccc tgggcaacag gcaaaaaata gagaccccat ctctattttt   40200
taaaaataaa ataaactggg agaaagaagc agggtcctcc ccagagcatc tttatcccta   40260
gtcacagacc tgacacctgt gttgggcaat ggctacttct agattgttta ccccctactgg   40320 gacttgtggt gaacatatgc acactttggt ttacagttgg gaccccctgat tttagcagga   40380 tggcccaatg gaatcagcta cagcagcttg acacacggta cctggagcag ctccatcagc   40440
tctacagtga cagcttccca atggagctgc ggcagtttct ggccccttgg attgagagtc   40500
aagattggta agtccttctt aagtgactct ccaaattgtt aggtttcagt ttgagtcaag   40560
agacatgaac tcttaatgtc atgccttgct gttccattaa aaaatgtatg ggtacaggtg   40620
atggggaaaa tgagatcagg agataaaggg gcaccctttg gtcttgtaaa gcctttttta   40680
tcttagaagg gcatgtgggc aactgtcttt gacacattga aaccgcctgt atggtggtgg   40740
atgtcttgaa ggttgatttg gacctcattt acttgggcag atcctctata tattctgata   40800
atccagtgat gtggtagaca tattttttct ctgaatgtga attctgtcat agctagaact   40860
ttgggttgat acttgtaatt ccccctttagt taaaggaagg agccacaggg gtgtattagt   40920
ctgttctcaa tttgctataa agaaatacct gagactgggt aatttataag aaaagaggtt   40980
taatcggctc atagttctgc aggctatata ggaagcatag cagcatctgc tgctggggag   41040
gcctcagcaa gcttccaatc atggcggaag gcagagaggg agcaggcagg tcacatggcc   41100
acagcaagag caagagagca aggggaggt gccacacact tttaaactat cagatctcac   41160
aagaactcac tgtctcgagg acagtatcaa cagggatggt attaaaccat tcatgagaaa   41220 cccacccccca tgatccagtc accttccacc aggccccacc tcaaacagtg ggggttacat   41280
ttcagtatga gatttgggca gggatgtaga tccaaactag atcacaggat aagggaagta   41340
gattccattc atagagcaga taatggcaca gatgtccagc aactattttc ttcacttttaa   41400 tatgctcagg ctcactactg attttggttt aattcaggcc agtgttaata tgacctggtt   41460
tttccagaat gcatactctg atttggtgaa gggccaggag gtgattcaca gatgttggag   41520
ataggccatc ccagcctggg attacttatt tgtactaata aatctgacca gagttaattg   41580
agggtttaaa gcaaaacagc atatctgtct actttgctca aatattttac aaatacaaca   41640
gattatgaga gtgggtaata atatctggaa taattgtttt tttgttttgt ggttttttt    41700 tttttttttt tgagatggag tctggctgta gcccaggctg gagtgcagtg gtacagtctc   41760
ggctcactgc acctctgcct cttggattca agcgattctc ccgcctcagc ctcccgagta   41820
gctgggatta caggtgccca ccaccacacc tggctaattt ttattttta gtagagacag   41880 cgtttcacca tgttggccag gttggtctgg aactcctgac ctcaggtgat ccgcctgcct   41940
cagcctccca aagtgctggg attacaggca tgagccacca tgcctggcct ggaataattg   42000
ttaataatta ttcattgat ggcatttat tgctgagcaa gaagaatcta acatgatgaa    42060
tgggttatag catcaggttt gctttgtttt tttgttttt tcctctttct tgatggtgat    42120
ttctgtgttt gtgtgtatgc gtcggcttca gagccattct ttatcattct tccttttcct   42180
```

-continued

```
agggcatatg cggccagcaa agaatcacat gccactttgg tgtttcataa tctcctggga   42240
gagattgacc agcagtatag ccgcttcctg caagagtcga atgttctcta tcagcacaat   42300
ctacgaagaa tcaagcagtt tcttcaggta tgatgagaaa ctgaggacaa ggagaaacag   42360
gacccgcaga gtcgggtgtt agtgttcttt cctggaagca tctctttct catttggcta    42420 agtaacgaga atctatcttg tattttcaat cacaggagaa gtaattagcc ctttctcaaa   42480
gctctgtata cttacccgtg agcatcatta cctgagaatc acttctcttg tcacagttga   42540
agtaataaag tgattgttat gttaatcata catgttagca tgttaacgcg gtccactgat   42600
aggaagatga ctctcactgt tacatgttaa atgtttgacc ataatgggat acttcttgac   42660
taagtcagta gcttccctgc aagaccagga tagtatactg tgtaaagact cagacaaggc   42720
caggcatggt ggctcacgcc tgtaatccca acaccttagg aggttgaggt gggaggattg   42780
cttgagcctg ggagttttga ccagcttgg gcaacataa caagacacca tctctacaga    42840 aattttttt aaaaactagc tgattgtggt ggcatgcacc tgtagtccca gctactcaga    42900
aggctgaggt gagaaaattg tttgagcctg ggaggtcgaa gctgcaataa gccgtgattg   42960
cgccactgca ctccagcctg gcggacagag tgagagccag tctcaaaaaa aaaaaaaaa   43020 gactcaggct aatgtgcctt ctgttacaga aatagtaacg acctccccctt cgccccccgc   43080 cgacagagag ccttcaccca ggctctgaag cctttgttcc gttgtttcct agaataaatg   43140
ctttccttga tgaatacatt agttttaagg tgccacagtt cagtccacat ctccatggtc   43200
tgctgctgat ttttattctc tttctctcct acttatagag caggtatctt gagaagccaa   43260
tggagattgc ccggattgtg gcccggtgcc tgtgggaaga atcacgcctt ctacagactg   43320
cagccactgc ggcccaggtg agacctgaga caaaacaaat ccctggtctg ggaggaatgg   43380
aaaatcaaac aactttataa tgagataaat tattagatct actaaaaaag aaggaaaaga   43440
aattaaatag atcaataatc ataaaaatac attgaaaaac tctaaaaaaa aagaaagttc   43500 cacccccccaa aatacattga aaaactctaa aaaaagaaa gttccaccaa aagaatccaa   43560
cagacccaat ggtttaaaag ttttgttttg ttctgacaaa ttttctttgt ttttcttttt   43620
ttttttttct gagacagagt tttgctcttg ttacccaggc tagagtgcaa tggcgcgatc   43680
ttggctcact gcaacctcca cctccagggt tcaagtgatt ctcctgcctc agcctcaaga   43740
gtagctggga ttataggcgt gtgccaccac acccagctaa ttttgtattt ttagtagaga   43800
cggggtttct tcatgttggt caggctggtc tcgaactcct gacctcaggt gatccgcccg   43860
cctcagcctc ccacagtgct gggattacag gcgtgagcca ctgtgcccgg cctgttctga   43920
caaactttca tagtacagat tattccaata tcattcaaac ttttccaaag tataggaaaa   43980
caagggatgt tttcagctta ttttatgagg ctggaaaaat cctcatatca aaacctaaaa   44040
aacagccagg tgtagtagct cacgcctgta atcccagcac tttgggaggc tgagacgggc   44100
agattgcctg agcctcagga gttcgagacc agctgggca atgtagcgag acctcatctc   44160
tctttttttt ttttttgag acagagtctc tctctgtcgt ccaggctgga gtgcagtggt   44220
gccatcttag ctcactgcaa cctccgcctc ccaggttcaa gcgattctct gcctcagcc   44280 tcccgactag ctgggactac aggtgtgtgc caccaagcct ggctaattt ttgtatttt    44340 tttagtagag atgggtttc accttgttag gcaggatggt cttgatctcc tgacttcatg   44400
atccaccggc cacagcctcc caaagtgctg ggattatagg catgagccac cacgcccagc   44460 ctttttttt tttttgagac agagtcttgc tctgttgcca ggctggagtg cagtggcgtg   44520
atctcagctc actgcaactt ctgcctccca ggttcaagct attcccctgc ctcagcctcc   44580
```

```
caagtagctg ggactacagg cgcgcgccac cacacccagc taattttttg tgtttttagt    44640
agagatgggg tttcactgtg ttagccagga tggtctcgat ctcttgacct cgtgatccgc    44700
ccgcctcggc ctcccaaagt gctgggatta caggcgtgag caaccgcacc tggcttaatt    44760
aaggatcttt ctaaacacaa gaaagaatat ttatcagaaa ccaaagggag catgatgcac    44820
agtggtgaaa cactattctc agtaaaaaca gcaaaagata aggatgtctt ttaccattga    44880
tactttctg agggatccag cctatgcaaa agaaaaaga aatgagggta caaatattgg     44940
aaagcaaggg acagaactct tattatttac agatagatag gtcttcctcg aagatccaag    45000
agaaacaaaa ctaacaataa caattggaac tagcaaggtt tagaaaggcc attgtataca    45060
agataaaatat ttttagaatc tgcagttccc ctaatcagta gcagcagtaa cctgttagaa    45120
gatgtaatga agtaaagat ctgggccagg cacgatgtct cacgcctgta atccaagcac     45180
tttgggaggc caaggtgggc agatcatgag gtcaagagat tgagaccatc ctggccaaca    45240
tgatgaaacc ccatctctac taaaaataca aaaattagct gggtgtggtg gtacgcgcct    45300
gtagtcccag ctactcggga agctgggggca ggagaatcgc ttgaacctgg gaggcggagg    45360
ttgtagtgaa ccaagattgc gccactgcac tcctgggcga cagagcgaga ctccgactga    45420
aaaaaaaaaa aaaaaaaaaa gaaagatctg attcatagta gtaaaactaa atgtatgcaa    45480
tttgcatata ctattggtat gtatgggaaa atatctggaa acacatatac taaatcatta    45540
aagtagtcgg tcataggaga cttttttact ttctgtgagg ggttttaccg tctttaatat    45600
cctataatca gggacatttt ttcttttct ccgtgacccc ctgctttta aaaaattgtg      45660
gtgaaataca cataacatta catttcaaat ttacctttgt aacctttgtt ttttttttt    45720
ttttttgaga cagtctcact ctgtcaccca ggctggagtg cagtggtgtg atcacagctc    45780
actgcagcct caaccacctg ggccctagcg atcctcctgc ctcagcctta tgagtagctg    45840
ggactacagg cacatgccac catgcccagc taattttttt tttttttttt tttggtagag    45900
atgggctctt gccatgtttc ccaggctggt gttgaactcc tgggctcatc aactgatgag    45960
aaagagctct ccaggcagaa agaagatcat gttcaaagac agaaacagaa atgtgtattc    46020
ttgggagaag tgtagaaagt tcagcatctg attgggtcgg ggaagacaag ctagtcaagg    46080
ccacatgatg ttttaattag tcatgcctaa cagtggggcc ctggaagagc agtttaccac    46140
aaggggccaa ctgcttcggt ttgaacccgc agccctgcca cttgctctgt aaccttaagt    46200
aaacaatttt tactctctct gttcctccaa tgggagtgat aacaataccct tcttcataga    46260
attaattcat acatgtaaaa tgcttagaac agtatctgac acataaatgc aaaataattt    46320
aactgctttc tgctgctgct gacatcacta tcatcaccct caccattact gtaggaaatg    46380
gggacccagt gaagaatttt ttttttttct tttgagacag agtctcactc tgtcacccag    46440
gccggagtgc agtgacgcga tttcggccca ctgcaacctc tgcctctcag gttcaagcga    46500
ttctcatgtc tcagcttccc aagtagctgg gattacaggc atgagccacc acactgggct    46560
aatttttgt atttttagtg agataggggtt tcaccatatt ggccaggctg gtctcaaact    46620
cctgacctca ggtgatccat ccacctcggc ctcccaaagt gctgggatta caggcataag    46680
ccactgtgtc cggcccctagt gaggaatttt aagcagaaaa ctgatatgct caggtgtgag    46740
cgaggtggta ggtaacactt actgtgcagt gccctgtagc ccaagaggtt agcacacagg    46800
catttgctca ggcagcacta ggattttctg ctgtggaaaa cctttgtatt ttatcctgct    46860
ccacaagata aaaataagtg gtttaagtca atttggatag aggctccaac ttaccatggg    46920
```

-continued

```
aggtaggaaa gccaaagtta tcccaaggat gttttcaatc gtacggatta ggggtctgca    46980
aactgtgagc gtggcccaaa tccagcctgc tgcttgtttt tgtaaatgag gttttttcgg    47040
aacccagcca cactcattta tttatgcatt atctgtggct gctttggtgc tgcagtggca    47100
gggctatttg tggcagggac tgtatgaccc aggaaaccaa aaatatttac cctctgtccc    47160
ttagagaaaa agtttgcaac ccctgatata aagctataag ttggttatt gtggcctcaa    47220 cccaggcctc actgctattt tttctgttta caatacctgg catgctctta agtgtctaga    47280
attggttaaa gatagaagag tggatgtaat ccctgctacc aagggctgtc aggctagttg    47340
ggattataag tacacaaaca ctcaaagtga gaaaacaca gaaaaggatg tgtgtcattt    47400
tgtctaagga agttgaataa gatttctcag gaaaagaaac atttgaactg aatttgaagg    47460
tgagtgagtt caggtgtgtt tgggctgaag cccaggccat gctgagtgga tagcgggtgg    47520
gaagagagtg tggaaacaca ctgcatgcag ggaagagttg ggagtctggg gtgaccaagg    47580
cacagggagg gaaagttgaa gttatcaatt gtgtgaaaca gctttctgtg ttggcctgag    47640
atgtttatag ctggaagcag tggggagcca atacagtttt ttacgaaggt attagaggtg    47700
ggtttctgtg ggtgatcgtt aatcatgttt tctcccttta agtgtagtcc tgcttgagaa    47760
atagacatga gaaggaatg aaggttaaaa catcagctgt attgttggta aaactagaat    47820
ggaaagtgtg gctgagctg gtaaccatag gggcttttcca atgcctgtgc cctgagttag    47880
atcttggggt agagagactg gatgtgcaga gcagcacccc caccccaccc cagccatcca    47940
tatggagctt cagctgccat agaccaacaa ggcagaggga taggcctcta gacctgcttc    48000
tagaaaccag gctgctgctc ttgcttatgg tgggccctag gaaggcaaga gtgagaggag    48060
ggaggcacca gctaggtgc tgggttcttt gaagatctgt gtgtacacag agtctttctc    48120
tccatcttac caatcagatg agtcactgtc actgtgggaa gaagtagggg catgggtcac    48180
cttcccaaaa cttctaagaa gttttgtattc tgtgggcttg gatagggacc atgggaaagg    48240
aagagaatgg ttgcccataa aactggctgt agtgtggcct caaacttctg gacttaaatg    48300
atcctcccac ctcagcctcc caagtagcta gaactacagg tatatgccac catgcccagc    48360
tagttaaaaa aaaatttttt tttttttttg gttgagatga ggtctcttc tatgttccct    48420 gggccggtct caaactccca gcctcaagtg atcctcctgc cttggtttcc caaagtgcta    48480
ggattatagg tgggagctac catgcctagc ccaagcctgt aatttttttt tttttttttt    48540
gagatggagt ttcacttttg ttgctcaggc tggagtgcat ggcgcagtct ggctcacca    48600 caacctccac ctcccgggtt caggcgattc tccttcctca gcctcccgag tagctgggat    48660
tacaggcatg caccaccaag ctcagctaac tttgtattt tagtagagat gggtttctcc    48720
gtgtcggtca ggctggtctc aaactcctga cctcaggtaa tctgcccacc ttggcctccc    48780
aaagtgctgg gattacaggc atcagccacc gcacctggca cgaacctgta atttttaagt    48840
ttcatatgct atttattttt tgttatttct ttaattcatt cattcattta ttcattcgag    48900
atggggcctc actatgttga ctaggctagt tttgaactcc tggcctcaag cagtcctccc    48960
acttcagcct tcccaagtgc tgatattata ggtgtgagct gctacatcca gccttctttc    49020 ttcttttttct ttttccatgt gctatttgac attttccaag gtaccagcct cccttctcc    49080 ccaagataat atctttaat atggaatttc atccctaggg caggactttt tttttattat    49140
ccctcagaaa tatactggac accacgttta agtagacatc caacatctgc tgtcataaat    49200
tgttttgaat ttttgacat acttgcccat gaggttttg aaggcataga ccatgtctta    49260
gctgaacatg tggtctctta gtgccataaa gggggtttat ggtatgacct gtgtagtgtc    49320
```

```
acctgtgtag tgacagcacc actgcctctg tttcccttcc tcttgtgatg gcagcagcgt   49380
ctcaagccaa acaagaaggg tagttagggt gggatggaag ctgggtagag gtattcctct   49440
ccccatagtt ctgtgttcac atgtgcattg acctccttt tggcagcaag ggggccaggc    49500
caaccacccc acagcagccg tggtgacgga aagcagcag atgctggagc agcaccttca    49560
ggatgtccgg aagagagtgc aggtgatgca agttacaagc ctcgggcagg gagctttcat   49620
taatttttt tttttttttt gagacagggt cttgctctgc cactcaggct gggctgcagt    49680
ggcatgatca cagctcactg cagcctcgac ctctcaggcc caagcgatcc tcctacctca   49740
tcctcccaag tagccgggac cacaggcatg caccaccacg cccagctaat taaaaaaaaa   49800
aaatttgtag atgggggt ctccctgtgt tgtccaggct gatcatgaac tcctgggctc      49860
aagtgatcct cccaactcag cctctcaaag tgctggcatt acaggcgtga gccactgcac   49920
ctggccaaca gggagccttc tcttggggat actgcctgca ggtcctgcat gtatcttttt   49980
tgaggttttg gcttcatttg aattctcctc agaaacttta tattttctgt tcccaaggaa   50040
atctttcttt acttctgttt ttttgtttgc ttattttaaa caggatctag aacagaaaat   50100
gaaagtggta gagaatctcc aggatgactt tgatttcaac tataaaaccc tcaagagtca   50160
aggaggcaag tgaatattag agatgttaaa atctctagaa agtgagtttg tgttgttgag   50220
ttgaaagact catttgtctt aactctgttt agatcttaag gcgggcgggg cgcaagggga   50280
gtacgggtcc tcaaaggagc ctggtcatta aggacaggag tattccctca ggtccaggag   50340
tattccctca ggtccaggag tattccctca ggtcaaggag tattccctca ggtcaaggag   50400
tattccctca ggtccaggag tattccctca ggtccaggag tattccctca ggtccaggag   50460
tattccctca ggtccaggag tattccctca ggtccaggag tattccctca ggtcaaggag   50520
tattccctca ggtccaggag tattccctca ggtccaggag tattccctca ggtccaggag   50580
tattccctca ggtccaggag tattccctca ggtccaggag tattccctca ggtcaaggag   50640
tattccctca ggtccaggag tattccctca ggtccaggag tattccctca ggtccaggag   50700
tattccctca ggtcaaggag tattccctca ggtccaggag tattccctca ggtccaggag   50760
tattccctca ggtccaggag tattccctca ggtccaggag tattccctca ggtccaggag   50820
tattccctca ggtccaggag tattccctca ggtccaggag tattccctca ggtccaggag   50880
tattccctca ggtcaaggag tattccctca ggtccaggag tattccctca ggtccaggag   50940
tattccctca ggtccaggag tattccctca ggtcaaggag tattccctca ggtcaaggag   51000
tattccctca ggtcaaggag ttttttcttc cttcgcagac atgcaagatc tgaatggaaa   51060
caaccagtca gtgaccaggc agaagatgca gcagctggaa cagatgctca ctgcgctgga   51120
ccagatgcgg agagtaaggg cataggtcgg accacttccc ccatgtgtct cgctcacttg   51180
cgggatttca gcgtcttgtg gcagaacttg cttggtttct aagaagttcc tgctctggag   51240
ttgactaaag aatgtggtta gagacagtct gaggaaatgt tttctgactt tgttttggtt   51300
tccaaccaga gcatcgtgag tgagctggcg gggcttttgt cagcgatgga gtacgtgcag   51360
aaaactctca cggacgagga gctggctgac tggaagaggc ggcaacagat tgcctgcatt   51420
ggaggcccgc caacatctg cctagatcgg ctagaaaact ggtaaaggat gaagaagct    51480
tttcctttct ttctcgaaag ctagattgaa ttctgatctt aactgcaggc ccacagaatt   51540
ggtactatat ctccaacgtg gggctttttc catattcaaa tttagcccaa gaattaaagt   51600
ttttacttta tttcggccag gcgctgtggc tcacacctgt aatcccagca ctttgggaga   51660
```

```
ccaagatggg cggatcactt gaggtcagga gtttgagacc agcctggcca acatggtgaa    51720
aacacatctc tactaaaaac ataaaaaaat tagccgggcg tggtggtgcg cacctgtagt    51780
cccagctact ctgggcggct gaggcaggag aatcacttga acctgggata tggaagttgc    51840
agtgagcgga gatcttacta ccgcacacca accagcctgg gagacagagt gagactccat    51900
ctcaaaaaaa taaaaataaa ataaagtttt tactttattt ggagaaactt tgttttaaaa    51960
aatgtattta tattattata ttttaagtat attttactta ataattcaat taaggctttt    52020
ggtttaactg tatttaacag atagacaaac cttttaattt tagttatttt agtaatctaa    52080
aatgacacat gcccttttta agggaaaaaa ttcaaataca gaaaattaat caagagaaga    52140 aaaaatttt aaatgaaatc atcagcagta ctagtagtta aaatttagtt gatgctcaat    52200
ctagacatct gtcattatgt atatacacat tatgtatata cacataaaga tagaaaattta    52260 tacagtttat attaggatca tttttttttc ttttttggga gtcagggtct cactgtgtta    52320
cccagtctag agtacagtta tgcagtcatg gctcactgga gccttgacct cctgggctca    52380
ggcagtcttc ccaccttagc cttctcagta gctgggacta caggcatgca ccaccacacc    52440
tggctaattt ttaaattttt tatagagaca gggtcttact tgttgcctg ggctggtctc    52500 aaattcctgg gctcaaggga tcatcccact tcggcctctc aaaagctctg gaattataga    52560
tgtgagctgc cgtgcccagc ccaggatctt cctttatatg cttttctgta atttgcactt    52620
ttaccttcat ccagcatatc ttactgcaac ccttcctgtg caaggcccta tagtgagcat    52680
gttgcaccag cttgccttag gagaaacttg agatacagag cctgcactgg aaatttagcg    52740
caactctaca tgagaatgcc tgtctattca tatcctcact aaccctgagt gttgttaatt    52800
tactgaaagc agttttaaat gcttcctgac cagggaacga agaagcttaa gttctgggaa    52860
tgggaggata gaagtgccag aaaagagctc aggagttcag aaatccctgc agcggtcccc    52920
ctccctctcc tttcactttc tgtctttctg gtcttttggt cttgttaca ctagtgataa    52980 accatcaaag aatgatggaa tgatgctaac ttctctcttt ttttaatttt tttgagacag    53040
agtctcactc tgtcacccag gttagagtgc agtggcatga tcttggctta ctgcaacctc    53100
ctcctcccag gttcaagcga ttcttagtca caaccttcca agtagctggg attacaggcc    53160
catgccacca tgcctggcta ttttttttgta ttttagtaga tcgacctgcc tcggcctctc    53220 aaattttttgg gattacaggt gtcagccact gcacctggcc taatatctct attcttggag    53280
atagatttaa tgagcttttt ctccctctct attcacttat tccttgtgca tgttatcaat    53340
attttgaaac ataatgtcat gtcctttgat cagttgaagg ctgacattga aaaggcttat    53400
ggggattggg tgttgtggct cacgcctgta aatcccaatg ctttgggagg cagagtcggg    53460
aggatcactt gaacccagga gtttgagacc agcctgggca acaaagtgag atcccatccc    53520
tacaaaaatt taaaaaacta gacatgtgcc attacacttc agcctgggtg acagagtgag    53580
actccatctc aaaaaactaa actaaactaa acaggcatgg tggcacacac ctatagttct    53640
agctactcag gaagctgagg taggaggatc actcatgtcc aggagttgga ggaggcagtg    53700
agctatgatc atgccattgc actgcactag gccacagagt gggaccctgt ctcaaaaaaa    53760 aaaaagaaa gaaagaaaag aaagggctca tgtagttcaa gcccttctct tcatgcaagg    53820
ggatgctaag gcccatgatg gtgaagggcc tggcaaagct tgcacagata gtgtgtgaca    53880
gagctggctc aaacccatct ttgggagctg tctaatctct ttttctgagt ctttatgttc    53940
atagacaagt taggatgagt aaagtaagtg ctaaattcca tatttcgtgt tctgcatatc    54000
tgggctcaga tgcttgtcat tttccagtga taactccatc aatgcctcct agtggtataa    54060
```

```
atttaatac ttcttgtgtg cccagcccc tcttagaaat ttgagatttt aggaagggac      54120
tagtaataaa aggtaaaata aattatttc tggccaggca tggtggctca cacctgtaat      54180
gccagtactt cgggaggtcg aggcagatgg atcacctgag gtcaggagtt caagaccagc    54240
ctggccaaca aggcaaaatc ccatctctac taaaaatgca aaaattatcc gggagtggtg    54300
gtgggtgcct gtaatcccag ctacttggga ggctgaggca ggagaatcac ttgaacttgg    54360
gaggcggagg ttgcagtgag ctgagactgt gccactgcac tccagcctgg caacagagt     54420 aagactctat ctcaaaaaaa aaaaaaaaa aaaaaggcc aggcgcagtg gcttacacct      54480
gtaatctctc aggaggctca ggcaggagaa tcacttgaac ccgggaaatg gaggttgcag    54540
tgagccgaga ttgcaccact gcactccagc tcaaaaaata aataaataaa taaattattt    54600
tcttttttta tttatttttt cagcatccac ccaacatggt gaaaaattcc tcttttctta    54660
atgtcactga actgtaaact taagatgaaa aattgtaaat tcatgctat atatatttca     54720 ccacaataaa aaaattcctt gttcttattg tagtggtctc catgtcttca gtatttcctt    54780 cccttctcc atctcacctg tatacattca ctttggtaat tagcatcttt cttaatttat     54840
tggcaggata acgtcattag cagaatctca acttcagacc cgtcaacaaa ttaagaaact    54900
ggaggagttg cagcaaaaag tttcctacaa aggggacccc attgtacagc accggccgat    54960
gctggaggag agaatcgtgg agctgtttag aaacttaatg aaaaggtaat ttagcatcct    55020 tgtcccttc cctcatctaa aaaataccta aagactcacg tggtagagtg agaggcgggc     55080
tgacttctgg tcatggccgt ggcgcgtgag cccatcttct ctttcctcag tgcctttgtg    55140
gtggagcggc agccctgcat gcccatgcat cctgaccggc ccctcgtcat caagaccggc    55200
gtccagttca ctactaaagt caggtaggcc atgccacttc catttccagt agagatttta    55260
ctgagggaca ctgttagggt gagggtagag ttggtggcca gggtcattct ttccaggtgt    55320
ggtgtcacag gcagtacact gttgcggggt tgaaatttgt tgccatacta tctgcttgct    55380
ctctgattct gatgtcaaaa gcaaagagc agtcatcttt ttgaaggtac ctgggcatat    55440
tcctatgatt gtagacctgg agtctcaggc cacagcttct ccttctgccc aagggacaaa    55500
ataatgtcat ctattttctg ttctttgagg ctactcttcc ctgtggattt taagggaaag    55560
agtaaggctt agtgatgggg aagctgagag gccccagggc aggtgggtgg tgggcctgta    55620
gggtgaggtg ttactttcac actcaagtca gaacaggtgt gctggggttt tgaccttctg    55680
cagcaaaatt tccctcctca gaaacttagt atggtgttcg gtttcaggat taatagaaca    55740
aaatgccagc tgcacagcat gtgttcctgt aatattttc attatatggc tttgattatc    55800
cttttgtgaa tctctcacaa ctttaagttg ttagttctta gatgttttct cagtacctt     55860 ggcttgaagg agtgatactc atctttgtt tttgtttgag acagggtctc actctcaccc     55920
aggctggtgt gcagtggcat gatctcagct cactgcaacc tccatctccc aggttcaagt    55980
gattcttgtg cctcagcctc ctgagtaact gggaatagag gtgcgtgcca ccacccgg     56040 ctaattttt tttttttgag acagagtctc gctcttcgg ccaggccaga gtgcgtgttg     56100
caatctcaac tcactgcaac ctccacctcc caggttcaag cgattctcct gccttagcct    56160
ccctgagtag ctggaccggc acactccacc atgcccggct aattttgta tttttagtag    56220 agacagggtt tctccatgtt ggccaggctg gtctcaaaac tcctgacctc agtaatccac    56280 ccacccggc ctccaaaagt gctgggatta cagatgtgag ccaccacgct cggccttttt    56340 tttttttt tttttttga gatggagtct ttctctatca cccaggctag agtgctgagg    56400
```

```
tgtgatctcg gatcactgca gcctctgcct cctgggttca agtgattctc ctgcctcagc    56460
ctcccaagta gctgggatta caggtacctg ccaccatgcc cggctgattt ttgtattttt    56520
agtagagacg gggtttcacc atcttggcca ggctggtctc gaactcctga ccttgtgatc    56580
cacctgcctt ggcctcccaa agtgctggga ttacaggtgt gagtcaccgc acccagccct    56640
attttaattt ttttaaagag agagataggg gccaggcacg gtggctctcg cctgtaatcc    56700
cagcactttg ggaggccaag gtgggtggat cacctgaggt cgggagttcg agaccatcct    56760
gaccaacatg gagaaactct gtctctacta aaaatacaaa attagctgag cgtggtggcg    56820
cgcgcctgta atcccagcta cttgagaggc tgaggcagga aatcacttg aacccaggag    56880 gcggaggttg cggtgaacgg agattgcgcc attgcactcc agcctgggta acgagagaaa    56940
ctgtctcaaa aaaaaaaaa gagaaagaga gataggatct cgctctgtca tctaggctag    57000
agtgcagtgg catgatcata gatcactgta gccttgaact cctgggcaca agtgatcctc    57060
ttgcctcagc ctcccgagta actgcgacta caggtacatg ctaccacacc ccgctaattt    57120 ttaaatttt tatagatgtg ggctctcact ttgttgccca gactgttatg gaactcctgg    57180
gctcaaggga tcctcccagc ttggcctccc acagtgctga gattatagat gtgagcctgt    57240
aattatagac agcttggcct atttacctgt tggaaatgaa gaattatgaa ttttacattt    57300
cttcaagaaa aggttatggg agagttactg actttttttc cttggatttt ttcttttttaa    57360 ataggttgct ggtcaaattc cctgagttga attatcagct taaaattaaa gtgtgcattg    57420
acaagtaagt actcctatct tagctctgtt tttcaaatga ggaatagaaa aatgagaact    57480
ttgacagaca tcatttgaac tagagactct gtctttattc agagatcttc attttgtgga    57540
caaaagtttt caaaagcctt ggggtgcatt gtcatttacg tgtctgaaca aagccacaaa    57600
gctgggggta cagatttgat ttgtggttgc tattgtgaca accagtccct ctttccttg    57660 tttagttttt tacttgtaca tgtcattcat gcatattata tataagactg agatcatgtg    57720
ttaattaacg actgggatac gttctgcaaa atgtatcatt aggcaatttt gttgtgcaaa    57780
tgttgtagag tatatagtcc ttacacaaac ctgggtggca gaacctactg cacacctacg    57840
ctatgtggca gagcctactg gtcgtaggct gtaaacctgt acagtatgtt actgtgctga    57900
ataccgtagg caattgtaac acatctcaat gaagtaggaa tttttcagct ccatgataat    57960
cttatgggac caccatcata tatgcatttt gttgttgacc gaaacgtcgt tatatattct    58020
ttccatacat agcatgtgga aagaatagat ctctttttt taattgttcc acactttacc    58080
atataatgga atacgcaaaa tttcacaata cctttcagga tgtaaaatac atatacccctt    58140 tgacgacatt agaaaagaga aaatgtgggc cgggcgcggt ggctcatgcc tgtaatccca    58200
gcactttggg aggccgaggc gggcggatca cgaggtcagg agatcgagac catcctgggt    58260
aacacggtga aacccgtctc tactaaaaa tacaaaaaaa ctagctgggc gtggtggcgg    58320
gcacctgtag tcccagctac tcaggaggct gaggcaggag aatggcatga acctgggagg    58380
tggagtttgc agtgagccaa gatcacacca ctgcactcca gcctgggcga cagagactcc    58440
atctcaaaaa aaaaaaaaa gaaagaaaa gagaaatgt ggctgggcgc ggtggctcac    58500
gcctgtaatc tcagcacttt gggaggctga ggtgggcaga tcacctgagg tcgagagttc    58560
gaaaccagcc cgaccaacat ggagaaacct tgtctctact aaaaatacaa aattagccag    58620
gtgtgttggc gcatgcccgt aatcccagct acacgggagg ctgaggcagg agaatcactt    58680
gaactcagga ggtggaggtt gtggtgagcc gagatcacac cattgcactc cagcctgggc    58740
aacaagagcg aaactatctc aaaaaaaaaa aagaaaaaa gaaagataa aatgcattct    58800
```

```
tattttttagt tgatgtaatt atgtggaaat ttcatgagga tgcactggaa aataatgaaa    58860
taagggagtt gacgaaggtg gtaggtttaa taagtacata tgcaatatga aacataggtt    58920 cccccttccta tggggaggca accaactgtg cctgctacgc agaggtgtta tgttgcgctg    58980
atcaactgta actgaatagt ttaaagaaat gcccaggagc acagaggttt tttcatgaca    59040
gtaaataaca ggtggtcaaa gtaggctttt tgaagaaaca cagagcctat tttattaaca    59100
acagtctgtg ttcttacaga gactctgggg acgttgcagc tctcagaggg taagttcagc    59160
ctagaggctt cctttgttc cgtttaacct aacttcatcc tccggctact tggtcaccta    59220
catagttgat tgttcccctg tgattcagat cccggaaatt taacattctg ggcacaaaca    59280
caaaagtgat gaacatggaa gaatccaaca acggcagcct ctctgcagaa ttcaaacact    59340
tggtatgtgg gaggagctcc ccttcacaaa gggcctctgg ctgccggaga gggctaggga    59400
gagcctcaca ggacacctgc cttttctttt tcttacagac cctgaggag cagagatgtg    59460 ggaatggggg ccgagccaat tgtgatgtaa gttttgttgg ggatgaaaga caactggggt    59520
gttttccttg agggagagag gggtaaagat ccttcttaat ccccagaatt agaaacatca    59580
acctgttctt tcagctgtag ttattccaaa aagtcacttc aggccaaagt gacatgaaca    59640
gaagttccat gtgccatgga gctctctggc ttggaacatt tccgtgaata tctgggagtt    59700
ggctcctcct taaggagaag tggaaagtcc cttgctgagt tgttctccac acccatgtgg    59760
tataaagcag ctttccacct tgcctggggc tttccaaatt ccccatccag ctcctgcggc    59820
tgaccctgct tggctccatt tttagtgccc tgttttctc tcccactgag gtgggataga    59880
gggtgtaaaa gcaacagatt tgagttaaac tttaaaataa atgaccaccct tgcattagct    59940 tgcttaggaa aagagtacat aaaataaaat gaacaaaaca aaacccatct tgttctttat    60000
cccccttatt ttctgctttt cattgattca gattattgga ttcttattgt caagaataaa    60060
ctttaaacaa acaaacaaaa aaaggtaaat gtgacggaag gctagttttc agtcattttt    60120 aaaattgtg atgccccgtt cttttttta catttgtccc ctgaacaatt cttcctcttt    60180
aaaatgtagc agtcctagct gggcgtgctg gctcacaccc cgtactttgg gatgccaagg    60240
caggctggtc acttgaggtc aggagttcaa gaccagcctg gccaacatgg tgaaagcccg    60300
tctctactaa agatacaaaa attagctggg tgtggtggtg cacgcctgta gtcccagtta    60360
ctggggaggc tgaggcatga gaatcgcttg aacctgagag gtggagcttg cagtgagcca    60420
agattttgcc actgcactct agcctgggca acagagtgaa actctgtctc aaaaaaataa    60480
ataaaataaa atgtagcagt cctttttaaa aatgtggaat tttacttgac agtagagtga    60540
agtagcctgt atgcaatgat atgggaaaat gtacatgaca tattaagaaa aagcaaaatg    60600
taaaataatt tgaatagtat tattagtata tgtgttttaa aaatacacta tactcttatg    60660
tgtattcata tgtatattaa gaaattctgg aggaatatac cagcagtgct atgtgtatta    60720
gtgctgctgt tggtatccat ggctattcta gactgtctct gtgatatttg cattttaaac    60780
tgaatatatt acttttataa tcagaaaaat agtattaaaa atgaattata atttaatttc    60840
ttttttcttt tttttttttg agtcggagtc tcgttctatc ggattgcagt ggtgcgatct    60900
cagctcactg caacctctgc ctcctaggtt caagcgattc tcctgtctca gcctcccaag    60960
tagctgggac gataggtgca tgccaccacg cctggctaat ttttgcattt ttagtagaga    61020
cagggtttca ccatattggt caggctggtc ttgaactcct gacctcgtga tccacccatc    61080
tcggcctccg aaagtgctgg gattacaggc atgagccgct gtgcccagac tagaattcaa    61140
```

-continued

```
tttttgagaa ttcattgaca actcttactt aaaataaggt tgctgtactg atgtgagaca    61200
ttgttgtagt cagtttggaa aacaatttgg cagtataaaa atgaacatac ctgtaaacca    61260
acggtgccat tcccaggatt taatagcaga gaaatctttg catatatgtc ccaggagaca    61320
tatataaagt ggacatcagc ctgattataa gctctaaatg caacccaaat aaatacccat    61380
caacattaga atgaatacat tatttgtggt atagacacaa tggaatactc cgcagctgtg    61440
aaaaggaata cactgcagat acacataacc atgtggattc atttcacatc aagtgaaaag    61500
tgaatcccaa aagaattcat tggagtccat aagtgtaagg ttcacaaatg tcccaaacta    61560
aacaatacct gcattgctta gataaacaaa tatggtaaaa ctgtaaaaaa acaaaacaaa    61620
acaagacaaa aagggctagg aaatgataaa cccaaaagac aaaatagcag ttatttctga    61680
gggaggaggg aagggggatgg ggttggggaa gggcacccag agaattttag gagtgatgga    61740
cttttcctta aattgaatgg tgggttcata ttgttttgtt attctttgtg ccttacgtat    61800
tttacaaata accaattgga tctatgtaat attataatac aaactgagta aaggattagg    61860
ttgaggatca cagcattgga agttcttggt gttgaagaga gtaagtgccg agcaagttgt    61920
gtccctggca gtttgtttgt gaccacctgg tggcttaccc ttcttggtgt ggtgaggctt    61980
ggcatgtcac tttccttggc tgtggctgtt agtactgaat gccattctct ctgaggaaaa    62040
gtgtccttct ctttttttatt gattgactga ttgattgaga cagagtctca ctctgtcacc    62100
caggctggag tgcagtggcg tgatctcggc tcactgcatc ctctgcctcc tgggttcaag    62160
cgattctcct gcctcagcct cctgagtagc tgggactaca ggcgcccact accacaccca    62220
gctaattttt gtattcttag tagaaacggg gtttcaccaa attattggcc aggctggtct    62280
cgaactcctg accatgtgat ccacctgcct cggcctccca aaatgctggg attgtaggtg    62340
tgagccatca cgctcagcct ttttttttat ttaatttaat ttttttttaa gacagggtct    62400
cactctgtca ccccagctag agtgcagtgg cacaatcata gctcgctgca gcctccatct    62460
cctaggctca agccatcctc ccacctcagc ctctcgagta gctggggcta taggtgtgca    62520
ccaccacacc cagctaattt ttgtatttttt tgcagagatg gagttttgct gtgctgctta    62580
gactggtctc gaactcctgg gctcaggcaa tcctcctgcc ttggcctccc aaagtgctgg    62640
gattacaggc atgagccacc acacctggcc taagagtgtc cttctcgtta ctgtaggctt    62700
ccctgattgt gactgaggag ctgcacctga tcacctttga daccgaggtg tatcaccaag    62760
gcctcaagat tgacctagag gtaagttctg cagcagaatc ggtgagaggc tacgtacagg    62820
ggtgactcag gacaaaaact tccactggga tttttacaag agaaggtgga atgattactg    62880
tttgcttaac actgtgttta ttttttgctta cttttctcca aaaaaatcct tggcatccca    62940
tctggcaata aagtcttgct tgaatgctta aagatgtgt gtatattcag ctttcagcaa    63000
acttgatatg aaaatctcta tttagaaatt gattggccgg gcgcggtggc tcacgcctgt    63060
aatcccagca ctttgggagg ctgaggcggg tggatcacga ggtcaggagt tcgagaccag    63120
cctggccaac atgacgaaac cccgtctcta ctaaaataca aaaattagct gggtatggtg    63180
gcggacgcct ataatcccag ctactcggga ggctgaggca ggagaatcac ttgaacctgg    63240
gaggcagagg ttgcagtgag ctgagattgt gccattgcac tccagcctgg gtgacagagt    63300
gagactccgt ctcaaaaaaa aaaaaagaa attagaactg actttataaa gtttgggcat    63360
aagagtctta gcagccagtg tgtttagtat acagaaaatt gtggcaatga cattctcctt    63420
tcccaacttt cttgattttt aaattaagat atacctagaa aagcaggaat cctggtctttt   63480 gattcctgag acctccctgt ttcatgtgaa gatacagctt caagtcttgg agaatgcctc    63540
```

```
caaggtctta aaaatgggga atctgtggat tgtgagtcaa gctttgagca agtcaggttt    63600
tacaagggac cggtatattc cgactgcagc ctgagttgtg tggccacgct gggcattctt    63660
tccactatga gtgctcactg agctgactca ctcacactcc tcgcctagag ttggcagcag    63720
gtgtggttta tggcatgtcc tttcattctg agccccgtga gatgcgggtg aagagatttc    63780
caaggctgtg agagcccctc tgcctcccca gctcagtccc cactccctcc gcagacccac    63840
tccttgccag ttgtggtgat ctccaacatc tgtcagatgc caaatgcctg ggcgtccatc    63900
ctgtggtaca acatgctgac caacaatccc aaggttagtg cccctccctt ttagttggtg    63960
ccccgggatc tcttgcgact taggggtacc tagtatagac aatgagcacc atccctcatc    64020
taaacaagca aatgtgttct ttccaataga atgtaaactt ttttaccaag cccccaattg    64080
gaacctggga tcaagtggcc gaggtcctga gctggcagtt ctcctccacc accaagcgag    64140
gactgagcat cgagcagctg actacactgg cagagaaact cttgggtccg catttcaccc    64200
cttctccctc ccgcccaccc gcccagaaaa gggatccggc ccatagggct gttcatttgg    64260
gccatgtcta ctgagcatta ggccatgttt cttttcctgag caaggcgctg tgctggtgcc    64320
aggaaacagg ggagttgggg agttggggtg cagagacagt ttgcagtttt cagtcgaggt    64380
gatcattttt gaggtgggag gtagatttct tttctcctgg ttgctgtctc attcacccac    64440
tctatctaac tttagaagat cttttaagtg tgtgttggaa ggtggcacta aaggcttgac    64500
attccctgtc cattttttta ataaactata ggctagttgg ttttttttgt cttattttat    64560
ttatttattt attttttttga gacgagtctt gctctgttgc ccaggctgga gtgcagtagt    64620
gtgatctcgg ctcactgcaa cctccgcctt ctgggttcaa gcgattcttc tgcctcggcc    64680
tcccgagtag ctgagactac aggtgctcac caccacgccc agctaatttt tgtattttta    64740
gtagagacgg ggttttacca tgttggccag gatagtctcc gtctcttcac ctcgtgatcc    64800
gcccacctcg gcctcctaaa gtgctgggat tacaggcttg agccactgtg cccagcgtag    64860
gctagttttt aaaaaagaat tagtggaata ttttatgtgc cacctgggct agaagtagct    64920
ttgttctaat aaagctgttg ccaccaaata cacctgtctg acacccgatg tcagcttgtt    64980
agtgagtgct gctgttggtt cccagcctac cacccgaggt tgggaagagc aggggacttt    65040
gttatatcac cctccatccc tgctgggcta cccagcaaca caagtgagtc aaatgatggg    65100
atagtgtttg tcctcatgtg cacacacaca acagtgccta ccttcaaaga tgtgaaagct    65160
gattattttg tggcccattg tgggatgaat gtgtgtgtgt tctgttttaa gaaataaacct    65220
cttgacccca agctgaaaat gtactacttg actcttttc tttccttcag gacctggtgt    65280
gaattattca gggtgtcaga tcacatgggc taaattttgc aaagtaagca atcttgttaa    65340
attctcgtgg gaatgggaat gctcacctgc acggctgtcg ttgagggctc tggcttgaag    65400
gccctgaact cttggtccag cggccagtag gacctgcctg aagtagacg ggcctgagga    65460
tttgggtgat gcactgcacc cctaggaagg gaagggctgg gatggcagta gacttggctt    65520
tcccattact cttttctcca ggaaaacatg gctggcaagg gcttctcctt ctgggtctgg    65580
ctggacaata tcattgacct tgtgaaaaag tacatcctgg cccttttggaa cgaagggtag    65640
gttggacaga gtgtgcacag atgtaaccaa gtccctgct ctcagcaagc cagtggcagg    65700
ggatggatgc cctgttagca ataacaacat tgttcctcct ccttggctcc aggtacatca    65760
tgggctttat cagtaaggag cgggagcggg ccatcttgag cactaagcct ccaggcacct    65820
tcctgctaag attcagtgaa agcagcaaag aaggaggcgt cactttcact tgggtggaga    65880
```

-continued

```
aggacatcag cggtaaggga ggctcccacc caccccacct gctggtggct gctgaggcct    65940
catcactgct tctagttgca agcacctact gcccctggt gggtggagat ggccttgact    66000
ccctgtttca ctcagactcg caaaacacat ttgcgtgact tctaaatcct tccagctgaa    66060
ggattggttt gctttgtttt gcttgctcca gtgactattt gttgagaatt ttgcaattta    66120
aattgtattc ttcatctctt tttctactta accctgttaa tatatcttac gcaagtagtt    66180
atattcaagt ttattttcta tgacccaact agtagcctct tcttaattag aagccagcct    66240
gaatatttcc acagtgccag gccactgaac agggtgttca gggtctcaac actagggtgg    66300
cttaagtctt ttccccttcg aggaaagaaa aaatgggcag ttttctctga gatgacctag    66360
ctgtaggttc catgatcttt ccttcccatg tcctgtgaca ggtaagaccc agatccagtc    66420
cgtggaacca tacacaaagc agcagctgaa caacatgtca tttgctgaaa tcatcatggg    66480
ctataagatc atggatgcta ccaatatcct ggtgtctcca ctggtctatc tctatcctga    66540
cattcccaag gaggaggcat tcggaaagta ttgtcggcca gagagccagg agcatcctga    66600
agctgaccca ggtagttgtt gattttccat gttcctggca tttaattttt gggaaaagtt    66660
ggaaattttg ggatccttgg aggatagata ggcaaatgcc tgaataacct gggggataat    66720
tatttctcct tatgggaaag aattgtagtg agtgcttttg ttggggtgac cgatgggatt    66780
tgagaggaga atcagaatca cttagagtag tgtagttcct gctccacaga gagtgcatga    66840
gtctaaagag gggatacagc ctgggcaata tggtgaaacc tcgtctctac aaaaaatcca    66900
aaaaaattac ccggtgtggt ggcacgcatt tgtagtcgta gctacttggg aggctgaggt    66960
gggaggatca cctgagccaa ggagttcaag gctgtagtga gcggtgatca tgccaccgca    67020
ctccagcctg gctgatagag tgagatactg tgtcaaaaaa taaaaataaa gagggggatca    67080
atacacatac gtcccccaaa acatgcctga aacacgagaa gggaaagtga gggcagttaa    67140
caggatgccc tgctggcaca gtgcttctta gtagatgcta gaaggtttga ggcccagatt    67200
tcagcccagc atatggcttt ttgcctgtaa ctgaaccatg tcagtgtgcc agatggtctg    67260
aagaaagggt ttctggagga aattattatt agctgcatgg gagtatggtt tacactagag    67320
tagaagagct gggagcatca cgtttgaagg ggaagacagt gactgggtgg aggggcaagg    67380
gattagtatt tagagtgtgc aactattgaa aataaggtat attttaatgt gtaagaggac    67440
atgtacttat atgttatata taaattattt tagctgggtg aagtggctca tgcctatagt    67500
cctagcactt tgggaggccc aggcgggagg atcacttgag cctgggagtt tgagaacagc    67560
ctagacaaca tagtgagacc ctatctatac aaaaataatt tttttaaat tagccacgtg    67620
tggtggtttg tgcctgtagt cctagctact cgggaggctg aggtgggagg attgcttaag    67680
cccaggaggt tgaggctgca gtgagccatg atcgcaccac tgcactccag cctgggtgac    67740
agagcaagac cttgactcac caaaaaaaaa aaaaaaaaa agagagagaa attaaaaata    67800
ctgtaatctc agctgggcat ggggggttcac acctgcagtc ctagcacttt gggaggctga    67860
agcaggagga tcacttgagg ccaggaactc aagaccagcc tggcaacata gcaagacccc    67920
actacacaca cacacacaca cacacacaaa gaagagaaag aaaaaaacga aacaaaactg    67980
taatctctgc agctgtcctc agtgtggagg gggtagccct gtctgttccc cttcagcact    68040
tgctgttttg actctctggg ttctttgtgc aggtcttgat ggggagtctc tggtttgcca    68100
ttctttgttt gatttaactt tctgtaatca taaagccaat gatgggcttt tttttttttt    68160
tttttttag actaagtctt gctctatcac ccaagctgga gtgcagtggc accatctcgg    68220
ctcactgcaa cctccaccctc ccggttcaag caattctcct gcctcagcct cccgagtagc    68280
```

```
tgggattatg ggcttgtgcc accatgccca gctgattttt gtattttttg tagagaaagg    68340
gtttcgccat gttggccagg ctggcctcga actcctgacc tcaggtgatc tgcccacttc    68400
agcctcccaa agtgctggga ttacaggcgt gagccactgt gcctggccta atgatgggct    68460
ctttaatgtg atcctttagg gttggcgcct tgccctagtt gctgttgaaa aactattttt    68520
tgtccaaata gcacacacac agaaacctac caacttccct cccactttt cctaggaatt    68580 ccttctgagg gatttcttga gatggggcag aatgggcttg gaagaggga gttggagcta    68640 attgaccgtt gcctttctcc tttgttgggg tcctgagtct tgttcctgct gtaagagtta    68700
ctcacttcct gtctgccacc tatctccctt tgcatgtgtg cttcagttgg gagatctgtt    68760
tatcagcccc tgccacacgg ctctttgttc cttctgcaga ggacgttggg gtcccacggc    68820
tggtcctttt gactcatttt gctttcaagg tcccacctcc cagtctgagg ctgcatcctc    68880
cattaccatc gccttcctg tgggctggga ggccaggtcc tttcctgccc agcgatgtca    68940
gcgtttcctc aggggccagg cactcatcag gagaaaggaa ctaattactt gagtaatttg    69000
ccttgccttg ctgagaggag tgtgccctga gggactccat gtgagtgtgg tgacgggtgt    69060
gggggtgtcc ctgtgttatt taaaatggg tgccttcagg acgatgagca tgtgaccatt    69120
tcctctctat ttccatcaca agagtattat ggtatgaggg tctcaggtta gattatcctc    69180
ccaagactct tctctcttcc ttctctactg gaagcccaca tagcatttcc ttatggcttg    69240
agggagaggt tcggagccac ttacaaatta gataaagtac atttacaatc ttgtacaaag    69300
ccacacaatg aagtcatttt tctcagcttt ttttttttt tttttttttt ttttgagcct    69360
gagtctcgct ctatcgtcca gactggagtg cagtggcgcg atcttgcttc actgaaacct    69420
ctgcctccca ggttcaagag attctcatac ctcagcctcc tgagtagctg ggattacaga    69480
catgcaccac tatgcctggc taattttttgg attttttagta gagaccgggt ttcaccctgt    69540
tggccaggct ggtctcgaac ccctgacctc aagtgatctt cccgcctggg cctcccaaag    69600
tgctgggatt ataggtgtga gccacagtgc ccagccttgt ttttgttttt gttttgtttt    69660
gacagtctgt cactctgtca cccaggctgg agtgcagtgg tgcgatctca cctcacttca    69720
gcctctgcct cccaggttca agtgattctc ctgtctcagc ctcctgagta gctgggatta    69780
caggcgtgcc accacgccca gctatttttg taatttcatt aaagacaggg ttccccatg    69840 ttggtgaggc tggtcttgaa ctcctggcct caagtgatcc acctgcttca gcctcccaaa    69900
gtgcagggat tacaggcatg agccactgtg cctggcctca gctatcttga atgctggaga    69960
attaaatcct tttctgtcta gggtgtcagc tccctaaggg ctgggccaaa acagttggat    70020
ttataagaca ctagagtctt gcctcagtag ctccctttgaa ttctgcactg aattgatcag    70080
tttcttggcc caaagtaaac tcagatggca gcccaagagc cactctgcag tgccttcttt    70140
cacatggtca tcatgctctc tgatccctca ggttctgtct aagcctcatg ttttatgacc    70200
gtgctgttct cagcccacct caccctgccc catgccttct caatggtttg ttcacctgaa    70260
ttccccagat tcatgccag tatccccaag gttccttgac ctcttggtgt aagcattcag    70320
catctaaaat tcatttttatt cccgtcaacg catttctaac tgtagaacaa gaattataaa    70380
tgacaaagct catagaaaat tggcaccttg tcttcccct ccctcttatt ttatacataa    70440
aagagaatat gggctgggca ttgtggccaa ggctgggcat gatagctcat acttgtaatc    70500
cagcactttg ggagggtgag gcagatggat cacctgaggt caggagttca agaccagcct    70560
ggccaacatg gtgaaacctc atctctacta aaattacaaa aaaaaaatta gctaggcatg    70620
```

```
gtggcagatg cctgtaatcc agctactcag gaggctgatg aaggagaatc acttgaaccc   70680
tggaggcaga ggttgtagag agccaagatg gcgctactgc actccaacct gggcgaaaga   70740
gagcaagact ccgtctcaaa aaaaaaaaag acaaaaatta gccaggcatg gtggtgccac   70800
ctgtagtccc agctgcttgg gagcctaagg caggagaatc gttttgacct gggagtagga   70860
ggttgcggta accgagattg tgccactgca cttgagcctg gcaacagag tgagactctg    70920 tctcaaaaca ataagaacaa cagcaacaaa agagagagac catgccttgc tccaggtctc   70980
ttagctattg aagatgtacc tggacccagg tctccggtct tctagttgaa gcaattgtac   71040
tgccttacaa agtcacattc tctttggtgc tttttgattg acgtatttat ccaactagaa   71100
agttactcat gccctcatcc aaaaatgtgg tagaggccag attagtgctg gtaggaataa   71160
gagatataac ctttggcttt ggaaccacaa gcattagcag tctccatgtt ctttaaagac   71220
ttggtgatat tggtatttag gctggacacc atgcaaagac tacacaggct cggttcctgc   71280
atgcagagaa gttatctaag agatatgacc aggccggaat agaatgctca gaccacgtgg   71340
aggctgttaa acttttacat aatctaggga agaagggac acaaggtggc attagtctag    71400
ggtcaggtgg gaaaaggtta tgctgaaaag tctctgcagc tcaggacagc tttgtgcaaa   71460
gaactgaagt tcacagctgc tagtgcctgg gagatcaaat agtataaatg agggcagaca   71520
accctgaggg gcagatggag cttttccagac aatcttggca tgaggatgag tgagtttcaa   71580
atcagtcctg ccgaggcaga tggcttcctc cagctctgct tactgaatgc gaagtcacag   71640
tcagtaagaa aactggtttt cttcttccca ggcgctgccc catacctgaa gaccaagttt   71700
atctgtgtga caccgtaagt ggcttccttt ccccgttttg ccttcatttc taatatcctc   71760
agttatccct gggaatggga cactgggtga gagttaatct gccaaaggtt ggaagcccct   71820
gggctatgtt tagtactcaa agtgaccttg tgtgtttaaa aagcttgagc ttttatttt    71880 ctgttggaga ccagagtttg atggcttgtg tgtgtgtgtt ttgttcttt tttttttttcc    71940 attgtgtctt gtcaaccccc cgtttcccct cctgctgccc cccatttcct acagaacgac   72000
ctgcagcaat accattgacc tgccgatgtc cccccgcact ttagattcat tgatgcagtt   72060
tggaaataat ggtgaaggtg ctgaaccctc agcaggaggg cagtttggtg agtatttggt   72120
tgacagactt tgtccctata agggaagttg gtcccctttg tgtgatgctc tcacatgtac   72180
acaccgagag ctggtcactc ggaatggtag gagattctag agctttgctt tccaaaagag   72240
atggtatgaa tgccacatgt gtgagtataa atcttctagc agccacactg gaaatagacg   72300
aacttaattt ttacaatata ttttatttaa cccactaaat ccaacatact ctcaatttaa   72360
catttcagaa aaagttgagg ctgggtgagt ggctcatgcc tgtaatccca gcactttggg   72420
aggccgaggt gggtggatca cttgaggtca ggagttcgag accagtctga ccaaaatctc   72480
taaaatataa aaattagctg ggcatggtgg cgcatacctg taatcccagc tactcaagaa   72540
gctgaggtgg gaggatcgct tgagcctggg aggtggaggt tgcagtgagc agagatcgtg   72600
ccactgcact ccagcctggg cgacagagtg agactccatc tcaaataaac aaaactaaac   72660 taaaagaaa aagttgagac cttttttat tcttttttt catactaagc ctttaaaatc       72720
cagtgggctt ttgacagcca cagcacagct cagtttggac aaaccaaatc tcaaatgctt   72780
ggtggccacg tgtgtctcgg ggctcctgaa ttaaacagta gatcaaggc agaagatctc     72840 aggacagcct tagagcttct gtaaacatgg agctctggga atcagttaag gtgggaatga   72900
gaaaggaccc ttcccgaggc aggtcctcc agggaggagg gtaaatctgg cttttctgac    72960
catccctggg ccttaagggg caggagattg gatagcagtg gtagcctggg ccctgtcctc   73020
```

-continued

```
tgaagggctg ggggcgtggc ctgccagttg cagagggtgg acaactgaac tagttttccc      73080
tgtctgtccc tccagagtcc ctcacctttg acatggagtt gacctcggag tgcgctacct      73140
cccccatgtg aggagctgag aacggaagct gcagaaagat acgactgagg cgcctacctg      73200
cattctgcca cccctcacac agccaaaccc cagatcatct gaaactacta actttgtggt      73260
tccagatttt ttttaatctc ctacttctgc tatctttgag caatctgggc acttttaaaa      73320
atagagaaat gagtgaatgt gggtgatctg cttttatcta aatgcaaata aggatgtgtt      73380
ctctgagacc catgatcagg ggatgtggcg ggggtggct agaggagaa aaaggaaatg       73440 tcttgtgttg ttttgttccc ctgccctcct ttctcagcag cttttttgtta ttgttgttgt     73500 tgttcttaga caagtgcctc ctggtgcctg cggcatcctt ctgcctgttt ctgtaagcaa      73560
atgccacagg ccacctatag ctacatactc ctggcattgc acttttttaac cttgctgaca     73620 tccaaataga agataggact atctaagccc taggtttctt tttaaattaa gaataataa       73680 caattaaagg gcaaaaaaca ctgtatcagc atagcctttc tgtatttaag aaacttaagc     73740
agccgggcat ggtggctcac gcctgtaatc ccagcacttt gggaggccga ggcggatcat     73800
aaggtcagga gatcaagacc atcctggcta acacggtgaa accccgtctc tactaaaagt    73860
acaaaaaatt agctgggtgt ggtggtgggc gcctgtagtc ccagctactc gggaggctga    73920
ggcaggagaa tcgcttgaac ctgagaggcg gaggttgcag tgagccaaaa ttgcaccact    73980
gcacactgca ctccatcctg ggcgacagtc tgagactctg tctcaaaaaa aaaaaaaaa     74040 aaaagaaact tcagttaaca gcctccttgg tgctttaagc attcagcttc cttcaggctg    74100
gtaatttata taatccctga aacgggcttc aggtcaaacc cttaagacat ctgaagctgc    74160
aacctggcct ttggtgttga aataggaagg tttaaggaga atctaagcat tttagacttt    74220
tttttataaa tagacttatt ttcctttgta atgtattggc cttttagtga gtaaggctgg    74280
gcagagggtg cttacaacct tgactcccct tctccctgga cttgatctgc tgtttcagag    74340
gctaggttgt ttctgtgggt gccttatcag ggctgggata cttctgattc tggcttcctt    74400
cctgccccac cctcccgacc ccag                                            74424
```

<210> SEQ ID NO 154
<211> LENGTH: 3455
<212> TYPE: DNA
<213> ORGANISM: H. sapiens
<220> FEATURE:
<221> NAME/KEY: CDS
<222> LOCATION: (241)...(2553)

<400> SEQUENCE: 154

```
ggtttccgga gctgcggcgg cgcagactgg gagggggagc cggggggttcc gacgtcgcag      60 ccgagggaac aagccccaac cggatcctgg acaggcaccc cggcttggcg ctgtctctcc     120
ccctcggctc ggagaggccc ttcggcctga gggagcctcg ccgccgtcc ccggcacacg       180 cgcagccccg gcctctcggc ctctgccgga gaacagttg gaccctga ttttagcagg         240 atg gcc caa tgg aat cag cta cag cag ctt gac aca cgg tac ctg gag         288
Met Ala Gln Trp Asn Gln Leu Gln Gln Leu Asp Thr Arg Tyr Leu Glu
  1               5                  10                  15 cag ctc cat cag ctc tac agt gac agc ttc cca atg gag ctg cgg cag         336
Gln Leu His Gln Leu Tyr Ser Asp Ser Phe Pro Met Glu Leu Arg Gln
             20                  25                  30 ttt ctg gcc cct tgg att gag agt caa gat tgg gca tat gcg gcc agc         384
Phe Leu Ala Pro Trp Ile Glu Ser Gln Asp Trp Ala Tyr Ala Ala Ser
         35                  40                  45
```

```
aaa gaa tca cat gcc act ttg gtg ttt cat aat ctc ctg gga gag att    432
Lys Glu Ser His Ala Thr Leu Val Phe His Asn Leu Leu Gly Glu Ile
 50                  55                  60 gac cag cag tat agc cgc ttc ctg caa gag tcg aat gtt ctc tat cag    480
Asp Gln Gln Tyr Ser Arg Phe Leu Gln Glu Ser Asn Val Leu Tyr Gln
 65                  70                  75                  80 cac aat cta cga aga atc aag cag ttt ctt cag agc agg tat ctt gag    528
His Asn Leu Arg Arg Ile Lys Gln Phe Leu Gln Ser Arg Tyr Leu Glu
                 85                  90                  95 aag cca atg gag att gcc cgg att gtg gcc cgg tgc ctg tgg gaa gaa    576
Lys Pro Met Glu Ile Ala Arg Ile Val Ala Arg Cys Leu Trp Glu Glu
            100                 105                 110 tca cgc ctt cta cag act gca gcc act gcg gcc cag caa ggg ggc cag    624
Ser Arg Leu Leu Gln Thr Ala Ala Thr Ala Ala Gln Gln Gly Gly Gln
        115                 120                 125 gcc aac cac ccc aca gca gcc gtg gtg acg gag aag cag cag atg ctg    672
Ala Asn His Pro Thr Ala Ala Val Val Thr Glu Lys Gln Gln Met Leu
    130                 135                 140 gag cag cac ctt cag gat gtc cgg aag aga gtg cag gat cta gaa cag    720
Glu Gln His Leu Gln Asp Val Arg Lys Arg Val Gln Asp Leu Glu Gln
145                 150                 155                 160 aaa atg aaa gtg gta gag aat ctc cag gat gac ttt gat ttc aac tat    768
Lys Met Lys Val Val Glu Asn Leu Gln Asp Asp Phe Asp Phe Asn Tyr
                165                 170                 175 aaa acc ctc aag agt caa gga gac atg caa gat ctg aat gga aac aac    816
Lys Thr Leu Lys Ser Gln Gly Asp Met Gln Asp Leu Asn Gly Asn Asn
            180                 185                 190 cag tca gtg acc agg cag aag atg cag cag ctg gaa cag atg ctc act    864
Gln Ser Val Thr Arg Gln Lys Met Gln Gln Leu Glu Gln Met Leu Thr
        195                 200                 205 gcg ctg gac cag atg cgg aga agc atc gtg agt gag ctg gcg ggg ctt    912
Ala Leu Asp Gln Met Arg Arg Ser Ile Val Ser Glu Leu Ala Gly Leu
    210                 215                 220 ttg tca gcg atg gag tac gtg cag aaa act ctc acg gac gag gag ctg    960
Leu Ser Ala Met Glu Tyr Val Gln Lys Thr Leu Thr Asp Glu Glu Leu
225                 230                 235                 240 gct gac tgg aag agg cgg caa cag att gcc tgc att gga ggc ccg ccc   1008
Ala Asp Trp Lys Arg Arg Gln Gln Ile Ala Cys Ile Gly Gly Pro Pro
                245                 250                 255 aac atc tgc cta gat cgg cta gaa aac tgg ata acg tca tta gca gaa   1056
Asn Ile Cys Leu Asp Arg Leu Glu Asn Trp Ile Thr Ser Leu Ala Glu
            260                 265                 270 tct caa ctt cag acc cgt caa caa att aag aaa ctg gag gag ttg cag   1104
Ser Gln Leu Gln Thr Arg Gln Gln Ile Lys Lys Leu Glu Glu Leu Gln
        275                 280                 285 caa aaa gtt tcc tac aaa ggg gac ccc att gta cag cac cgg ccg atg   1152
Gln Lys Val Ser Tyr Lys Gly Asp Pro Ile Val Gln His Arg Pro Met
    290                 295                 300 ctg gag gag aga atc gtg gag ctg ttt aga aac tta atg aaa agt gcc   1200
Leu Glu Glu Arg Ile Val Glu Leu Phe Arg Asn Leu Met Lys Ser Ala
305                 310                 315                 320 ttt gtg gtg gag cgg cag ccc tgc atg ccc atg cat cct gac cgg ccc   1248
Phe Val Val Glu Arg Gln Pro Cys Met Pro Met His Pro Asp Arg Pro
                325                 330                 335 ctc gtc atc aag acc ggc gtc cag ttc act act aaa gtc agg ttg ctg   1296
Leu Val Ile Lys Thr Gly Val Gln Phe Thr Thr Lys Val Arg Leu Leu
            340                 345                 350 gtc aaa ttc cct gag ttg aat tat cag ctt aaa att aaa gtg tgc att   1344
Val Lys Phe Pro Glu Leu Asn Tyr Gln Leu Lys Ile Lys Val Cys Ile
```

```
                355              360              365
gac aaa gac tct ggg gac gtt gca gct ctc aga gga tcc cgg aaa ttt    1392
Asp Lys Asp Ser Gly Asp Val Ala Ala Leu Arg Gly Ser Arg Lys Phe
    370              375              380 aac att ctg ggc aca aac aca aaa gtg atg aac atg gaa gaa tcc aac    1440
Asn Ile Leu Gly Thr Asn Thr Lys Val Met Asn Met Glu Glu Ser Asn
385              390              395              400 aac ggc agc ctc tct gca gaa ttc aaa cac ttg acc ctg agg gag cag    1488
Asn Gly Ser Leu Ser Ala Glu Phe Lys His Leu Thr Leu Arg Glu Gln
                405              410              415 aga tgt ggg aat ggg ggc cga gcc aat tgt gat gct tcc ctg att gtg    1536
Arg Cys Gly Asn Gly Gly Arg Ala Asn Cys Asp Ala Ser Leu Ile Val
            420              425              430 act gag gag ctg cac ctg atc acc ttt gag acc gag gtg tat cac caa    1584
Thr Glu Glu Leu His Leu Ile Thr Phe Glu Thr Glu Val Tyr His Gln
        435              440              445 ggc ctc aag att gac cta gag acc cac tcc ttg cca gtt gtg gtg atc    1632
Gly Leu Lys Ile Asp Leu Glu Thr His Ser Leu Pro Val Val Val Ile
    450              455              460 tcc aac atc tgt cag atg cca aat gcc tgg gcg tcc atc ctg tgg tac    1680
Ser Asn Ile Cys Gln Met Pro Asn Ala Trp Ala Ser Ile Leu Trp Tyr
465              470              475              480 aac atg ctg acc aac aat ccc aag aat gta aac ttt ttt acc aag ccc    1728
Asn Met Leu Thr Asn Asn Pro Lys Asn Val Asn Phe Phe Thr Lys Pro
                485              490              495 cca att gga acc tgg gat caa gtg gcc gag gtc ctg agc tgg cag ttc    1776
Pro Ile Gly Thr Trp Asp Gln Val Ala Glu Val Leu Ser Trp Gln Phe
            500              505              510 tcc tcc acc acc aag cga gga ctg agc atc gag cag ctg act aca ctg    1824
Ser Ser Thr Thr Lys Arg Gly Leu Ser Ile Glu Gln Leu Thr Thr Leu
        515              520              525 gca gag aaa ctc ttg gga cct ggt gtg aat tat tca ggg tgt cag atc    1872
Ala Glu Lys Leu Leu Gly Pro Gly Val Asn Tyr Ser Gly Cys Gln Ile
    530              535              540 aca tgg gct aaa ttt tgc aaa gaa aac atg gct ggc aag ggc ttc tcc    1920
Thr Trp Ala Lys Phe Cys Lys Glu Asn Met Ala Gly Lys Gly Phe Ser
545              550              555              560 ttc tgg gtc tgg ctg gac aat atc att gac ctt gtg aaa aag tac atc    1968
Phe Trp Val Trp Leu Asp Asn Ile Ile Asp Leu Val Lys Lys Tyr Ile
                565              570              575 ctg gcc ctt tgg aac gaa ggg tac atc atg ggc ttt atc agt aag gag    2016
Leu Ala Leu Trp Asn Glu Gly Tyr Ile Met Gly Phe Ile Ser Lys Glu
            580              585              590 cgg gag cgg gcc atc ttg agc act aag cct cca ggc acc ttc ctg cta    2064
Arg Glu Arg Ala Ile Leu Ser Thr Lys Pro Pro Gly Thr Phe Leu Leu
        595              600              605 aga ttc agt gaa agc agc aaa gaa gga ggc gtc act ttc act tgg gtg    2112
Arg Phe Ser Glu Ser Ser Lys Glu Gly Gly Val Thr Phe Thr Trp Val
    610              615              620 gag aag gac atc agc ggt aag acc cag atc cag tcc gtg gaa cca tac    2160
Glu Lys Asp Ile Ser Gly Lys Thr Gln Ile Gln Ser Val Glu Pro Tyr
625              630              635              640 aca aag cag cag ctg aac aac atg tca ttt gct gaa atc atc atg ggc    2208
Thr Lys Gln Gln Leu Asn Asn Met Ser Phe Ala Glu Ile Ile Met Gly
                645              650              655 tat aag atc atg gat gct acc aat atc ctg gtg tct cca ctg gtc tat    2256
Tyr Lys Ile Met Asp Ala Thr Asn Ile Leu Val Ser Pro Leu Val Tyr
            660              665              670 ctc tat cct gac att ccc aag gag gag gca ttc gga aag tat tgt cgg    2304
```

-continued

| | | | | | | | | | | | | | | |
|---|---|---|---|---|---|---|---|---|---|---|---|---|---|---|
| Leu | Tyr | Pro | Asp | Ile | Pro | Lys | Glu | Glu | Ala | Phe | Gly | Lys | Tyr | Cys | Arg |
| | | 675 | | | | 680 | | | | | 685 | | | | |

| cca | gag | agc | cag | gag | cat | cct | gaa | gct | gac | cca | ggt | agc | gct | gcc | cca | 2352 |
|---|---|---|---|---|---|---|---|---|---|---|---|---|---|---|---|---|
| Pro | Glu | Ser | Gln | Glu | His | Pro | Glu | Ala | Asp | Pro | Gly | Ser | Ala | Ala | Pro | |
| | 690 | | | | | 695 | | | | 700 | | | | | | |

| tac | ctg | aag | acc | aag | ttt | atc | tgt | gtg | aca | cca | acg | acc | tgc | agc | aat | 2400 |
|---|---|---|---|---|---|---|---|---|---|---|---|---|---|---|---|---|
| Tyr | Leu | Lys | Thr | Lys | Phe | Ile | Cys | Val | Thr | Pro | Thr | Thr | Cys | Ser | Asn | |
| 705 | | | | | 710 | | | | | 715 | | | | | 720 | |

| acc | att | gac | ctg | ccg | atg | tcc | ccc | cgc | act | tta | gat | tca | ttg | atg | cag | 2448 |
|---|---|---|---|---|---|---|---|---|---|---|---|---|---|---|---|---|
| Thr | Ile | Asp | Leu | Pro | Met | Ser | Pro | Arg | Thr | Leu | Asp | Ser | Leu | Met | Gln | |
| | | | | | 725 | | | | | 730 | | | | | 735 | |

| ttt | gga | aat | aat | ggt | gaa | ggt | gct | gaa | ccc | tca | gca | gga | ggg | cag | ttt | 2496 |
|---|---|---|---|---|---|---|---|---|---|---|---|---|---|---|---|---|
| Phe | Gly | Asn | Asn | Gly | Glu | Gly | Ala | Glu | Pro | Ser | Ala | Gly | Gly | Gln | Phe | |
| | | | | 740 | | | | | 745 | | | | | 750 | | |

| gag | tcc | ctc | acc | ttt | gac | atg | gag | ttg | acc | tcg | gag | tgc | gct | acc | tcc | 2544 |
|---|---|---|---|---|---|---|---|---|---|---|---|---|---|---|---|---|
| Glu | Ser | Leu | Thr | Phe | Asp | Met | Glu | Leu | Thr | Ser | Glu | Cys | Ala | Thr | Ser | |
| | | 755 | | | | | 760 | | | | | 765 | | | | |

| ccc | atg | tga | ggagctgaga | acggaagctg | cagaaagata | cgactgaggc | 2593 |
|---|---|---|---|---|---|---|---|
| Pro | Met | * | | | | | |
| | 770 | | | | | | | gcctacctgc attctgccac ccctcacaca gccaaacccc agatcatctg aaactactaa     2653 ctttgtggtt ccagattttt tttaatctcc tacttctgct atctttgagc aatctgggca     2713 cttttaaaaa tagagaaatg agtgaatgtg ggtgatctgc ttttatctaa atgcaaataa     2773 ggatgtgttc tctgagaccc atgatcaggg gatgtggcgg ggggtggcta gagggagaaa     2833 aaggaaatgt cttgtgttgt tttgttcccc tgccctcctt tctcagcagc ttttttgttat     2893 tgttgttgtt gttcttagac aagtgcctcc tggtgcctgc ggcatccttc tgcctgtttc     2953 tgtaagcaaa tgccacaggc cacctatagc tacatactcc tggcattgca cttttttaacc     3013 ttgctgacat ccaaatagaa gataggacta tctaagccct aggtttcttt ttaaattaag     3073 aaataataac aattaaaggg caaaaaacac tgtatcagca tagccttttct gtatttaaga     3133 aacttaagca gccgggcatg gtggctcacg cctgtaatcc cagcactttg ggaggccgag     3193 gcggatcata aggtcaggag atcaagacca tcctggctaa cacggtgaaa ccccgtctct     3253 actaaaagta caaaaaatta gctgggtgtg gtggtgggcg cctgtagtcc cagctactcg     3313 ggaggctgag gcaggagaat cgcttgaacc tgagaggcgg aggttgcagt gagccaaaat     3373 tgcaccactg cacactgcac tccatcctgg gcgacagtct gagactctgt ctcaaaaaaa     3433 aaaaaaaaaa aaaaaaaaaa aa     3455

<210> SEQ ID NO 155
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 155
gtgcgcgcga gcccgaaatc     20

<210> SEQ ID NO 156
<211> LENGTH: 24
<212> TYPE: DNA
<213> ORGANISM: Artificial Sequence
<220> FEATURE:
<223> OTHER INFORMATION: PCR Primer

<400> SEQUENCE: 156

```
acatgccact ttggtgtttc ataa                                          24
```

```
<210> SEQ ID NO 157
<211> LENGTH: 27
<212> TYPE: DNA
<213> ORGANISM: Artificial Sequence
<220> FEATURE:
<223> OTHER INFORMATION: PCR Primer

<400> SEQUENCE: 157
tcttcgtaga ttgtgctgat agagaac                                       27
```

```
<210> SEQ ID NO 158
<211> LENGTH: 29
<212> TYPE: DNA
<213> ORGANISM: Artificial Sequence
<220> FEATURE:
<223> OTHER INFORMATION: PCR Probe

<400> SEQUENCE: 158
cagtatagcc gcttcctgca agagtcgaa                                     29
```

```
<210> SEQ ID NO 159
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 159
agcctctgca ccctcatgtt                                               20
```

```
<210> SEQ ID NO 160
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 160
ctcctaaatt aagaacttct                                               20
```

```
<210> SEQ ID NO 161
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 161
ttttgcatga tgtaaccact                                               20
```

```
<210> SEQ ID NO 162
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 162
tattgaaaat tatctaattc                                               20
```

```
<210> SEQ ID NO 163
<211> LENGTH: 20
<212> TYPE: DNA
<213> ORGANISM: Artificial Sequence
```

```
<220> FEATURE:
<223> OTHER INFORMATION: Antisense oligonucleotide

<400> SEQUENCE: 163
ttgggccatc ctgctaaaat                                                      20

<210> SEQ ID NO 164
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 164
attcacttgc ctccttgact                                                      20

<210> SEQ ID NO 165
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 165
atgcccttac tctccgcatc                                                      20

<210> SEQ ID NO 166
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 166
ctgaacttac cctctgagag                                                      20

<210> SEQ ID NO 167
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 167
aaatgcggac ccaagagttt                                                      20

<210> SEQ ID NO 168
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 168
cttgttccct cggctgcgac                                                      20

<210> SEQ ID NO 169
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 169
gcctgtccag gatccggttg                                                      20
```

<210> SEQ ID NO 170
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 170
gaagggcctc tccgagccga                                                20

<210> SEQ ID NO 171
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 171
ggcggcgagg ctccctcagg                                                20

<210> SEQ ID NO 172
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 172
tccggcagag gccgagaggc                                                20

<210> SEQ ID NO 173
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 173
ccatcctgct aaaatcaggg                                                20

<210> SEQ ID NO 174
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 174
ccattgggcc atcctgctaa                                                20

<210> SEQ ID NO 175
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 175
tgtcaagctg ctgtagctga                                                20

<210> SEQ ID NO 176
<211> LENGTH: 20
<212> TYPE: DNA
<213> ORGANISM: Artificial Sequence
<220> FEATURE:
<223> OTHER INFORMATION: Antisense oligonucleotide

```
<400> SEQUENCE: 176
aactgccgca gctccattgg                                                     20

<210> SEQ ID NO 177
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 177
tcttgactct caatccaagg                                                     20

<210> SEQ ID NO 178
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 178
cgcatatgcc caatcttgac                                                     20

<210> SEQ ID NO 179
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 179
cgactcttgc aggaagcggc                                                     20

<210> SEQ ID NO 180
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 180
tcgtagattg tgctgataga                                                     20

<210> SEQ ID NO 181
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 181
agaaactgct tgattcttcg                                                     20

<210> SEQ ID NO 182
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 182
gatacctgct ctgaagaaac                                                     20

<210> SEQ ID NO 183
```

```
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 183
ttctcaagat acctgctctg                                                   20

<210> SEQ ID NO 184
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 184
ttggcttctc aagatacctg                                                   20

<210> SEQ ID NO 185
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 185
gtgattcttc ccacaggcac                                                   20

<210> SEQ ID NO 186
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 186
atctgctgct tctccgtcac                                                   20

<210> SEQ ID NO 187
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 187
ccagcatctg ctgcttctcc                                                   20

<210> SEQ ID NO 188
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 188
tgaaggtgct gctccagcat                                                   20

<210> SEQ ID NO 189
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 189
```
ttctgttcta gatcctgcac                                               20

<210> SEQ ID NO 190
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 190
ctggagattc tctaccactt                                               20

<210> SEQ ID NO 191
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 191
aagtcatcct ggagattctc                                               20

<210> SEQ ID NO 192
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 192
aatcaaagtc atcctggaga                                               20

<210> SEQ ID NO 193
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 193
gttgaaatca aagtcatcct                                               20

<210> SEQ ID NO 194
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 194
ttatagttga aatcaaagtc                                               20

<210> SEQ ID NO 195
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 195
gggttttata gttgaaatca                                               20

<210> SEQ ID NO 196
<211> LENGTH: 20
<212> TYPE: DNA

```
<213> ORGANISM: Artificial Sequence
<220> FEATURE:
<223> OTHER INFORMATION: Antisense oligonucleotide

<400> SEQUENCE: 196
cttgagggtt ttatagttga                                               20

<210> SEQ ID NO 197
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 197
tgactcttga gggttttata                                               20

<210> SEQ ID NO 198
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 198
ctccttgact cttgagggtt                                               20

<210> SEQ ID NO 199
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 199
catgtctcct tgactcttga                                               20

<210> SEQ ID NO 200
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 200
attcagatct tgcatgtctc                                               20

<210> SEQ ID NO 201
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 201
tggttgtttc cattcagatc                                               20

<210> SEQ ID NO 202
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 202
tggtcactga ctggttgttt                                               20
```

```
<210> SEQ ID NO 203
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 203
tccagctgct gcatcttctg                                          20

<210> SEQ ID NO 204
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 204
gagcatctgt tccagctgct                                          20

<210> SEQ ID NO 205
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 205
cttctccgca tctggtccag                                          20

<210> SEQ ID NO 206
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 206
ttctgcacgt actccatcgc                                          20

<210> SEQ ID NO 207
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 207
cagccagctc ctcgtccgtg                                          20

<210> SEQ ID NO 208
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 208
ctcttccagt cagccagctc                                          20

<210> SEQ ID NO 209
<211> LENGTH: 20
<212> TYPE: DNA
<213> ORGANISM: Artificial Sequence
<220> FEATURE:
```

<223> OTHER INFORMATION: Antisense oligonucleotide

<400> SEQUENCE: 209
tgccgcctct tccagtcagc 20

<210> SEQ ID NO 210
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 210
ccagttttct agccgatcta 20

<210> SEQ ID NO 211
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 211
acgttatcca gttttctagc 20

<210> SEQ ID NO 212
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 212
agttgagatt ctgctaatga 20

<210> SEQ ID NO 213
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 213
tctgaagttg agattctgct 20

<210> SEQ ID NO 214
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 214
cctttgtagg aaactttttg 20

<210> SEQ ID NO 215
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 215
aggcactttt cattaagttt 20

<210> SEQ ID NO 216
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 216
ttgaccagca acctgacttt                                           20

<210> SEQ ID NO 217
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 217
agctgataat tcaactcagg                                           20

<210> SEQ ID NO 218
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 218
ttttaagctg ataattcaac                                           20

<210> SEQ ID NO 219
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 219
ctttaatttt aagctgataa                                           20

<210> SEQ ID NO 220
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 220
gcacacttta attttaagct                                           20

<210> SEQ ID NO 221
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 221
tcaatgcaca ctttaatttt                                           20

<210> SEQ ID NO 222
<211> LENGTH: 20
<212> TYPE: DNA
<213> ORGANISM: Artificial Sequence
<220> FEATURE:
<223> OTHER INFORMATION: Antisense oligonucleotide

```
<400> SEQUENCE: 222
cccagaatgt taaatttccg                                              20

<210> SEQ ID NO 223
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 223
agaggctgcc gttgttggat                                              20

<210> SEQ ID NO 224
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 224
aagtgtttga attctgcaga                                              20

<210> SEQ ID NO 225
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 225
tctctgctcc ctcagggtca                                              20

<210> SEQ ID NO 226
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 226
atcaggtgca gctcctcagt                                              20

<210> SEQ ID NO 227
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 227
aggtgatcag gtgcagctcc                                              20

<210> SEQ ID NO 228
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 228
ctcaaaggtg atcaggtgca                                              20

<210> SEQ ID NO 229
<211> LENGTH: 20
```

```
<212> TYPE: DNA
<213> ORGANISM: Artificial Sequence
<220> FEATURE:
<223> OTHER INFORMATION: Antisense oligonucleotide

<400> SEQUENCE: 229
gaggccttgg tgatacacct                                               20

<210> SEQ ID NO 230
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 230
tcaatcttga ggccttggtg                                               20

<210> SEQ ID NO 231
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 231
ctaggtcaat cttgaggcct                                               20

<210> SEQ ID NO 232
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 232
ggtctctagg tcaatcttga                                               20

<210> SEQ ID NO 233
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 233
aaggagtggg tctctaggtc                                               20

<210> SEQ ID NO 234
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 234
ctggcaagga gtgggtctct                                               20

<210> SEQ ID NO 235
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 235
```
accacaactg gcaaggagtg                                                    20

<210> SEQ ID NO 236
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 236
tctgacagat gttggagatc                                                    20

<210> SEQ ID NO 237
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 237
tggcatctga cagatgttgg                                                    20

<210> SEQ ID NO 238
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 238
gcatttggca tctgacagat                                                    20

<210> SEQ ID NO 239
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 239
ttcttgggat tgttggtcag                                                    20

<210> SEQ ID NO 240
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 240
gtcagctgct cgatgctcag                                                    20

<210> SEQ ID NO 241
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 241
tcccaagagt ttctctgcca                                                    20

<210> SEQ ID NO 242
<211> LENGTH: 20
<212> TYPE: DNA
<213> ORGANISM: Artificial Sequence -continued

```
<220> FEATURE:
<223> OTHER INFORMATION: Antisense oligonucleotide

<400> SEQUENCE: 242
catgtgatct gacaccctga                                               20

<210> SEQ ID NO 243
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 243
tagcccatgt gatctgacac                                               20

<210> SEQ ID NO 244
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 244
gccatgtttt ctttgcaaaa                                               20

<210> SEQ ID NO 245
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 245
ccttgccagc catgttttct                                               20

<210> SEQ ID NO 246
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 246
gaagcccttg ccagccatgt                                               20

<210> SEQ ID NO 247
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 247
aaggagaagc ccttgccagc                                               20

<210> SEQ ID NO 248
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 248
cccagaagga gaagcccttg                                               20
```

<210> SEQ ID NO 249
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 249
tccagccaga cccagaagga                                                 20

<210> SEQ ID NO 250
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 250
tctttgctgc tttcactgaa                                                 20

<210> SEQ ID NO 251
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 251
atgttgttca gctgctgctt                                                 20

<210> SEQ ID NO 252
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 252
atgacatgtt gttcagctgc                                                 20

<210> SEQ ID NO 253
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 253
agcaaatgac atgttgttca                                                 20

<210> SEQ ID NO 254
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 254
atttcagcaa atgacatgtt                                                 20

<210> SEQ ID NO 255
<211> LENGTH: 20
<212> TYPE: DNA
<213> ORGANISM: Artificial Sequence
<220> FEATURE:
<223> OTHER INFORMATION: Antisense oligonucleotide

```
<400> SEQUENCE: 255
tgatgatttc agcaaatgac                                                    20

<210> SEQ ID NO 256
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 256
ttatagccca tgatgatttc                                                    20

<210> SEQ ID NO 257
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 257
tgatcttata gcccatgatg                                                    20

<210> SEQ ID NO 258
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 258
atccatgatc ttatagccca                                                    20

<210> SEQ ID NO 259
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 259
ggtagcatcc atgatcttat                                                    20

<210> SEQ ID NO 260
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 260
aatgtcagga tagagataga                                                    20

<210> SEQ ID NO 261
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 261
gcctcctcct tgggaatgtc                                                    20

<210> SEQ ID NO 262
```

```
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 262
tccgaatgcc tcctccttgg                                                  20

<210> SEQ ID NO 263
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 263
tactttccga atgcctcctc                                                  20

<210> SEQ ID NO 264
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 264
gacaatactt tccgaatgcc                                                  20

<210> SEQ ID NO 265
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 265
ctacctgggt cagcttcagg                                                  20

<210> SEQ ID NO 266
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 266
ataaacttgg tcttcaggta                                                  20

<210> SEQ ID NO 267
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 267
gtcgttggtg tcacacagat                                                  20

<210> SEQ ID NO 268
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 268
```

```
tgcaggtcgt tggtgtcaca                                               20

<210> SEQ ID NO 269
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 269
attgctgcag gtcgttggtg                                               20

<210> SEQ ID NO 270
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 270
atggtattgc tgcaggtcgt                                               20

<210> SEQ ID NO 271
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 271
ggtcaatggt attgctgcag                                               20

<210> SEQ ID NO 272
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 272
gacatcggca ggtcaatggt                                               20

<210> SEQ ID NO 273
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 273
caatgaatct aaagtgcggg                                               20

<210> SEQ ID NO 274
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 274
tgcatcaatg aatctaaagt                                               20

<210> SEQ ID NO 275
<211> LENGTH: 20
<212> TYPE: DNA
```

```
<213> ORGANISM: Artificial Sequence
<220> FEATURE:
<223> OTHER INFORMATION: Antisense oligonucleotide

<400> SEQUENCE: 275
caaactgcat caatgaatct                                               20

<210> SEQ ID NO 276
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 276
atttccaaac tgcatcaatg                                               20

<210> SEQ ID NO 277
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 277
aactgccctc ctgctgaggg                                               20

<210> SEQ ID NO 278
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 278
ggtgagggac tcaaactgcc                                               20

<210> SEQ ID NO 279
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 279
cagtcgtatc tttctgcagc                                               20

<210> SEQ ID NO 280
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 280
agatagcaga agtaggagat                                               20

<210> SEQ ID NO 281
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 281
aaagtgccca gattgctcaa                                               20
```

<210> SEQ ID NO 282
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 282
tttttaaaag tgcccagatt                                          20

<210> SEQ ID NO 283
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 283
cagatcaccc acattcactc                                          20

<210> SEQ ID NO 284
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 284
tgcatttaga taaaagcaga                                          20

<210> SEQ ID NO 285
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 285
gaacacatcc ttatttgcat                                          20

<210> SEQ ID NO 286
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 286
atcatgggtc tcagagaaca                                          20

<210> SEQ ID NO 287
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 287
cacatcccct gatcatgggt                                          20

<210> SEQ ID NO 288
<211> LENGTH: 20
<212> TYPE: DNA
<213> ORGANISM: Artificial Sequence
<220> FEATURE:

<223> OTHER INFORMATION: Antisense oligonucleotide

<400> SEQUENCE: 288
agacatttcc tttttctccc 20

<210> SEQ ID NO 289
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 289
accaggaggc acttgtctaa 20

<210> SEQ ID NO 290
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 290
gcaggcacca ggaggcactt 20

<210> SEQ ID NO 291
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 291
gcttacagaa acaggcagaa 20

<210> SEQ ID NO 292
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 292
aggtggcctg tggcatttgc 20

<210> SEQ ID NO 293
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 293
gtatgtagct ataggtggcc 20

<210> SEQ ID NO 294
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 294
gcaatgccag gagtatgtag 20

-continued

```
<210> SEQ ID NO 295
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 295
ttaaaaagtg caatgccagg                                              20

<210> SEQ ID NO 296
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 296
ggcttagata gtcctatctt                                              20

<210> SEQ ID NO 297
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 297
taaaaagaaa cctagggctt                                              20

<210> SEQ ID NO 298
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 298
atacagaaag gctatgctga                                              20

<210> SEQ ID NO 299
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 299
ttaagtttct taaatacaga                                              20

<210> SEQ ID NO 300
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 300
gcatctgctg cttctccgtc                                              20

<210> SEQ ID NO 301
<211> LENGTH: 20
<212> TYPE: DNA
<213> ORGANISM: Artificial Sequence
<220> FEATURE:
<223> OTHER INFORMATION: Antisense oligonucleotide
```

```
<400> SEQUENCE: 301
cagcatctgc tgcttctccg                                               20

<210> SEQ ID NO 302
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 302
tccagcatct gctgcttctc                                               20

<210> SEQ ID NO 303
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 303
ctccagcatc tgctgcttct                                               20

<210> SEQ ID NO 304
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 304
tgctccagca tctgctgctt                                               20

<210> SEQ ID NO 305
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 305
tgctgctcca gcatctgctg                                               20

<210> SEQ ID NO 306
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 306
ggtgctgctc cagcatctgc                                               20

<210> SEQ ID NO 307
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 307
aaggtgctgc tccagcatct                                               20

<210> SEQ ID NO 308
<211> LENGTH: 20
```

```
<212> TYPE: DNA
<213> ORGANISM: Artificial Sequence
<220> FEATURE:
<223> OTHER INFORMATION: Antisense oligonucleotide

<400> SEQUENCE: 308
tgggattgtt ggtcagcatg                                           20

<210> SEQ ID NO 309
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 309
attcttggga ttgttggtca                                           20

<210> SEQ ID NO 310
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 310
acattcttgg gattgttggt                                           20

<210> SEQ ID NO 311
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 311
cacattcttg ggattgttgg                                           20

<210> SEQ ID NO 312
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 312
ttcacattct tgggattgtt                                           20

<210> SEQ ID NO 313
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 313
agttcacatt cttgggattg                                           20

<210> SEQ ID NO 314
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 314
```

```
gaagttcaca ttcttgggat                                              20

<210> SEQ ID NO 315
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 315
agattatgaa acaccaaagt                                              20

<210> SEQ ID NO 316
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 316
ggagattatg aaacaccaaa                                              20

<210> SEQ ID NO 317
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 317
caggagatta tgaaacacca                                              20

<210> SEQ ID NO 318
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 318
tcccaggaga ttatgaaaca                                              20

<210> SEQ ID NO 319
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 319
ctcccaggag attatgaaac                                              20

<210> SEQ ID NO 320
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 320
ctctcccagg agattatgaa                                              20

<210> SEQ ID NO 321
<211> LENGTH: 20
<212> TYPE: DNA
<213> ORGANISM: Artificial Sequence
```

```
<220> FEATURE:
<223> OTHER INFORMATION: Antisense oligonucleotide

<400> SEQUENCE: 321
atctctccca ggagattatg                                              20

<210> SEQ ID NO 322
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 322
cttgccagcc atgttttctt                                              20

<210> SEQ ID NO 323
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 323
cccttgccag ccatgttttc                                              20

<210> SEQ ID NO 324
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 324
agcccttgcc agccatgttt                                              20

<210> SEQ ID NO 325
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 325
gagaagccct tgccagccat                                              20

<210> SEQ ID NO 326
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 326
aggagaagcc cttgccagcc                                              20

<210> SEQ ID NO 327
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 327
gaaggagaag cccttgccag                                              20
```

```
<210> SEQ ID NO 328
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 328
aagcccttgc cagccatgtt                                                  20

<210> SEQ ID NO 329
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 329
agaagccctt gccagccatg                                                  20

<210> SEQ ID NO 330
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 330
agaaggagaa gcccttgcca                                                  20

<210> SEQ ID NO 331
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 331
ccagaaggag aagcccttgc                                                  20

<210> SEQ ID NO 332
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 332
acccagaagg agaagccctt                                                  20

<210> SEQ ID NO 333
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 333
tgcctcctcc ttgggaatgt                                                  20

<210> SEQ ID NO 334
<211> LENGTH: 20
<212> TYPE: DNA
<213> ORGANISM: Artificial Sequence
<220> FEATURE:
<223> OTHER INFORMATION: Antisense oligonucleotide
```

```
<400> SEQUENCE: 334
aatgcctcct ccttgggaat                                              20

<210> SEQ ID NO 335
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 335
cgaatgcctc ctccttggga                                              20

<210> SEQ ID NO 336
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 336
ttccgaatgc ctcctccttg                                              20

<210> SEQ ID NO 337
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 337
tttccgaatg cctcctcctt                                              20

<210> SEQ ID NO 338
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 338
actttccgaa tgcctcctcc                                              20

<210> SEQ ID NO 339
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 339
ttgcaggaag cggctatact                                              20

<210> SEQ ID NO 340
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 340
tcttgcagga agcggctata                                              20

<210> SEQ ID NO 341
```

```
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 341
actcttgcag gaagcggcta                                               20

<210> SEQ ID NO 342
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 342
gactcttgca ggaagcggct                                               20

<210> SEQ ID NO 343
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 343
tcgactcttg caggaagcgg                                               20

<210> SEQ ID NO 344
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 344
ttcgactctt gcaggaagcg                                               20

<210> SEQ ID NO 345
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 345
cattcgactc ttgcaggaag                                               20

<210> SEQ ID NO 346
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 346
tcttatagcc catgatgatt                                               20

<210> SEQ ID NO 347
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 347
```
gatcttatag cccatgatga                                              20

<210> SEQ ID NO 348
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 348
atgatcttat agcccatgat                                              20

<210> SEQ ID NO 349
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 349
ccatgatctt atagcccatg                                              20

<210> SEQ ID NO 350
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 350
gcatccatga tcttatagcc                                              20

<210> SEQ ID NO 351
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 351
tagcatccat gatcttatag                                              20

<210> SEQ ID NO 352
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 352
gtagcatcca tgatcttata                                              20

<210> SEQ ID NO 353
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 353
aaaggctatg ctgatacagt                                              20

<210> SEQ ID NO 354
<211> LENGTH: 20
<212> TYPE: DNA

```
<213> ORGANISM: Artificial Sequence
<220> FEATURE:
<223> OTHER INFORMATION: Antisense oligonucleotide

<400> SEQUENCE: 354
agaaaggcta tgctgataca                                               20

<210> SEQ ID NO 355
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 355
acagaaaggc tatgctgata                                               20

<210> SEQ ID NO 356
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 356
tacagaaagg ctatgctgat                                               20

<210> SEQ ID NO 357
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 357
aatacagaaa ggctatgctg                                               20

<210> SEQ ID NO 358
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 358
aaatacagaa aggctatgct                                               20

<210> SEQ ID NO 359
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 359
ttaaatacag aaaggctatg                                               20

<210> SEQ ID NO 360
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 360
tcttaaatac agaaaggcta                                               20
```

```
<210> SEQ ID NO 361
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 361
ggtctcagag aacacatcct                                              20

<210> SEQ ID NO 362
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 362
tgggtctcag agaacacatc                                              20

<210> SEQ ID NO 363
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 363
catgggtctc agagaacaca                                              20

<210> SEQ ID NO 364
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 364
tcatgggtct cagagaacac                                              20

<210> SEQ ID NO 365
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 365
tgatcatggg tctcagagaa                                              20

<210> SEQ ID NO 366
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 366
cctgatcatg ggtctcagag                                              20

<210> SEQ ID NO 367
<211> LENGTH: 20
<212> TYPE: DNA
<213> ORGANISM: Artificial Sequence
<220> FEATURE:
```

<223> OTHER INFORMATION: Antisense oligonucleotide

<400> SEQUENCE: 367
cccctgatca tgggtctcag        20

<210> SEQ ID NO 368
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 368
cagacccaga aggagaagcc        20

<210> SEQ ID NO 369
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 369
cagccagacc cagaaggaga        20

<210> SEQ ID NO 370
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 370
ccagccagac ccagaaggag        20

<210> SEQ ID NO 371
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 371
gtccagccag acccagaagg        20

<210> SEQ ID NO 372
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 372
tgtccagcca gacccagaag        20

<210> SEQ ID NO 373
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 373
attgtccagc cagacccaga        20

```
<210> SEQ ID NO 374
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 374
atattgtcca gccagaccca                                              20

<210> SEQ ID NO 375
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 375
catgatctta tagcccatga                                              20

<210> SEQ ID NO 376
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 376
tccatgatct tatagcccat                                              20

<210> SEQ ID NO 377
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 377
catccatgat cttatagccc                                              20

<210> SEQ ID NO 378
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 378
agcatccatg atcttatagc                                              20

<210> SEQ ID NO 379
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 379
tggtagcatc catgatctta                                              20

<210> SEQ ID NO 380
<211> LENGTH: 20
<212> TYPE: DNA
<213> ORGANISM: Artificial Sequence
<220> FEATURE:
<223> OTHER INFORMATION: Antisense oligonucleotide
```

```
<400> SEQUENCE: 380
ttggtagcat ccatgatctt                                                      20

<210> SEQ ID NO 381
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 381
gatattggta gcatccatga                                                      20

<210> SEQ ID NO 382
<211> LENGTH: 2924
<212> TYPE: DNA
<213> ORGANISM: M. musculus
<220> FEATURE:
<221> NAME/KEY: CDS
<222> LOCATION: (173)...(2341)

<400> SEQUENCE: 382
gtcgacccac gcgtccgcgc tgaggtacaa ccccgctcgg tgtcgcctga ccgcgtcggc          60
taggagaggc caggcggccc tcgggagccc agcagctcgc gcctggagtc agcgcaggcc         120
ggccagtcgg gcctcagccc cggagacagt cgagacccct gactgcagca gg atg gct        178
                                                          Met Ala
                                                            1 cag tgg aac cag ctg cag cag ctg gac aca cgc tac ctg gag cag ctg          226
Gln Trp Asn Gln Leu Gln Gln Leu Asp Thr Arg Tyr Leu Glu Gln Leu
        5                   10                  15 cac cag ctg tac agc gac acg ttc ccc atg gag ctg cgg cag ttc ctg          274
His Gln Leu Tyr Ser Asp Thr Phe Pro Met Glu Leu Arg Gln Phe Leu
    20                  25                  30 gca cct tgg att gag agt caa gac tgg gca tat gca gcc agc aaa gag          322
Ala Pro Trp Ile Glu Ser Gln Asp Trp Ala Tyr Ala Ala Ser Lys Glu
35                  40                  45                  50 tca cat gcc acg ttg gtg ttt cat aat ctc ttg ggt gaa att gac cag          370
Ser His Ala Thr Leu Val Phe His Asn Leu Leu Gly Glu Ile Asp Gln
                55                  60                  65 caa tat agc cga ttc ctg caa gag tcc aat gtc ctc tat cag cac aac          418
Gln Tyr Ser Arg Phe Leu Gln Glu Ser Asn Val Leu Tyr Gln His Asn
            70                  75                  80 ctt cga aga atc aag cag ttt ctg cag agc agg tat ctt gag aag cca          466
Leu Arg Arg Ile Lys Gln Phe Leu Gln Ser Arg Tyr Leu Glu Lys Pro
        85                  90                  95 atg gaa att gcc cgg atc gtg gcc cga tgc ctg tgg gaa gag tct cgc          514
Met Glu Ile Ala Arg Ile Val Ala Arg Cys Leu Trp Glu Glu Ser Arg
    100                 105                 110 ctc ctc cag acg gca gcc acg gca gcc cag caa ggg ggc cag gcc aac          562
Leu Leu Gln Thr Ala Ala Thr Ala Ala Gln Gln Gly Gly Gln Ala Asn
115                 120                 125                 130 cac cca aca gcc gcc gta gtg aca gag aag cag cag atg ttg gag cag          610
His Pro Thr Ala Ala Val Val Thr Glu Lys Gln Gln Met Leu Glu Gln
                135                 140                 145 cat ctt cag gat gtc cgg aag cga gtg cag gat cta gaa cag aaa atg          658
His Leu Gln Asp Val Arg Lys Arg Val Gln Asp Leu Glu Gln Lys Met
            150                 155                 160 aag gtg gtg gag aac ctc cag gac gac ttt gat ttc aac tac aaa acc          706
Lys Val Val Glu Asn Leu Gln Asp Asp Phe Asp Phe Asn Tyr Lys Thr
        165                 170                 175
```

-continued

| | | |
|---|---|---|
| ctc aag agc caa gga gac atg cag gat ctg aat gga aac aac cag tct<br>Leu Lys Ser Gln Gly Asp Met Gln Asp Leu Asn Gly Asn Asn Gln Ser<br>180                            185                      190 | 754 | |
| gtg acc aga cag aag atg cag cag ctg gaa cag atg ctc aca gcc ctg<br>Val Thr Arg Gln Lys Met Gln Gln Leu Glu Gln Met Leu Thr Ala Leu<br>195                            200                      205                      210 | 802 | |
| gac cag atg cgg aga agc att gtg agt gag ctg gcg ggg ctc ttg tca<br>Asp Gln Met Arg Arg Ser Ile Val Ser Glu Leu Ala Gly Leu Leu Ser<br>                      215                      220                      225 | 850 | |
| gca atg gag tac gtg cag aag aca ctg act gat gaa gag ctg gct gac<br>Ala Met Glu Tyr Val Gln Lys Thr Leu Thr Asp Glu Glu Leu Ala Asp<br>                230                      235                      240 | 898 | |
| tgg aag agg cgg cag cag atc gcg tgc atc gga ggc cct ccc aac atc<br>Trp Lys Arg Arg Gln Gln Ile Ala Cys Ile Gly Gly Pro Pro Asn Ile<br>            245                      250                      255 | 946 | |
| tgc ctg gac cgt ctg gaa aac tgg ata act tca tta gca gaa tct caa<br>Cys Leu Asp Arg Leu Glu Asn Trp Ile Thr Ser Leu Ala Glu Ser Gln<br>260                            265                      270 | 994 | |
| ctt cag acc cgc caa caa att aag aaa ctg gag gag ctg cag cag aaa<br>Leu Gln Thr Arg Gln Gln Ile Lys Lys Leu Glu Glu Leu Gln Gln Lys<br>275                            280                      285                      290 | 1042 | |
| gtg tcc tac aag ggc gac cct atc gtg cag cac cgg ccc atg ctg gag<br>Val Ser Tyr Lys Gly Asp Pro Ile Val Gln His Arg Pro Met Leu Glu<br>                          295                      300                      305 | 1090 | |
| gag agg atc gtg gag ctg ttc aga aac tta atg aag agt gcc ttc gtg<br>Glu Arg Ile Val Glu Leu Phe Arg Asn Leu Met Lys Ser Ala Phe Val<br>                      310                      315                      320 | 1138 | |
| gtg gag cgg cag ccc tgc atg ccc atg cac ccg gac cgg ccc tta gtc<br>Val Glu Arg Gln Pro Cys Met Pro Met His Pro Asp Arg Pro Leu Val<br>325                            330                      335 | 1186 | |
| atc aag act ggt gtc cag ttt acc acg aaa gtc agg ttg ctg gtc aaa<br>Ile Lys Thr Gly Val Gln Phe Thr Thr Lys Val Arg Leu Leu Val Lys<br>340                            345                      350 | 1234 | |
| ttt cct gag ttg aat tat cag ctt aaa att aaa gtg tgc att gat aaa<br>Phe Pro Glu Leu Asn Tyr Gln Leu Lys Ile Lys Val Cys Ile Asp Lys<br>355                            360                      365                      370 | 1282 | |
| gac tct ggg gat gtt gct gcc ctc aga ggg tct cgg aaa ttt aac att<br>Asp Ser Gly Asp Val Ala Ala Leu Arg Gly Ser Arg Lys Phe Asn Ile<br>                      375                      380                      385 | 1330 | |
| ctg ggc acg aac aca aaa gtg atg aac atg gag gag tct aac aac ggc<br>Leu Gly Thr Asn Thr Lys Val Met Asn Met Glu Glu Ser Asn Asn Gly<br>                390                      395                      400 | 1378 | |
| agc ctg tct gca gag ttc aag cac ctg acc ctt agg gag cag aga tgt<br>Ser Leu Ser Ala Glu Phe Lys His Leu Thr Leu Arg Glu Gln Arg Cys<br>            405                      410                      415 | 1426 | |
| ggg aat gga ggc cgt gcc aat tgt gat gcc tcc ttg atc gtg act gag<br>Gly Asn Gly Gly Arg Ala Asn Cys Asp Ala Ser Leu Ile Val Thr Glu<br>420                            425                      430 | 1474 | |
| gag ctg cac ctg atc acc ttc gag act gag gtg tac cac caa ggc ctc<br>Glu Leu His Leu Ile Thr Phe Glu Thr Glu Val Tyr His Gln Gly Leu<br>435                            440                      445                      450 | 1522 | |
| aag att gac cta gag acc cac tcc ttg cca gtt gtg gtg atc tcc aac<br>Lys Ile Asp Leu Glu Thr His Ser Leu Pro Val Val Val Ile Ser Asn<br>                      455                      460                      465 | 1570 | |
| atc tgt cag atg cca aat gct tgg gca tca atc ctg tgg tat aac atg<br>Ile Cys Gln Met Pro Asn Ala Trp Ala Ser Ile Leu Trp Tyr Asn Met<br>                      470                      475                      480 | 1618 | |
| ctg acc aat aac ccc aag aac gtg aac ttc ttc act aag ccg cca att<br>Leu Thr Asn Asn Pro Lys Asn Val Asn Phe Phe Thr Lys Pro Pro Ile<br>485                            490                      495 | 1666 | |

```
gga acc tgg gac caa gtg gcc gag gtg ctc agc tgg cag ttc tcg tcc        1714
Gly Thr Trp Asp Gln Val Ala Glu Val Leu Ser Trp Gln Phe Ser Ser
    500                 505                 510 acc acc aag cga ggg ctg agc atc gag cag ctg aca acg ctg gct gag        1762
Thr Thr Lys Arg Gly Leu Ser Ile Glu Gln Leu Thr Thr Leu Ala Glu
515                 520                 525                 530 aag ctc cta ggg cct ggt gtg aac tac tca ggg tgt cag atc aca tgg        1810
Lys Leu Leu Gly Pro Gly Val Asn Tyr Ser Gly Cys Gln Ile Thr Trp
                535                 540                 545 gct aaa ttc tgc aaa gaa aac atg gct ggc aag ggc ttc tcc ttc tgg        1858
Ala Lys Phe Cys Lys Glu Asn Met Ala Gly Lys Gly Phe Ser Phe Trp
            550                 555                 560 gtc tgg cta gac aat atc atc gac ctt gtg aaa aag tat atc ttg gcc        1906
Val Trp Leu Asp Asn Ile Ile Asp Leu Val Lys Lys Tyr Ile Leu Ala
        565                 570                 575 ctt tgg aat gaa ggg tac atc atg ggt ttc atc agc aag gag cgg gag        1954
Leu Trp Asn Glu Gly Tyr Ile Met Gly Phe Ile Ser Lys Glu Arg Glu
    580                 585                 590 cgg gcc atc cta agc aca aag ccc ccg ggc acc ttc cta ctg cgc ttc        2002
Arg Ala Ile Leu Ser Thr Lys Pro Pro Gly Thr Phe Leu Leu Arg Phe
595                 600                 605                 610 agc gag agc agc aaa gaa gga ggg gtc act ttc act tgg gtg gaa aag        2050
Ser Glu Ser Ser Lys Glu Gly Gly Val Thr Phe Thr Trp Val Glu Lys
                615                 620                 625 gac atc agt ggc aag acc cag atc cag tct gta gag cca tac acc aag        2098
Asp Ile Ser Gly Lys Thr Gln Ile Gln Ser Val Glu Pro Tyr Thr Lys
            630                 635                 640 cag cag ctg aac aac atg tca ttt gct gaa atc atc atg ggc tat aag        2146
Gln Gln Leu Asn Asn Met Ser Phe Ala Glu Ile Ile Met Gly Tyr Lys
        645                 650                 655 atc atg gat gcg acc aac atc ctg gtg tct cca ctt gtc tac ctc tac        2194
Ile Met Asp Ala Thr Asn Ile Leu Val Ser Pro Leu Val Tyr Leu Tyr
    660                 665                 670 ccc gac att ccc aag gag gag gca ttt gga aag tac tgt agg ccc gag        2242
Pro Asp Ile Pro Lys Glu Glu Ala Phe Gly Lys Tyr Cys Arg Pro Glu
675                 680                 685                 690 agc cag gag cac ccc gaa gcc gac cca ggt agt gct gcc ccg tac ctg        2290
Ser Gln Glu His Pro Glu Ala Asp Pro Gly Ser Ala Ala Pro Tyr Leu
                695                 700                 705 aag acc aag ttc atc tgt gtg aca cca ttc att gat gca gtt tgg aaa        2338
Lys Thr Lys Phe Ile Cys Val Thr Pro Phe Ile Asp Ala Val Trp Lys
            710                 715                 720 taa cggtgaaggt gctgagccct cagcaggagg gcagtttgag tcgctcacgt             2391
 * ttgacatgga tctgacctcg gagtgtgcta cctcccccat gtgaggagct gaaaccagaa      2451
gctgcagaga cgtgacttga gacacctgcc ccgtgctcca cccctaagca gccgaacccc     2511
atatcgtctg aaactcctaa ctttgtggtt ccagattttt ttttttaatt tcctacttct      2571
gctatctttg ggcaatctgg gcactttta aaagagagaa atgagtgagt gtgggtgata      2631
aactgttatg taaagaggag agcacctctg agtctgggga tggggctgag agcagaaggg     2691
aggcaaaggg gaacacctcc tgtcctgccc gcctgccctc cttttttcagc agctcggggg    2751 ttggttgtta gacaagtgcc tcctggtgcc catggctacc tgttccccca ctctgtgagc     2811
tgatacccca ttctgggaac tcctggctct gcactttcaa ccttgctaat atccacatag     2871
aagctaggac taagcccagg aggttcctct ttaaattaaa aaaaaaaaaa aaa            2924
```

```
<210> SEQ ID NO 383
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 383
tggtattgct gcaggtcgtt                                                  20

<210> SEQ ID NO 384
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 384
cggcaggtca atggtattgc                                                  20

<210> SEQ ID NO 385
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 385
ggacatcggc aggtcaatgg                                                  20

<210> SEQ ID NO 386
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 386
ttgtacctca gcgcggacgc                                                  20

<210> SEQ ID NO 387
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 387
aaaagtgccc agattgccc                                                   19

<210> SEQ ID NO 388
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 388
aaaagtgccc agattgcc                                                    18

<210> SEQ ID NO 389
<211> LENGTH: 17
<212> TYPE: DNA
<213> ORGANISM: Artificial Sequence
<220> FEATURE:
<223> OTHER INFORMATION: Antisense oligonucleotide
```

```
<400> SEQUENCE: 389
aaagtgccca gattgcc                                              17

<210> SEQ ID NO 390
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 390
gctgcaggtc gttggtgtca                                           20

<210> SEQ ID NO 391
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 391
ttctacctcg cgcgatttac                                           20

<210> SEQ ID NO 392
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 392
gtacagttat gcgcggtaga                                           20

<210> SEQ ID NO 393
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 393
ttagaatacg tcgcgttatg                                           20

<210> SEQ ID NO 394
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 394
cgttattaac ctccgttgaa                                           20

<210> SEQ ID NO 395
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 395
ctgctagcct ctggatttga                                           20

<210> SEQ ID NO 396
<211> LENGTH: 20
```

```
<212> TYPE: DNA
<213> ORGANISM: Artificial Sequence
<220> FEATURE:
<223> OTHER INFORMATION: Antisense oligonucleotide

<400> SEQUENCE: 396
ctcttactgt gctgtggaca                                              20

<210> SEQ ID NO 397
<211> LENGTH: 15
<212> TYPE: DNA
<213> ORGANISM: Artificial Sequence
<220> FEATURE:
<223> OTHER INFORMATION: PCR Primer

<400> SEQUENCE: 397
gaggcccgcc caaca                                                   15

<210> SEQ ID NO 398
<211> LENGTH: 26
<212> TYPE: DNA
<213> ORGANISM: Artificial Sequence
<220> FEATURE:
<223> OTHER INFORMATION: PCR Primer

<400> SEQUENCE: 398
ttctgctaat gacgttatcc agtttt                                       26

<210> SEQ ID NO 399
<211> LENGTH: 14
<212> TYPE: DNA
<213> ORGANISM: Artificial Sequence
<220> FEATURE:
<223> OTHER INFORMATION: PCR Probe

<400> SEQUENCE: 399
ctgcctagat cggc                                                    14

<210> SEQ ID NO 400
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 400
attcttggga ttgttggtct t                                            21

<210> SEQ ID NO 401
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 401
ctccagcatc tgctgcttct t                                            21

<210> SEQ ID NO 402
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 402
```

```
tttgatcgag gttagccgtg                                              20

<210> SEQ ID NO 403
<211> LENGTH: 21
<212> TYPE: DNA
<213> ORGANISM: Artificial Sequence
<220> FEATURE:
<223> OTHER INFORMATION: Antisense Oligonucleotide
<220> FEATURE:
<221> NAME/KEY: misc_feature
<222> LOCATION: 1-19
<223> OTHER INFORMATION: bases at these positions are RNA

<400> SEQUENCE: 403
cgagaggcgg acgggaccgt t                                            21

<210> SEQ ID NO 404
<211> LENGTH: 21
<212> TYPE: DNA
<213> ORGANISM: Artificial Sequence
<220> FEATURE:
<223> OTHER INFORMATION: Antisense Oligonucleotide
<220> FEATURE:
<221> NAME/KEY: misc_feature
<222> LOCATION: 3, 4, 6, 8, 9, 10, 11, 12,
      14, 15, 16, 17, 19, 20, 21
<223> OTHER INFORMATION: bases at these positions are RNA

<400> SEQUENCE: 404
ttgctctccg cctgccctgg c                                            21

<210> SEQ ID NO 405
<211> LENGTH: 19
<212> TYPE: RNA
<213> ORGANISM: Artificial Sequence
<220> FEATURE:
<223> OTHER INFORMATION: Antisense Oligonucleotide

<400> SEQUENCE: 405
cgagaggcgg acgggaccg                                               19

<210> SEQ ID NO 406
<211> LENGTH: 19
<212> TYPE: DNA
<213> ORGANISM: Artificial Sequence
<220> FEATURE:
<223> OTHER INFORMATION: Antisense Oligonucleotide
<220> FEATURE:
<221> NAME/KEY: misc_feature
<222> LOCATION: 1, 2, 4, 6, 7, 8, 9, 10, 12, 13,
      14, 15, 17, 18, 19
<223> OTHER INFORMATION: bases at these positions are RNA

<400> SEQUENCE: 406
gctctccgcc tgccctggc                                               19
```

ANTISENSE OLIGONUCLEOTIDE MODULATION OF STAT3 EXPRESSION This application is a divisional of U.S. application Ser. No. 10/773,678, filed Feb. 6, 2004 now U.S Pat. No. 7,098,192.

FIELD OF THE INVENTION

This invention relates to compositions and methods for modulating expression of the human STAT3 gene, which encodes a naturally present DNA-binding protein involved in signal transduction and transcriptional activation, and is implicated in disease. This invention is also directed to methods for inhibiting STAT3-mediated signal transduction and transcriptional activation; these methods can be used diagnostically or therapeutically. Furthermore, this invention is directed to treatment of conditions associated with expression of the human STAT3 gene.

BACKGROUND OF THE INVENTION

The STAT (signal transducers and activators of transcription) family of proteins are DNA-binding proteins that play a dual role in signal transduction and activation of transcription. Presently, there are six distinct members of the STAT family (STAT1, STAT2, STAT3, STAT4, STAT5, and STAT6) and several isoforms (STAT1•, STAT1•, STAT3• and STAT3•). The activities of the STATs are modulated by various cytokines and mitogenic stimuli. Binding of a cytokine to its receptor results in the activation of Janus protein tyrosine kinases (JAKs) associated with these receptors. This in turn, phosphorylates STAT, resulting in translocation to the nucleus and transcriptional activation of STAT responsive genes. Phosphorylation on a specific tyrosine residue on the STATs results in their activation, resulting in the formation of homodimers and/or heterodimers of STAT which bind to specific gene promoter sequences. Events mediated by cytokines through STAT activation include cell proliferation and differentiation and prevention of apoptosis.

The specificity of STAT activation is due to specific cytokines, i.e. each STAT is responsive to a small number of specific cytokines. Other non-cytokine signaling molecules, such as growth factors, have also been found to activate STATs. Binding of these factors to a cell surface receptor associated with protein tyrosine kinase also results in phosphorylation of STAT.

STAT3 (also acute phase response factor (APRF)), in particular, has been found to be responsive to interleukin-6 (IL-6) as well as epidermal growth factor (EGF) (Darnell, Jr., J. E., et al., *Science*, 1994, 264, 1415-1421). In addition, STAT3 has been found to have an important role in signal transduction by interferons (Yang, C.-H., et al., *Proc. Natl. Acad. Sci. USA*, 1998, 95, 5568-5572). Evidence exists suggesting that STAT3 may be regulated by the MAPK pathway. ERK2 induces serine phosphorylation and also associates with STAT3 (Jain, N., et al., *Oncogene*, 1998, 17, 3157-3167).

STAT3 is expressed in most cell types (Zhong, Z., et al., *Proc. Natl. Acad. Sci. USA*, 1994, 91, 4806-4810). It induces the expression of genes involved in response to tissue injury and inflammation. STAT3 has also been shown to prevent apoptosis through the expression of bcl-2 (Fukada, T., et al., *Immunity*, 1996, 5, 449-460).

Aberrant expression of or constitutive expression of STAT3 is associated with a number of disease processes. STAT3 has been shown to be involved in cell transformation.

It is constitutively activated in v-src-transformed cells (Yu, C.-L., et al., *Science*, 1995, 269, 81-83). Constitutively active STAT3 also induces STAT3 mediated gene expression and is required for cell transformation by src (Turkson, J., et al., *Mol. Cell. Biol.*, 1998, 18, 2545-2552). STAT3 is also constitutively active in Human T cell lymphotropic virus I (HTLV-I) transformed cells (Migone, T.-S. et al., *Science*, 1995, 269, 79-83).

Constitutive activation and/or overexpression of STAT3 appears to be involved in several forms of cancer, including myeloma, breast carcinomas, prostate cancer, brain tumors, head and neck carcinomas, melanoma, leukemias and lymphomas, particularly chronic myelogenous leukemia and multiple myeloma. Niu et al., *Cancer Res.*, 1999, 59, 5059-5063. Breast cancer cell lines that overexpress EGFR constitutively express phosphorylated STAT3 (Sartor, C. I., et al., *Cancer Res.*, 1997, 57, 978-987; Garcia, R., et al., *Cell Growth and Differentiation*, 1997, 8, 1267-1276). Activated STAT3 levels were also found to be elevated in low grade glioblastomas and medulloblastomas (Cattaneo, E., et al., *Anticancer Res.*, 1998, 18, 2381-2387).

Cells derived from both rat and human prostate cancers have been shown to have constitutively activated STAT3, with STAT3 activation being correlated with malignant potential. Expression of a dominant-negative STAT3 was found to significantly inhibit the growth of human prostate cells. Ni et al., *Cancer Res.*, 2000, 60, 1225-1228.

STAT3 has also been found to be constitutively activated in some acute leukemias (Gouilleux-Gruart, V., et al., *Leuk. Lymphoma*, 1997, 28, 83-88) and T cell lymphoma (Yu, C.-L., et al., *J. Immunol.*, 1997, 159, 5206-5210). Interestingly, STAT3 has been found to be constitutively phosphorylated on a serine residue in chronic lymphocytic leukemia (Frank, D. A., et al., *J. Clin. Invest.*, 1997, 100, 3140-3148). In addition, antisense oligonucleotides to STAT3 have been shown to promote apoptosis in non small cell lung cancer cells (Song et al., *Oncogene* 22:4150, 2003) and prostate cancer cells (Mora et al., *Cancer Res.* 62:6659, 2002).

STAT3 has been found to be constitutively active in myeloma tumor cells, both in culture and in bone marrow mononuclear cells from patients with multiple myeloma. These cells are resistant to Fas-mediated apoptosis and express high levels of Bcl-xL. STAT3 signaling was shown to be essential for survival of myeloma tumor cells by conferring resistance to apoptosis. Thus STAT3 is a potential target for therapeutic intervention in multiple myeloma and other cancers with activated STAT3 signaling. There is a distinct medical need for novel therapies for chemoresistant myeloma. Velcade was approved in May 2003 with an 188 evaluable patient pivotal trial based on tumor shrinkage, not survival. 28% showed a partial tresponse. The data is currently under FDA review.

Catlett-Falcone, R., et al., *Immunity*, 1999, 10, 105-115. A gene therapy approach in a syngeneic mouse tumor model system has been used to inhibit activated STAT3 in vivo using a dominant-negative STAT3 variant. This inhibition of activated STAT3 signaling was found to suppress B16 melanoma tumor growth and induce apoptosis of B16 tumor cells in vivo. Interestingly, the number of apoptotic cells (95%) exceeded the number of transfected cells, indicating a possible antitumor "bystander effect" in which an inflammatory response (tumor infiltration by acute and chronic inflammatory cells) may participate in killing of residual tumor cells. Niu et al., *Cancer Res.*, 1999, 59, 5059-5063. Constitutively activated STAT3 is also associated with chronic myelogenous leukemia.

STAT3 may also play a role in inflammatory diseases including rheumatoid arthritis. Activated STAT3 has been found in the synovial fluid of rheumatoid arthritis patients (Sengupta, T. K., et al., *J. Exp. Med.*, 1995, 181, 1015-1025) and cells from inflamed joints (Wang, F., et al., *J. Exp. Med.*, 1995, 182, 1825-1831).

Multiple forms of STAT3 exist, generated by alternative splicing. STAT3• is a short form of STAT3 (also, STAT3•) that differs predominately by the absence of 55 amino acid residues at the C-terminus. This domain contains the trans-activation domain, and thus, STAT3• may act as a negative regulator of STAT3 function (Caldenhoven, E., et al., *J. Biol. Chem.*, 1996, 271, 13221-13227). STAT3• has been found to be more stable and have greater DNA-binding activity than STAT3•, while STAT3• is more transcriptionally active.

There are currently several approaches for inhibiting STAT3 expression. U.S. Pat. Nos. 5,719,042 and 5,844,082 to Akira, S. and Kishimoto, T. disclose the use of inhibitors of APRF, including antibodies, antisense nucleic acids and ribozymes for the treatment of IL-6 associated diseases, such as inflammatory diseases, leukemia, and cancer. Schreiber, R. D., et al., in U.S. Pat. Nos. 5,731,155; 5,582,999; and 5,463,023, disclose methods of inhibiting transcriptional activation using short peptides that bind p91. Darnell, J. E., et al., in U.S. Pat. No. 5,716,622, disclose peptides containing the DNA binding domain of STATs, chimeric proteins containing the DNA binding domain, and antibodies to STATs for inhibiting STAT transcriptional activation.

The use of an antisense oligonucleotide targeted to the translation start region of human STAT3 has been disclosed (Grandis, J. R., et al., *J. Clin. Invest.*, 1998, 102, 1385-1392). In this report, a phosphorothioate oligodeoxynucleotide complementary to the translation start region of STAT3 inhibited TGF-β stimulated cell growth mediated by the epidermal growth factor receptor (EGFR).

There remains an unmet need for therapeutic compositions and methods targeting expression of STAT3, and disease processes associated therewith.

SUMMARY OF THE INVENTION

The present invention provides oligonucleotides which are targeted to nucleic acids encoding STAT3 and are capable of modulating STAT3 expression. The present invention also provides chimeric oligonucleotides targeted to nucleic acids encoding human STAT3. The oligonucleotides of the invention are believed to be useful both diagnostically and therapeutically, and are believed to be particularly useful in the methods of the present invention.

The present invention also comprises methods of modulating the expression of human STAT3, in cells and tissues, using the oligonucleotides of the invention. Methods of inhibiting STAT3 expression are provided; these methods are believed to be useful both therapeutically and diagnostically. These methods are also useful as tools, for example, for detecting and determining the role of STAT3 in various cell functions and physiological processes and conditions and for diagnosing conditions associated with expression of STAT3.

The present invention also comprises methods for diagnosing and treating inflammatory diseases, particularly rheumatoid arthritis, and cancers, including those of the breast, prostate, head and neck, and brain, myelomas and melanomas and leukemias and lymphomas. These methods are believed to be useful, for example, in diagnosing STAT3-associated disease progression. These methods employ the oligonucleotides of the invention. These methods are believed to be useful both therapeutically, including prophylactically, and as clinical research and diagnostic tools.

DETAILED DESCRIPTION OF THE INVENTION

STAT3 plays an important role in cytokine signal transduction. Overexpression and/or constitutive activation of STAT3 is associated with a number of inflammatory diseases and cancers. As such, this DNA-binding protein represents an attractive target for treatment of such diseases. In particular, modulation of the expression of STAT3 may be useful for the treatment of diseases such as rheumatoid arthritis, breast cancer, prostate cancer, brain cancer, head and neck cancer, myelomas, melanomas, leukemias and lymphomas.

The present invention employs antisense compounds, particularly oligonucleotides, for use in modulating the function of nucleic acid molecules encoding STAT3, ultimately modulating the amount of STAT3 produced. This is accomplished by providing oligonucleotides which specifically hybridize with nucleic acids, preferably mRNA, encoding STAT3.

This relationship between an antisense compound such as an oligonucleotide and its complementary nucleic acid target, to which it hybridizes, is commonly referred to as "antisense". "Targeting" an oligonucleotide to a chosen nucleic acid target, in the context of this invention, is a multistep process. The process usually begins with identifying a nucleic acid sequence whose function is to be modulated. This may be, as examples, a cellular gene (or mRNA made from the gene) whose expression is associated with a particular disease state, or a foreign nucleic acid from an infectious agent. In the present invention, the targets are nucleic acids encoding STAT3; in other words, a gene encoding STAT3, or mRNA expressed from the STAT3 gene mRNA which encodes STAT3 is presently the preferred target. The targeting process also includes determination of a site or sites within the nucleic acid sequence for the antisense interaction to occur such that modulation of gene expression will result.

In accordance with this invention, persons of ordinary skill in the art will understand that messenger RNA includes not only the information to encode a protein using the three letter genetic code, but also associated ribonucleotides which form a region known to such persons as the 5'-untranslated region, the 3'-untranslated region, the 5' cap region and intron/exon junction ribonucleotides. Thus, oligonucleotides may be formulated in accordance with this invention which are targeted wholly or in part to these associated ribonucleotides as well as to the informational ribonucleotides. The oligonucleotide may therefore be specifically hybridizable with a transcription initiation site region, a translation initiation codon region, a 5' cap region, an intron/exon junction, coding sequences, a translation termination codon region or sequences in the 5'- or 3'-untranslated region. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon." A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formyl-methionine (prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding STAT3, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region," "AUG region" and "translation initiation codon region" refer to a portion of such an mRNA or gene that encompasses from about 25 to about 50 contiguous nucleotides in either direction (i.e., 5' or 3') from a translation initiation codon. This region is a preferred target region. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. This region is a preferred target region. The open reading frame (ORF) or "coding region," which is known in the art to refer to the region between the translation initiation codon and the translation termination codon, is also a region which may be targeted effectively. Other preferred target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns", which are excised from a pre-mRNA transcript to yield one or more mature mRNA. The remaining (and therefore translated) regions are known as "exons" and are spliced together to form a continuous mRNA sequence. mRNA splice sites, i.e., exon-exon or intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. Targeting particular exons in alternatively spliced mRNAs may also be preferred. It has also been found that introns can also be effective, and therefore preferred, target regions for antisense compounds targeted, for example, to DNA or pre-mRNA.

Once the target site or sites have been identified, oligonucleotides are chosen which are sufficiently complementary to the target, i.e., hybridize sufficiently well and with sufficient specificity, to give the desired modulation.

"Hybridization", in the context of this invention, means hydrogen bonding, also known as Watson-Crick base pairing, between complementary bases, usually on opposite nucleic acid strands or two regions of a nucleic acid strand. Guanine and cytosine are examples of complementary bases which are known to form three hydrogen bonds between them. Adenine and thymine are examples of complementary bases which form two hydrogen bonds between them.

"Specifically hybridizable" and "complementary" are terms which are used to indicate a sufficient degree of complementarity such that stable and specific binding occurs between the DNA or RNA target and the oligonucleotide.

It is understood that an oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment or, in the case of in vitro assays, under conditions in which the assays are conducted.

Hybridization of antisense oligonucleotides with mRNA interferes with one or more of the normal functions of mRNA. The functions of mRNA to be interfered with include all vital functions such as, for example, translocation of the RNA to the site of protein translation, translation of protein from the RNA, splicing of the RNA to yield one or more mRNA species, and catalytic activity which may be engaged in by the RNA. Binding of specific protein(s) to the RNA may also be interfered with by antisense oligonucleotide hybridization to the RNA.

The overall effect of interference with mRNA function is modulation of expression of STAT3. In the context of this invention "modulation" means either inhibition or stimulation; i.e., either a decrease or increase in expression. This modulation can be measured in ways which are routine in the art, for example by Northern blot assay of mRNA expression, or reverse transcriptase PCR, as taught in the examples of the instant application or by Western blot or ELISA assay of protein expression, or by an immunoprecipitation assay of protein expression. Effects on cell proliferation or tumor cell growth can also be measured, as taught in the examples of the instant application. Inhibition is presently preferred.

In addition to the well known antisense effects of oligonucleotides, it has also been found that oligonucleotide analogs having at least one phosphorothioate bond can induce stimulation of a local immune response. This is described in U.S. Pat. No. 5,663,153 which is commonly assigned to the assignee of the present invention and is herein incorporated by reference in its entirety. This immunostimulatory effect does not appear to be related to any antisense effect which these oligonucleotide analogs may or may not possess. These oligonucleotide analogs are useful as immunopotentiators, either alone or in combination with other therapeutic modalities, such as drugs, particularly antiinfective and anticancer drugs, and surgical procedures to increase efficacy. In addition, the antiinfective and anticancer effects already possessed by certain antisense oligonucleotide analogs are enhanced through such immune stimulation.

It has also been found that oligonucleotide analogs having at least one phosphorothioate bond can be used to induce stimulation of a systemic or humoral immune response.

Thus, these oligonucleotides are also useful as immunopotentiators of an antibody response, either alone or in combination with other therapeutic modalities. U.S. Pat. No. 5,663,153.

It is presently believed, therefore, that, in addition to the antisense effects of oligonucleotides targeted to STAT3, oligonucleotides containing at least one phosphorothioate backbone linkage may be useful in eliciting an immune response which may add to the antitumor "bystander effect" already observed with dominant negative inhibitors of STAT3 signaling. Niu et al., *Cancer Res.*, 1999, 59, 5059-5063. This effect is believed to be related to tumor infiltration by acute and chronic inflammatory cells which may participate in killing of residual tumor cells. Thus the therapeutic effects of antisense oligonucleotides targeted to STAT3 may be potentiated by the immunostimulatory properties of the oligonucleotides themselves. Alternatively, oligonucleotides which may not be targeted to STAT3 but which contain at least one phosphorothioate backbone linkage may be used as adjuvants in combination with antisense or other inhibitors of STAT3.

The oligonucleotides of this invention can be used in diagnostics, therapeutics, prophylaxis, and as research reagents and in kits. Since the oligonucleotides of this invention hybridize to nucleic acids encoding STAT3, sandwich, colorimetric and other assays can easily be constructed to exploit this fact. Provision of means for detecting hybridization of oligonucleotide with the STAT3 gene or mRNA can routinely be accomplished. Such provision may include enzyme conjugation, radiolabelling or any other suitable detection systems. Kits for detecting the presence or absence of STAT3 may also be prepared.

The present invention is also suitable for diagnosing abnormal inflammatory states or certain cancers in tissue or other samples from patients suspected of having an inflammatory disease such as rheumatoid arthritis or cancers such as breast, brain, or head and neck cancer, melanomas, myelomas, leukemias and lymphomas. A number of assays may be formulated employing the present invention, which assays will commonly comprise contacting a tissue sample with an oligonucleotide of the invention under conditions selected to permit detection and, usually, quantitation of such inhibition. In the context of this invention, to "contact" tissues or cells with an oligonucleotide or oligonucleotides means to add the oligonucleotide(s), usually in a liquid carrier, to a cell suspension or tissue sample, either in vitro or ex vivo, or to administer the oligonucleotide(s) to cells or tissues within an animal.

The oligonucleotides of this invention may also be used for research purposes. Thus, the specific hybridization exhibited by the oligonucleotides may be used for assays, purifications, cellular product preparations and in other methodologies which may be appreciated by persons of ordinary skill in the art.

In the context of this invention, the term "oligonucleotide" refers to an oligomer or polymer of ribonucleic acid or deoxyribonucleic acid. This term includes oligonucleotides composed of naturally-occurring nucleobases, sugars and covalent intersugar (backbone) linkages as well as oligonucleotides having non-naturally-occurring portions which function similarly. Such modified or substituted oligonucleotides are often preferred over native forms because of desirable properties such as, for example, enhanced cellular uptake, enhanced binding to target and increased stability in the presence of nucleases.

The antisense compounds in accordance with this invention preferably comprise from about 5 to about 50 nucleobases. Particularly preferred are antisense oligonucleotides comprising from about 8 to about 30 nucleobases (i.e. from about 8 to about 30 linked nucleosides). As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2=, 3= or 5=hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3= to 5=phosphodiester linkage.

While the preferred form of antisense compound is a single-stranded antisense oligonucleotide, in many species the introduction of double-stranded structures, such as double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing.

The first evidence that dsRNA could lead to gene silencing in animals came in 1995 from work in the nematode, *Caenorhabditis elegans* (Guo and Kempheus, *Cell*, 1995, 81, 611-620). Montgomery et al. have shown that the primary interference effects of dsRNA are posttranscriptional (Montgomery et al., *Proc. Natl. Acad. Sci. USA*, 1998, 95, 15502-15507). The posttranscriptional antisense mechanism defined in *Caenorhabditis elegans* resulting from exposure to double-stranded RNA (dsRNA) has since been designated RNA interference (RNAi). This term has been generalized to mean antisense-mediated gene silencing involving the introduction of dsRNA leading to the sequence-specific reduction of endogenous targeted mRNA levels (Fire et al., *Nature*, 1998, 391, 806-811). Recently, it has been shown that it is, in fact, the single-stranded RNA oligomers of antisense polarity of the dsRNAs which are the potent inducers of RNAi (Tijsterman et al., *Science*, 2002, 295, 694-697). The use of these double stranded RNA molecules (short interfering RNA or siRNA) for targeting and inhibiting the expression of STAT3 mRNA is also contemplated. These double stranded RNA molecules target regions similar to those targeted by antisense oligocleotides and have similar effects. These double stranded RNA molecules are generally 19-21 base pairs in length, but may range between 8 and 50 nucleobases. The production of siRNA molecules is described in a general sense in the examples provided below, but it will be appreciated that any desired siRNA targeted to STAT3 may be synthesized by conventional oligonucleotide synthesis techniques. Once the sequence of the antisense strand is known, the complementary sense strand is synthesized based on base pairing. The sense and antisense strands are then combined to form the siRNA.

Oligomer and Monomer Modifications

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are generally preferred. In addition, linear compounds may have internal nucleobase complementarity and may therefore fold in a manner as to produce a fully or partially double-stranded compound. Within oligonucleotides, the phosphate groups are commonly referred to as forming the internucleoside linkage or in conjunction with the sugar ring the backbone of the oligonucleotide. The normal internucleoside linkage that makes up the backbone of RNA and DNA is a 3' to 5' phosphodiester linkage.

Modified Internucleoside Linkages

Specific examples of preferred antisense oligomeric compounds useful in this invention include oligonucleotides containing modified e.g. non-naturally occurring internucleoside linkages. As defined in this specification, oligonucleotides having modified internucleoside linkages include internucleoside linkages that retain a phosphorus atom and internucleoside linkages that do not have a phosphorus atom. For the purposes of this specification, and as sometimes referenced in the art, modified oligonucleotides that do not have a phosphorus atom in their internucleoside backbone can also be considered to be oligonucleosides.

In the *C. elegans* system, modification of the internucleotide linkage (phosphorothioate) did not significantly interfere with RNAi activity. Based on this observation, it is suggested that certain preferred oligomeric compounds of the invention can also have one or more modified internucleoside linkages. A preferred phosphorus containing modified internucleoside linkage is the phosphorothioate internucleoside linkage.

Preferred modified oligonucleotide backbones containing a phosphorus atom therein include, for example, phosphorothioates, chiral phosphorothioates, phosphoro-dithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and borano-phosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

In more preferred embodiments of the invention, oligomeric compounds have one or more phosphorothioate and/or heteroatom internucleoside linkages, in particular —CH$_2$—NH—O—CH$_2$—, —CH$_2$—N(CH$_3$)—O—CH$_2$— [known as a methylene (methylimino) or MMI backbone], —CH$_2$—O—N(CH$_3$)—CH$_2$—, —CH$_2$—N(CH$_3$)—N(CH$_3$)—CH$_2$— and —O—N(CH$_3$)—CH$_2$—CH$_2$— [wherein the native phosphodiester internucleotide linkage is represented as —O—P(=O) (OH)—O—CH$_2$—]. The MMI type internucleoside linkages are disclosed in the above referenced U.S. Pat. No. 5,489,677. Preferred amide internucleoside linkages are disclosed in the above referenced U.S. Pat. No. 5,602,240.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH$_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

Oligomer Mimetics

Another preferred group of oligomeric compounds amenable to the present invention includes oligonucleotide mimetics. The term mimetic as it is applied to oligonucleotides is intended to include oligomeric compounds wherein only the furanose ring or both the furanose ring and the internucleotide linkage are replaced with novel groups, replacement of only the furanose ring is also referred to in the art as being a sugar surrogate. The heterocyclic base moiety or a modified heterocyclic base moiety is maintained for hybridization with an appropriate target nucleic acid. One such oligomeric compound, an oligonucleotide mimetic that has been shown to have excellent hybridization properties, is referred to as a peptide nucleic acid (PNA). In PNA oligomeric compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone.

Representative United States patents that teach the preparation of PNA oligomeric compounds include, but are not limited to, U.S. Pat. Nos. 5,539,082; 5,714,331; and 5,719,262, each of which is herein incorporated by reference. Further teaching of PNA oligomeric compounds can be found in Nielsen et al., Science, 1991, 254, 1497-1500.

One oligonucleotide mimetic that has been reported to have excellent hybridization properties is peptide nucleic acids (PNA). The backbone in PNA compounds is two or more linked aminoethylglycine units which gives PNA an amide containing backbone. The heterocyclic base moieties are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

PNA has been modified to incorporate numerous modifications since the basic PNA structure was first prepared. The basic structure is shown below:

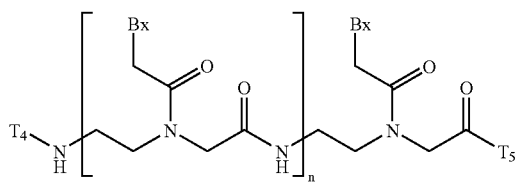

wherein

Bx is a heterocyclic base moiety;

$T_4$ is hydrogen, an amino protecting group, —C(O)$R_5$, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, alkylsulfonyl, arylsulfonyl, a chemical functional group, a reporter group, a conjugate group, a D or L α-amino acid linked via the α-carboxyl group or optionally through the ω-carboxyl group when the amino acid is aspartic acid or glutamic acid or a peptide derived from D, L or mixed D and L amino acids linked through a carboxyl group, wherein the substituent groups are selected from hydroxyl, amino, alkoxy, carboxy, benzyl, phenyl, nitro, thiol, thioalkoxy, halogen, alkyl, aryl, alkenyl and alkynyl;

$T_5$ is —OH, —N($Z_1$) $Z_2$, $R_5$, D or L α-amino acid linked via the α-amino group or optionally through the ω-amino group when the amino acid is lysine or ornithine or a peptide derived from D, L or mixed D and L amino acids linked through an amino group, a chemical functional group, a reporter group or a conjugate group;

$Z_1$ is hydrogen, $C_1$-$C_6$ alkyl, or an amino protecting group;

$Z_2$ is hydrogen, $C_1$-$C_6$ alkyl, an amino protecting group, —C(=O)—(CH$_2$)$_n$-J-$Z_3$, a D or L α-amino acid linked via the α-carboxyl group or optionally through the ω-carboxyl group when the amino acid is aspartic acid or glutamic acid or a peptide derived from D, L or mixed D and L amino acids linked through a carboxyl group;

$Z_3$ is hydrogen, an amino protecting group, —$C_1$-$C_6$ alkyl, —C(=O)—CH$_3$, benzyl, benzoyl, or —(CH$_2$)$_n$—N(H)$Z_1$;

each J is O, S or NH;

$R_5$ is a carbonyl protecting group; and n is from 2 to about 50.

Another class of oligonucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. A preferred class of linking groups have been selected to give a non-ionic oligomeric compound. The non-ionic morpholino-based oligomeric compounds are less likely to have undesired interactions with cellular proteins. Morpholino-based oligomeric compounds are non-ionic mimics of oligonucleotides which are less likely to form undesired interactions with cellular proteins (Dwaine A. Braasch and David R. Corey, Biochemistry, 2002, 41(14), 4503-4510). Morpholino-based oligomeric compounds are disclosed in U.S. Pat. No. 5,034,506, issued Jul. 23, 1991. The morpholino class of oligomeric compounds have been prepared having a variety of different linking groups joining the monomeric subunits.

Morpholino nucleic acids have been prepared having a variety of different linking groups ($L_2$) joining the monomeric subunits. The basic formula is shown below:

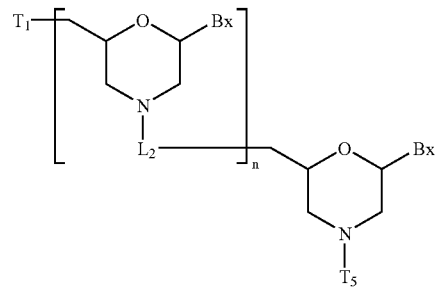

wherein $T_1$ is hydroxyl or a protected hydroxyl;

$T_5$ is hydrogen or a phosphate or phosphate derivative;

$L_2$ is a linking group; and n is from 2 to about 50.

A further class of oligonucleotide mimetic is referred to as cyclohexenyl nucleic acids (CeNA). The furanose ring normally present in an DNA/RNA molecule is replaced with a cyclohenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (see Wang et al., J. Am. Chem. Soc., 2000, 122, 8595-8602). In general the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation. Furthermore the incorporation of CeNA into a sequence targeting RNA was stable to serum and able to activate E. Coli RNase resulting in cleavage of the target RNA strand.

The general formula of CeNA is shown below:

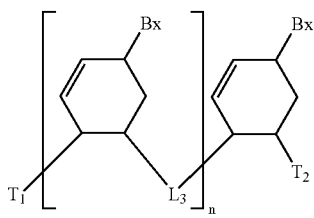

wherein
each Bx is a heterocyclic base moiety;
$T_1$ is hydroxyl or a protected hydroxyl; and
$T_2$ is hydroxyl or a protected hydroxyl.

Another class of oligonucleotide mimetic (anhydrohexitol nucleic acid) can be prepared from one or more anhydrohexitol nucleosides (see, wouters and Herdewijn, *Bioorg. Med. Chem. Lett.*, 1999, 9, 1563-1566) and would have the general formula:

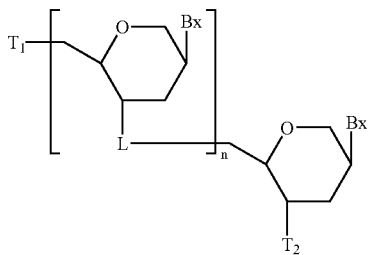

A further preferred modification includes Locked Nucleic Acids (LNAS) in which the 2'-hydroxyl group is linked to the 4' carbon atom of the sugar ring thereby forming a 2'-C, 4'-C-oxymethylene linkage thereby forming a bicyclic sugar moiety. The linkage is preferably a methylene $(-CH_2-)_n$ group bridging the 2' oxygen atom and the 4' carbon atom wherein n is 1 or 2 (Singh et al., Chem. Commun., 1998, 4, 455-456). LNA and LNA analogs display very high duplex thermal stabilities with complementary DNA and RNA (Tm=+3 to +10 C), stability towards 3'-exonucleolytic degradation and good solubility properties. The basic structure of LNA showing the bicyclic ring system is shown below:

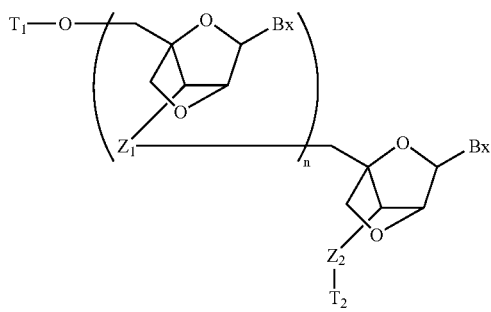

The conformations of LNAs determined by 2D NMR spectroscopy have shown that the locked orientation of the LNA nucleotides, both in single-stranded LNA and in duplexes, constrains the phosphate backbone in such a way as to introduce a higher population of the N-type conformation (Petersen et al., J. Mol. Recognit., 2000, 13, 44-53). These conformations are associated with improved stacking of the nucleobases (Wengel et al., Nucleosides Nucleotides, 1999, 18, 1365-1370).

LNA has been shown to form exceedingly stable LNA: LNA duplexes (Koshkin et al., J. Am. Chem. Soc., 1998, 120, 13252-13253). LNA:LNA hybridization was shown to be the most thermally stable nucleic acid type duplex system, and the RNA-mimicking character of LNA was established at the duplex level. Introduction of 3 LNA monomers (T or A) significantly increased melting points (Tm=+15/+11) toward DNA complements. The universality of LNA-mediated hybridization has been stressed by the formation of exceedingly stable LNA:LNA duplexes. The RNA-mimicking of LNA was reflected with regard to the N-type conformational restriction of the monomers and to the secondary structure of the LNA:RNA duplex.

LNAs also form duplexes with complementary DNA, RNA or LNA with high thermal affinities. Circular dichroism (CD) spectra show that duplexes involving fully modified LNA. (esp. LNA:RNA) structurally resemble an A-form RNA:RNA duplex. Nuclear magnetic resonance (NMR) examination of an LNA:DNA duplex confirmed the 3'-endo conformation of an LNA monomer. Recognition of double-stranded DNA has also been demonstrated suggesting strand invasion by LNA. Studies of mismatched sequences show that LNAs obey the Watson-Crick base pairing rules with generally improved selectivity compared to the corresponding unmodified reference strands.

Novel types of LNA-oligomeric compounds, as well as the LNAs, are useful in a wide range of diagnostic and therapeutic applications. Among these are antisense applications, PCR applications, strand-displacement oligomers, substrates for nucleic acid polymerases and generally as nucleotide based drugs. Potent and nontoxic antisense oligonucleotides containing LNAs have been described (Wahlestedt et al., Proc. Natl. Acad. Sci. U.S. A., 2000, 97, 5633-5638.) The authors have demonstrated that LNAs confer several desired properties to antisense agents. LNA/DNA copolymers were not degraded readily in blood serum and cell extracts. LNA/DNA copolymers exhibited potent antisense activity in assay systems as disparate as G-protein-coupled receptor signaling in living rat brain and detection of reporter genes in *Escherichia coli*. Lipofectin-mediated efficient delivery of LNA into living human breast cancer cells has also been accomplished.

The synthesis and preparation of the LNA monomers adenine, cytosine, guanine, 5-methyl-cytosine, thymine and uracil, along with their oligomerization, and nucleic acid recognition properties have been described (Koshkin et al., Tetrahedron, 1998, 54, 3607-3.630). LNAs and preparation thereof are also described in WO 98/39352 and WO 99/14226.

The first analogs of LNA, phosphorothioate-LNA and 2'-thio-LNAs, have also been prepared (Kumar et al., Bioorg. Med. Chem. Lett., 1998, 8, 2219-2222). Preparation of locked nucleoside analogs containing oligodeoxyribonucleotide duplexes as substrates for nucleic acid polymerases has also been described (Wengel et al., PCT International Application WO 98-DK393 19980914). Furthermore, synthesis of 2'-amino-LNA, a novel conformationally restricted high-affinity oligonucleotide analog with a handle has been described in the art (Singh et al., J. Org. Chem., 1998, 63, 10035-10039). In addition, 2'-Amino- and 2'-methylamino-LNA's have been prepared and the thermal stability of their duplexes with complementary RNA and DNA strands has been previously reported.

Further oligonucleotide mimetics have been prepared to include bicyclic and tricyclic nucleoside analogs having the formulas (amidite monomers shown):

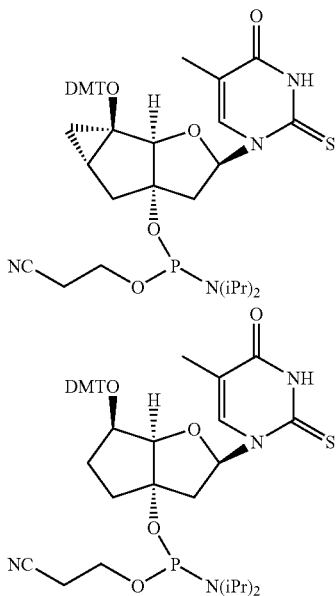

(see Steffens et al., *Helv. Chim. Acta,* 1997, 80, 2426-2439; Steffens et al., *J. Am. Chem. Soc.,* 1999, 121, 3249-3255; and Renneberg et al., *J. Am. Chem. Soc.,* 2002, 124, 5993-6002). These modified nucleoside analogs have been oligomerized using the phosphoramidite approach and the resulting oligomeric compounds containing tricyclic nucleoside analogs have shown increased thermal stabilities (Tm's) when hybridized to DNA, RNA and itself. Oligomeric compounds containing bicyclic nucleoside analogs have shown thermal stabilities approaching that of DNA duplexes.

Another class of oligonucleotide mimetic is referred to as phosphonomonoester nucleic acids incorporate a phosphorus group in a backbone the backbone. This class of oligonucleotide mimetic is reported to have useful physical and biological and pharmacological properties in the areas of inhibiting gene expression (antisense oligonucleotides, ribozymes, sense oligonucleotides and triplex-forming oligonucleotides), as probes for the detection of nucleic acids and as auxiliaries for use in molecular biology.

The general formula (for definitions of Markush variables see: U.S. Pat. Nos. 5,874,553 and 6,127,346 herein incorporated by reference in their entirety) is shown below.

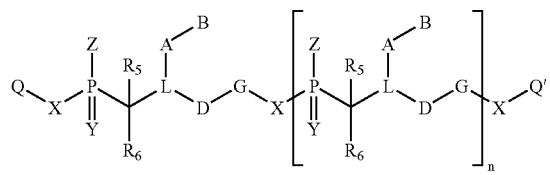

Another oligonucleotide mimetic has been reported wherein the furanosyl ring has been replaced by a cyclobutyl moiety.

Modified Sugars

Oligomeric compounds of the invention may also contain one or more substituted sugar moieties. Preferred oligomeric compounds comprise a sugar substituent group selected from: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3]_2$, where n and m are from 1 to about 10. Other preferred oligonucleotides comprise a sugar substituent group selected from: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., *Helv. Chim. Acta,* 1995, 78, 486-504) i.e., an alkoxyalkoxy group. A further preferred modification includes 2'-dimethylaminooxyethoxy, i.e., a $O(CH_2)_2 ON(CH_3)$, group, also known as 2'-DMAOE, as described in examples hereinbelow, and 2'-dimethylamino-ethoxyethoxy (also known in the art as 2'-O-dimethyl-amino-ethoxy-ethyl or 2'-DMAEOE), i.e., 2'-O—$CH_2$—O—$CH_2$—N($CH_3$)$_2$.

Other preferred sugar substituent groups include methoxy (—O—$CH_3$), aminopropoxy (—$OCH_2CH_2CH_2NH_2$), allyl (—$CH_2$—CH=$CH_2$), —O-allyl (—O—$CH_2$—CH=$CH_2$) and fluoro (F). 2'-Sugar substituent groups may be in the arabino (up) position or ribo (down) position. A preferred 2'-arabino modification is 2'-F. Similar modifications may also be made at other positions on the oligomeric compound, particularly the 3' position of the sugar on the 3' terminal nucleoside or in 2'-5' linked oligonucleotides and the 5' position of 5' terminal nucleotide. Oligomeric compounds may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

Further representative sugar substituent groups include groups of formula $I_a$ or $II_a$:

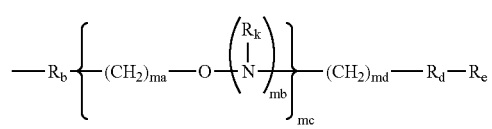

-continued

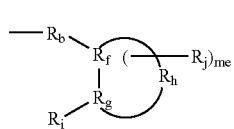

wherein:
R$_b$ is O, S or NH;
R$_d$ is a single bond, O, S or C(=O);
R$_e$ is C$_1$-C$_{10}$ alkyl, N(R$_k$)(R$_m$), N(R$_k$)(R$_n$), N=C(R$_p$)(R$_q$), N=C(R$_p$)(R$_r$) or has formula III$_a$;

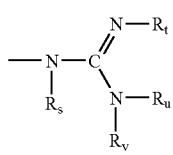

R$_p$ and R$_q$ are each independently hydrogen or C$_1$-C$_{10}$ alkyl;
R$_R$ is —R$_x$—R$_y$;
each R$_s$, R$_t$, R$_u$ and R$_v$ is, independently, hydrogen, C(O)R$_w$, substituted or unsubstituted C$_1$-C$_{10}$ alkyl, substituted or unsubstituted C$_2$-C$_{10}$ alkenyl, substituted or unsubstituted C$_2$-C$_{10}$ alkynyl, alkylsulfonyl, arylsulfonyl, a chemical functional group or a conjugate group, wherein the substituent groups are selected from hydroxyl, amino, alkoxy, carboxy, benzyl, phenyl, nitro, thiol, thioalkoxy, halogen, alkyl, aryl, alkenyl and alkynyl;

or optionally, R$_u$ and R$_v$, together form a phthalimido moiety with the nitrogen atom to which they are attached;

each R$_w$ is, independently, substituted or unsubstituted C$_1$-C$_{10}$ alkyl, trifluoromethyl, cyanoethyloxy, methoxy, ethoxy, t-butoxy, allyloxy, 9-fluorenylmethoxy, 2-(trimethylsilyl)-ethoxy, 2,2,2-trichloroethoxy, benzyloxy, butyryl, iso-butyryl, phenyl or aryl;

R$_k$ is hydrogen, a nitrogen protecting group or —R$_x$—R$_y$;
R$_p$ is hydrogen, a nitrogen protecting group or —R$_x$—R$_y$;
R$_x$ is a bond or a linking moiety;
R$_y$ is a chemical functional group, a conjugate group or a solid support medium;

each R$_m$ and R$_n$ is, independently, H, a nitrogen protecting group, substituted or unsubstituted C$_1$-C$_{10}$ alkyl, substituted or unsubstituted C$_1$-C$_{10}$ alkenyl, substituted or unsubstituted C$_2$-C$_{10}$ alkynyl, wherein the substituent groups are selected from hydroxyl, amino, alkoxy, carboxy, benzyl, phenyl, nitro, thiol, thioalkoxy, halogen, alkyl, aryl, alkenyl, alkynyl; NH$_3^+$, N(R$_u$)(R$_v$), guanidino and acyl where said acyl is an acid amide or an ester;

or R$_m$ and R$_n$, together, are a nitrogen protecting group, are joined in a ring structure that optionally includes an additional heteroatom selected from N and O or are a chemical functional group;

R$_i$ is OR$_z$, SR$_z$, or N(R$_z$)$_2$;
each R$_z$ is, independently, H, C$_1$-C$_8$ alkyl, C$_1$-C$_8$ haloalkyl, C(=NH)N(H)R$_u$, C(=O)N(H)R$_u$ or OC(=O)N(H)R$_u$;

R$_f$, R$_g$ and R$_h$ comprise a ring system having from about 4 to about 7 carbon atoms or having from about 3 to about 6 carbon atoms and 1 or 2 heteroatoms wherein said heteroatoms are selected from oxygen, nitrogen and sulfur and wherein said ring system is aliphatic, unsaturated aliphatic, aromatic, or saturated or unsaturated heterocyclic;

R$_j$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, N(R$_k$)(R$_m$)OR$_k$, halo, SR$_k$ or CN;

m$_a$ is 1 to about 10;
each mb is, independently, 0 or 1;
mc is 0 or an integer from 1 to 10;
md is an integer from 1 to 10;
me is from 0, 1 or 2; and
provided that when mc is 0, md is greater than 1.

Representative substituents groups of Formula I are disclosed in U.S. patent application Ser. No. 09/130,973, filed Aug. 7, 1998, entitled "Capped 2'-Oxyethoxy Oligonucleotides," hereby incorporated by reference in its entirety.

Representative cyclic substituent groups of Formula II are disclosed in U.S. patent application Ser. No. 09/123,108, filed Jul. 27, 1998, entitled "RNA Targeted 2'-Oligomeric compounds that are Conformationally Preorganized," hereby incorporated by reference in its entirety.

Particularly preferred sugar substituent groups include O[(CH$_2$)$_n$O]$_m$CH$_3$, O(CH$_2$)$_n$OCH$_3$, O(CH$_2$)$_n$NH$_2$, O(CH$_2$)$_n$CH$_3$, O(CH$_2$)$_n$ONH$_2$, and O(CH$_2$)$_n$ON[(CH$_2$)$_n$CH$_3$)]$_2$, where n and m are from 1 to about 10.

Representative guanidino substituent groups that are shown in formula III and IV are disclosed in co-owned U.S. patent application Ser. No. 09/349,040, entitled "Functionalized oligomers", filed Jul. 7, 1999, hereby incorporated by reference in its entirety.

Representative acetamido substituent groups are disclosed in U.S. Pat. No. 6,147,200 which is hereby incorporated by reference in its entirety.

Representative dimethylaminoethyloxyethyl substituent groups are disclosed in International Patent Application PCT/US99/17895, entitled "2'-O-Dimethylaminoethyloxyethyl-Oligomeric compounds", filed Aug. 6, 1999, hereby incorporated by reference in its entirety.

Modified Nucleobases/Naturally Occurring Nucleobases

Oligomeric compounds may also include nucleobase (often referred to in the art simply as "base" or "heterocyclic base moiety") modifications or substitutions. As used herein, "unmodified" or "natural" nucleobases include the purine bases adenine (A) and guanine (G), and the pyrimidine bases thymine (T), cytosine (C) and uracil (U). Modified nucleobases also referred herein as heterocyclic base moieties include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289-302, Crooke, S. T. and Lebleu, B., ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyl-adenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278) and are presently preferred base substitutions, even more particularly when combined with 2'-O-methoxyethyl sugar modifications.

In one aspect of the present invention oligomeric compounds are prepared having polycyclic heterocyclic compounds in place of one or more heterocyclic base moieties. A number of tricyclic heterocyclic compounds have been previously reported. These compounds are routinely used in antisense applications to increase the binding properties of the modified strand to a target strand. The most studied modifications are targeted to guanosines hence they have been termed G-clamps or cytidine analogs. Many of these polycyclic heterocyclic compounds have the general formula:

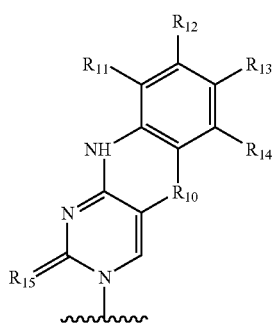

Representative cytosine analogs that make 3 hydrogen bonds with a guanosine in a second strand include 1,3-diazaphenoxazine-2-one ($R_{10=}$ O, $R_{11}$-$R_{14}$=H) [Kurchavov, et al., *Nucleosides and Nucleotides*, 1997, 16, 1837-1846], 1,3-diazaphenothiazine-2-one ($R_{10}$=S, $R_{11}$-$R_{14}$=H), [Lin, K.-Y.; Jones, R. J.; Matteucci, M. J. Am. Chem. Soc. 1995, 117, 3873-3874] and 6,7,8,9-tetrafluoro-1,3-diazaphenoxazine-2-one ($R_{10}$=O, $R_{11}$-$R_{14}$=F) [Wang, J.; Lin, K.-Y., Matteucci, M. Tetrahedron Lett. 1998, 39, 8385-8388]. Incorporated into oligonucleotides these base modifications were shown to hybridize with complementary guanine and the latter was also shown to hybridize with adenine and to enhance helical thermal stability by extended stacking interactions (also see U.S. patent application entitled "Modified Peptide Nucleic Acids" filed May 24, 2002, Ser. No. 10/155, 920; and U.S. patent application entitled "Nuclease Resistant Chimeric Oligonucleotides" filed May 24, 2002, Ser. No. 10/013,295, both of which are commonly owned with this application and are herein incorporated by reference in their entirety).

Further helix-stabilizing properties have been observed when a cytosine analog/substitute has an aminoethoxy moiety attached to the rigid 1,3-diazaphenox-azine-2-one scaffold ($R_{10=}$ O, $R_{11}$=—O—$(CH_2)_2$—$NH_2$, $R_{12-14}$=H) [Lin, K.-Y.; Matteucci, M. J. Am. Chem. Soc. 1998, 120, 8531-8532]. Binding studies demonstrated that a single incorporation could enhance the binding affinity of a model oligonucleotide to its complementary target DNA or RNA with a $\Delta T_m$ of up to 18° relative to 5-methyl cytosine ($dC5^{me}$), which is the highest known affinity enhancement for a single modification, yet. On the other hand, the gain in helical stability does not compromise the specificity of the oligonucleotides. The $T_m$ data indicate an even greater discrimination between the perfect match and mismatched sequences compared to $dC5^{me}$. It was suggested that the tethered amino group serves as an additional hydrogen bond donor to interact with the Hoogsteen face, namely the O6, of a complementary guanine thereby forming 4 hydrogen bonds. This means that the increased affinity of G-clamp is mediated by the combination of extended base stacking and additional specific hydrogen bonding.

Further tricyclic heterocyclic compounds and methods of using them that are amenable to the present invention are disclosed in U.S. Pat. No. 6,028,183, which issued on May 22, 2000, and U.S. Pat. No. 6,007,992, which issued on Dec. 28, 1999, the contents of both are commonly assigned with this application and are incorporated herein in their entirety.

The enhanced binding affinity of the phenoxazine derivatives together with their uncompromised sequence specificity makes them valuable nucleobase analogs for the development of more potent antisense-based drugs. In fact, promising data have been derived from in vitro experiments demonstrating that heptanucleotides containing phenoxazine substitutions are capable to activate RNaseH, enhance cellular uptake and exhibit an increased antisense activity [Lin, K-Y; Matteucci, M. J. Am. Chem. Soc. 1998, 120, 8531-8532]. The activity enhancement was even more pronounced in case of G-clamp, as a single substitution was shown to significantly improve the in vitro potency of a 20mer 2'-deoxyphosphorothioate oligonucleotides [Flanagan, W. M.; Wolf, J. J.; Olson, P.; Grant, D.; Lin, K.-Y.; Wagner, R. W.; Matteucci, M. Proc. Natl. Acad. Sci. USA, 1999, 96, 3513-3518]. Nevertheless, to optimize oligonucleotide design and to better understand the impact of these heterocyclic modifications on the biological activity, it is important to evaluate their effect on the nuclease stability of the oligomers.

Further modified polycyclic heterocyclic compounds useful as heterocyclic bases are disclosed in but not limited to, the above noted U.S. Pat. No. 3,687,808, as well as U.S. Pat. Nos. 4,845,205; 5,130,302; 5,134,066; 5,175,273; 5,367, 066; 5,432,272; 5,434,257; 5,457,187; 5,459,255; 5,484, 908; 5,502,177; 5,525,711; 5,552,540; 5,587,469; 5,594, 121, 5,596,091; 5,614,617; 5,645,985; 5,646,269; 5,750, 692; 5,830,653; 5,763,588; 6,005,096; and 5,681,941, and U.S. patent application Ser. No. 09/996,292 filed Nov. 28, 2001, certain of which are commonly owned with the instant application, and each of which is herein incorporated by reference.

The oligonucleotides of the present invention also include variants in which a different base is present at one or more of the nucleotide positions in the oligonucleotide. For example, if the first nucleotide is an adenosine, variants may be produced which contain thymidine, guanosine or cytidine at this position. This may be done at any of the positions of the oligonucleotide. Thus, a 20-mer may comprise 60 variations (20 positions×3 alternates at each position) in which the original nucleotide is substituted with any of the three alternate nucleotides. These oligonucleotides are then tested using the methods described herein to determine their ability to inhibit expression of HCV mRNA and/or HCV replication.

Conjugates

A further preferred substitution that can be appended to the oligomeric compounds of the invention involves the linkage of one or more moieties or conjugates which enhance the activity, cellular distribution or cellular uptake of the resulting oligomeric compounds. In one embodiment such modified oligomeric compounds are prepared by covalently attaching conjugate groups to functional groups such as hydroxyl or amino groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, phospholipids, biotin, phenazine, folate, phenanthridine, anthraquinone, acridine, fluoresceins, rhodamines, coumarins., and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992 the entire disclosure of which is incorporated herein by reference. Conjugate moieties include but are not limited to lipid moieties such as a cholesterol moiety (Letsinger et al., *Proc. Natl. Acad. Sci. USA*, 1989, 86, 6553-6556), cholic acid (Manoharan et al., *Bioorg. Med. Chem. Let.*, 1994, 4, 1053-1060), a thioether, e.g., hexyl-S-tritylthiol (Manoharan et al., *Ann. N.Y. Acad. Sci.*, 1992, 660, 306-309; Manoharan et al., *Bioorg. Med. Chem. Let.*, 1993, 3, 2765-2770), a thiocholesterol (Oberhauser et al., *Nucl. Acids Res.*, 1992, 20, 533-538), an aliphatic chain, e.g., dodecandiol or undecyl residues (Saison-Behmoaras et al., *EMBO J.*, 1991, 10, 1111-1118; Kabanov et al., *FEBS Lett.*, 1990, 259, 327-330; Svinarchuk et al., *Biochimie*, 1993, 75, 49-54), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36, 3651-3654; Shea et al., *Nucl. Acids Res.*, 1990, 18, 3777-3783), a polyamine or a polyethylene glycol chain (Manoharan et al., *Nucleosides & Nucleotides*, 1995, 14, 969-973), or adamantane acetic acid (Manoharan et al., *Tetrahedron Lett.*, 1995, 36, 3651-3654), a palmityl moiety (Mishra et al., *Biochim. Biophys. Acta*, 1995, 1264, 229-237), or an octadecylamine or hexylamino-carbonyl-oxycholesterol moiety (Crooke et al., *J. Pharmacol. Exp. Ther.*, 1996, 277, 923-937.

The oligomeric compounds of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative United States patents that teach the preparation of such oligonucleotide conjugates include, but are not limited to, U.S. Pat. Nos. 4,828,979; 4,948,882; 5,218, 105; 5,525,465; 5,541,313; 5,545,730; 5,552,538; 5,578, 717, 5,580,731; 5,580,731; 5,591,584; 5,109,124; 5,118, 802; 5,138,045; 5,414,077; 5,486,603; 5,512,439; 5,578, 718; 5,608,046; 4,587,044; 4,605,735; 4,667,025; 4,762, 779; 4,789,737; 4,824,941; 4,835,263; 4,876,335; 4,904, 582; 4,958,013; 5,082,830; 5,112,963; 5,214,136; 5,082, 830; 5,112,963; 5,214,136; 5,245,022; 5,254,469; 5,258, 506; 5,262,536; 5,272,250; 5,292,873; 5,317,098; 5,371, 241, 5,391,723; 5,416,203, 5,451,463; 5,510,475; 5,512, 667; 5,514,785; 5,565,552; 5,567,810; 5,574,142; 5,585, 481; 5,587,371; 5,595,726; 5,597,696; 5,599,923; 5,599,928 and 5,688,941, certain of which are commonly owned with the instant application, and each of which is herein incorporated by reference.

Chimeric Oligomeric Compounds

It is not necessary for all positions in an oligomeric compound to be uniformly modified, and in fact more than one of the aforementioned modifications may be incorporated in a single oligomeric compound or even at a single monomeric subunit such as a nucleoside within a oligomeric compound. The present invention also includes oligomeric compounds which are chimeric oligomeric compounds. "Chimeric" oligomeric compounds or "chimeras," in the context of this invention, are oligomeric compounds that contain two or more chemically distinct regions, each made up of at least one monomer unit, i.e., a nucleotide in the case of a nucleic acid based oligomer.

Chimeric oligomeric compounds typically contain at least one region modified so as to confer increased resistance to nuclease degradation, increased cellular uptake, and/or increased binding affinity for the target nucleic acid. An additional region of the oligomeric compound may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of inhibition of gene expression. Consequently, comparable results can often be obtained with shorter oligomeric compounds when chimeras are used, compared to for example phosphorothioate deoxyoligonucleotides hybridizing to the same target region. Cleavage of the RNA target can be routinely detected by gel electrophoresis and, if necessary, associated nucleic acid hybridization techniques known in the art.

Chimeric oligomeric compounds of the invention may be formed as composite structures of two or more oligonucleotides, oligonucleotide analogs, oligonucleosides and/or oligonucleotide mimetics as described above. Such oligomeric compounds have also been referred to in the art as hybrids hemimers, gapmers or inverted gapmers. Representative United States patents that teach the preparation of such hybrid structures include, but are not limited to, U.S. Pat. Nos. 5,013,830; 5,149,797; 5,220,007; 5,256,775; 5,366, 878; 5,403,711; 5,491,133; 5,565,350; 5,623,065; 5,652, 355; 5,652,356; and 5,700,922, certain of which are commonly owned with the instant application, and each of which is herein incorporated by reference in its entirety.

3'-endo Modifications

In one aspect of the present invention oligomeric compounds include nucleosides synthetically modified to induce a 3'-endo sugar conformation. A nucleoside can incorporate synthetic modifications of the heterocyclic base, the sugar moiety or both to induce a desired 3'-endo sugar conformation. These modified nucleosides are used to mimic RNA like nucleosides so that particular properties of an oligomeric compound can be enhanced while maintaining the desirable 3'-endo conformational geometry. There is an apparent preference for an RNA type duplex (A form helix, predominantly 3'-endo) as a requirement (e.g. trigger) of RNA interference which is supported in part by the fact that duplexes composed of 2'-deoxy-2'-F-nucleosides appears efficient in triggering RNAi response in the *C. elegans* system. Properties that are enhanced by using more stable 3'-endo nucleosides include but aren't limited to modulation of pharmacokinetic properties through modification of protein binding, protein off-rate, absorption and clearance; modulation of nuclease stability as well as chemical stability; modulation of the binding affinity and specificity of the oligomer (affinity and specificity for enzymes as well as for complementary sequences); and increasing efficacy of RNA cleavage. The present invention provides oligomeric triggers of RNAi having one or more nucleosides modified in such a way as to favor a C3'-endo type conformation.

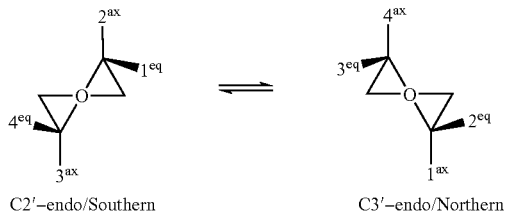

Scheme 1

C2'-endo/Southern      C3'-endo/Northern

Nucleoside conformation is influenced by various factors including substitution at the 2', 3' or 4'-positions of the pentofuranosyl sugar. Electronegative substituents generally prefer the axial positions, while sterically demanding substituents generally prefer the equatorial positions (Principles of Nucleic Acid. Structure, Wolfgang Sanger, 1984, Springer-Verlag.) Modification of the 2' position to favor the 3'-endo conformation can be achieved while maintaining the 2'-OH as a recognition element, as illustrated in FIG. 2, below (Gallo et al., Tetrahedron (2001), 57, 5707-5713. Harry-O'kuru et al., J. Org. Chem., (1997), 62(6), 1754-1759 and Tang et al., J. Org. Chem. (1999), 64, 747-754.) Alternatively, preference for the 3'-endo conformation can be achieved by deletion of the 2'-OH as exemplified by 2'deoxy-2'F-nucleosides (Kawasaki et al., J. Med. Chem. (1993), 36, 831-841), which adopts the 3'-endo conformation positioning the electronegative fluorine atom in the axial position. Other modifications of the ribose ring, for example substitution at the 4'-position to give 4'-F modified nucleosides (Guillerm et al., Bioorganic and Medicinal Chemistry Letters (1995), 5, 1455-1460 and Owen et al., J. Org. Chem. (1976), 41, 3010-3017), or for example modification to yield methanocarba nucleoside analogs (Jacobson et al., J. Med. Chem. Lett. (2000), 43, 2196-2203 and Lee et al., Bioorganic and Medicinal Chemistry Letters (2001), 11, 1333-1337) also induce preference for the 3'-endo conformation. Along similar lines, oligomeric triggers of RNAi response might be composed of one or more nucleosides modified in such a way that conformation is locked into a C3'-endo type conformation, i.e. Locked Nucleic Acid (LNA, Singh et al, Chem. Commun. (1998), 4, 455-456), and ethylene bridged Nucleic Acids (ENA, Morita et al, Bioorganic & Medicinal Chemistry Letters (2002), 12, 73-76.) Examples of modified nucleosides amenable to the present invention are shown below in Table I. These examples are meant to be representative and not exhaustive.

TABLE I

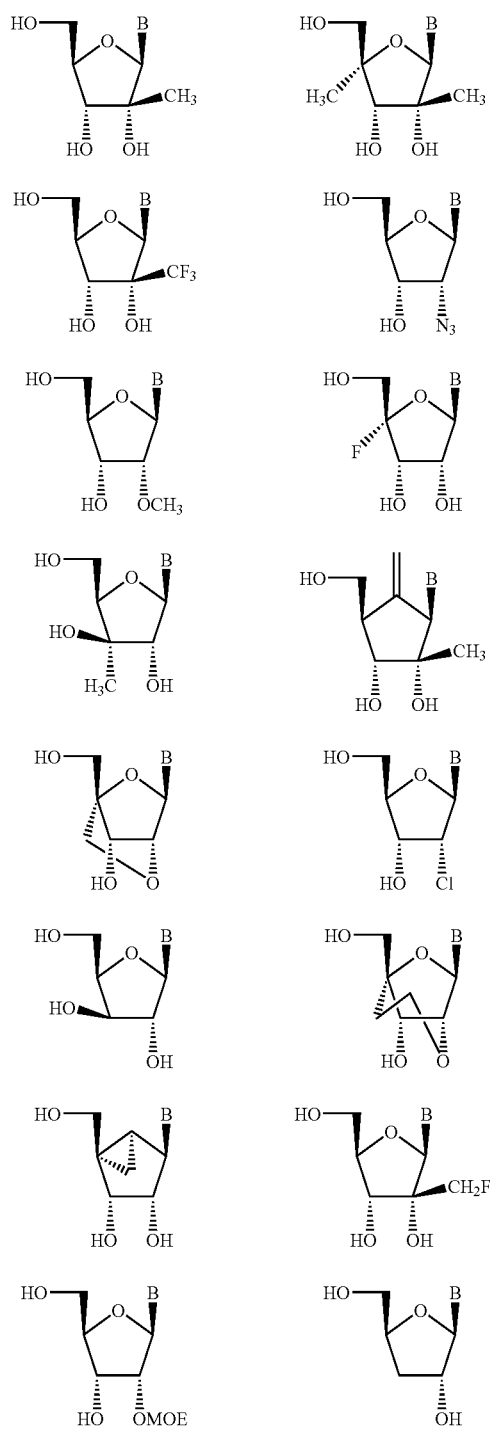

TABLE I-continued

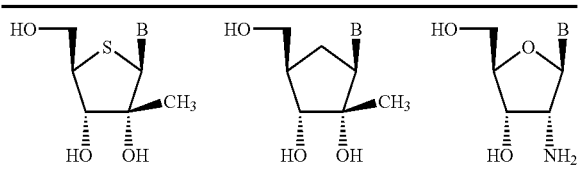

The preferred conformation of modified nucleosides and their oligomers can be estimated by various methods such as molecular dynamics calculations, nuclear magnetic resonance spectroscopy and CD measurements. Hence, modifications predicted to induce RNA like conformations, A-form duplex geometry in an oligomeric context, are selected for use in the modified oligoncleotides of the present invention. The synthesis of numerous of the modified nucleosides amenable to the present invention are known in the art (see for example, Chemistry of Nucleosides and Nucleotides Vol 1-3, ed. Leroy B. Townsend, 1988, Plenum press., and the examples section below.) Nucleosides known to be inhibitors/substrates for RNA dependent RNA polymerases (for example HCV NS5B In one aspect, the present invention is directed to oligonucleotides that are prepared having enhanced properties compared to native RNA against nucleic acid targets. A target is identified and an oligonucleotide is selected having an effective length and sequence that is complementary to a portion of the target sequence. Each nucleoside of the selected sequence is scrutinized for possible enhancing modifications. A preferred modification would be the replacement of one or more RNA nucleosides with nucleosides that have the same 3'-endo conformational geometry. Such modifications can enhance chemical and nuclease stability relative to native RNA while at the same time being much cheaper and easier to synthesize and/or incorporate into an oligonulceotide. The selected sequence can be further divided into regions and the nucleosides of each region evaluated for enhancing modifications that can be the result of a chimeric configuration. Consideration is also given to the 5' and 3'-termini as there are often advantageous modifications that can be made to one or more of the terminal nucleosides. The oligomeric compounds of the present invention include at least one 5'-modified phosphate group on a single strand or on at least one 5'-position of a double stranded sequence or sequences. Further modifications are also considered such as internucleoside linkages, conjugate groups, substitute sugars or bases, substitution of one or more nucleosides with nucleoside mimetics and any other modification that can enhance the selected sequence for its intended target.

The terms used to describe the conformational geometry of homoduplex nucleic acids are "A Form" for RNA and "B Form" for DNA. The respective conformational geometry for RNA and DNA duplexes was determined from X-ray diffraction analysis of nucleic acid fibers (Arnott and Hukins, *Biochem. Biophys. Res. Comm.*, 1970, 47, 1504.) In general, RNA:RNA duplexes are more stable and have higher melting temperatures (Tm's) than DNA:DNA duplexes (Sanger et al., Principles of Nucleic Acid Structure, 1984, Springer-Verlag; New York, N.Y.; Lesnik et al., Biochemistry, 1995, 34, 10807-10815; Conte et al., Nucleic Acids Res., 1997, 25, 2627-2634). The increased stability of RNA has been attributed to several structural features, most notably the improved base stacking interactions that result from an A-form geometry (Searle et al., Nucleic Acids Res., 1993, 21, 2051-2056). The presence of the 2' hydroxyl in RNA biases the sugar toward a C3' endo pucker, i.e., also designated as Northern pucker, which causes the duplex to favor the A-form geometry. In addition, the 2' hydroxyl groups of RNA can form a network of water mediated hydrogen bonds that help stabilize the RNA duplex (Egli et al., Biochemistry, 1996, 35, 8489-8494). On the other hand, deoxy nucleic acids prefer a C2' endo sugar pucker, i.e., also known as Southern pucker, which is thought to impart a less stable B-form geometry (Sanger, W. (1984) Principles of Nucleic Acid Structure, Springer-Verlag, New York, N.Y.). As used herein, B-form geometry is inclusive of both C2'-endo pucker and O4'-endo pucker. This is consistent with Berger, et. al., *Nucleic Acids Research*, 1998, 26, 2473-2480, who pointed out that in considering the furanose conformations which give rise to B-form duplexes consideration should also be given to a O4'-endo pucker contribution.

DNA:RNA hybrid duplexes, however, are usually less stable than pure RNA:RNA duplexes, and depending on their sequence may be either more or less stable than DNA:DNA duplexes (Searle et al., *Nucleic Acids Res.*, 1993, 21, 2051-2056). The structure of a hybrid duplex is intermediate between A- and B-form geometries, which may result in poor stacking interactions (Lane et al., *Eur. J. Biochem.*, 1993, 215, 297-306; Fedoroff et al., *J. Mol. Biol.*, 1993, 233, 509-523; Gonzalez et al., *Biochemistry*, 1995, 34, 4969-4982; Horton et al., *J. Mol. Biol.*, 1996, 264, 521-533). The stability of the duplex formed between a target RNA and a synthetic sequence is central to therapies such as but not limited to antisense and RNA interference as these mechanisms require the binding of a synthetic oligonucleotide strand to an RNA target strand. In the case of antisense, effective inhibition of the mRNA requires that the antisense DNA have a very high binding affinity with the mRNA. Otherwise the desired interaction between the synthetic oligonucleotide strand and target mRNA strand will occur infrequently, resulting in decreased efficacy.

One routinely used method of modifying the sugar puckering is the substitution of the sugar at the 2'-position with a substituent group that influences the sugar geometry. The influence on ring conformation is dependant on the nature of the substituent at the 2'-position. A number of different substituents have been studied to determine their sugar puckering effect. For example, 2'-halogens have been studied showing that the 2'-fluoro derivative exhibits the largest population (65%) of the C3'-endo form, and the 2'-iodo exhibits the lowest population (7%). The populations of adenosine (2'-OH) versus deoxyadenosine (2'-H) are 36% and 19%, respectively. Furthermore, the effect of the 2'-fluoro group of adenosine dimers (2'-deoxy-2'-fluoroadenosine-2'-deoxy-2'-fluoro-adenosine) is further correlated to the stabilization of the stacked conformation.

As expected, the relative duplex stability can be enhanced by replacement of 2'-OH groups with 2'-F groups thereby increasing the C3'-endo population. It is assumed that the highly polar nature of the 2'-F bond and the extreme preference for C3'-endo puckering may stabilize the stacked conformation in an A-form duplex. Data from UV hypochromicity, circular dichroism, and $^1$H NMR also indicate that the degree of stacking decreases as the electronegativity of the halo substituent decreases. Furthermore, steric bulk at the 2'-position of the sugar moiety is better accommodated in an A-form duplex than a B-form duplex. Thus, a 2'-substituent on the 3'-terminus of a dinucleoside monophosphate is thought to exert a number of effects on the stacking conformation: steric repulsion, furanose puckering preference, electrostatic repulsion, hydrophobic attraction, and hydrogen bonding capabilities. These substituent effects are thought to be determined by the molecular size, electronegativity, and hydrophobicity of the substituent. Melting temperatures of complementary strands is also increased with the 2'-substituted adenosine diphosphates. It is not clear whether the 3'-endo preference of the conformation or the presence of the substituent is responsible for the increased binding. However, greater overlap of adjacent bases (stacking) can be achieved with the 3'-endo conformation.

One synthetic 2'-modification that imparts increased nuclease resistance and a very high binding affinity to nucleotides is the 2-methoxyethoxy (2'-MOE, 2'-OCH$_2$CH$_2$OCH$_3$) side chain (Baker et al., *J. Biol. Chem.*, 1997, 272, 11944-12000). One of the immediate advantages of the 2'-MOE substitution is the improvement in binding affinity, which is greater than many similar 2' modifications such as O-methyl, O-propyl, and O-aminopropyl. Oligonucleotides having the 2'-O-methoxyethyl substituent also have been shown to be antisense inhibitors of gene expression with promising features for in vivo use (Martin, P., *Helv. Chim. Acta*, 1995, 78, 486-504; Altmann et al., *Chimia*, 1996, 50, 168-176; Altmann et al., *Biochem. Soc. Trans.*, 1996, 24, 630-637; and Altmann et al., *Nucleosides Nucleotides*, 1997, 16, 917-926). Relative to DNA, the oligonucleotides having the 2'-MOE modification displayed improved RNA affinity and higher nuclease resistance. Chimeric oligonucleotides having 2'-MOE substituents in the wing nucleosides and an internal region of deoxy-phosphorothioate nucleotides (also termed a gapped oligonucleotide or gapmer) have shown effective reduction in the growth of tumors in animal models at low doses. 2'-MOE substituted oligonucleotides have also shown outstanding promise as antisense agents in several disease states. One such MOE substituted oligonucleotide is presently being investigated in clinical trials for the treatment of CMV retinitis.

Chemistries Defined

Unless otherwise defined herein, alkyl means $C_1$-$C_{12}$, preferably $C_1$-$C_8$, and more preferably $C_1$-$C_6$, straight or (where possible) branched chain aliphatic hydrocarbyl.

Unless otherwise defined herein, heteroalkyl means $C_1$-$C_{12}$, preferably $C_1$-$C_8$, and more preferably $C_1$-$C_6$, straight or (where possible) branched chain aliphatic hydrocarbyl containing at least one, and preferably about 1 to about 3, hetero atoms in the chain, including the terminal portion of the chain. Preferred heteroatoms include N, O and S.

Unless otherwise defined herein, cycloalkyl means $C_3$-$C_{12}$, preferably $C_3$-$C_8$, and more preferably $C_3$-$C_6$, aliphatic hydrocarbyl ring.

Unless otherwise defined herein, alkenyl means $C_2$-$C_{12}$, preferably $C_2$-$C_8$, and more preferably $C_2$-$C_6$ alkenyl, which may be straight or (where possible) branched hydrocarbyl moiety, which contains at least one carbon-carbon double bond.

Unless otherwise defined herein, alkynyl means $C_2$-$C_{12}$, preferably $C_2$-$C_8$, and more preferably $C_2$-$C_6$ alkynyl, which may be straight or (where possible) branched hydrocarbyl moiety, which contains at least one carbon-carbon triple bond.

Unless otherwise defined herein, heterocycloalkyl means a ring moiety containing at least three ring members, at least one of which is carbon, and of which 1, 2 or three ring members are other than carbon. Preferably the number of carbon atoms varies from 1 to about 12, preferably 1 to about 6, and the total number of ring members varies from three to about 15, preferably from about 3 to about 8. Preferred ring heteroatoms are N, O and S. Preferred heterocycloalkyl groups include morpholino, thiomorpholino, piperidinyl, piperazinyl, homopiperidinyl, homopiperazinyl, homomorpholino, homothiomorpholino, pyrrolodinyl, tetrahydrooxazolyl, tetrahydroimidazolyl, tetrahydrothiazolyl, tetrahydroisoxazolyl, tetrahydropyrrazolyl, furanyl, pyranyl, and tetrahydroisothiazolyl.

Unless otherwise defined herein, aryl means any hydrocarbon ring structure containing at least one aryl ring. Preferred aryl rings have about 6 to about 20 ring carbons. Especially preferred aryl rings include phenyl, napthyl, anthracenyl, and phenanthrenyl.

Unless otherwise defined herein, hetaryl means a ring moiety containing at least one fully unsaturated ring, the ring consisting of carbon and non-carbon atoms. Preferably the ring system contains about 1 to about 4 rings. Preferably the number of carbon atoms varies from 1 to about 12, preferably 1 to about 6, and the total number of ring members varies from three to about 15, preferably from about 3 to about 8. Preferred ring heteroatoms are N, O and S. Preferred hetaryl moieties include pyrazolyl, thiophenyl, pyridyl, imidazolyl, tetrazolyl, pyridyl, pyrimidinyl, purinyl, quinazolinyl, quinoxalinyl, benzimidazolyl, benzothiophenyl, etc.

Unless otherwise defined herein, where a moiety is defined as a compound moiety, such as hetarylalkyl (hetaryl and alkyl), aralkyl (aryl and alkyl), etc., each of the sub-moieties is as defined herein.

Unless otherwise defined herein, an electron withdrawing group is a group, such as the cyano or isocyanato group that draws electronic charge away from the carbon to which it is attached. Other electron withdrawing groups of note include those whose electronegativities exceed that of carbon, for example halogen, nitro, or phenyl substituted in the ortho- or para-position with one or more cyano, isothiocyanato, nitro or halo groups.

Unless otherwise defined herein, the terms halogen and halo have their ordinary meanings. Preferred halo (halogen) substituents are Cl, Br, and I. The aforementioned optional substituents are, unless otherwise herein defined, suitable substituents depending upon desired properties. Included are halogens (Cl, Br, I), alkyl, alkenyl, and alkynyl moieties, $NO_2$, $NH_3$ (substituted and unsubstituted), acid moieties (e.g. —$CO_2H$, —$OSO_3H_2$, etc.), heterocycloalkyl moieties, hetaryl moieties, aryl moieties, etc.

In all the preceding formulae, the squiggle (~) indicates a bond to an oxygen or sulfur of the 5'-phosphate.

Phosphate protecting groups include those described in U.S. Pat. No. 5,760,209, U.S. Pat. No. 5,614,621, U.S. Pat. No. 6,051,699, U.S. Pat. No. 6,020,475, U.S. Pat. No. 6,326,478, U.S. Pat. No. 6,169,177, U.S. Pat. No. 6,121,437, U.S. Pat. No. 6,465,628 each of which is expressly incorporated herein by reference in its entirety.

The oligonucleotides in accordance with this invention (single stranded or double stranded) preferably comprise from about 8 to about 80 nucleotides, more preferably from about 12-50 nucleotides and most preferably from about 15 to 30 nucleotides. As is known in the art, a nucleotide is a base-sugar combination suitably bound to an adjacent nucleotide through a phosphodiester, phosphorothioate or other covalent linkage.

The oligonucleotides of the present invention also include variants in which a different base is present at one or more of the nucleotide positions in the oligonucleotide. For example, if the first nucleotide is an adenosine, variants may be produced which contain thymidine, guanosine or cytidine at this position. This may be done at any of the positions of the oligonucleotide. Thus, a 20-mer may comprise 60 variations (20 positions×3 alternates at each position) in which the original nucleotide is substituted with any of the three alternate nucleotides. These oligonucleotides are then tested using the methods described herein to determine their ability to inhibit expression of STAT3 mRNA.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of the routineer. It is well known to use similar techniques to prepare oligonucleotides such as the phosphorothioates and 2'-alkoxy or 2'-alkoxyalkoxy derivatives, including 2'-O-methoxyethyl oligonucleotides (Martin, P., Helv. Chim. Acta 1995, 78, 486-504). It is also well known to use similar techniques and commercially available modified amidites and controlled-pore glass (CPG) products such as biotin, fluorescein, acridine or psoralen-modified amidites and/or CPG (available from Glen Research, Sterling, Va.) to synthesize fluorescently labeled, biotinylated or other conjugated oligonucleotides.

The antisense compounds of the present invention include bioequivalent compounds, including pharmaceutically acceptable salts and prodrugs. This is intended to encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to pharmaceutically acceptable salts of the nucleic acids of the invention and prodrugs of such nucleic acids. A Pharmaceutically acceptable salts@ are physiologically and pharmaceutically acceptable salts of the nucleic acids of the invention: i.e., salts that retain the desired biological activity of the parent compound and do not impart undesired toxicological effects thereto (see, for example, Berge et al., "Pharmaceutical Salts," *J. of Pharma Sci.* 1977, 66, 1-19).

For oligonucleotides, examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The oligonucleotides of the invention may additionally or alternatively be prepared to be delivered in a Aprodrug@ form. The term Aprodrug@ indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993.

For therapeutic or prophylactic treatment, oligonucleotides are administered in accordance with this invention oligonucleotide compounds of the invention may be formulated in a pharmaceutical composition, which may include pharmaceutically acceptable carriers, thickeners, diluents, buffers, preservatives, surface active agents, neutral or cationic lipids, lipid complexes, liposomes, penetration enhancers, carrier compounds and other pharmaceutically acceptable carriers or excipients and the like in addition to the oligonucleotide. Such compositions and formulations are comprehended by the present invention.

Pharmaceutical compositions comprising the oligonucleotides of the present invention may include penetration enhancers in order to enhance the alimentary delivery of the oligonucleotides. Penetration enhancers may be classified as belonging to one of five broad categories, i.e., fatty acids, bile salts, chelating agents, surfactants and non-surfactants (Lee et al., *Critical Reviews in Therapeutic Drug Carrier Systems* 1991, 8, 91-192; Muranishi, *Critical Reviews in Therapeutic Drug Carrier Systems* 1990, 7, 1-33). One or more penetration enhancers from one or more of these broad categories may be included. Various fatty acids and their derivatives which act as penetration enhancers include, for example, oleic acid, lauric acid, capric acid, myristic acid, palmitic acid, stearic acid, linoleic acid, linolenic acid, dicaprate, tricaprate, recinleate, monoolein (a.k.a. 1-monooleoyl-rac-glycerol), dilaurin, caprylic acid, arachidonic acid, glyceryl 1-monocaprate, 1-dodecylazacycloheptan-2-one, acylcarnitines, acylcholines, mono- and di-glycerides and physiologically acceptable salts thereof (i.e., oleate, laurate, caprate, myristate, palmitate, stearate, linoleate, etc.) (Lee et al., *Critical Reviews in Therapeutic Drug Carrier Systems* 1991, page 92; Muranishi, *Critical Reviews in Therapeutic Drug Carrier Systems* 1990, 7, 1; El-Hariri et al., *J. Pharm. Pharmacol.* 1992 44, 651-654).

The physiological roles of bile include the facilitation of dispersion and absorption of lipids and fat-soluble vitamins (Brunton, Chapter 38 In: *Goodman & Gilman's The Pharmacological Basis of Therapeutics,* 9th Ed., Hardman et al., eds., McGraw-Hill, New York, N.Y., 1996, pages 934-935). Various natural bile salts, and their synthetic derivatives, act as penetration enhancers. Thus, the term "bile salt" includes any of the naturally occurring components of bile as well as any of their synthetic derivatives.

Complex formulations comprising one or more penetration enhancers may be used. For example, bile salts may be used in combination with fatty acids to make complex formulations.

Chelating agents include, but are not limited to, disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines) [Lee et al., *Critical Reviews in Therapeutic Drug Carrier Systems* 1991, page 92; Muranishi, *Critical Reviews in Therapeutic Drug Carrier Systems* 1990, 7, 1-33; Buur et al., *J. Control Rel.* 1990, 14, 43-51). Chelating agents have the added advantage of also serving as DNase inhibitors.

Surfactants include, for example, sodium lauryl sulfate, polyoxyethylene-9-lauryl ether and polyoxyethylene-20-cetyl ether (Lee et al., *Critical Reviews in Therapeutic Drug Carrier Systems* 1991, page 92); and perfluorochemical emulsions, such as FC-43 (Takahashi et al., *J. Pharm. Phamacol.* 1988, 40, 252-257).

Non-surfactants include, for example, unsaturated cyclic ureas, 1-alkyl- and 1-alkenylazacyclo-alkanone derivatives (Lee et al., *Critical Reviews in Therapeutic Drug Carrier Systems* 1991, page 92); and non-steroidal anti-inflammatory agents such as diclofenac sodium, indomethacin and phenylbutazone (Yamashita et al., *J. Pharm. Pharmacol.* 1987, 39, 621-626).

As used herein, "carrier compound" refers to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. In contrast to a carrier compound, a "pharmaceutically acceptable carrier" (excipient) is a pharmaceutically acceptable solvent, suspending agent or any other pharmacologically inert vehicle for delivering one or more nucleic acids to an animal. The pharmaceutically acceptable carrier may be liquid or solid and is selected with the planned manner of administration in mind so as to provide for the desired bulk, consistency, etc., when combined with a nucleic acid and the other components of a given pharmaceutical composition. Typical pharmaceutically acceptable carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrates (e.g., starch, sodium starch glycolate, etc.); or wetting agents (e.g., sodium lauryl sulphate, etc.). Sustained release oral delivery systems and/or enteric coatings for orally administered dosage forms are described in U.S. Pat. Nos. 4,704,295; 4,556,552; 4,309,406; and 4,309,404.

The compositions of the present invention may additionally contain other adjunct components conventionally found in pharmaceutical compositions, at their art-established usage levels. Thus, for example, the compositions may contain additional compatible pharmaceutically-active materials such as, e.g., antipruritics, astringents, local anesthetics or anti-inflammatory agents, or may contain additional materials useful in physically formulating various dosage forms of the composition of present invention, such as dyes, flavoring agents, preservatives, antioxidants, opacifiers, thickening agents and stabilizers. However, such materials, when added, should not unduly interfere with the biological activities of the components of the compositions of the invention.

Regardless of the method by which the oligonucleotides of the invention are introduced into a patient, colloidal dispersion systems may be used as delivery vehicles to enhance the in vivo stability of the oligonucleotides and/or to target the oligonucleotides to a particular organ, tissue or cell type. Colloidal dispersion systems include, but are not limited to, macromolecule complexes, nanocapsules, microspheres, beads and lipid-based systems including oil-in-water emulsions, micelles, mixed micelles, liposomes and lipid:oligonucleotide complexes of uncharacterized structure. A preferred colloidal dispersion system is a plurality of liposomes. Liposomes are microscopic spheres having an aqueous core surrounded by one or more outer layers made up of lipids arranged in a bilayer configuration (see, generally, Chonn et al., *Current Op. Biotech.* 1995, 6, 698-708).

The pharmaceutical compositions of the present invention may be administered in a number of ways depending upon whether local or systemic treatment is desired and upon the area to be treated. Administration may be topical (including ophthalmic, vaginal, rectal, intranasal, epidermal, and transdermal), oral or parenteral. Parenteral administration includes intravenous drip, subcutaneous, intraperitoneal or intramuscular injection, pulmonary administration, e.g., by inhalation or insufflation, or intracranial, e.g., intrathecal or intraventricular, administration oligonucleotides with at least one 2'-O-methoxyethyl modification are believed to be particularly useful for oral administration.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water or non-aqueous media, capsules, sachets or tablets. Thickeners, flavoring agents, diluents, emulsifiers, dispersing aids or binders may be desirable.

Compositions for parenteral administration may include sterile aqueous solutions which may also contain buffers, diluents and other suitable additives. In some cases it may be more effective to treat a patient with an oligonucleotide of the invention in conjunction with other traditional therapeutic modalities in order to increase the efficacy of a treatment regimen. In the context of the invention, the term "treatment regimen" is meant to encompass therapeutic, palliative and prophylactic modalities. For example, a patient may be treated with conventional chemotherapeutic agents, particularly those used for tumor and cancer treatment. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine (CA), 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide, trimetrexate, teniposide., cisplatin, gemcitabine and diethylstilbestrol (DES). See, generally, *The Merck Manual of Diagnosis and Therapy,* 15th Ed. 1987, pp. 1206-1228, Berkow et al., eds., Rahway, N.J. When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide).

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in vitro and in in vivo animal models. In general, dosage is from 0.01•g to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01•g to 100 g per kg of body weight, once or more daily, to once every 20 years.

The following examples illustrate the present invention and are not intended to limit the same.

EXAMPLES

Example 1

Synthesis of Oligonucleotides

Unmodified oligodeoxynucleotides are synthesized on an automated DNA synthesizer (Applied Biosystems model 380B) using standard phosphoramidite chemistry with oxidation by iodine. β-cyanoethyldiisopropyl-phosphoramidites are purchased from Applied Biosystems (Foster City, Calif.). For phosphorothioate oligonucleotides, the standard oxidation bottle was replaced by a 0.2 M solution of $^3$H-1,2-benzodithiole-3-one 1,1-dioxide in acetonitrile for the stepwise thiation of the phosphite linkages. The thiation cycle wait step was increased to 68 seconds and was followed by the capping step. Cytosines may be 5-methyl cytosines. (5-methyl deoxycytidine phosphoramidites available from Glen Research, Sterling, Va. or Amersham Pharmacia Biotech, Piscataway, N.J.)

2'-methoxy oligonucleotides are synthesized using 2'-methoxy β-cyanoethyldiisopropyl-phosphoramidites (Chemgenes, Needham, Mass.) and the standard cycle for unmodified oligonucleotides, except the wait step after pulse delivery of tetrazole and base is increased to 360 seconds. Other 2'-alkoxy oligonucleotides are synthesized by a modification of this method, using appropriate 2'-modified amidites such as those available from Glen Research, Inc., Sterling, Va.

2'-fluoro oligonucleotides are synthesized as described in Kawasaki et al. (J. Med. Chem. 1993, 36, 831-841). Briefly, the protected nucleoside $N^6$-benzoyl-2'-deoxy-2'-fluoroadenosine is synthesized utilizing commercially available 9-β-D-arabinofuranosyladenine as starting material and by modifying literature procedures whereby the 2'-a-fluoro atom is introduced by a $S_N$2-displacement of a 2'-β-O-trifyl group. Thus $N^6$-benzoyl-9-β-D-arabinofuranosyladenine is selectively protected in moderate yield as the 3',5'-ditetrahydropyranyl (THP) intermediate. Deprotection of the THP and $N^6$-benzoyl groups is accomplished using standard methodologies and standard methods are used to obtain the 5'-dimethoxytrityl-(DMT) and 5'-DMT-3'-phosphoramidite intermediates.

The synthesis of 2'-deoxy-2'-fluoroguanosine is accomplished using tetraisopropyldisiloxanyl (TPDS) protected 9-β-D-arabinofuranosylguanine as starting material, and conversion to the intermediate diisobutyryl-arabinofuranosylguanosine. Deprotection of the TPDS group is followed by protection of the hydroxyl group with THP to give diisobutyryl di-THP protected arabinofuranosylguanine. Selective O-deacylation and triflation is followed by treatment of the crude product with fluoride, then deprotection of the THP groups. Standard methodologies are used to obtain the 5'-DMT- and 5'-DMT-3'-phosphoramidites.

Synthesis of 2'-deoxy-2'-fluorouridine is accomplished by the modification of a known procedure in which 2,2'-anhydro-1-β-D-arabinofuranosyluracil is treated with 70% hydrogen fluoride-pyridine. Standard procedures are used to obtain the 5'-DMT and 5'-DMT-3'phosphoramidites.

2'-deoxy-2'-fluorocytidine is synthesized via amination of 2'-deoxy-2'-fluorouridine, followed by selective protection to give $N^4$-benzoyl-2'-deoxy-2'-fluorocytidine. Standard procedures are used to obtain the 5'-DMT and 5'-DMT-3'phosphoramidites.

2'-(2-methoxyethyl)-modified amidites were synthesized according to Martin, P. (Helv. Chim. Acta 1995, 78, 486-506). For ease of synthesis, the last nucleotide may be a deoxynucleotide. 2'-O—$CH_2CH_2OCH_3$ cytosines may be 5-methyl cytosines.

Synthesis of 5-Methyl cytosine monomers 2,2'-Anhydro[1-(β-D-arabinofuranosyl)-5-methyluridine]

5-Methyluridine (ribosylthymine, commercially available through Yamasa, Choshi, Japan) (72.0 g, 0.279 M), diphenylcarbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid which was crushed to a light tan powder (57 g, 85% crude yield). The material was used as is for further reactions.

2'-O-Methoxyethyl-5-methyluridine 2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155-160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product.

2'-O-Methoxyethyl-5'-O-dimethoxytrityl-5-methyluridine

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/Hexane/Acetone (5:5:1) containing 0.5% $Et_3NH$. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyluridine

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by tlc by first quenching the tlc sample with the addition of MeOH. Upon completion of the reaction, as judged by tlc, MeOH (50 mL) was added and the mixture evaporated at 35° C. The residue was dissolved in $CHCl_3$ (800 mL) and extracted with 2×200 mL of saturated sodium bicarbonate and 2×200 mL of saturated NaCl. The water layers were back extracted with 200 mL of $CHCl_3$. The combined organics were dried with sodium sulfate and evaporated to give 122 g of residue (approx. 90% product). The residue was purified on a 3.5 kg silica gel column and eluted using EtOAc/Hexane (4:1). Pure product fractions were evaporated to yield 96 g (84%).

3'-O-Acetyl-2'-O-methoxyethyl-5'-O-dimethoxytrityl-5-methyl-4-triazoleuridine A first solution was prepared by dissolving 3'-O-acetyl-2'-O-methoxyethyl-5'-O-dimethoxytrityl-5-methyluridine (96 g, 0.144 M) in $CH_3CN$ (700 mL) and set aside. Triethylamine (189 mL, 1.44 M) was added to a solution of triazole (90 g, 1.3 M) in $CH_3CN$ (1 L), cooled to −5° C. and stirred for 0.5 h using an overhead stirrer. $POCl_3$ was added dropwise, over a 30 minute period, to the stirred solution maintained at 0-10° C., and the resulting mixture stirred for an additional 2 hours. The first solution was added dropwise, over a 45 minute period, to the later solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of $NaHCO_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine

A solution of 3'-O-acetyl-2'-O-methoxyethyl-5'-O-dimethoxytrityl-5-methyl-4-triazoleuridine (103 g, 0.141 M) in dioxane (500 mL) and $NH_4OH$ (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with $NH_3$ gas was added and the vessel heated to 100° C. for 2 hours (tlc showed complete conversion). The vessel contents were evaporated to dryness and the residue was dissolved in EtOAc (500 mL) and washed once with saturated NaCl (20.0 mL). The organics were dried over sodium sulfate and the solvent was evaporated to give 85 g (95%) of the title compound.

$N^4$-Benzoyl-2'-O-methoxyethyl-5'-O-dimethoxytrityl-5-methyl-cytidine

2'-O-Methoxyethyl-5'-O-dimethoxytrityl-5-methyl-cytidine (85 g, 0.134 M) was dissolved in DMF (800 mL) and benzoic anhydride (37.2 g, 0.165 M) was added with stirring. After stirring for 3 hours, tlc showed the reaction to be approximately 95% complete. The solvent was evaporated and the residue azeotroped with MeOH (200 mL). The residue was dissolved in $CHCl_3$ (700 mL) and extracted with saturated $NaHCO_3$ (2×300 mL) and saturated NaCl (2×300 mL), dried over $MgSO_4$ and evaporated to give a residue (96 g). The residue was chromatographed on a 1.5 kg silica column using EtOAc/Hexane (1:1) containing 0.5% $Et_3NH$ as the eluting solvent. The pure product fractions were evaporated to give 90 g (90%) of the title compound.

$N^4$-Benzoyl-2'-O-methoxyethyl-5'-O-dimethoxytrityl-5-methylcytidine-3'-amidite $N^4$-Benzoyl-2'-O-methoxyethyl-5'-O-dimethoxytrityl-5-methylcytidine (74 g, 0.10 M) was dissolved in $CH_2Cl_2$ (1 L). Tetrazole diisopropylamine (7.1 g) and 2-cyanoethoxy-tetra(isopropyl)phosphite (40.5 mL, 0.123 M) were added with stirring, under a nitrogen atmosphere. The resulting mixture was stirred for 20 hours at room temperature (tlc showed the reaction to be 95% complete). The reaction mixture was extracted with saturated $NaHCO_3$ (1×300 mL) and saturated NaCl (3×300 mL). The aqueous washes were back-extracted with $CH_2Cl_2$ (300 mL), and the extracts were combined, dried over $MgSO_4$ and concentrated. The residue obtained was chromatographed on a 1.5 kg silica column using EtOAc\Hexane (3:1) as the eluting solvent. The pure fractions were combined to give 90.6 g (87%) of the title compound.

5-methyl-2'-deoxycytidine (5-me-C) containing oligonucleotides were synthesized according to published methods (Sanghvi et al., *Nucl. Acids Res.* 1993, 21, 3197-3203) using commercially available phosphoramidites (Glen Research, Sterling Va. or ChemGenes, Needham Mass.).

2=-O-(dimethylaminooxyethyl) nucleoside amidites

2'-(Dimethylaminooxyethoxy) nucleoside amidites [also known in the art as 2'-O-(dimethylaminooxyethyl) nucleoside amidites] are prepared as described in the following paragraphs. Adenosine, cytidine and guanosine nucleoside amidites are prepared similarly to the thymidine (5-methyluridine) except the exocyclic amines are protected with a benzoyl moiety in the case of adenosine and cytidine and with isobutyryl in the case of guanosine.

5'-O-tert-Butyldiphenylsilyl-$O^2$-2-anhydro-5-methyluridine $O^2$-2'-anhydro-5-methyluridine (Pro. Bio. Sint., Varese, Italy, 100.0 g, 0.416 mmol), dimethylaminopyridine (0.66 g, 0.013 eq, 0.0054 mmol) were dissolved in dry pyridine (500 ml) at ambient temperature under an argon atmosphere and with mechanical stirring tert-Butyldiphenylchlorosilane (125.8 g, 119.0 mL, 1.1 eq, 0.458 mmol) was added in one portion. The reaction was stirred for 16 h at ambient temperature. TLC (Rf 0.22, ethyl acetate) indicated a complete reaction. The solution was concentrated under reduced pressure to a thick oil. This was partitioned between dichloromethane (1 L) and saturated sodium bicarbonate (2×1 L) and brine (1 L). The organic layer was dried over sodium sulfate and concentrated under reduced pressure to a thick oil. The oil was dissolved in a 1:1 mixture of ethyl acetate and ethyl ether (600 mL) and the solution was cooled to −10° C. The resulting crystalline product was collected by filtration, washed with ethyl ether (3×200 mL) and dried (40° C., 1 mm Hg, 24 h) to 149 g (74.8%) of white solid. TLC and NMR were consistent with pure product.

5'-O-tert-Butyldiphenylsilyl-2'-O-(2-hydroxyethyl)-5-methyluridine

In a 2 L stainless steel, unstirred pressure reactor was added borane in tetrahydrofuran (1.0 M, 2.0 eq, 622 mL). In the fume hood and with manual stirring, ethylene glycol (350 mL, excess) was added cautiously at first until the evolution of hydrogen gas subsided. 5'-O-tert-Butyldiphenylsilyl-$O^2$-2'-anhydro-5-methyluridine (149 g, 0.311 mol) and sodium bicarbonate (0.074 g, 0.003 eq) were added with manual stirring. The reactor was sealed and heated in an oil bath until an internal temperature of 160° C. was reached and then maintained for 16 h (pressure<100 psig). The reaction vessel was cooled to ambient and opened. TLC (Rf 0.67 for desired product and Rf 0.82 for ara-T side product, ethyl acetate) indicated about 70% conversion to the product. In order to avoid additional side product formation, the reaction was stopped, concentrated under reduced pressure (10 to 1 mm Hg) in a warm water bath (40-100° C.) with the more extreme conditions used to remove the ethylene glycol. [Alternatively, once the low boiling solvent is gone, the remaining solution can be partitioned between ethyl acetate and water. The product will be in the organic phase.] The residue was purified by column chromatography (2 kg silica gel, ethyl acetate-hexanes gradient 1:1 to 4:1). The appropriate fractions were combined, stripped and dried to product as a white crisp foam (84 g, 50%), contaminated starting material (17.4 g) and pure reusable starting material 20 g. The yield based on starting material less pure recovered starting material was 58%. TLC and NMR were consistent with 99% pure product.

2'-O-([2-phthalimidoxy)ethyl]-5'-t-butyldiphenylsilyl-5-methyluridine

5'-O-tert-Butyldiphenylsilyl-2'-O-(2-hydroxyethyl)-5-methyluridine (20 g, 36.98 mmol) was mixed with triphenylphosphine (11.63 g, 44.36 mmol) and N-hydroxyphthalimide (7.24 g, 44.36 mmol). It was then dried over $P_2O_5$ under high vacuum for two days at 40° C. The reaction mixture was flushed with argon and dry THF (369 mL, Aldrich, sure seal bottle) was added to get a clear solution. Diethyl-azodicarboxylate (6.98 mL, 44.36 mmol) was added dropwise to the reaction mixture. The rate of addition is maintained such that resulting deep red coloration is just discharged before adding the next drop. After the addition was complete, the reaction was stirred for 4 hrs. By that time TLC showed the completion of the reaction (ethylacetate:hexane, 60:40). The solvent was evaporated in vacuum. Residue obtained was placed on a flash column and eluted with ethyl acetate:hexane (60:40), to get 2'-O-([2-phthalimidoxy)ethyl]-5'-t-butyldiphenylsilyl-5-methyluridine as white foam (21.819, 86%).

5'-O-tert-butyldiphenylsilyl-2'-O-[(2-formadoximinooxy)ethyl]-5-methyluridine 2'-O-([2-phthalimidoxy)ethyl]-5'-t-butyldiphenylsilyl-5-methyluridine (3.1 g, 4.5 mmol) was dissolved in dry $CH_2Cl_2$ (4.5 mL) and methylhydrazine (300 mL, 4.64 mmol) was added dropwise at −10° C. to 0° C. After 1 hr the mixture was filtered, the filtrate was washed with ice cold $CH_2Cl_2$ and the combined organic phase was washed with water, brine and dried over anhydrous $Na_2SO_4$. The solution was concentrated to get 2'-O-(aminooxyethyl) thymidine, which was then dissolved in MeOH (67.5 mL). To this formaldehyde (20% aqueous solution, w/w, 1.1 eg.) was added and the mixture for 1 hr. Solvent was removed under vacuum; residue chromatographed to get 5'-O-tert-butyldiphenylsilyl-2'-O-[(2-formadoximinooxy)ethyl]-5-methyluridine as white foam (1.95, 78%).

5'-O-tert-Butyldiphenylsilyl-2'-O-[N,N-dimethylaminooxyethyl]-5-methyluridine 5'-O-tert-butyldiphenylsilyl-2'-O-[(2-formadoximinooxy) ethyl]-5-methyluridine (1.77 g, 3.12 mmol) was dissolved in a solution of 1M pyridinium p-toluenesulfonate (PPTS) in dry MeOH (30.6 mL). Sodium cyanoborohydride (0.39 g, 6.13 mmol) was added to this solution at 10° C. under inert atmosphere. The reaction mixture was stirred for 10 minutes at 10° C. After that the reaction vessel was removed from the ice bath and stirred at room temperature for 2 hr, the reaction monitored by TLC (5% MeOH in $CH_2Cl_2$). Aqueous $NaHCO_3$ solution (5%, 10 mL) was added and extracted with ethyl acetate (2×20 mL). Ethyl acetate phase was dried over anhydrous $Na_2SO_4$, evaporated to dryness. Residue was dissolved in a solution of 1M PPTS in MeOH (30.6 mL). Formaldehyde (20% w/w, 30 mL, 3.37 mmol) was added and the reaction mixture was stirred at room temperature for 10 minutes. Reaction mixture cooled to 10° C. in an ice bath, sodium cyanoborohydride (0.39 g, 6.13 mmol) was added and reaction mixture stirred at 10° C. for 10 minutes. After 10 minutes, the reaction mixture was removed from the ice bath and stirred at room temperature for 2 hrs. To the reaction mixture 5% $NaHCO_3$ (25 mL) solution was added and extracted with ethyl acetate (2×25 mL). Ethyl acetate layer was dried over anhydrous $Na_2SO_4$ and evaporated to dryness. The residue obtained was purified by flash column chromatography and eluted with 5% MeOH in $CH_2Cl_2$ to get 5'-O-tert-butyldiphenylsilyl-2'-O-[N,N-dimethylaminooxyethyl]-5-methyluridine as a white foam (14.6 g, 80%).

2'-O-(dimethylaminooxyethyl)-5-methyluridine

Triethylamine trihydrofluoride (3.91 mL, 24.0 mmol) was dissolved in dry THF and triethylamine (1.67 mL, 12 mmol, dry, kept over KOH). This mixture of triethylamine-2HF was then added to 5'-O-tert-butyldiphenylsilyl-2'-O-[N,N-dimethylaminooxyethyl]-5-methyluridine (1.40 g, 2.4 mmol) and stirred at room temperature for 24 hrs. Reaction was monitored by TLC (5% MeOH in $CH_2Cl_2$). Solvent was removed under vacuum and the residue placed on a flash column and eluted with 10% MeOH in $CH_2Cl_2$ to get 2'-O-(dimethylaminooxyethyl)-5-methyluridine (766 mg, 92.5%).

5'-O-DMT-2'-O-(dimethylaminooxyethyl)-5-methyluridine

2'-O-(dimethylaminooxyethyl)-5-methyluridine (750 mg, 2.17 mmol) was dried over $P_2O_5$ under high vacuum overnight at 40° C. It was then co-evaporated with anhydrous pyridine (20 mL). The residue obtained was dissolved in pyridine (11 mL) under argon atmosphere. 4-dimethylaminopyridine (26.5 mg, 2.60 mmol), 4,4'-dimethoxytrityl chloride (880 mg, 2.60 mmol) was added to the mixture and the reaction mixture was stirred at room temperature until all of the starting material disappeared. Pyridine was removed under vacuum and the residue chromatographed and eluted with 10% MeOH in $CH_2Cl_2$ (containing a few drops of pyridine) to get 5'-O-DMT-2'O-(dimethylamino-oxyethyl)-5-methyluridine (1.13 g, 80%).

5'-O-DMT-2'-O-(2-N,N-dimethylaminooxyethyl)-5-methyluridine-3'-[(2-cyanoethyl)-N,N-diisoproylphosphoramidite]

5'-O-DMT-2'-O-(dimethylaminooxyethyl)-5-methyluridine (1.08 g, 1.67 mmol) was co-evaporated with toluene (20 mL). To the residue N,N-diisopropylamine tetrazonide (0.29 g, 1.67 mmol) was added and dried over $P_2O_5$ under high vacuum overnight at 40° C. Then the reaction mixture was dissolved in anhydrous acetonitrile (8.4 mL) and 2-cyanoethyl-N,N,$N^1$,$N^1$-tetraisopropylphosphoramidite (2.12 mL, 6.08 mmol) was added. The reaction mixture was stirred at ambient temperature for 4 hrs under inert atmosphere. The progress of the reaction was monitored by TLC (hexane:ethyl acetate 1:1). The solvent was evaporated, then the residue was dissolved in ethyl acetate (70 mL) and washed with 5% aqueous $NaHCO_3$ (40 mL). Ethyl acetate layer was dried over anhydrous $Na_2SO_4$ and concentrated. Residue obtained was chromatographed (ethyl acetate as eluent) to get 5'-O-DMT-2'-O-(2-N,N-dimethylaminooxyethyl)-5-methyluridine-3'-[(2-cyanoethyl)-N,N-diisopropylphosphoramidite] as a foam (1.04 g, 74.9%).

Oligonucleotides having methylene(methylimino) (MMI) backbones are synthesized according to U.S. Pat. No. 5,378,825, which is coassigned to the assignee of the present invention and is incorporated herein in its entirety. For ease of synthesis, various nucleoside dimers containing MMI linkages are synthesized and incorporated into oligonucleotides. Other nitrogen-containing backbones are synthesized according to WO 92/20823 which is also coassigned to the assignee of the present invention and incorporated herein in its entirety.

Oligonucleotides having amide backbones are synthesized according to De Mesmaeker et al. (*Acc. Chem. Res.* 1995, 28, 366-374). The amide moiety is readily accessible by simple and well-known synthetic methods and is compatible with the conditions required for solid phase synthesis of oligonucleotides.

Oligonucleotides with morpholino backbones are synthesized according to U.S. Pat. No. 5,034,506 (Summerton and Weller).

Peptide-nucleic acid (PNA) oligomers are synthesized according to P. E. Nielsen et al. (*Science* 1991, 254, 1497-1500).

After cleavage from the controlled pore glass column (Applied Biosystems) and deblocking in concentrated ammonium hydroxide at 55° C. for 18 hours, the oligonucleotides are purified by precipitation twice out of 0.5 M NaCl with 2.5 volumes ethanol. Synthesized oligonucleotides were analyzed by polyacrylamide gel electrophoresis on denaturing gels or capillary gel electrophoresis and judged to be at least 85% full length material. The relative amounts of phosphorothioate and phosphodiester linkages obtained in synthesis were periodically checked by $^{31}P$ nuclear magnetic resonance spectroscopy, and for some studies oligonucleotides were purified by HPLC, as described by Chiang et al. (*J. Biol. Chem.* 1991, 266, 18162). Results obtained with HPLC-purified material were similar to those obtained with non-HPLC purified material.

Alternatively, oligonucleotides were synthesized in 96 well plate format via solid phase P(III) phosphoramidite chemistry on an automated synthesizer capable of assembling 96 sequences simultaneously in a standard 96 well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyl-di-isopropyl phosphoramidites were purchased from commercial vendors (e.g. PE-Applied Biosystems, Foster City, Calif., or Pharmacia, Piscataway, N.J.). Non-standard nucleosides are synthesized as per published methods. They are utilized as base protected beta-cyanoethyldiisopropyl phosphoramidites.

Oligonucleotides were cleaved from support and deprotected with concentrated $NH_4OH$ at elevated temperature (55-60° C.) for 12-16 hours and the released product then dried in vacuo. The dried product was then re-suspended in sterile water to afford a master plate from which all analytical and test plate samples are then diluted utilizing robotic pipettors.

Example 2

Human STAT3 Oligodeoxynucleotide Sequences

Antisense oligonucleotides were designed to target human STAT3. Target sequence data are from the APRF cDNA sequence published by Akira, S. et al. (*Cell*, 1994, 77, 63-71); Genbank accession number L29277, provided herein as SEQ ID NO: 1. A set of oligodeoxynucleotides were synthesized with phosphorothioate linkages. 2'-deoxy cytosines were 5-methyl cytosines. These oligonucleotide sequences are shown in Table 1. An additional set of oligonucleotides was synthesized as chimeric oligonucleotides ("gapmers") 20 nucleotides in length, composed of a central "gap" region consisting of ten 2'-deoxynucleotides, which is flanked on both sides (5' and 3' directions) by five-nucleotide "wings." The wings are composed of 2'-methoxyethyl (2'-MOE)nucleotides. The internucleoside (backbone) linkages are phosphorothioate (P=S) throughout the oligonucleotide. All 2'-MOE cytosines and 2'-deoxy cytosines were 5-methyl-cytosines. These oligonucleotide sequences are shown in Table 2.

An appropriate cell line, typically expressing high levels of STAT3, is chosen for in vitro studies. Cell culture conditions are those standard for that particular cell line. Oligonucleotide treatment is for four hours and mRNA usually isolated 24 to 48 hours following initial treatment. mRNA is isolated using the RNAEASY7 kit (Qiagen, Santa Clarita, Calif.).

TABLE 1

Nucleotide Sequences of Human STAT3 Phosphorothioate Oligodeoxynucleotides

| ISIS NO. | NUCLEOTIDE SEQUENCE[1] (5' -> 3') | SEQ ID NO: | TARGET GENE NUCLEOTIDE CO-ORDINATES[2] | GENE TARGET REGION |
|---|---|---|---|---|
| 106691 | GTCTGCGCCGCCGCCCCGAA | 2 | 0010-0029 | 5'-UTR |
| 106692 | GGCCGAAGGGCCTCTCCGAG | 3 | 0130-0149 | 5'-UTR |
| 106693 | TCCTGTTTCTCCGGCAGAGG | 4 | 0202-0221 | AUG |
| 106694 | CATCCTGTTTCTCCGGCAGA | 5 | 0204-0223 | AUG |
| 106695 | GCCATCCTGTTTCTCCGGCA | 6 | 0206-0225 | AUG |
| 106696 | GGGCCATCCTGTTTCTCCGG | 7 | 0208-0227 | AUG |
| 106697 | TTGGGCCATCCTGTTTCTCC | 8 | 0210-0229 | AUG |
| 106698 | CATTGGGCCATCCTGTTTCT | 9 | 0212-0231 | AUG |
| 106699 | TCCATTGGGCCATCCTGTTT | 10 | 0214-0233 | AUG |
| 106700 | ATTCCATTGGGCCATCCTGT | 11 | 0216-0235 | AUG |
| 106701 | TGATTCCATTGGGCCATCCT | 12 | 0218-0237 | AUG |
| 106702 | GCTGATTCCATTGGGCCATC | 13 | 0220-0239 | AUG |
| 106703 | TAGCTGATTCCATTGGGCCA | 14 | 0222-0241 | AUG |
| 106704 | TGTAGCTGATTCCATTGGGC | 15 | 0224-0243 | coding |
| 106705 | CTGTAGAGCTGATGGAGCTG | 16 | 0269-0288 | coding |
| 106706 | CCCAATCTTGACTCTCAATC | 17 | 0331-0350 | coding |
| 106707 | CCCAGGAGATTATGAAACAC | 18 | 0386-0405 | coding |
| 106708 | ACATTCGACTCTTGCAGGAA | 19 | 0431-0450 | coding |
| 106709 | TCTGAAGAAACTGCTTGATT | 20 | 0475-0494 | coding |
| 106710 | GGCCACAATCCGGGCAATCT | 21 | 0519-0538 | coding |
| 106711 | TGGCTGCAGTCTGTAGAAGG | 22 | 0562-0581 | coding |
| 106712 | CTGCTCCAGCATCTGCTGCT | 23 | 0639-0658 | coding |
| 106713 | TTTCTGTTCTAGATCCTGCA | 24 | 0684-0703 | coding |
| 106714 | TAGTTGAAATCAAAGTCATC | 25 | 0728-0747 | coding |
| 106715 | TTCCATTCGATCTTGCATG | 26 | 0772-0791 | coding |
| 106716 | TCTGTTCCAGCTGCTGCATC | 27 | 0817-0836 | coding |
| 106717 | TCACTCACGATGCTTCTCCG | 28 | 0860-0879 | coding |
| 106718 | GAGTTTTCTGCACGTACTCC | 29 | 0904-0923 | coding |
| 106719 | ATCTGTTGCCGCCTCTTCCA | 30 | 0947-0968 | coding |
| 106720 | CTAGCCGATCTAGGCAGATG | 31 | 0991-1010 | coding |

TABLE 1-continued

Nucleotide Sequences of Human STAT3 Phosphorothioate Oligodeoxynucleotides

| ISIS NO. | NUCLEOTIDE SEQUENCE[1] (5' -> 3') | SEQ ID NO: | TARGET GENE NUCLEOTIDE CO-ORDINATES[2] | GENE TARGET REGION |
|---|---|---|---|---|
| 106721 | CGGGTCTGAAGTTGAGATTC | 32 | 1034-1053 | coding |
| 106722 | CGGCCGGTGCTGTACAATGG | 33 | 1110-1129 | coding |
| 106723 | TTTCATTAAGTTTCTGAACA | 34 | 1155-1174 | coding |
| 106724 | AGGATGCATGGGCATGCAGG | 35 | 1200-1219 | coding |
| 106725 | GACCAGCAACCTGACTTTAG | 36 | 1260-1279 | coding |
| 106726 | ATGCACACTTTAATTTTAAG | 37 | 1304-1323 | coding |
| 106727 | TTCCGGGATCCTCTGAGAGC | 38 | 1349-1368 | coding |
| 106728 | TTCCATGTTCATCACTTTTG | 39 | 1392-1411 | coding |
| 106729 | GTCAAGTGTTTGAATTCTGC | 40 | 1436-1455 | coding |
| 106730 | CAATCAGGGAAGCATCACAA | 41 | 1495-1514 | coding |
| 106731 | TACACCTCGGTCTCAAAGGT | 42 | 1538-1557 | coding |
| 106732 | TGACAAGGAGTGGGTCTCTA | 43 | 1581-1600 | coding |
| 106733 | CGCCCAGGCATTTGGCATCT | 44 | 1626-1645 | coding |
| 106734 | CATTCTTGGGATTGTTGGTC | 45 | 1669-1688 | coding |
| 106735 | CACTTGGTCCCAGGTTCCAA | 46 | 1713-1732 | coding |
| 106736 | CCCGCTTGGTGGTGGACGAG | 47 | 1756-1775 | coding |
| 106737 | AGTTCACACCAGGCCCTAGG | 48 | 1816-1835 | coding |
| 106738 | GTTTTCTTTGCAGAAGTTAG | 49 | 1860-1879 | coding |
| 106739 | ATATTGTCTAGCCAGACCCA | 50 | 1904-1923 | coding |
| 106740 | AACCCATGATGTACCCTTCA | 51 | 1963-1982 | coding |
| 106741 | GCTTAGTGCTCAAGATGGCC | 52 | 2005-2024 | coding |
| 106742 | GCTGCTTTCACTGAAGCGCA | 53 | 2043-2062 | coding |
| 106743 | GTGAAAGTGACGCCTCCTTC | 54 | 2066-2085 | coding |
| 106744 | CTGATGTCCTTCTCCACCCA | 55 | 2087-2106 | coding |
| 106745 | ACTGGATCTGGGTCTTACCG | 56 | 2107-2126 | coding |
| 106746 | AAATGACATGTTGTTCAGCT | 57 | 2151-2170 | coding |
| 106747 | GCCCATGATGATTTCAGCAA | 58 | 2169-2188 | coding |
| 106748 | TATTGGTAGCATCCATGATC | 59 | 2194-2213 | coding |
| 106749 | ATAGACAAGTGGAGACAACA | 60 | 2217-2236 | coding |
| 106750 | TTGGGAATGTCAGGATAGAG | 61 | 2237-2256 | coding |
| 106751 | CTCCTGGCTCTCTGGCCGAC | 62 | 2280-2299 | coding |
| 106752 | ACCTGGGTCAGCTTCAGGAT | 63 | 2301-2320 | coding |
| 106753 | CACAGATAAACTTGGTCTTC | 64 | 2338-2357 | coding |
| 106754 | ATCGGCAGGTCAATGGTATT | 65 | 2378-2397 | coding |
| 106755 | CCAAACTGCATCAATGAATC | 66 | 2414-2433 | coding |
| 106756 | GGTTCAGCACCTTCACCATT | 67 | 2438-2457 | coding |

TABLE 1-continued

Nucleotide Sequences of Human STAT3
Phosphorothioate Oligodeoxynucleotides

| ISIS NO. | NUCLEOTIDE SEQUENCE[1] (5' -> 3') | SEQ ID NO: | TARGET GENE NUCLEOTIDE CO-ORDINATES[2] | GENE TARGET REGION |
|---|---|---|---|---|
| 106757 | GAGGGACTCAAACTGCCCTC | 68 | 2466-2485 | coding |
| 106758 | CAACTCCATGTCAAAGGTGA | 69 | 2484-2503 | coding |
| 106759 | TTCTCAGCTCCTCACATGGG | 70 | 2525-2544 | STOP |
| 106760 | CGTTCTCAGCTCCTCACATG | 71 | 2527-2546 | STOP |
| 106761 | TCCGTTCTCAGCTCCTCACA | 72 | 2529-2548 | STOP |
| 106762 | CTTCCGTTCTCAGCTCCTCA | 73 | 2531-2550 | STOP |
| 106763 | AGCTTCCGTTCTCAGCTCCT | 74 | 2533-2552 | STOP |
| 106764 | AGAATGCAGGTAGGCGCCTC | 75 | 2569-2588 | 3'-UTR |
| 106765 | ACCACAAAGTTAGTAGTTTC | 76 | 2623-2642 | 3'-UTR |
| 106766 | TGCTCAAAGATAGCAGAAGT | 77 | 2665-2684 | 3'-UTR |
| 106767 | ATTCACTCATTTCTCTATTT | 78 | 2701-2720 | 3'-UTR |
| 106768 | CATTTAGATAAAAGCAGATC | 79 | 2727-2746 | 3'-UTR |
| 106769 | ACATCCTTATTTGCATTTAG | 80 | 2740-2759 | 3'-UTR |
| 106770 | GATCATGGGTCTCAGAGAAC | 81 | 2760-2779 | 3'-UTR |

[1] "C" residues are 5-methyl-cytosines; all linkages are phosphorothioate linkages.
[2] Coordinates from Genbank Accession No. L29277, locus name "HUMAPRF", SEQ ID NO. 1.

TABLE 2

Nucleotide Sequences of Human STAT3
Chimeric (deoxy gapped) Phosphorothioate
Oligonucleotides

| ISIS NO. | NUCLEOTIDE SEQUENCE[1] (5' -> 3') | SEQ ID NO: | TARGET GENE NUCLEOTIDE CO-ORDINATES[2] | GENE TARGET REGION |
|---|---|---|---|---|
| 106771 | GTCTGCGCCGCCGCCCCGAA | 2 | 0010-0029 | 5'-UTR |
| 106772 | GGCCGAAGGGCCTCTCCGAG | 3 | 0130-0149 | 5'-UTR |
| 106773 | TCCTGTTTCTCCGGCAGAGG | 4 | 0202-0221 | AUG |
| 106774 | CATCCTGTTTCTCCGGCAGA | 5 | 0204-0223 | AUG |
| 106775 | GCCATCCTGTTTCTCCGGCA | 6 | 0206-0225 | AUG |
| 106776 | GGGCCATCCTGTTTCTCCGG | 7 | 0208-0227 | AUG |
| 106777 | TTGGGCCATCCTGTTTCTCC | 8 | 0210-0229 | AUG |
| 106778 | CATTGGGCCATCCTGTTTCT | 9 | 0212-0231 | AUG |
| 106779 | TCCATTGGGCCATCCTGTTT | 10 | 0214-0233 | AUG |
| 106780 | ATTCCATTGGGCCATCCTGT | 11 | 0216-0235 | AUG |
| 106781 | TGATTCCATTGGGCCATCCT | 12 | 0218-0237 | AUG |
| 106782 | GCTGATTCCATTGGGCCATC | 13 | 0220-0239 | AUG |
| 106783 | TAGCTGATTCCATTGGGCCA | 14 | 0222-0241 | AUG |
| 106784 | TGTAGCTGATTCCATTGGGC | 15 | 0224-0243 | coding |
| 106785 | CTGTAGAGCTGATGGAGCTG | 16 | 0269-0288 | coding |
| 106786 | CCCAATCTTGACTCTCAATC | 17 | 0331-0350 | coding |
| 106787 | CCCAGGAGATTATGAAACAC | 18 | 0386-0405 | coding |
| 106788 | ACATTCGACTCTTGCAGGAA | 19 | 0431-0450 | coding |
| 106789 | TCTGAAGAAACTGCTTGATT | 20 | 0475-0494 | coding |
| 106790 | GGCCACAATCCGGGCAATCT | 21 | 0519-0538 | coding |
| 106791 | TGGCTGCAGTCTGTAGAAGG | 22 | 0562-0581 | coding |
| 106792 | CTGCTCCAGCATCTGCTGCT | 23 | 0639-0658 | coding |
| 106793 | TTTCTGTTCTAGATCCTGCA | 24 | 0684-0703 | coding |
| 106794 | TAGTTGAAATCAAAGTCATC | 25 | 0728-0747 | coding |
| 106795 | TTCCATTCAGATCTTGCATG | 26 | 0772-0791 | coding |
| 106796 | TCTGTTCCAGCTGCTGCATC | 27 | 0817-0836 | coding |
| 106797 | TCACTCACGATGCTTCTCCG | 28 | 0860-0879 | coding |
| 106798 | GAGTTTTCTGCACGTACTCC | 29 | 0904-0923 | coding |
| 106799 | ATCTGTTGCCGCCTCTTCCA | 30 | 0947-0968 | coding |
| 106800 | CTAGCCGATCTAGGCAGATG | 31 | 0991-1010 | coding |
| 106801 | CGGGTCTGAAGTTGAGATTC | 32 | 1034-1053 | coding |
| 106802 | CGGCCGGTGCTGTACAATGG | 33 | 1110-1129 | coding |
| 106803 | TTTCATTAAGTTTCTGAACA | 34 | 1155-1174 | coding |
| 106804 | AGGATGCATGGGCATGCAGG | 35 | 1200-1219 | coding |
| 106805 | GACCAGCAACCTGACTTTAG | 36 | 1260-1279 | coding |
| 106806 | ATGCACACTTTAATTTTAAG | 37 | 1304-1323 | coding |
| 106807 | TTCCGGGATCCTCTGAGAGC | 38 | 1349-1368 | coding |
| 106808 | TTCCATGTTCATCACTTTTG | 39 | 1392-1411 | coding |
| 106809 | GTCAAGTGTTTGAATTCTGC | 40 | 1436-1455 | coding |
| 106810 | CAATCAGGGAAGCATCACAA | 41 | 1495-1514 | coding |
| 106811 | TACACCTCGGTCTCAAAGGT | 42 | 1538-1557 | coding |
| 106812 | TGACAAGGAGTGGGTCTCTA | 43 | 1581-1600 | coding |
| 106813 | CGCCCAGGCATTTGGCATCT | 44 | 1626-1645 | coding |
| 106814 | CATTCTTGGGATTGTTGGTC | 45 | 1669-1688 | coding |
| 106815 | CACTTGGTCCCAGGTTCCAA | 46 | 1713-1732 | coding |
| 106816 | CCCGCTTGGTGGTGGACGAG | 47 | 1756-1775 | coding |
| 106817 | AGTTCACACCAGGCCCTAGG | 48 | 1816-1835 | coding |
| 106818 | GTTTTCTTTGCAGAAGTTAG | 49 | 1860-1879 | coding |
| 106819 | ATATTGTCTAGCCAGACCCA | 50 | 1904-1923 | coding |
| 106820 | AACCCATGATGTACCCTTCA | 51 | 1963-1982 | coding |

TABLE 2-continued

Nucleotide Sequences of Human STAT3 Chimeric (deoxy gapped) Phosphorothioate Oligonucleotides

| ISIS NO. | NUCLEOTIDE SEQUENCE[1] (5' -> 3') | SEQ ID NO: | TARGET GENE NUCLEOTIDE CO-ORDINATES[2] | GENE TARGET REGION |
|---|---|---|---|---|
| 106821 | GCTTAGTGCTCAAGATGGCC | 52 | 2005-2024 | coding |
| 106822 | GCTGCTTTCACTGAAGCGCA | 53 | 2043-2062 | coding |
| 106823 | GTGAAAGTGACGCCTCCTTC | 54 | 2066-2085 | coding |
| 106824 | CTGATGTCCTTCTCCACCCA | 55 | 2087-2106 | coding |
| 106825 | ACTGGATCTGGGTCTTACCG | 56 | 2107-2126 | coding |
| 106826 | AAATGACATGTTGTTCAGCT | 57 | 2151-2170 | coding |
| 106827 | GCCCATGATGATTTCAGCAA | 58 | 2169-2188 | coding |
| 106828 | TATTGGTAGCATCCATGATC | 59 | 2194-2213 | coding |
| 106829 | ATAGACAAGTGGAGACAACA | 60 | 2217-2236 | coding |
| 106830 | TTGGGAATGTCAGGATAGAG | 61 | 2237-2256 | coding |
| 106831 | CTCCTGGCTCTCTGGCCGAC | 62 | 2280-2299 | coding |
| 106832 | ACCTGGGTCAGCTTCAGGAT | 63 | 2301-2320 | coding |
| 106833 | CACAGATAAACTTGGTCTTC | 64 | 2338-2357 | coding |
| 106834 | ATCGGCAGGTCAATGGTATT | 65 | 2378-2397 | coding |
| 106835 | CCAAACTGCATCAATGAATC | 66 | 2414-2433 | coding |
| 106836 | GGTTCAGCACCTTCACCATT | 67 | 2438-2457 | coding |
| 106837 | GAGGGACTCAAACTGCCCTC | 68 | 2466-2485 | coding |
| 106838 | CAACTCCATGTCAAAGGTGA | 69 | 2484-2503 | coding |
| 106839 | TTCTCAGCTCCTCACATGGG | 70 | 2525-2544 | STOP |
| 106840 | CGTTCTCAGCTCCTCACATG | 71 | 2527-2546 | STOP |
| 106841 | TCCGTTCTCAGCTCCTCACA | 72 | 2529-2548 | STOP |
| 106842 | CTTCCGTTCTCAGCTCCTCA | 73 | 2531-2550 | STOP |
| 106843 | AGCTTCCGTTCTCAGCTCCT | 74 | 2533-2552 | STOP |
| 106844 | AGAATGCAGGTAGGCGCCTC | 75 | 2569-2588 | 3'-UTR |
| 106845 | ACCACAAAGTTAGTAGTTTC | 76 | 2623-2642 | 3'-UTR |
| 106846 | TGCTCAAAGATAGCAGAAGT | 77 | 2665-2684 | 3'-UTR |
| 106847 | ATTCACTCATTTCTCTATTT | 78 | 2701-2720 | 3'-UTR |
| 106848 | CATTTAGATAAAAGCAGATC | 79 | 2727-2746 | 3'-UTR |
| 106849 | ACATCCTTATTTGCATTTAG | 80 | 2740-2759 | 3'-UTR |
| 106850 | GATCATGGGTCTCAGAGAAC | 81 | 2760-2779 | 3'-UTR |

[1]Emboldened residues are 2'-methoxyethoxy residues, 2'-methoxyethoxy cytosine residues and 2'-OH cytosine residues are 5-methyl-cytosines; all linkages are phosphorothioate linkages.
[2]Coordinates from Genbank Accession No. L29277, locus name "HUMAPRF", SEQ ID NO. 1.

Oligonucleotide activity is assayed by quantitation of STAT3 mRNA levels by real-time PCR (RT-PCR) using the ABI PRISM™ 7700 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR, in which amplification products are quantitated after the PCR is completed, products in RT-PCR are quantitated as they accumulate. This is accomplished by including in the PCR reaction an oligonucleotide probe that anneals specifically between the forward and reverse PCR primers, and contains two fluorescent dyes. A reporter dye (e.g., JOE or FAM, PE-Applied Biosystems, Foster City, Calif.) is attached to the 5' end of the probe and a quencher dye (e.g., TAMRA, PE-Applied Biosystems, Foster City, Calif.) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated with each cycle, additional reporter dye molecules are cleaved from their respective probes, and the fluorescence intensity is monitored at regular (six-second) intervals by laser optics built into the ABI PRISM™ 7700 Sequence Detection System. In each assay, a series of parallel reactions containing serial dilutions of mRNA from untreated control samples generates a standard curve that is used to quantitate the percent inhibition after antisense oligonucleotide treatment of test samples.

RT-PCR reagents are obtained from PE-Applied Biosystems, Foster City, Calif. RT-PCR reactions are carried out by adding 25•l PCR cocktail (1×TAQMAN7 buffer A, 5.5 nM $MgCl_2$, 300 •M each of dATP, dCTP and dGTP, 600 •M of dUTP, 100 nM each of forward primer, reverse primer, and probe, 20 U RNAse inhibitor, 1.25 units AMPLITAQ GOLD7, and 12.5 U MuLV reverse transcriptase) to 96 well plates containing 25 •l poly(A) mRNA solution. The RT reaction is carried out by incubation for 30 minutes at 48° C. following a 10 minute incubation at 95° C. to activate the AMPLITAQ GOLD7, 40 cycles of a two-step PCR protocol are carried out: 95° C. for 15 seconds. (denaturation) followed by 60° C. for 1.5 minutes (annealing/extension).

STAT3 PCR primers and a probe can be designed using commercial software (e.g. Oligo 5.0).

Example 3

Mouse STAT3 Oligonucleotide Sequences

Antisense oligonucleotides were designed to target mouse STAT3. Target sequence data are from the STAT3 cDNA sequence submitted by Zhong, Z.; Genbank accession number U06922, provided herein as SEQ ID NO: 82. Oligonucleotides were synthesized as chimeric oligonucleotides ("gapmers") 20 nucleotides in length, composed of a central "gap" region consisting of ten 2'-deoxynucleotides, which is flanked on both sides (5' and 3' directions) by five-nucleotide "wings." The wings are composed of 2'-methoxyethyl (2'-MOE) nucleotides. The internucleoside (backbone) linkages are phosphorothioate (P=S) throughout the oligonucleotide. All 2'-MOE cytosines were 5-methyl-cytosines. Oligonucleotide sequences are shown in Table 3.

The B lymphoma cell line, BCL1 was obtained from ATCC (Rockville, Md.). BCL1 cells were cultured in RPMI 1640 medium.

BCL1 cells (5×10⁶ cells in PBS) were transfected with oligonucleotides by electroporation, at 200V, 1000° F. using a BTX Electro Cell Manipulator 600 (Genetronics, San Diego, Calif.). For an initial screen, BCL1 were electroporated with 10 •M oligonucleotide and RNA collected 24 hours later. Controls without oligonucleotide were subjected to the same electroporation conditions.

Total cellular RNA was isolated using the RNEASY7 kit (Qiagen, Santa Clarita, Calif.). RNAse protection experiments were conducted using RIBOQUANT™ kits and template sets according to the manufacturer's instructions (Pharmingen, San Diego, Calif.). Northern blotting was performed as described in Chiang, M-Y. et al. (*J. Biol. Chem.*, 1991, 266, 18162-18171), using a rat cDNA probe prepared by Xho I/Sal I restriction digest of psvsport-1 plasmid (ATCC, Rockville, Md.). mRNA levels were quantitated using a PhosphorImager (Molecular Dynamics, Sunnyvale, Calif.).

TABLE 3

Nucleotide Sequences of Mouse STAT3 Chimeric (deoxy gapped) Phosphorothioate Oligodeoxynucleotides

| ISIS NO. | NUCLEOTIDE SEQUENCE[1] (5' -> 3') | SEQ ID NO: | TARGET GENE NUCLEOTIDE CO-ORDINATES[2] | GENE TARGET REGION |
|---|---|---|---|---|
| 17136 | GTTCCACTGAGCCATCCTGC | 83 | 0064-0083 | AUG |
| 17137 | TTCAGGTAGCGTGTGTCCAG | 84 | 0096-0115 | coding |
| 17138 | ATGTGACTCTTTGCTGGCTG | 85 | 0205-0224 | coding |
| 17139 | CCAAGAGATTATGAAACACC | 86 | 0233-0252 | coding |
| 17140 | GCTCCAACATCTGCTGCTTC | 87 | 0485-0504 | coding |
| 17141 | GCTCTTCATCAGTCAGTGTC | 88 | 0767-0786 | coding |
| 17142 | ATCTGACACCCTGAGTAGTT | 89 | 1680-1699 | coding |
| 17143 | GCCAGACCCAGAAGGAGAAG | 90 | 1742-1761 | coding |
| 17144 | CGCTCCTTGCTGATGAAACC | 91 | 1827-1846 | coding |
| 17145 | AACTTGGTCTTCAGGTACGG | 92 | 2178-2197 | coding |
| 17146 | ATCAATGAATCTAAAGTGCG | 93 | 2253-2272 | coding |
| 17147 | TCAGCACCTTCACCGTTATT | 94 | 2283-2302 | coding |
| 17148 | ACTCAAACTGCCCTCCTGCT | 95 | 2309-2328 | coding |
| 17149 | GGTTTCAGCTCCTCACATGG | 96 | 2374-2393 | STOP |
| 17150 | TAAAAAAAAAAATCTGGAAC | 97 | 2485-2504 | 3'-UTR |
| 17151 | AAGATAGCAGAAGTAGGAAA | 98 | 2506-2525 | 3'-UTR |
| 17152 | AAAAAGTGCCCAGATTGCCC | 99 | 2527-2546 | 3'-UTR |
| 17153 | ATCACCCACACTCACTCATT | 100 | 2557-2645 | 3'-UTR |
| 17154 | CCTTTGCCTCCCTTCTGCTC | 101 | 2626-2645 | 3'-UTR |
| 17155 | TGAAAAAGGAGGGCAGGCGG | 102 | 2665-2684 | 3'-UTR |
| 17156 | CACCAGGAGGCACTTGTCTA | 103 | 2705-2724 | 3'-UTR |
| 17157 | AACCTCCTGGGCTTAGTCCT | 104 | 2822-2841 | 3'-UTR |
| 23176 | AAAAAGTGCGCAGATTGCCC | 105 | | 1 base mismatch control |
| 23177 | AAAAAGTCCGCTGATTGCCC | 106 | | 3 base mismatch control |
| 23178 | AAAAACTCCGCTGAATGCCC | 107 | | 5 base mismatch control |

[1]All 2'-MOE cytosine residues are 5-methyl-cytosines; all linkages are phosphorothioate linkages.
[2]Co-ordinates from Genbank Accession No. U06922, locus name "MMU06922", SEQ ID NO. 82.

Results are shown in Table 4. Oligonucleotides 17138 (SEQ ID NO. 85), 17139 (SEQ ID NO. 86), 17140 (SEQ ID NO. 87), 17143 (SEQ ID. NO. 90), 17144 (SEQ ID NO. 91), 17152 (SEQ ID NO. 99), 17153 (SEQ ID NO. 100), 17156 (SEQ ID NO. 103), and 17157 (SEQ ID NO. 104) gave better than 45% inhibition in this assay.

TABLE 4

Inhibition of Mouse STAT3 mRNA expression in BCL1 Cells by Chimeric (deoxy gapped) Phosphorothioate Oligonucleotides

| ISIS No: | SEQ ID NO: | GENE TARGET REGION | % mRNA EXPRESSION | % mRNA INHIBITION |
|---|---|---|---|---|
| control | — | — | 100% | 0% |
| 17136 | 83 | AUG | 75% | 25% |
| 17137 | 84 | coding | 75% | 25% |
| 17138 | 85 | coding | 37% | 63% |
| 17139 | 86 | coding | 41% | 59% |
| 17140 | 87 | coding | 40% | 60% |
| 17141 | 88 | coding | 62% | 38% |
| 17142 | 89 | coding | 70% | 30% |
| 17143 | 90 | coding | 42% | 58% |
| 17144 | 91 | coding | 55% | 45% |
| 17145 | 92 | coding | 89% | 11% |
| 17146 | 93 | coding | 91% | 9% |
| 17147 | 94 | coding | 70% | 30% |
| 17148 | 95 | coding | 69% | 31% |
| 17149 | 96 | STOP | 70% | 30% |
| 17150 | 97 | 3'-UTR | 95% | 5% |
| 17151 | 98 | 3'-UTR | 92% | 8% |
| 17152 | 99 | 3'-UTR | 25% | 75% |
| 17153 | 100 | 3'-UTR | 44% | 56% |
| 17154 | 101 | 3'-UTR | 80% | 20% |
| 17155 | 102 | 3'-UTR | 78% | 22% |
| 17156 | 103 | 3'-UTR | 40% | 60% |
| 17157 | 104 | 3'-UTR | 53% | 47% |

Example 4

Dose Response of Antisense Chimeric (Deoxy Gapped) Phosphorothioate Oligonucleotide Effects on Mouse STAT3 Protein Levels in BCL1 Cells ISIS 17152 (SEQ ID. NO. 99) was chosen for further study. The effect of this oligonucleotide on protein levels was determined by Western blot. ISIS 23177 (SEQ ID NO. 10), a 3 base mismatch, was used as a control. BCL1 cells were grown, treated and processed as described in Example 2.

Nuclear extracts from primary B cells and B lymphoma cell lines were prepared as described in Karras, J. G., et al. (*J. Exp. Med.*, 1997, 185, 1035-10.42).

Western blotting was performed as described in Karras, J. G. et al. (*J. Immunol.*, 1996, 157, 2299). STAT1 and STAT3 antibodies were obtained from UBI (Lake Placid, NY).

Results are shown in Table 5. ISIS 17152 (SEQ ID NO. 99) was significantly better at reducing STAT3 protein levels than the mismatch control.

TABLE 5

Dose Response of BCL1 cells to STAT3 Chimeric (deoxy gapped) Phosphorothioate Oligonucleotides

| ISIS # | SEQ ID NO: | ASO Gene Target | Dose | % protein Expression | % protein Inhibition |
|---|---|---|---|---|---|
| control | — | — | — | 100% | — |
| 17152 | 99 | 3'-UTR | 10 nM | 41.7% | 58.3% |
| " | " | " | 15 nM | 42.5% | 57.5% |
| " | " | " | 20 nM | 26.5% | 73.5% |
| 23177 | 106 | control | 10 nM | 75.1% | 24.9% |
| " | " | " | 15 nM | 67.6% | 32.4% |
| " | " | " | 20 nM | 62.6% | 37.4% |

Example 5

Inhibition of BCL1 Proliferation by STAT3 Antisense Chimeric (Deoxy Gapped) Phosphorothioate Oligonucleotide The effect of ISIS 17152 (SEQ ID NO. 99) on BCL1 proliferation was determined. BCL1 cells contain constitutively active STAT3 which is thought to be responsible for their proliferation. BCL1 cells were grown, treated and processed as described in Example 2.

$1 \times 10^5$ BCL1 cells were incubated in 96-well plates in 200 •L complete. RPMI following electroporation. Cultures were pulsed with 1 •Ci of [$^3$H]-thymidine for the last 8 hours of culture and cells were harvested and analyzed for thymidine incorporation as described in Francis, D. A. et al. (*Int. Immunol.*, 1995, 7, 151-161) 48 hours after electroporation.

Results are shown in Table 6. ISIS 17152 (SEQ ID NO. 99) was able to reduce BCL1 cell proliferation by approximately 50% whereas the mismatch control had no effect.

TABLE 6

Inhibition of BCL1 Cell Proliferation with STAT3 Chimeric (deoxy gapped) Phosphorothioate Oligonucleotides

| ISIS # | SEQ ID NO: | ASO Gene Target | Dose | % Cell Proliferation | % Cell Inhibition |
|---|---|---|---|---|---|
| control | — | — | — | 100% | — |
| 17152 | 99 | 3'-UTR | 10 nM | 78.5% | 21.5% |
| " | " | " | 15 nM | 54.4% | 45.6% |
| " | " | " | 20 nM | 50.2% | 49.8% |
| 23177 | 106 | control | 10 nM | 117.0% | — |
| " | " | " | 15 nM | 99.7% | 0.3% |
| " | " | " | 20 nM | 107.0% | — |

Example 6

Inhibition of BCL1 IgM Secretion by STAT3 Antisense Chimeric (Deoxy Gapped) Phosphorothioate Oligonucleotides The effect of ISIS 17152 (SEQ ID. NO. 99) on IgM secretion levels was determined. STAT3 has been implicated in regulation of IgM expression (Faris, M., et al., *Immunology*, 1997, 90, 350-357). BCL1 cells were grown, treated and processed as described in Example 2.

$1 \times 10^6$ BCL1 cells were incubated in 12-well plates in 2 mL complete RPMI following electroporation. Supernatant was replaced at 24 hour post electroporation with fresh medium. 48 hours later, supernatants were harvested, centrifuged to remove cells, and assayed for IgM content using the OPT-EIA™ ELISA kit (Pharmingen, San-Diego, Calif.) and capture and detecting antibodies for mouse IgM (Southern Biotechnology, Birmingham, Ala.).

Results are shown in Table 7. ISIS 17152 (SEQ ID NO. 99) was significantly better at reducing IgM secretion than the mismatch control.

TABLE 7

Inhibition of BCL1 IgM secretion by STAT3 Chimeric (deoxy gapped) Phosphorothioate Oligonucleotides

| ISIS # | SEQ ID NO: | ASO Gene Target | Dose | % IgM Expression | % IgM Inhibition |
|---|---|---|---|---|---|
| control | — | — | — | 100% | — |
| 17152 | 99 | 3'-UTR | 5 nM | 34.2% | 65.8% |
| " | " | " | 15 nM | 23.1% | 76.9% |
| 23177 | 106 | control | 5 nM | 110.0% | — |
| " | " | " | 15 nM | 80.8% | 19.2% |

Example 7

Induction of Chemokines in BCL1 Cells Following Treatment with STAT3 Antisense Chimeric (Deoxy Gapped) Phosphorothioate Oligonucleotide The effect of ISIS 17152 (SEQ ID. NO. 99) on chemokine levels was determined. BCL1 cells were grown, treated and processed as described in Example 2. Chemokine gene expression was induced in BCL1 cells by addition of 10 •M of a CpG-containing oligonucleotide to the media 16 hours following antisense oligonucleotide electroporation. CpG-containing oligonucleotides are immune-stimulatory (Krieg, A. M., et al., *Nature*, 1995, 374, 546-549). The levels of chemokines were measured eight hours later using RNase protection assay as described in Example 2 with a mouse chemokine template set, Mck-5 (Pharmingen, San Diego, Calif.).

Results are shown in Table 8. ISIS 17152 (SEQ ID. NO. 99) was able to induce the expression of the chemokines, RANTES, MIP-1 • and MIP-1 • whereas the mismatch control had minimal effect.

TABLE 8

Induction of Chemokines in BCL1 Cells Following Treatment with STAT3 Chimeric (deoxy gapped) Phosphorothioate Oligonucleotides

| ISIS # | SEQ ID NO: | ASO Gene Target | Dose | % RANTES mRNA | % MIP1a mRNA | % MIP1b mRNA |
|---|---|---|---|---|---|---|
| control | — | — | — | 100% | 100% | 100% |
| 17152 | 99 | 3'-UTR | 5 nM | 236% | 201% | 133% |
| " | " | " | 10 nM | 266% | 258% | 150% |
| " | " | " | 20 nM | 257% | 254% | 159% |
| 23178 | 107 | control | 5 nM | 96% | 123% | 96.5% |
| " | " | " | 10 nM | 70.2% | 116% | 87.1% |
| " | " | " | 20 nM | 56% | 106% | 73.3% |

Example 8

Effect of STAT3 Antisense Oligonucleotides in a Murine Model for Rheumatoid Arthritis Collagen-induced arthritis (CIA) is used as a murine model for arthritis (Mussener, A., et al., *Clin. Exp. Immunol.*, 1997, 107, 485-493). Female DBA/1LacJ mice (Jackson Laboratories, Bar Harbor, Me.) between the ages of 6 and 8 weeks are used to assess the activity of STAT3 antisense oligonucleotides.

On day 0, the mice are immunized at the base of the tail with 100 µg of bovine type II collagen which is emulsified in Complete Freund's Adjuvant (CFA). On day 7, a second booster dose of collagen is administered by the same route. On day 14, the mice are injected subcutaneously with 100 µg of LPS. Oligonucleotide is administered intraperitoneally daily (10 mg/kg bolus) starting on day −3 and continuing for the duration of the study.

Weights are recorded weekly. Mice are inspected daily for the onset of CIA. Paw widths are rear ankle widths of affected and unaffected joints and are measured three times a week using a constant tension caliper. Limbs are clinically evaluated and graded on a scale from 0-4 (with 4 being the highest).

Example 9

Effect of STAT3 Antisense Oligonucleotides on Growth of Human MDA-MB231 Tumors in Nude Mice MDA-MB231 human breast carcinoma cells are obtained from the American Type Culture Collection (Bethesda, Md.). Serially transplanted MDA-MB231 tumors are established subcutaneously in nude mice. Beginning two weeks later, STAT3 antisense oligonucleotides, in saline, are administered intravenously daily for 14 days at dosages of 60 mg/kg and 6 mg/kg. Control oligonucleotides are also administered at these doses, and a saline control is also given. Tumor growth rates are monitored for the two-week period of oligonucleotide administration. Activity of the STAT3 antisense oligonucleotides is measured by a reduction in tumor growth. A lower-dose study can also be conducted using the same oligonucleotides at 6 mg/kg and 0.6 mg/kg.

Example 10

Effect of STAT3 Antisense Oligonucleotides on U-87 Human Glioblastoma Cells Following Subcutaneous Xenografts into Nude Mice The U-87 human glioblastoma cell line is obtained from the ATCC (Rockville Md.) and maintained in Iscove's DMEM medium supplemented with heat-inactivated 10% fetal calf serum. Nude mice are injected subcutaneously with $2 \times 10^7$ cells. Mice are injected intraperitoneally with STAT3 antisense oligonucleotides at dosages of either 2 mg/kg or 20 mg/kg for 21 consecutive days beginning 7 days after xenografts are implanted. Tumor volumes are measured on days 14, 21, 24, 31 and 35. Activity is measured by reduced tumor volume compared to saline or sense oligonucleotide control.

Example 11

Effect of STAT3 Antisense Oligonucleotides on Intracerebral U-87 Glioblastoma Xenografts into Nude Mice U-87 cells are implanted in the brains of nude mice. Mice are treated via continuous intraperitoneal administration of STAT3 antisense oligonucleotides at 20 mg/kg, control sense oligonucleotide (20 mg/kg) or saline beginning on day 7 after xenograft implantation. Activity of the STAT3 antisense oligonucleotides is measured by an increase in survival time compared to controls.

Example 12

Additional Antisense Oligonucleotides Targeted to Human STAT3

An additional set of oligonucleotides targeted to SEQ ID NO: 1 was designed and synthesized as chimeric oligonucleotides ("gapmers") 20 nucleotides in length, composed of a central "gap" region consisting of ten 2'-deoxynucleotides, which is flanked on both sides (5' and 3' directions) by five-nucleotide "wings." The wings are composed of 2'-methoxyethyl (2'-MOE)nucleotides (shown in bold). The internucleoside (backbone) linkages are phosphorothioate (P=S) throughout the oligonucleotide. All 2'-MOE cytosines and 2'-deoxy cytosines were 5-methyl-cytosines. These oligonucleotide sequences are shown in Table 9.

TABLE 9

Nucleotide Sequences of Additional Chimeric (deoxy gapped) Phosphorothioate Oligonucleotides targeted to Human STAT3

| ISIS NO. | NUCLEOTIDE SEQUENCE[1] (5' -> 3') | TARGET GENE NUCLEOTIDE CO-ORDINATES[2] | GENE TARGET REGION | SEQ ID NO: |
|---|---|---|---|---|
| 113169 | ATGTGATTCTTTGCTGGCCG | 357 | 5' UTR | 108 |
| 113170 | AGCTGATTCCATTGGGCCAT | 221 | AUG | 109 |
| 113171 | CCAGGAGATTATGAAACACC | 385 | Coding | 110 |
| 113172 | ACCGTGTGTCAAGCTGCTGT | 241 | Coding | 111 |
| 113173 | CCATTGGGAAGCTGTCACTG | 286 | Coding | 112 |
| 113174 | TGTGATTCTTTGCTGGCCGC | 356 | Coding | 113 |

TABLE 9-continued

Nucleotide Sequences of Additional Chimeric (deoxy gapped) Phosphorothioate Oligonucleotides targeted to Human STAT3

| ISIS NO. | NUCLEOTIDE SEQUENCE[1] (5' -> 3') | TARGET GENE NUCLEOTIDE CO-ORDINATES[2] | GENE TARGET REGION | SEQ ID NO: |
|---|---|---|---|---|
| 113175 | GCGGCTATACTGCTGGTCAA | 411 | Coding | 114 |
| 113176 | GCTCCAGCATCTGCTGCTTC | 637 | Coding | 115 |
| 113177 | GATTCTTCCCACAGGCACCG | 539 | Coding | 116 |
| 113178 | TGATTCTTCCCACAGGCACC | 540 | Coding | 117 |
| 113179 | ATCCTGAAGGTGCTGCTCCA | 651 | Coding | 118 |
| 113180 | CGGACATCCTGAAGGTGCTG | 656 | Coding | 119 |
| 113181 | CCCGCCAGCTCACTCACGAT | 869 | Coding | 120 |
| 113182 | AGTCAGCCAGCTCCTCGTCC | 928 | Coding | 121 |
| 113183 | CCAGTCAGCCAGCTCCTCGT | 930 | Coding | 122 |
| 113184 | CGCCTCTTCCAGTCAGCCAG | 938 | Coding | 123 |
| 113185 | GGCCGGTGCTGTACAATGGG | 1109 | Coding | 124 |
| 113186 | ATCCTCTCCTCCAGCATCGG | 1127 | Coding | 125 |
| 113187 | CCGCTCCACCACAAAGGCAC | 1176 | Coding | 126 |
| 113188 | CGTCCCCAGAGTCTTTGTCA | 1324 | Coding | 127 |
| 113189 | TTGTGTTTGTGCCCAGAATG | 1375 | Coding | 128 |
| 113190 | GCTCGGCCCCCATTCCCACA | 1472 | Coding | 129 |
| 113191 | AGGCATTTGGCATCTGACAG | 1621 | Coding | 130 |
| 113192 | CTTGGGATTGTTGGTCAGCA | 1665 | Coding | 131 |
| 113193 | CTCGGCCACTTGGTCCCAGG | 1719 | Coding | 132 |
| 113194 | CCCCGCTTGGTGGTGGACGA | 1757 | Coding | 133 |
| 113195 | CCCCGCTTGGTGGTGGACG | 1758 | Coding | 134 |
| 113196 | GGAGAAGCCCTTGCCAGCCA | 1881 | Coding | 135 |
| 113197 | TTCATTCCAAAGGGCCAAGA | 1947 | Coding | 136 |
| 113198 | CCCGCTCCTTGCTGATGAAA | 1981 | Coding | 137 |
| 113199 | GTGCTCAAGATGGCCCGCTC | 2000 | Coding | 138 |
| 113200 | CCCAAGTGAAAGTGACGCCT | 2071 | Coding | 139 |
| 113201 | ACCCAAGTGAAAGTGACGCC | 2072 | Coding | 140 |
| 113202 | CCGAATGCCTCCTCCTTGGG | 2252 | Coding | 141 |
| 113203 | GCCGACAATACTTCCCGAAT | 2266 | Coding | 142 |
| 113204 | GATGCTCCTGGCTCTCTGGC | 2284 | Coding | 143 |
| 113205 | TCAATGAATCTAAAGCGCGG | 2404 | Coding | 144 |
| 113206 | GACTCAAACTGCCCTCCTGC | 2462 | Coding | 145 |
| 113207 | ATCACCCACATTCACTCATT | 2710 | 3' UTR | 146 |
| 113208 | AAAAGTGCCCAGATTGC | 2682 | 3' UTR | 147 |
| 113209 | AAAAGTGCCCAGATTGCTCA | 2679 | 3' UTR | 148 |
| 113210 | TAAAAGTGCCCAGATTGCTC | 2680 | 3' UTR | 149 |
| 113211 | AAGCAGATCACCCACATTCA | 2716 | 3' UTR | 150 |

These oligonucleotides were screened by Northern blot analysis in U266 cells at an oligonucleotide concentration of 2.5 μM. U266 human myeloma cell lines (originally obtained from American Type Culture Collection) were maintained in RPMI 1640 medium supplemented with 10% fetal calf serum. Cells (15×10[6] cells in PBS) were transfected with oligonucleotides at 200V with a single 6-millisecond pulse using a BTX Electro Square Porator T820 (Genetronics, San Diego Calif.). The cells were incubated for 24 hours before RNA extraction.

Total cellular RNA was isolated using the Rneasy kit (Qiagen, Santa Clarita, Calif.). Northern blotting was performed on 15 μg of RNA using a cDNA probe prepared from MB-MDA 468 RNA by standard RT-PCR followed by a nested primer reaction. Signals were quantitated using a Molecular Phosphorimager.

Results for selected compounds (expressed as percent of control mRNA expression and percent inhibition of mRNA expression) are shown in Table 10.

TABLE 10

Inhibition of Human STAT3 mRNA expression in U266 Cells by Chimeric (deoxy gapped) Phosphorothioate Oligonucleotides

| ISIS No: | SEQ ID NO: | GENE TARGET REGION | % mRNA EXPRESSION | % mRNA INHIBITION |
|---|---|---|---|---|
| None | — | — | 100 | — |
| 17148 | 95 | Coding | 95.1 | 4.9 |
| 17152 | 99 | 3' UTR | 82.5 | 17.5 |
| 113170 | 109 | AUG | 89.6 | 10.4 |
| 113171 | 110 | Coding | 110.2 | — |
| 113172 | 111 | Coding | 96.1 | 3.9 |
| 113173 | 112 | Coding | 119 | — |
| 113175 | 114 | Coding | 75.8 | 24.2 |
| 113176 | 115 | Coding | 72.3 | 27.7 |
| 113178 | 117 | Coding | 143.9 | — |
| 113181 | 120 | Coding | 105.4 | — |
| 113184 | 123 | Coding | 104.3 | — |
| 113187 | 126 | Coding | 55.9 | 44.1 |
| 113189 | 128 | Coding | 163.9 | — |
| 113199 | 139 | Coding | 64.4 | 35.6 |
| 113207 | 146 | 3' UTR | 123.6 | — |
| 113209 | 148 | 3' UTR | 71.4 | 28.6 |
| 113210 | 149 | 3' UTR | 72.2 | 27.8 |
| 113211 | 150 | 3' UTR | 116.5 | — |

Dose-response experiments were conducted for ISIS 113176, 129987, 113187, 129991, 113209, 129995, 113210 and 129999 as well as ISIS 17148 and the mouse STAT3 oligo ISIS 114054. Results are shown in Table 11.

TABLE 11

Percent inhibition of human STAT3 mRNA expression with antisense oligonucleotides - dose response

| ISIS # | SEQ ID NO: | Percent inhibition of STAT3 expression Oligo concentration | | |
|---|---|---|---|---|
| | | 2.5 μM | 5 μM | 10 μM |
| 17148 | 95 | 8 | 54 | 60 |
| 114054 | | 4 | 17 | 15 |
| 113176 | | 33 | 67 | 79 |
| 129987 | | 5 | 5 | 29 |
| 113187 | | 44 | 56 | 75 |
| 129991 | | 21 | 22 | 26 |
| 113209 | | 43 | 54 | 73 |
| 129995 | | 5 | 32 | 25 |
| 113210 | | 36 | 50 | 76 |
| 129999 | | 31 | 8 | — |

ISIS 17148, 113176, 113187, 113209 and 113210 were shown to reduce STAT3 expression by over 50% at one or more oligonucleotide concentrations. These compounds are therefore preferred.

Example 13

Antisense Inhibition of STAT3 Causes Apoptotic Cell Death in Mouse Melanoma Cells Mouse B16 melanoma cells were grown in RPMI 1640 (Life Technologies, Inc., Grand Island, N.Y.) medium supplemented with 10% fetal bovine serum, 2 mM L-glutamine, 1 mM sodium pyruvate, 1% MEM nonessential amino acids and 100 IU/ml penicillin/streptomycin.

Cells were treated with ISIS 17152, targeted to mouse STAT3, or the 3-base mismatch control, ISIS 28084 (AAAAAGAGGCCTGATTGCCC; SEQ ID NO: 151). Cells were transfected with oligonucleotide using LipofectAMINE PLUSJ reagent (GibcoBRL). Oligonucleotide was pre-complexed with LipofectAMINE PLUSJ by adding the oligonucleotide to 100 μl serum-free RPMI 1640 medium, then 6 μl LipofectAMINE PLUSJ reagent was added, the sample was mixed well and incubated for 15 minutes at room temperature. An additional 4 μl of LipofectAMINE PLUSJ reagent was diluted to 100 μl in serum-free RPMI. This diluted LipofectAMINE PLUSJ was mixed with the pre-complexed oligonucleotide/LipofectAMINE PLUSJ mixture and incubated for 15 minutes at room temperature. 800 μl of serum-free RPMI 1640 was added, and the resulting oligonucleotide-LipofectAMINE PLUSJ-medium mixture (approximately 1 ml) was added to cells in a 6-well plate. After 3 hours incubation, 1 ml of RPMI 1640 supplemened with 20% fetal bovine serum was added. Oligonucleotide concentrations were 200 nM or 300 nM.

24 hours after transfection, cells were counted to determine the effect of antisense treatment on cell death. Cells were harvested at 24 hours post transfection for western blot analysis and at 48 hours post-transfection for Annexin-V staining for apoptosis.

Effects of oligonucleotide on cell number are shown in Table 12.

TABLE 12

Effect of antisense inhibition of STAT3 on cell number

| | 200 nM | | 300 nM | |
|---|---|---|---|---|
| Expt | ISIS 28084 (3 mismatch) | ISIS 17152 | ISIS 28084 (3 mismatch) | ISIS 17152 |
| 1 | $10.2 \times 10^5$ | $3.8 \times 10^5$ | | |
| 2 | $5.0 \times 10^5$ | $6.8 \times 10^5$ | $9.1 \times 10^5$ | $3.5 \times 10^5$ |
| 3 | $3.5 \times 10^5$ | $1.8 \times 10^5$ | $3.3 \times 10^5$ | $2.2 \times 10^5$ |

Thus treatment with STAT3 antisense oligonucleotide increased cell death (decreased cell number).

Apoptosis in B16 cells was measured by staining with Annexin V-PE (Clontech) and flow cytometry analysis 48 hours after antisense treatment. Positive staining for Annexin-V indicates apoptosis is occurring. Mock-transfected cells and control oligonucleotide-treated cell cultures had 11.37% and 10.15% of cells staining positive for Annexin-V. In contrast, ISIS 17152-treated cells were 29.84% positive for Annexin-V, indicating a nearly threefold increase in apoptotic cells. It should be noted that in general, the percent of apoptosis in B16 cells is likely to have been underestimated since detached dead cells are washed off in processing.

Western blot analysis was done on cells 24 hours after antisense treatment, using an anti-STAT3 antibody (K15, Santa Cruz Biotechnology, Santa Cruz, Calif.). ISIS 17152 at 200 nM or 300 nM significantly reduced STAT3 protein production in B16 cells.

Example 14

Effect of STAT3 Antisense Oligonucleotides on Melanoma Tumors

Six-week-old female C57BL mice were purchased from the National Cancer Center (Frederick Md.) and maintained under approved conditions. Mice were shaved in the left flank area and injected subcutaneously with $2 \times 10^5$ B16 melanoma cells in 100 μl of PBS. After 7-10 days, B16 tumors with a diameter of 3-6 mm were established. Tumor volume was calculated according to the formula $V=0.52 \times a^2 \times b$ (a, smallest superficial diameter; b, largest superficial diameter).

Beginning two weeks later, STAT3 antisense oligonucleotides, in saline, are administered intravenously daily for 14 days at dosages of 60 mg/kg and 6 mg/kg. Control oligonucleotides are also administered at these doses, and a saline control is also given. Tumor growth rates are monitored for the two-week period of oligonucleotide administration. Activity of the STAT3 antisense oligonucleotides is measured by a reduction in tumor growth. A lower-dose study can also be conducted using the same oligqnucleotides at 6 mg/kg and 0.6 mg/kg.

Example 15

Effect of STAT3 Antisense Oligonucleotides on Leukemic Large Granular Lymphocytes (LGL)

LGL leukemia is a lymphoproliferative disease with autoimmune features and LGL cells are known to be insensitive to Fas-dependent cell death despite high levels of Fas and FasL expression. (Lamy et al., *Blood,* 1998, 92, 4771-7). STAT3 antisense oligonucleotides were tested for their ability to sensitize LGL cells to the apoptotic signal in these cells.

LGL leukemic cells were obtained from patients who met the clinical criteria of T cell (CD3+) LGL leukemia with increased LGL counts and clonal TCR gene rearrangements. All patients had chronic disease not requiring treatment at the time of analysis. Purified leukemic LGL cells were placed in 24-well plates at a concentration of $2\times10^6/0.5$ mL of complete medium (RPMI-1640 medium supplemented with 10% fetal bovine serum, 2 mM L-glutamine, 10 U/mL penicillin, and 100 ug/mL streptomycin, all from Gibco Life Technologies, Gaithersburg, Md.). Cells were incubated with either ISIS 17148 antisense oligonucleotide (SEQ ID NO: 95) or the control, ISIS 16094 (SEQ ID NO: 152). Antisense oligonucleotide delivery to LGL leukemic cells was by passive uptake and no transfection reagents were included in the reaction.

Both ISIS 17148 and ISIS 16094 are 20 nucleotides in length, composed of a central "gap" region consisting of ten 2'-deoxynucleotides, which is flanked on both sides (5' and 3' directions) by five-nucleotide "wings." The wings are composed of 2'-methoxyethyl (2'-MOE)nucleotides. The internucleoside (backbone) linkages are phosphorothioate (P=S) throughout the oligonucleotide. All 2'-MOE cytosines and 2'-deoxy cytosines were 5-methyl-cytosines.

Extracts of LGL cells treated with antisense oligonucleotides (1 uM dosing for ISIS 17148 and the control) from three patients were obtained and assayed for STAT3 protein levels by Western blot. Sensitization of the LGL cells to Fas-mediated apoptosis was also measured by flow cytometry in cells treated with antisense oligonucleotides at doses of 1, 2 and 5 uM. By Western analysis, a reduction in STAT3 protein levels ranged from 25 to 45%. Sensitivity to Fas-mediated apoptosis was also significantly increased in the antisense treated cells and was dose dependent. Measurements of percent specific apoptosis in duplicate reactions revealed an increase in apoptosis from 5% in untreated cells to levels of 6, 17 and 24% in antisense-treated cells at 1, 2, and 5 uM, respectively. Levels of apoptosis in control oligonucleotide treated cells remained at 6% at all doses.

Example 16

Induction of Apoptosis in the Human Myeloma Cell Line U266 Following Stat3 Antisense Oligonucleotide Treatment Methods Cell Culture U266 cells (ATCC, Bethesda, Md.) were cultured in RPMI 1640 medium supplemented with 10% heat-inactivated fetal bovine serum (Sigma Chemical Company, St. Louis, Mo.), 10 mM Hepes, pH 7.2, 50 •M 2-ME, 2 mM L-glutamine, 100 U/ml penicillin, and 100 •g/ml streptomycin (Gibco, Grand Island, N.Y.).

Oligonucleotide Synthesis and Transfection of U266 Cells

2'-O-methoxyethylribose modified phosphorothioate oligonucleotides were synthesized on an automated DNA synthesizer (Applied Biosystems model 380B), as described above. Chimeric oligonucleotides were employed in these studies; the chimeric oligonucleotides contain 2'-O-methoxyethyl modified residues flanking a 2'-deoxynucleotide/phosphorothioate region (gap) that supports RNase H activation. Oligonucleotides were analyzed by capillary gel electrophoresis and judged to be at least 85% full-length material. U266 ($1\times10^7$ cells in PBS) were transfected with oligonucleotides by electroporation, at 175V, 1000 µF using a BTX Electro Cell Manipulator 600 (Genetronics, San Diego, Calif.).

Flow Cytometric Analysis of Apoptosis $10\times10^6$ U266 cells were electroporated with oligonucleotides and cultured for 48 hours before analysis of phosphatidylserine expression was performed as a measure of apoptosis using the Annexin-V staining kit (Clontech, Palo Alto, Calif.) according to the manufacturer's instructions. Briefly, the cells were resuspended in 0.2 mL of staining buffer (10 mM HEPES, pH 7.4, 140 mM NaCl, 5 mM $CaCl_2$) and 10 µL of propidium iodide (50 µg/ml) and 5 µL of Annexin V reagent were added at 4° C. for 10 minutes. The samples were then diluted with FacsFlow buffer and analyzed on a Becton Dickinson FACScan (Mountain View, Calif.).

Results

Antisense Inhibition of STAT3 Induces Apoptosis of U266 Multiple Myeloma Cells.

In order to examine the importance of STAT3 expression in multiple myeloma cells, a, series of 20 mer STAT3 antisense oligonucleotides were designed and synthesized, using phosphorothioate chemistry and incorporating 2'-O-methoxyethyl modifications to improve hybridization affinity and nuclease resistance. Screens performed in U266 MM cells identified several sequences that optimally inhibited STAT3 mRNA expression, as determined by Northern blotting. Two antisense oligonucleotides, ISIS 17148 (SEQ ID NO: 95) and ISIS 113176 (SEQ ID NO: 115) were found to potently inhibit STAT3 mRNA expression in U266 cells following electroporation in a dose-dependent fashion. Control oligonucleotide containing 5 mismatched bases within the 2'-deoxyphosphorothioate central gap region failed to inhibit STAT3 mRNA expression, demonstrating a hybridization-dependent mechanism of target reduction.

Further characterization of the STAT3 antisense oligonucleotides was performed, using western blotting of nuclear extracts from U266 cells to evaluate STAT3 protein reduction following oligonucleotide transfection. The STAT3 antisense oligonucleotides were found to dose-dependently inhibit STAT3 protein expression in a manner that correlated well with the mRNA inhibition, when evaluated 48 hours after transfection. The five base mismatch control oligonucleotide at the highest dose did not show any effect, further suggesting an antisense mechanism of action.

Previously published data using a dominant negative expression vector encoding STAT3 lacking an intact transactivation domain suggested that STAT3 was a survival factor for MM cells (Catlett-Falcone et al., Immunity 10: 105, 1999). Changes in the proliferative index of STAT3 antisense transfected U266 cells as well as reduced viabililty in culture following STAT3 antisense transfection led us to determine whether reduction of wild type STAT3 protein would also induce an apoptotic response. Transfection of U266 cells with either ISIS 17148 or 113176 was found to result in increased levels of annexin V staining as assessed by flow cytometry. This effect contrasted to that of control oligonucleotides, either an antisense oligonucleotide targeted to a gene not expressed by U266 cells or the 5 base mismatch control oligonucleotide. These data further support an anti-apoptotic role for STAT3 in multiple myeloma.

Example 17

Design of Phenotypic Assays and In Vivo Studies for the Use of STAT3 Inhibitors

Phenotypic Assays

Once STAT3 inhibitors have been identified by the methods disclosed herein, the compounds are further investigated in one or more phenotypic assays, each having measurable endpoints predictive of efficacy in the treatment of a particular disease state or condition. Phenotypic assays, kits and reagents for their use are well known to those skilled in the art and are herein used to investigate the role and/or association of STAT3 in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with STAT3 inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest. Analysis of the genotype of the cell (measurement of the expression of one or more of the genes of the cell) after treatment is also used as an indicator of the efficacy or potency of STAT3 inhibitors. Hallmark genes, or those genes suspected to be associated with a specific disease state, condition, or phenotype, are measured in both treated and untreated cells.

Example 18

Antisense Inhibition of Human STAT3 by Chimeric Phosphorothioate Oligonucleotides having 2'-MOE Wings and a Deoxy Gap In accordance with the present invention, an additional series of oligonucleotides was designed to target different regions of the human STAT 3, using published sequences (GenBank accession number L29277, incorporated herein as SEQ ID NO: 1, the complement of nucleotides 4189213 to 4263636 of the sequence with the GenBank accession number NT_010755.13, incorporated herein As SEQ ID NO: 153 and GenBank accession number NM_139276.1, incorporated herein as SEQ ID NO: 154). The oligonucleotides are shown in Table 13. "Target site" indicates the first (5'-most) nucleotide number on the particular target sequence to which the oligonucleotide binds. All compounds in Table 13 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE) nucleotides. The internucleoside (backbone) linkages are phosphorothioate (P=S) throughout the oligonucleotide. All cytidine residues are 5-methylcytidines.

The compounds were analyzed for their effect on STAT3 mRNA levels in A549 cells. The human lung carcinoma cell line A549 was obtained from the American Type Culture Collection (ATCC) (Manassas, Va.). A549 cells were routinely cultured in DMEM basal media (Invitrogen Corporation, Carlsbad, Calif.) supplemented with 10% fetal calf serum (Invitrogen Corporation, Carlsbad, Calif.), 100 units/mL penicillin, and 100 ug/mL streptomycin (Invitrogen Corporation, Carlsbad, Calif.). Cells were routinely passaged by trypsinization and dilution when they reached 90% confluence.

ISIS 18078 was used as a control oligonucleotide and was used at 75 nM. ISIS 18078 (GTGCGCGCGAGC-CCGAAATC, SEQ ID NO: 155) is an chimeric oligonucleotide ("gapmers") 20 nucleotides in length, composed of a central "gap" region consisting of nine 2'-deoxynucleotides, which is flanked on both sides (5' and 3' directions) by five-nucleotide and six-nucleotide "wings", respectively. The wings are composed of 2'-methoxyethyl (2'-MOE) nucleotides. The internucleoside (backbone) linkages are phosphorothioate (P=S) throughout the oligonucleotide. All cytidine residues are 5-methylcytidines.

When cells reached 65-75% confluency, they were treated with oligonucleotide. For cells grown in 96-well plates, wells were washed once with 100 L OPTI-MEM-1 reduced-serum medium (Invitrogen Corporation, Carlsbad, Calif.) and then treated with 130 L of OPTI-MEM-1 containing 3.75 g/mL LIPOFECTIN (Invitrogen Corporation, Carlsbad, Calif.) and 75 nM of the compounds in Table 13. Cells were treated and data were obtained in duplicate. Untreated cells served as controls. After 4-7 hours of treatment at 37° C., the medium was replaced with fresh medium. Cells were harvested 16-24 hours after oligonucleotide treatment. STAT3 mRNA levels in A549 cells were quantitated by real-time PCR as described by other methods herein.

Probes and primers to human STAT3 were designed to hybridize to a human STAT3 sequence, using published sequence information (incorporated herein as SEQ ID NO: 1). For STAT 3 the PCR primers were:
forward primer: ACATGCCACTTTGGTGTTTCATAA (SEQ ID NO: 156)
reverse primer: TCTTCGTAGATTGTGCTGATA-GAGAAC (SEQ ID NO: 157) and the PCR probe was: FAM-CAGTATAGCCGCTTCCTGCAAGAGTCGAA-TAMRA (SEQ ID NO: 158) where FAM is the fluorescent reporter dye and TAMRA is the quencher dye. This primer probe set is referred to as PPS 199. Gene target quantities obtained by real time RT-PCR are normalized by quantifying total RNA using RiboGreen™ (Molecular Probes, Inc. Eugene, Oreg.). In this assay, 170 μL of RiboGreen™ working reagent (RiboGreen™ reagent diluted 1:350 in 10 mM Tris-HCl, 1 mM EDTA, pH 7.5) is pipetted into a 96-well plate containing 30 μL purified, cellular RNA. The plate is read in a CytoFluor 4000 (PE Applied Biosystems) with excitation at 485 nm and emission at 530 nm.

The results of the antisense oligonucleotide treatments are the average of 2 experiments and are shown in Table 13. Data are expressed as percent inhibition relative to untreated control cells.

TABLE 13

Inhibition of human STAT 3 mRNA levels by chimeric phosphorothioate oligonucleotides having 2'-MOE wings and a deoxy gap

| Isis # | Region | Target Seq ID No | Target Site | Sequence | % Inhib | Seq ID No |
|---|---|---|---|---|---|---|
| 337245 | intron | 153 | 6814 | AGCCTCTGCACCCTCATGTT | 77 | 159 |
| 337246 | intron | 153 | 6868 | CTCCTAAATTAAGAACTTCT | 37 | 160 |
| 337247 | intron | 153 | 14801 | TTTTGCATGATGTAACCACT | 87 | 161 |
| 337248 | intron | 153 | 34820 | TATTGAAAATTATCTAATTC | 0 | 162 |
| 337249 | coding | 153 | 40369 | TTGGGCCATCCTGCTAAAAT | 48 | 163 |
| 337250 | exon: intron | 153 | 50156 | ATTCACTTGCCTCCTTGACT | 51 | 164 |
| 337251 | intron: exon | 153 | 51124 | ATGCCCTTACTCTCCGCATC | 74 | 165 |
| 337252 | exon: intron | 153 | 59140 | CTGAACTTACCCTCTGAGAG | 60 | 166 |
| 337253 | exon: intron | 153 | 64176 | AAATGCGGACCCAAGAGTTT | 49 | 167 |
| 337254 | 5' UTR | 1 | 56 | CTTGTTCCCTCGGCTGCGAC | 57 | 168 |
| 337255 | 5' UTR | 1 | 79 | GCCTGTCCAGGATCCGGTTG | 75 | 169 |
| 337256 | 5' UTR | 1 | 126 | GAAGGGCCTCTCCGAGCCGA | 67 | 170 |
| 337257 | 5' UTR | 1 | 148 | GGCGGCGAGGCTCCCTCAGG | 80 | 171 |
| 337258 | 5' UTR | 1 | 193 | TCCGGCAGAGGCCGAGAGGC | 56 | 172 |
| 337259 | 5' UTR | 154 | 225 | CCATCCTGCTAAAATCAGGG | 58 | 173 |
| 337260 | 5' UTR | 154 | 233 | CCATTGGGCCATCCTGCTAA | 62 | 174 |
| 337261 | coding | 1 | 235 | TGTCAAGCTGCTGTAGCTGA | 79 | 175 |
| 337262 | coding | 1 | 299 | AACTGCCGCAGCTCCATTGG | 74 | 176 |
| 337263 | coding | 1 | 326 | TCTTGACTCTCAATCCAAGG | 79 | 177 |
| 337264 | coding | 1 | 339 | CGCATATGCCCAATCTTGAC | 81 | 178 |
| 337265 | coding | 1 | 426 | CGACTCTTGCAGGAAGCGGC | 92 | 179 |
| 337266 | coding | 1 | 453 | TCGTAGATTGTGCTGATAGA | 61 | 180 |
| 337267 | coding | 1 | 470 | AGAAACTGCTTGATTCTTCG | 62 | 181 |
| 337268 | coding | 1 | 484 | GATACCTGCTCTGAAGAAAC | 75 | 182 |
| 337269 | coding | 1 | 491 | TTCTCAAGATACCTGCTCTG | 74 | 183 |
| 337270 | coding | 1 | 496 | TTGGCTTCTCAAGATACCTG | 89 | 184 |
| 337271 | coding | 1 | 541 | GTGATTCTTCCCACAGGCAC | 85 | 185 |
| 337272 | coding | 1 | 629 | ATCTGCTGCTTCTCCGTCAC | 74 | 186 |
| 337273 | coding | 1 | 634 | CCAGCATCTGCTGCTTCTCC | 73 | 187 |
| 337274 | coding | 1 | 647 | TGAAGGTGCTGCTCCAGCAT | 74 | 188 |
| 337275 | coding | 1 | 683 | TTCTGTTCTAGATCCTGCAC | 82 | 189 |
| 337276 | coding | 1 | 708 | CTGGAGATTCTCTACCACTT | 91 | 190 |
| 337277 | coding | 1 | 716 | AACTCATCCTGGAGATTCTC | 79 | 191 |
| 337278 | coding | 1 | 721 | AATCAAAGTCATCCTGGAGA | 69 | 192 |

TABLE 13-continued

Inhibition of human STAT 3 mRNA levels
by chimeric phosphorothioate oligonucleotides
having 2'-MOE wings and a deoxy gap

| Isis # | Region | Target Seq ID No | Target Site | Sequence | % Inhib | Seq ID No |
|---|---|---|---|---|---|---|
| 337279 | coding | 1 | 726 | CTTGAAATCAAAGTCATCCT | 78 | 193 |
| 337280 | coding | 1 | 731 | TTATAGTTGAAATCAAAGTC | 45 | 194 |
| 337281 | coding | 1 | 736 | GGGTTTTATAGTTGAAATCA | 16 | 195 |
| 337282 | coding | 1 | 741 | CTTGAGGGTTTTATAGTTGA | 58 | 196 |
| 337283 | coding | 1 | 746 | TGACTCTTGAGGGTTTTATA | 71 | 197 |
| 337284 | coding | 1 | 751 | CTCCTTGACTCTTGAGGGTT | 91 | 198 |
| 337285 | coding | 1 | 756 | CATGTCTCCTTGACTCTTGA | 78 | 199 |
| 337286 | coding | 1 | 768 | ATTCAGATCTTGCATGTCTC | 77 | 200 |
| 337287 | coding | 1 | 779 | TGGTTGTTTCCATTCAGATC | 82 | 201 |
| 337288 | coding | 1 | 790 | TGGTCACTGACTGGTTGTTT | 84 | 202 |
| 337289 | coding | 1 | 812 | TCCAGCTGCTGCATCTTCTG | 83 | 203 |
| 337290 | coding | 1 | 822 | GAGCATCTGTTCCAGCTGCT | 80 | 204 |
| 337291 | coding | 1 | 848 | CTTCTCCGCATCTGGTCCAG | 66 | 205 |
| 337292 | coding | 1 | 899 | TTCTGCACGTACTCCATCGC | 81 | 206 |
| 337293 | coding | 1 | 925 | CAGCCAGCTCCTCGTCCGTG | 92 | 207 |
| 337294 | coding | 1 | 935 | CTCTTCCAGTCAGCCAGCTC | 75 | 208 |
| 337295 | coding | 1 | 941 | TGCCGCCTCTTCCAGTCAGC | 82 | 209 |
| 337296 | coding | 1 | 999 | CCAGTTTTCTAGCCGATCTA | 80 | 210 |
| 337297 | coding | 1 | 1006 | ACGTTATCCAGTTTTCTAGC | 72 | 211 |
| 337298 | coding | 1 | 1025 | AGTTGAGATTCTGCTAATGA | 74 | 212 |
| 337299 | coding | 1 | 1030 | TCTGAAGTTGAGATTCTGCT | 80 | 213 |
| 337300 | coding | 1 | 1085 | CCTTTGTAGGAAACTTTTTG | 23 | 214 |
| 337301 | coding | 1 | 1162 | AGGCACTTTTCATTAAGTTT | 73 | 215 |
| 337302 | coding | 1 | 1262 | TTGACCAGCAACCTGACTTT | 61 | 216 |
| 337303 | coding | 1 | 1286 | AGCTGATAATTCAACTCAGG | 85 | 217 |
| 337304 | coding | 1 | 1291 | TTTTAAGCTGATAATTCAAC | 15 | 218 |
| 337305 | coding | 1 | 1297 | CTTTAATTTTAAGCTGATAA | 25 | 219 |
| 337306 | coding | 1 | 1302 | GCACACTTTAATTTTAAGCT | 77 | 220 |
| 337307 | coding | 1 | 1307 | TCAATGCACACTTTAATTTT | 53 | 221 |
| 337308 | coding | 1 | 1364 | CCCAGAATGTTAAATTTCCG | 70 | 222 |
| 337309 | coding | 1 | 1414 | AGAGGCTGCCGTTGTTGGAT | 73 | 223 |
| 337310 | coding | 1 | 1433 | AAGTGTTTGAATTCTGCAGA | 73 | 224 |
| 337311 | coding | 1 | 1452 | TCTCTGCTCCCTCAGGGTCA | 61 | 225 |
| 337312 | coding | 1 | 1517 | ATCAGGTGCAGCTCCTCAGT | 78 | 226 |
| 337313 | coding | 1 | 1522 | AGGTGATCAGGTGCAGCTCC | 61 | 227 |

TABLE 13-continued

Inhibition of human STAT 3 mRNA levels by chimeric phosphorothioate oligonucleotides having 2'-MOE wings and a deoxy gap

| Isis # | Region | Target Seq ID No | Target Site | Sequence | % Inhib | Seq ID No |
|---|---|---|---|---|---|---|
| 337314 | coding | 1 | 1527 | CTCAAAGGTGATCAGGTGCA | 75 | 228 |
| 337315 | coding | 154 | 1571 | GAGGCCTTGGTGATACACCT | 46 | 229 |
| 337316 | coding | 154 | 1579 | TCAATCTTGAGGCCTTGGTG | 59 | 230 |
| 337317 | coding | 154 | 1584 | CTAGGTCAATCTTGAGGCCT | 55 | 231 |
| 337318 | coding | 1 | 1569 | GGTCTCTAGGTCAATCTTGA | 74 | 232 |
| 337319 | coding | 1 | 1577 | AAGGAGTGGGTCTCTAGGTC | 38 | 233 |
| 337320 | coding | 154 | 1602 | CTGGCAAGGAGTGGGTCTCT | 74 | 234 |
| 337321 | coding | 154 | 1609 | ACCACAACTGGCAAGGAGTG | 80 | 235 |
| 337322 | coding | 1 | 1609 | TCTGACAGATGTTGGAGATC | 69 | 236 |
| 337323 | coding | 1 | 1614 | TGGCATCTGACAGATGTTGG | 79 | 237 |
| 337324 | coding | 1 | 1619 | GCATTTGGCATCTGACAGAT | 79 | 238 |
| 337325 | coding | 1 | 1667 | TTCTTGGGATTGTTGGTCAG | 75 | 239 |
| 337326 | coding | 1 | 1778 | GTCAGCTGCTCGATGCTCAG | 78 | 240 |
| 337327 | coding | 154 | 1823 | TCCCAAGAGTTTCTCTGCCA | 84 | 241 |
| 337328 | coding | 1 | 1838 | CATGTGATCTGACACCCTGA | 85 | 242 |
| 337329 | coding | 1 | 1843 | TAGCCCATGTGATCTGACAC | 88 | 243 |
| 337330 | coding | 154 | 1885 | GCCATGTTTTCTTTGCAAAA | 59 | 244 |
| 337331 | coding | 1 | 1873 | CCTTGCCAGCCATGTTTTCT | 88 | 245 |
| 337332 | coding | 1 | 1878 | GAAGCCCTTGCCAGCCATGT | 91 | 246 |
| 337333 | coding | 154 | 1903 | AAGGAGAAGCCCTTGCCAGC | 90 | 247 |
| 337334 | coding | 154 | 1908 | CCCAGAAGGAGAAGCCCTTG | 85 | 248 |
| 337335 | coding | 154 | 1918 | TCCAGCCAGACCCAGAAGGA | 86 | 249 |
| 337336 | coding | 1 | 2048 | TCTTTGCTGCTTTCACTGAA | 79 | 250 |
| 337337 | coding | 1 | 2144 | ATGTTGTTCAGCTGCTGCTT | 76 | 251 |
| 337338 | coding | 1 | 2149 | ATGACATGTTGTTCAGCTGC | 80 | 252 |
| 337339 | coding | 1 | 2154 | AGCAAATGACATGTTGTTCA | 84 | 253 |
| 337340 | coding | 1 | 2159 | ATTTCAGCAAATGACATGTT | 72 | 254 |
| 337341 | coding | 1 | 2164 | TGATGATTTCAGCAAATGAC | 74 | 255 |
| 337342 | coding | 1 | 2174 | TTATAGCCCATGATGATTTC | 81 | 256 |
| 337343 | coding | 1 | 2179 | TGATCTTATAGCCCATGATG | 84 | 257 |
| 337344 | coding | 1 | 2184 | ATCCATGATCTTATAGCCCA | 90 | 258 |
| 337345 | coding | 1 | 2190 | GGTAGCATCCATGATCTTAT | 86 | 259 |
| 337346 | coding | 1 | 2232 | AATGTCAGGATAGAGATAGA | 55 | 260 |
| 337347 | coding | 1 | 2246 | GCCTCCTCCTTGGGAATGTC | 88 | 261 |
| 337348 | coding | 154 | 2273 | TCCGAATGCCTCCTCCTTGG | 92 | 262 |
| 337349 | coding | 154 | 2278 | TACTTTCCGAATGCCTCCTC | 65 | 263 |

TABLE 13-continued

Inhibition of human STAT 3 mRNA levels
by chimeric phosphorothioate oligonucleotides
having 2'-MOE wings and a deoxy gap

| Isis # | Region | Target Seq ID No | Target Site | Sequence | % Inhib | Seq ID No |
|---|---|---|---|---|---|---|
| 337350 | coding | 154 | 2283 | GACAATACTTTCCGAATGCC | 84 | 264 |
| 337351 | coding | 1 | 2303 | CTACCTGGGTCAGCTTCAGG | 74 | 265 |
| 337352 | coding | 1 | 2333 | ATAAACTTGGTCTTCAGGTA | 80 | 266 |
| 337353 | coding | 1 | 2351 | GTCGTTGGTGTCACACAGAT | 81 | 267 |
| 337354 | coding | 1 | 2356 | TGCAGGTCGTTGGTGTCACA | 62 | 268 |
| 337355 | coding | 1 | 2361 | ATTGCTGCAGGTCGTTGGTG | 61 | 269 |
| 337356 | coding | 1 | 2366 | ATGGTATTGCTGCAGGTCGT | 75 | 270 |
| 337357 | coding | 1 | 2371 | GGTCAATGGTATTGCTGCAG | 71 | 271 |
| 337358 | coding | 1 | 2381 | GACATCGGCAGGTCAATGGT | 77 | 272 |
| 337359 | coding | 154 | 2423 | CAATGAATCTAAAGTGCGGG | 57 | 273 |
| 337360 | coding | 154 | 2428 | TGCATCAATGAATCTAAAGT | 71 | 274 |
| 337361 | coding | 1 | 2413 | CAAACTGCATCAATGAATCT | 61 | 275 |
| 337362 | coding | 1 | 2418 | ATTTCCAAACTGCATCAATG | 69 | 276 |
| 337363 | coding | 1 | 2456 | AACTGCCCTCCTGCTGAGGG | 63 | 277 |
| 337364 | coding | 1 | 2469 | GGTGAGGGACTCAAACTGCC | 70 | 278 |
| 337365 | 3' UTR | 1 | 2550 | CAGTCGTATCTTTCTGCAGC | 84 | 279 |
| 337366 | 3' UTR | 1 | 2658 | AGATAGCAGAAGTAGGAGAT | 66 | 280 |
| 337367 | 3' UTR | 1 | 2678 | AAAGTGCCCAGATTGCTCAA | 82 | 281 |
| 337368 | 3' UTR | 1 | 2684 | TTTTTAAAAGTGCCCAGATT | 59 | 282 |
| 337369 | 3' UTR | 1 | 2713 | CAGATCACCCACATTCACTC | 88 | 283 |
| 337370 | 3' UTR | 1 | 2729 | TGCATTTAGATAAAAGCAGA | 78 | 284 |
| 337371 | 3' UTR | 1 | 2744 | GAACACATCCTTATTTGCAT | 76 | 285 |
| 337372 | 3' UTR | 1 | 2759 | ATCATGGGTCTCAGAGAACA | 88 | 286 |
| 337373 | 3' UTR | 154 | 2790 | CACATCCCCTGATCATGGGT | 70 | 287 |
| 337374 | 3' UTR | 154 | 2826 | AGACATTTCCTTTTTCTCCC | 67 | 288 |
| 337375 | 3' UTR | 154 | 2908 | ACCAGGAGGCACTTGTCTAA | 89 | 289 |
| 337376 | 3' UTR | 154 | 2914 | GCAGGCACCAGGAGGCACTT | 83 | 290 |
| 337377 | 3' UTR | 154 | 2941 | CCTTACAGAAACAGGCAGAA | 78 | 291 |
| 337378 | 3' UTR | 154 | 2959 | AGGTGGCCTGTGGCATTTGC | 16 | 292 |
| 337379 | 3' UTR | 154 | 2971 | GTATGTAGCTATAGGTGGCC | 71 | 293 |
| 337380 | 3' UTR | 154 | 2983 | GCAATGCCAGGAGTATGTAG | 83 | 294 |
| 337381 | 3' UTR | 154 | 2992 | TTAAAAGTGCAATGCCAGG | 86 | 295 |
| 337382 | 3' UTR | 154 | 3032 | GGCTTAGATAGTCCTATCTT | 84 | 296 |
| 337383 | 3' UTR | 154 | 3047 | TAAAAAGAAACCTAGGGCTT | 81 | 297 |

TABLE 13-continued

Inhibition of human STAT 3 mRNA levels
by chimeric phosphorothioate oligonucleotides
having 2'-MOE wings and a deoxy gap

| Isis # | Region | Target Seq ID No | Target Site | Sequence | % Inhib | Seq ID No |
|---|---|---|---|---|---|---|
| 337384 | 3' UTR | 154 | 3108 | ATACAGAAAGGCTATGCTGA | 89 | 298 |
| 337385 | 3' UTR | 154 | 3121 | TTAAGTTTCTTAAATACAGA | 70 | 299 |

As shown in Table 13, SEQ ID Nos 159, 161, 165, 166, 169, 170, 171, 174, 175, 176, 177, 178, 179, 180, 181, 182, 183, 184, 185, 186, 187, 188, 189, 190, 191, 192, 193, 197, 198, 199, 200, 201, 202, 203, 204, 205, 206, 207, 208, 209, 210, 211, 212, 213, 215, 216, 217, 220, 222, 223, 224, 225, 226, 227, 228, 232, 234, 235, 236, 237, 238, 239, 240, 241, 242, 243, 245, 246, 247, 248, 249, 250, 251, 252, 253, 254, 255, 256, 257, 258, 259, 261, 262, 263, 264, 265, 266, 267, 268, 269, 270, 271, 272, 274, 275, 276, 277, 278, 279, 280, 281, 283, 284, 285, 286, 287, 288, 289, 290, 291, 293, 294, 295, 296, 297, 298 and 299 inhibited human STAT3 expression at least 60%.

Example 19

Chimeric Phosphorothioate Oligonucleotides Targeted to Human STAT3 having 2'-MOE Wings and a Deoxy Gap In accordance with the present invention, an additional series of oligonucleotides was designed to target different regions of the human STAT 3, using published sequences (GenBank accession number L29277, incorporated herein as SEQ ID NO: 1, GenBank accession number NM_139276.1, incorporated herein as SEQ ID NO: 154). The oligonucleotides are shown in Table 14. "Target site" indicates the first (5'-most) nucleotide number on the particular target sequence to which the oligonucleotide binds. All compounds in Table 14 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE) nucleotides. The internucleoside (backbone) linkages are phosphorothioate (P=S) throughout the oligonucleotide. All cytidine residues are 5-methylcytidines.

TABLE 14

Chimeric phosphorothioate oligonucleotides
targeted to human STAT3 having 2'-MOE
wings and a deoxy gap

| Isis # | Region | Target Seq ID No | Target Site | Sequence | Seq ID No |
|---|---|---|---|---|---|
| 345752 | coding | 1 | 631 | GCATCTGCTGCTTCTCCGTC | 300 |
| 345753 | coding | 1 | 633 | CAGCATCTGCTGCTTCTCCG | 301 |
| 345754 | coding | 1 | 635 | TCCAGCATCTGCTGCTTCTC | 302 |
| 345755 | coding | 1 | 636 | CTCCAGCATCTGCTGCTTCT | 303 |
| 345756 | coding | 1 | 638 | TGCTCCAGCATCTGCTGCTT | 304 |
| 345757 | coding | 1 | 641 | TGCTGCTCCAGCATCTGCTG | 305 |
| 345758 | coding | 1 | 643 | GGTGCTGCTCCAGCATCTGC | 306 |
| 345759 | coding | 1 | 645 | AAGGTGCTGCTCCAGCATCT | 307 |
| 345760 | coding | 1 | 1663 | TGGGATTGTTGGTCAGCATG | 308 |
| 345761 | coding | 1 | 1668 | ATTCTTGGGATTGTTGGTCA | 309 |
| 345762 | coding | 1 | 1670 | ACATTCTTGGGATTGTTGGT | 310 |
| 345763 | coding | 1 | 1671 | CACATTCTTGGGATTGTTGG | 311 |
| 345764 | coding | 1 | 1673 | TTCACATTCTTGGGATTGTT | 312 |
| 345765 | coding | 1 | 1675 | AGTTCACATTCTTGGGATTG | 313 |
| 345766 | coding | 1 | 1677 | GAAGTTCACATTCTTGGGAT | 314 |
| 345767 | coding | 1 | 380 | AGATTATGAAACACCAAAGT | 315 |
| 345768 | coding | 1 | 382 | GGAGATTATGAAACACCAAA | 316 |
| 345769 | coding | 1 | 384 | CAGGAGATTATGAAACACCA | 317 |
| 345770 | coding | 1 | 387 | TCCCAGGAGATTATGAAACA | 318 |
| 345771 | coding | 1 | 388 | CTCCCAGGAGATTATGAAAC | 319 |
| 345772 | coding | 1 | 390 | CTCTCCCAGGAGATTATGAA | 320 |
| 345773 | coding | 1 | 392 | ATCTCTCCCAGGAGATTATG | 321 |
| 345774 | coding | 1 | 1872 | CTTGCCAGCCATGTTTTCTT | 322 |
| 345775 | coding | 1 | 1874 | CCCTTGCCAGCCATGTTTTC | 323 |
| 345776 | coding | 1 | 1876 | AGCCCTTGCCAGCCATGTTT | 324 |
| 345777 | coding | 1 | 1880 | GAGAAGCCCTTGCCAGCCAT | 325 |
| 345778 | coding | 1 | 1882 | AGGAGAAGCCCTTGCCAGCC | 326 |
| 345779 | coding | 154 | 1904 | GAAGGAGAAGCCCTTGCCAG | 327 |
| 345780 | coding | 1 | 1877 | AAGCCCTTGCCAGCCATGTT | 328 |
| 345781 | coding | 1 | 1879 | AGAAGCCCTTGCCAGCCATG | 329 |
| 345782 | coding | 154 | 1905 | AGAAGGAGAAGCCCTTGCCA | 330 |

TABLE 14-continued

Chimeric phosphorothioate oligonucleotides targeted to human STAT3 having 2'-MOE wings and a deoxy gap

| Isis # | Region | Target Seq ID No | Target Site | Sequence | Seq ID No |
|---|---|---|---|---|---|
| 345783 | coding | 154 | 1907 | CCAGAAGGAGAAGCCCTTGC | 331 |
| 345784 | coding | 154 | 1909 | ACCCAGAAGGAGAAGCCCTT | 332 |
| 345785 | coding | 1 | 2247 | TGCCTCCTCCTTGGGAATGT | 333 |
| 345786 | coding | 1 | 2249 | AATGCCTCCTCCTTGGGAAT | 334 |
| 345787 | coding | 1 | 2251 | CGAATGCCTCCTCCTTGGGA | 335 |
| 345788 | coding | 154 | 2274 | TTCCGAATGCCTCCTCCTTG | 336 |
| 345789 | coding | 154 | 2275 | TTTCCGAATGCCTCCTCCTT | 337 |
| 345790 | coding | 154 | 2277 | ACTTTCCGAATGCCTCCTCC | 338 |
| 345791 | coding | 1 | 420 | TTGCAGGAAGCGGCTATACT | 339 |
| 345792 | coding | 1 | 422 | TCTTGCAGGAAGCGGCTATA | 340 |
| 345793 | coding | 1 | 424 | ACTCTTGCAGGAAGCGGCTA | 341 |
| 345794 | coding | 1 | 425 | GACTCTTGCAGGAAGCGGCT | 342 |
| 345795 | coding | 1 | 427 | TCGACTCTTGCAGGAAGCGG | 343 |
| 345796 | coding | 1 | 428 | TTCGACTCTTGCAGGAAGCG | 344 |
| 345797 | coding | 1 | 430 | CATTCGACTCTTGCAGGAAG | 345 |
| 345798 | coding | 1 | 2176 | TCTTATAGCCCATGATGATT | 346 |
| 345799 | coding | 1 | 2178 | GATCTTATAGCCCATGATGA | 347 |
| 345800 | coding | 1 | 2180 | ATGATCTTATAGCCCATGAT | 348 |
| 345801 | coding | 1 | 2182 | CCATGATCTTATAGCCCATG | 349 |
| 345802 | coding | 1 | 2186 | GCATCCATGATCTTATAGCC | 350 |
| 345803 | coding | 1 | 2188 | TAGCATCCATGATCTTATAG | 351 |
| 345804 | coding | 1 | 2189 | GTAGCATCCATGATCTTATA | 352 |
| 345805 | 3' UTR | 154 | 3102 | AAAGGCTATGCTGATACAGT | 353 |
| 345806 | 3' UTR | 154 | 3104 | AGAAAGGCTATGCTATACA | 354 |
| 345807 | 3' UTR | 154 | 3106 | ACAGAAAGGCTATGCTGATA | 355 |
| 345808 | 3' UTR | 154 | 3107 | TACAGAAAGGCTATGCTGAT | 356 |
| 345809 | 3' UTR | 154 | 3109 | AATACAGAAAGGCTATGCTG | 357 |
| 345810 | 3' UTR | 154 | 3110 | AAATACAGAAAGGCTATGCT | 358 |
| 345811 | 3' UTR | 154 | 3112 | TTAAATACAGAAAGGCTATG | 359 |
| 345812 | 3' UTR | 154 | 3114 | TCTTAAATACAGAAAGGCTA | 360 |
| 345813 | 3' UTR | 1 | 2753 | GGTCTCAGAGAACACATCCT | 361 |
| 345814 | 3' UTR | 1 | 2755 | TGGGTCTCAGAGAACACATC | 362 |
| 345815 | 3' UTR | 1 | 2757 | CATGGGTCTCAGAGAACACA | 363 |
| 345816 | 3' UTR | 1 | 2758 | TCATGGGTCTCAGAGAACAC | 364 |
| 345817 | 3' UTR | 1 | 2761 | TGATCATGGGTCTCAGAGAA | 365 |
| 345818 | 3' UTR | 1 | 2763 | CCTGATCATGGGTCTCAGAG | 366 |
| 345819 | 3' UTR | 1 | 2765 | CCCCTGATCATGGGTCTCAG | 367 |
| 345820 | coding | 154 | 1912 | CAGACCCAGAAGGAGAAGCC | 368 |
| 345822 | coding | 154 | 1916 | CAGCCAGACCCAGAAGGAGA | 369 |
| 345823 | coding | 154 | 1917 | CCAGCCAGACCCAGAAGGAG | 370 |
| 345824 | coding | 154 | 1919 | GTCCAGCCAGACCCAGAAGG | 371 |
| 345825 | coding | 154 | 1920 | TGTCCAGCCAGACCCAGAAG | 372 |
| 345826 | coding | 154 | 1922 | ATTGTCCAGCCAGACCCAGA | 373 |
| 345827 | coding | 154 | 1924 | ATATTGTCCAGCCAGACCCA | 374 |
| 345828 | coding | 1 | 2181 | CATGATCTTATAGCCCATGA | 375 |
| 345829 | coding | 1 | 2183 | TCCATGATCTTATAGCCCAT | 376 |
| 345830 | coding | 1 | 2185 | CATCCATGATCTTATAGCCC | 377 |
| 345831 | coding | 1 | 2187 | AGCATCCATGATCTTATAGC | 378 |
| 345832 | coding | 1 | 2191 | TGGTAGCATCCATGATCTTA | 379 |
| 345833 | coding | 1 | 2192 | TTGGTAGCATCCATGATCTT | 380 |
| 345834 | coding | 1 | 2196 | GATATTGCTAGCATCCATGA | 381 |

Example 20

Chimeric Phosphorothioate Oligonucleotides Targeted to Mouse STAT3, having 2'-MOE Wings and a Deoxy Gap In accordance with the present invention, an additional series of oligonucleotides was designed to target different regions of the mouse STAT 3 RNA, using published sequences (GenBank accession number U06922.1, incorporated herein as SEQ ID NO: 82, GenBank accession number U30709.1, incorporated herein as SEQ ID NO: 382). The oligonucleotides are shown in Table 15. "Target site" indicates the first (5'-most) nucleotide number on the particular target sequence to which the oligonucleotide binds. All compounds in Table 15 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines.

TABLE 15

Chimeric phosphorothioate oligonucleotides targeted to mouse STAT3 having 2'-MOE wings and a deoxy gap

| Isis # | Region | Target Seq ID No | Target Site | Sequence | Seq ID No |
|---|---|---|---|---|---|
| 29800 | coding | 82 | 2213 | TGGTATTGCTGCAGGTCGTT | 383 |
| 29801 | coding | 82 | 2224 | CGGCAGGTCAATGGTATTGC | 384 |
| 29802 | coding | 82 | 2230 | GGACATCGGCAGGTCAATGG | 385 |
| 29806 | 5' UTR | 382 | 11 | TTGTACCTCAGCGCGGACGC | 386 |
| 134027 | coding | 82 | 2309 | ACTCAAACTGCCCTCCTGCT | 95 |
| 337354 | coding | 82 | 2204 | TGCAGGTCGTTGGTGTCACA | 268 |
| 345821 | coding | 82 | 1742 | GCCAGACCCAGAAGGAGAAG | 90 |

In a further embodiment, an additional series of oligonucleotides was designed to target mouse STAT 3 RNA, using published sequences (GenBank accession number U06922.1, incorporated herein as SEQ ID NO: 82). The compounds are shown in Table 16. "Target site" indicates the first (5'-most) nucleotide number on the particular sequence to which the compound binds. All compounds in Table 16 are chimeric oligonucleotides, composed of a "gap" region consisting of twelve 2'-deoxynucleotides, which is flanked on both sides (5' and 3' directions) by "wings" consisting of 2'-methoxyethyl (2'-MOE)nucleotides. The number of 2'-MOE nucleotides in the gaps vary from a length of 2 to 5 nucleotides, with the 2'-deoxynucleotides in plain type and the 2'-MOE nucleotides in bold type. The exact structure of each oligonucleotide is designated in Table 16 as the "wing" structure. A designation of 5~10~5, for example, indicates that the first and last 5 nucleotides are 2'-MOE nucleotides and the central 10 nucleotides are 2'deoxynucleotides. The internucleoside (backbone) linkages are phosphorothioate (P=S) throughout the oligonucleotide. Unmodified cytidine residues which are underscored; all other cytidine residues are 5-methylcytidines.

TABLE 16

Chimeric phosphorothioate oligonucleotides targeted to mouse STAT3, having 2'-MOE wings and a deoxy gap

| ISIS # | Region | TARGET SEQ ID NO | TARGET SITE | SEQUENCE | WING STRUCTURE | SEQ ID NO |
|---|---|---|---|---|---|---|
| 133003 | 3' UTR | 82 | 2527 | AAAAAGTGCCCAGATTGCCC | 5-12-5 | 99 |
| 346030 | 3' UTR | 82 | 2527 | AAAAGTG<u>CCC</u>GATTGCCC | 4-10-5 | 387 |
| 346031 | 3' UTR | 82 | 2528 | AAAAGTG<u>CCC</u>AGATTGCC | 4-10-4 | 388 |
| 346032 | 3' UTR | 82 | 2528 | AAAGTG<u>CCC</u>AGATTGCC | 3-10-4 | 389 |

In a further embodiment of the present invention, an additional series of oligonucleotides was designed to target different regions of the mouse STAT 3 RNA, using published sequence (GenBank accession number U06922.1, incorporated herein as SEQ ID NO: 82). The oligonucleotides are shown in Table 17. "Target site" indicates the first (5'-most) nucleotide number on the particular target sequence to which the oligonucleotide binds. All compounds in table 17 are uniformly composed of 2'-methoxyethyl (2'-MOE) nucleotides. The internucleoside (backbone) linkages are phosphorothioate (P=S) throughout the oligonucleotide, and all cytidine residues are 5-methylcytidines.

TABLE 17

Phosphorothioated uniform 2' MOE oligonucleotides targeted to mouse STAT3

| Isis # | Region | Target Seq ID No | Target Site | Sequence | Seq ID No |
|---|---|---|---|---|---|
| 29803 | coding | 82 | 2253 | ATCAATGAATCTAAAGTGCG | 93 |
| 29805 | coding | 82 | 2206 | GCTGCAGGTCGTTGGTGTCA | 390 |

Example 21

Antisense Inhibition of Human STAT 3 by Chimeric Oligonucleotides having 2'-MOE Wings and a Deoxy Gap: Dose Response In accordance with the present invention, a subset of the antisense oligonucleotides targeted to human STAT3 was further investigated in dose-response studies. The compounds were analyzed for their effect on human STAT 3 mRNA levels in T-24 cells.

The transitional cell bladder carcinoma cell line T-24 was obtained from the American Type Culture Collection (ATCC) (Manassas, Va.). T-24 cells were routinely cultured in complete McCoy's 5A basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence. Cells were seeded into 96-well plates (Falcon-Primaria#3872) at a density of 7000 cells/well for use in RT-PCR analysis.

Control oligonucleotides used were ISIS 129695 (TTCTACCTCGCGCGATTTAC, SEQ ID NO: 391), ISIS 129694 (GTACAGTTATGCGCGGTAGA SEQ ID NO: 392), ISIS 129690 (TTAGAATACGTCGCGTTATG SEQ ID NO: 393), ISIS 129686 (CGTTATTAACCTCCGTTGAA SEQ ID NO: 394)., ISIS 116847 (CTGCTAGC- CTCTGGATTTGA, SEQ ID NO: 395) and ISIS 113529 (CTCTTACTGTGCTGTGGACA SEQ ID NO: 396). These are universal scrambled control oligonucleotides.

T-24 cells were treated with 18.75, 37.5, 75, or 150 nM of oligonucleotide mixed with 3 ug/mL LIPOFECTIN per 100 nM oligonucleotide as described by other examples herein. Untreated cells served as controls. Following 16 hours of treatment, RNA was prepared from cells for subsequent real-time PCR analysis.

Human STAT3 mRNA expression levels were quantitated by real-time PCR using primer probe set PPS 199 and gene target quantities were normalized using Ribogreen as described in other examples herein. Data are averages from two experiments are shown in Table 18. A "−" or "+" designation indicates a decrease or increase of STAT 3 mRNA expression, respectively, relative to untreated control cells.

TABLE 18

Inhibition of human STAT 3 mRNA levels by chimeric phosphorothioate oligonucleotides having 2'-MOE wings and a deoxy gap: dose response
Percent change of STAT3 expression using PPS 199

| Isis # | Seq ID No | Oligonucleotide Concentration | | | |
|---|---|---|---|---|---|
| | | 18.75 nM | 37.5 nM | 75 nM | 150 nM |
| 106747 | 58 | −37 | −48 | −71 | −84 |
| 337247 | 161 | −23 | −43 | −62 | −75 |
| 337270 | 184 | −29 | −41 | −67 | −87 |
| 337276 | 190 | −40 | −61 | −76 | −81 |
| 337284 | 198 | −49 | −64 | −69 | −72 |
| 337293 | 207 | −26 | −49 | −66 | −79 |
| 337303 | 217 | −44 | −61 | −69 | −72 |
| 337332 | 246 | −63 | −79 | −87 | −92 |
| 337333 | 247 | −48 | −73 | −82 | −88 |
| 337344 | 258 | −27 | −47 | −63 | −77 |
| 337348 | 262 | −61 | −77 | −82 | −86 |
| 337384 | 298 | −40 | −55 | −71 | −80 |
| 129695 | 391 | +5 | +2 | +8 | 0 |
| 129694 | 392 | +4 | −3 | −4 | −10 |
| 129690 | 393 | +2 | +7 | +6 | +8 |
| 129686 | 394 | +2 | +1 | −5 | +1 |
| 116847 | 395 | +7 | +4 | +8 | +5 |
| 113529 | 396 | +1 | −1 | −11 | −26 |

As shown in Table 18, the compounds tested inhibit human STAT3 mRNA expression in a dose-dependent manner.

The dose-response was repeated in T-24 cells and gene target quantities were measured using a different primer-probe set, called PPS 2033 herein. PPS 2033 comprises probes and primers to human STAT3 were designed to hybridize to a human STAT3 sequence, using published sequence information (incorporated herein as SEQ ID NO: XXX). For PPS 2033 the PCR primers were: forward primer: GAGGCCCGCCCAACA (SEQ ID NO: 397) reverse primer: TTCTGCTAATGACGTTATCCAGTTTT (SEQ ID NO: 398) and the PCR probe was: FAM-CTGC-CTAGATCGGC-TAMRA (SEQ ID NO: 399) where FAM is the fluorescent reporter dye and TAMRA is the quencher dye. Gene target quantities obtained by real time RT-PCR are normalized by quantifying total RNA using RiboGreen™ (Molecular Probes, Inc. Eugene, Oreg.). Control oligonucleotides used were ISIS 129695 (SEQ ID NO: 391), ISIS 129694 (SEQ ID NO: 392), ISIS 129690 (SEQ ID NO: 393), ISIS 129686 (SEQ ID NO: 394), ISIS 116847 (SEQ ID NO: 395) and ISIS 113529 (SEQ ID NO: 396).

T-24 cells were treated with 18.75, 37.5, 75, or 150 nM of oligonucleotide mixed with 3 ug/mL LIPOFECTIN per 100 nM oligonucleotide as described by other examples herein. Untreated cells served as controls. Following 16 hours of treatment, RNA was prepared from cells for subsequent real-time PCR analysis.

Human STAT3 mRNA expression levels were quantitated by real-time PCR using primer probe set PPS 2033 and gene target quantities were normalized using Ribogreen as described in other examples herein. Data are averages from two experiments are shown in Table 19. A "−" or "+" designation indicates a decrease or increase of STAT 3 mRNA expression, respectively, relative to untreated control cells.

TABLE 19

Inhibition of human STAT 3 mRNA levels by chimeric phosphorothioate oligonucleotides having 2'-MOE wings and a deoxy gap: dose response
Percent change of STAT3 expression using PPS 2033

| Isis # | Seq ID No | Oligonucleotide Concentration | | | |
|---|---|---|---|---|---|
| | | 18.75 nM | 37.5 nM | 75 nM | 150 nM |
| 106747 | 58 | −32 | −48 | −62 | −76 |
| 337247 | 161 | +17 | −21 | −53 | −69 |
| 337270 | 184 | −16 | −27 | −67 | −87 |
| 337276 | 190 | −34 | −58 | −75 | −81 |
| 337284 | 198 | −49 | −62 | −66 | −68 |
| 337293 | 207 | −26 | −49 | −67 | −79 |
| 337303 | 217 | −47 | −59 | −69 | −71 |
| 337332 | 246 | −66 | −79 | −85 | −91 |
| 337333 | 247 | −46 | −70 | −82 | −90 |
| 337344 | 258 | −17 | −37 | −60 | −76 |
| 337348 | 262 | −53 | −76 | −83 | −86 |
| 337384 | 298 | −41 | −59 | −69 | −80 |
| 129695 | 391 | −4 | +2 | +8 | +3 |
| 129694 | 392 | +19 | −1 | +7 | +2 |
| 129690 | 393 | +4 | +10 | +8 | +11 |
| 129686 | 394 | +20 | +16 | +25 | +9 |
| 116847 | 395 | +45 | +33 | +22 | −2 |
| 113529 | 396 | +1 | +12 | −11 | −24 |

As shown in Table 19, measurement of target gene quantities using PPS 2033 demonstrates that the compounds tested inhibit human STAT3 mRNA expression in a dose-dependent manner.

An additional dose-response experiment was preformed in A549 cells. A549 cells were treated with 18.75, 37.5, 75, or 150 nM of oligonucleotide mixed with 3 ug/mL LIPO-FECTIN per 100 nM oligonucleotide as described by other examples herein. Control oligonucleotides used were ISIS 129686 (SEQ ID NO: 394) and ISIS 129690 (SEQ ID NO: 393). Untreated cells served as controls. Following 16 hours of treatment. RNA was prepared from cells for subsequent real-time PCR analysis.

Human STAT3 mRNA expression levels were quantitated by real-time PCR using primer probe set PPS 199 and gene target quantities were normalized using Ribogreen as described in other examples herein. Data are averages from two experiments are shown in Table 20. A "−" or "+" designation in the dose response results indicates a decrease or increase of STAT 3 mRNA expression, respectively, relative to untreated control cells.

TABLE 20

Inhibition of human STAT 3 mRNA levels by chimeric phosphorothioate oligonucleotides having 2'-MOE wings and a deoxy gap: dose response
Percent change of STAT3 expression in A549 cells using PPS 199

| | | Oligonucleotide Concentration | | | |
|---|---|---|---|---|---|
| Isis # | Seq ID No | 18.75 nM | 37.5 nM | 75 nM | 150 nM |
| 106734 | 45 | −2 | −16 | −56 | −73 |
| 337332 | 246 | −31 | −61 | −77 | −87 |
| 337333 | 247 | −8 | −39 | −59 | −75 |
| 337348 | 262 | −26 | −43 | −55 | −77 |
| 129686 | 394 | +27 | +23 | +22 | +19 |
| 129690 | 393 | +30 | +27 | +16 | +27 |

As shown in Table 20, the compounds tested inhibit human STAT3 mRNA expression in A549 cells in a dose-dependent manner.

Example 22

Design and Screening of Duplexed Antisense Compounds Targeting STAT3

In accordance with the present invention, a series of nucleic acid duplexes comprising the antisense compounds of the present invention and their complements can be designed to target STAT3. The nucleobase sequence of the antisense strand of the duplex comprises at least a portion of an oligonucleotide targeted to STAT3 as disclosed herein. The ends of the strands may be modified by the addition of one or more natural or modified nucleobases to form an overhang. The sense strand of the dsRNA is then designed and synthesized as the complement of the antisense strand and may also contain modifications or additions to either terminus. For example, in one embodiment, both strands of the dsRNA duplex would be complementary over the central nucleobases, each having overhangs at one or both termini.

For example, a duplex comprising an antisense strand having the sequence CGAGAGGCGGACGGGACCG (SEQ ID NO: 405) and having a two-nucleobase overhang of deoxythymidine(dT) would have the following structure:

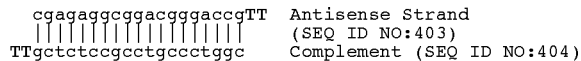
```
cgagaggcggacgggaccgTT   Antisense Strand
|||||||||||||||||||     (SEQ ID NO:403)
TTgctctccgcctgccctggc   Complement (SEQ ID NO:404)
```

In another embodiment, a duplex comprising an antisense strand having the same sequence CGAGAGGCGGACGG-GACCG may be prepared with blunt ends (no single stranded overhang) as shown:

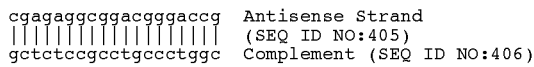
```
cgagaggcggacgggaccg    Antisense Strand
|||||||||||||||||||    (SEQ ID NO:405)
gctctccgcctgccctggc    Complement (SEQ ID NO:406)
```

RNA strands of the duplex can be synthesized by methods disclosed herein or purchased from Dharmacon Research Inc., (Lafayette, Colo.). Once synthesized, the complementary strands are annealed. The single strands are aliquoted and diluted to a concentration of 50 uM. Once diluted, 30 uL of each strand is combined with 15 uL of a 5× solution of annealing buffer. The final concentration of said buffer is 100 mM potassium acetate, 30 mM HEPES-KOH pH 7.4, and 2 mM magnesium acetate. The final volume is 75 uL. This solution is incubated for 1 minute at 90° C. and then centrifuged for 15 seconds. The tube is allowed to sit for 1 hour at 37° C. at which time the dsRNA duplexes are used in experimentation. The final concentration of the dsRNA duplex is 20 uM. This solution can be stored frozen (−20° C.) and freeze-thawed up to 5 times.

Once prepared, the duplexed antisense compounds are evaluated for their ability to modulate STAT3.

When cells reached 80% confluency, they are treated with duplexed antisense compounds of the invention. For cells grown in 96-well plates, wells are washed once with 200 •L OPTI-MEM-1 reduced-serum medium (Gibco BRL) and then treated with 130 μL of OPTI-MEM-1 containing 12 μg/mL LIPOFECTIN (Gibco BRL) and the desired duplex antisense compound at a final concentration of 200 nM (a ratio of 6 μg/mL LIPOFECTIN per 100 nM duplex antisense compound). After 5 hours of treatment, the medium is replaced with fresh medium. Cells are harvested 16 hours after treatment, at which time RNA is isolated and target reduction measured by RT-PCR.

A series of nucleic acid duplexes comprising the antisense compounds of the present invention and their complements was designed to target STAT3 mRNA, using published sequence (GenBank Accession number L29277, incorporated herein as SEQ ID NO: 1). The nucleobase sequence of the antisense strand of the duplex is 20 nucleotides in length. The sequences of the antisense strand are listed in Table 21. The sense strand of the dsRNA is designed and synthesized as the complement of the antisense strand.

All compounds in Table 21 are oligodeoxynucleotides, 21 nucleotides in length with the two nucleotides on the 3' end being the TT overhang and with phosphodiester internucleoside linkages (backbones) throughout. These sequences are shown to contain thymine (T) but one of skill in the art will appreciate that thymine (T) is generally replaced by uracil (U) in RNA sequences.

TABLE 21 dsRNAs targeted to human STAT3

| ISIS # | REGION | TARGET SITE | TARGET SEQ ID | SEQUENCE | SEQ ID NO |
|---|---|---|---|---|---|
| 330249 | coding | 1669 | 1 | ATTCTTGGGATTGTTGGTCTT | 400 |
| 330247 | coding | 637 | 1 | CTCCAGCATCTGCTGCTTCTT | 401 |

The compounds in Table 21 were tested for their effects on human STAT3 expression in A549 cells. ISIS 330249 targets the same site as the antisense oligonucleotid ISIS 106734 (SEQ ID NO: 45) and ISIS 330247 targets the same site as the antisense oligonucleotide ISIS 113176 (SEQ ID NO: 115); thus, ISIS 106734 and ISIS 113176 were also tested. A549 cells were treated with oligonucleotide mixed with LIPOFECTIN (Invitrogen Corporation, Carlsbad, Calif.) as described herein. Oligonucleotide concentrations used are indicated in Table 22. The control oligonucleotide used was ISIS 129698 (TTTGATCGAGGTTAGCCGTG, SEQ ID NO: 402). Cells were treated with oligonucleotide for 4 hours and harvested an additional 16 hours later. Untreated cells served as a control.

Human STAT3 mRNA expression levels were quantitated by real-time PCR using primer probe set PPS 199 and gene target quantities were normalized using Ribogreen as described in other examples herein. Data are averages from two experiments are shown in Table 22. A "−" or "+" designation indicates a decrease or increase of STAT 3 mRNA expression, respectively, relative to untreated control cells. Where present, "N.D." indicates not determined.

TABLE 22

Inhibition of STAT 3 mRNA levels by dsRNAs Percent change in STAT3 mRNA expression in A549 cells by duplex antisense compounds

| | | Oligonucleotide Concentration | | | | | |
|---|---|---|---|---|---|---|---|
| Isis # | SEQ ID NO | 12.5 nM | 25 nM | 50 nM | 100 nM | 200 nM | 400 nM |
| 330249 | 400 | −64 | −70 | −80 | −83 | −87 | −81 |
| 106734 | 45 | −5 | −5 | −40 | −56 | −67 | −77 |
| 330247 | 401 | +11 | −19 | −15 | −16 | −20 | −48 |
| 113176 | 115 | +8 | +17 | +6 | 0 | −22 | −34 |
| 129698 | 402 | N.D. | N.D. | +41 | +42 | +1 | +22 |

Example 23

Inhibition of Tumor Growth in LNCaP Mouse Model of Prostate Carcinoma

The LNCaP murine model of human prostate carcinoma is described in Kiyama et al., Cancer Res. 63:3575-3584, 2003, incorporated herein by reference. Briefly, LNCaP human prostatic carcinoma cells were cultured and maintained in RPMI medium (Life Technologies, Inc., Carlsbad, Calif.) supplemented with 5% heat inactivated fetal calf serum (FCS). About 1×10' LNCaP cells' were inoculated subcutaneously with 0.1 ml of Matrigel (Becton Dickinson Labware, Franklin Lakes, N.J.) in the flank region of 6-8 week old male athymic nude mice (Harlan Sprague Dawley, Inc., Indianapolis, Ind.) via a 27 gauge needle under methoxyfluorane anesthesia. Mice bearing tumors between 300 and 500 mm$^3$ in volume were castrated via a scrotal approach and randomly assigned to treatment with 10 mg/kg of either ISIS 113176 human antisense or ISIS 129987 human mismatch control STAT 3 oligonucleotide intraperitoneally five times per week for the first week followed by three times per week thereafter. Treatment commenced beginning one day after castration. Tumor volumes and serum prostate specific antigen (PSA) measurements were performed once weekly. Tumor volumes were calculated by the formula L×W×H×0.5236 (Gleave et al., Cancer Res. 51:1598-1605, 1992). Blood samples were obtained from tail vein incisions of mice, and serum PSA levels were determined by an enzymatic immunoassay kit with a lower limit of sensitivity of 0.2 µg/liter (Abbott IMX, Montreal, Quebec, Canada) according to the manufacturer's protocol.

ISIS 113176 suppressed the induction of serum PSA levels and tumor growth in the LNCaP xenograft model in castrated nude mice. Similar treatment of mice with the mismatch control oligonucleotide ISIS 129987 had no effect. The observed STAT3 antisense oligonucleotide-mediated effects on PSA and tumor volume were significantly different from mismatch oligonucleotide ISIS 129987 or saline treated controls (student's t-test, p<0.05). Treatment effects were demonstrated out to the end of the observation perion (10 weeks post-castration). To address the potential target-specific toxicit of this approach, normal mice were treated subcutaneously with an optimized murine STAT3 antisense oligonucleotide (up to 50 mg/kg three times per week for 2 weeks) and pharmacodynamic and toxological effects were evaluated in the blood, liver and bone marrow. STAT3 antisense oligonucleotide treatment resulted in 85% liver mRNA reduction and significant inhibition of STAT3 protein in the bone marrow pre-monocytic subpopulation. No overt changes were observed in complete blood counts, liver histology or bone marrow subpopulations in animals treated with STAT3 antisense oligonucleotide. Liver and bone marrow expression of STAT3 was significantly reduced by treatment with STAT3 antisense oligonucleotide. Thus, antisense oligonucleotides to STAT 3 represent a therapeutic opportunity for treatment of prostate cancer.

What is claimed is:

1. A modified or unmodified antisense compound 20 to 30 nucleobases in length targeted to a nucleic acid molecule encoding human STAT 3, comprising the nucleotide sequence shown in SEQ ID NO: 184, or a pharmaceutically acceptable salt thereof.

2. The antisense compound of claim 1, which comprises at least one modified internucleoside linkage.

3. The antisense compound of claim 2, wherein said modified internucleoside likage linkage is a phosphorothioate linkage.

4. The antisense compound of claim 3, which comprises at least one modified sugar moiety.

5. The antisense compound of claim 4, wherein said modified sugar moiety is a 2'-O-(2-methoxyethyl) moiety.

6. The antisense compound of claim 5, which comprises at least one modified nucleobase.

7. The antisense compound of claim 6, wherein said modified nucleobase is a 5-methyl cytosine.

8. The antisense compound of claim 1, wherein all internucleoside linkages are phosphorothioate, nucleotides 1-5 and 16-20 reading from the 5' end to 3' end of SEQ ID NO:

184 each comprise a 2'-O-(2-methoxyethyl) sugar, or a pharmaceutically acceptable salt thereof.

9. The antisense compound of claim 8, wherein all cytidine residues are 5-methylcytidines.

10. The antisense compound of claim 9, wherein said pharmaceutically acceptable salt is a sodium salt.

11. A pharmaceutical composition, comprising said antisense compound of claim 1 and a pharmaceutically acceptable carrier or diluent.

12. An antisense oligonucleotide, consisting of the nucleotide sequence shown in SEQ ID NO: 184, wherein every intemucleoside linkage is a phosphorothioate linkage, nucleotides 1-5 and 16-20 reading from the 5' end to the 3' end each comprise a 2'-O-(2-methoxyethyl) sugar, nucleotides 6-15 are 2'-deoxynucleotides, every cytidine residue is a 5-methylcytidine, and which is in the form of a sodium salt.

13. A pharmaceutical composition, comprising said antisense oligonucleotide of claim 12, and a pharmaceutically acceptable carrier or diluent.

* * * * *